(12) United States Patent
Lieber et al.

(10) Patent No.: US 9,200,041 B2
(45) Date of Patent: *Dec. 1, 2015

(54) METHODS AND SYSTEMS FOR ADENOVIRUS INTERACTION WITH DESMOGLEIN 2 (DSG2)

(71) Applicant: University of Washington through its Center for Commercialization, Seattle, WA (US)

(72) Inventors: Andre Lieber, Seattle, WA (US); Hongjie Wang, Seattle, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/066,353

(22) Filed: Oct. 29, 2013

(65) Prior Publication Data

US 2014/0107014 A1    Apr. 17, 2014

Related U.S. Application Data

(63) Continuation of application No. 13/158,246, filed on Jun. 10, 2011.

(60) Provisional application No. 61/470,663, filed on Apr. 1, 2011, provisional application No. 61/430,091, filed on Jan. 5, 2011, provisional application No. 61/353,652, filed on Jun. 10, 2010.

(51) Int. Cl.

| | | |
|---|---|---|
| *C07K 14/075* | (2006.01) | |
| *A61K 38/16* | (2006.01) | |
| *C12N 15/861* | (2006.01) | |
| *G01N 33/53* | (2006.01) | |
| *C07K 14/005* | (2006.01) | |
| *A61K 39/395* | (2006.01) | |
| *C07K 16/28* | (2006.01) | |
| *C12N 7/00* | (2006.01) | |
| *C12N 15/86* | (2006.01) | |
| *A61K 45/06* | (2006.01) | |
| *G01N 33/50* | (2006.01) | |

(52) U.S. Cl.
CPC ............. *C07K 14/005* (2013.01); *A61K 38/162* (2013.01); *A61K 39/39558* (2013.01); *A61K 45/06* (2013.01); *C07K 16/28* (2013.01); *C12N 7/00* (2013.01); *C12N 15/86* (2013.01); *G01N 33/5076* (2013.01); *C07K 2317/76* (2013.01); *C12N 2710/10322* (2013.01); *C12N 2710/10343* (2013.01); *C12N 2710/10345* (2013.01)

(58) Field of Classification Search
CPC ....... A61K 38/00; A61K 38/16; C07K 14/47; C07K 14/075; A01N 37/18; C12N 15/861; G01N 33/53
USPC .......................................... 530/350; 514/3.7
See application file for complete search history.

(56) References Cited

U.S. PATENT DOCUMENTS 7,560,527 B1    7/2009 Legrand et al.

FOREIGN PATENT DOCUMENTS

| WO | 99/41359 | 8/1999 |
| WO | 00/42208 | 7/2000 |
| WO | 2005/040333 A2 | 5/2005 |
| WO | WO 2005040333 A2 * | 5/2005 |

OTHER PUBLICATIONS

DeCrescenzo et al., Real-Time Monitoring of the Interactions of Two-Stranded de NoVo Designed Coiled-Coils: Effect of Chain Length on the Kinetic and Thermodynamic Constants of Binding, Biochem. 42:1754-1763 (2003).*
Tuve et al., "A New Group B Adenovirus Receptor Is Expressed at High Levels on Human Stem and Tumor Cells," J. Virol. 80:12109-20 (2006).*
Wang et al., "Desmoglein 2 is a receptor for adenovirus serotypes 3, 7, 11, and 14," Nat. Med. 17:96-104 (Jan. 2011).*
UnitProt Accession No. P04501 accessed Oct. 16, 2014 at URL: uniprot.org/uniprot/P04501.*
Wheeler, et al. "Understanding resistance to EGFR inhibitors—impact on future treatment strategies," 2010. Nat Rev Clin Oncol 7:493-507.
Wu, et al. "Bacteroides fragilis enterotoxin cleaves the zolula adherens protein, E-cadherin," 1998. Proc Natl Acad Sci USA 95:14979-14984.
Yang, et al. "Development and Characterization of a Recombinant Madin-Darby Canine Kidney Cell Line That Expresses Rat Multidrug Resistance-Associate Protein 1(rMRP1)," 2004. AAPS J 6:77-85.
Yashiro, et al. "Decreased expression of the adhesion molecule desmolglein-2 is associated with diffuse-type gastric carcinoma," 2006. Eur J Cancer 42:2397-2403.
Zeng, et al. "A ligand-pseudoreceptor system based on de novo designed peptides for the generation of adenoviral vectors with altered tropism," 2008. J Gene Med 10:355-367.
Arnberg, "Adenovirus receptors: implications for tropism, treatment and targeting," 2009. Rev Med Virol19:165-178.
Chitaev, et al. "Direct Ca2+-dependent Heterophilic Interaction between Desmosomal Cadherins, Desmoglein and Desmocollin, Contributes to Cell-Cell Adhesion," 1997. J Cell Bioi 138:193-201.
Coyne, et al. "CAR: A virus receptor within the tight junction," 2005. Adv Drug Deilv Rev 57:869-882.
Coyne, et al. "Coxsackievirus Entry across Epithelial Tight Junctions Requires Occludin and the Small GTPases Rab34 and Rab5," 2007. Cell Host Microbe 2:181-192.
Disis, et al. "Enhancing Cancer Vaccine Efficacy via Modulation of the Tumor Microenvironment," 2009. Clin Cancer Res 15:6476-6478.

(Continued)

*Primary Examiner* — Julie Ha
*Assistant Examiner* — Kristina M Hellman
(74) *Attorney, Agent, or Firm* — McDonnell Boehnen Hulbert & Berghoff LLP

(57) ABSTRACT

The present invention provides compositions, compounds, and methods relating to recombinant adenoviral-based polypeptides for treating disorders associated with epithelial tissues.

19 Claims, 27 Drawing Sheets

(56) References Cited

OTHER PUBLICATIONS

Fender, et al. "Synthesis, cellular localization, and quantification of penton-dodecahedron in serotype 3 adenovirus-infected cells," 2005. Virology 340:167-173.

Granio, et al. "Adenovirus 5-Fiber 35 Chimeric Vector Mediates Efficient Apical Correction of the Cystic Fibrosis Transmembrane Conductance Regulator Defect in Cystic Fibrosis Primary Airway Epithelia," 2010. Hum Gene Ther 21:251-269.

Harper, et al. "Advances in Platinum Chemotherapeutics," 2010. Chemistry 16:7064-7077.

Kalin, et al. "Macropinocytotic Uptake and Infection of Human Epithelial Cells with Species B2 Adenovirus Type 35," 2010. J Virol 84:5336-5350.

Keim, et al. "Generation and Characterization of Monoclonal Antibodies Against the Proregion of Human Desmoglein-2," 2008. Hybridoma (Larchmt) 27:249-258.

Kirby, et al. "Identification of Contact Residues and Definition of the CAR-Binding Site of Adenovirus Type 5 Fiber Protein," 2000. J Virol74:2804-2813.

Latorre, et al. 2005. "Viral oncoprotein-induced mislocalization of select PDZ proteins disrupts tight junctions and causes polarity defects in epithelial cells," J Cell Sci 118:4283-4293.

Lee, et al. "Targeting YB-1 in HER-2 Overexpressing Breast Cancer Cells Induces Apoptosis via the mTOR/STAT3 Pathway and Supresses Tumor Growth in Mice," 2008. Cancer Res 68:8661-8666.

Litowski, et al. "Designing Heterodimeric Two-stranded-Helical Coiled-coils," 2002. J Bioi Chem 277:37272-37279.

Lortat-Jacob, et al. "Kinetic Analysis of Adenovirus Fiber Binding to Its Receptor Reveals an Avidity Mechanism for Trimeric Receptor-Ligand Interactions," 2001. J Bioi Chem 276:9009-9015.

Ni, et al. "Evaluation of adenovirus vectors containing serotype 35 fibers for tumor targeting," 2006. Cancer Gene Ther 13:1072-1081.

Persson, et al. "Adenovirus type 11 binding alters the conformation of its receptor CD46," 2007. Nat Struct Mol Bioi 14:164-166.

Sanchez, et al. "Outbreak of Adenovirus 35 Pneumonia among Adult Residents and Staff of a Chronic Care Psychiatric Facility," 1997. J Infect Dis 176:760-763.

Shayakhmetov, et al. "Dependence of Adenovirus Infectivity on Length of the Fiber Shaft Domain," 2000. J Virol 74:10274-10286.

Shayakhmetov, et al. "Efficient Gene Transfer into Human CD341 Cells by a Retargeted Adenovirus Vector," 2000. J Virol 74:2567-2583.

Sonoda, et al. "Clostridiump erfringensE nterotoxinF ragmentR emovesS pecificC laudins from Tight Junction Strands: Evidence for Direct Involvement of Claudins in Tight Junction Barrier," 1999. J Cell Bioi 147:195-204.

Tuve, et al. "Role of Cellular Heparan Sulfate Proteoglycans in Infection of Human Adenovirus Serotype 3 and 35," 2008. PLoS Pat hog 4:e1000189.

Tuve, et al. "A New Group B Adenovirus Receptor Is Expressed at High Levels on Human Stem and Tumor Cells," 2006. J Virol 80:12109-12120.

Walters, et al. "Adenovirus Fiber Disrupts CAR-Mediated Intercellular Adhesion Allowing Virus Escape," 2002. Cell 110:789-799.

Yang, et al. "Conditionally Replciating Adenovirus Expressing TIMP2 for Ovarian Cancer Cancer Therapy," 2011. Clin Cancer Res 17:538-549.

Bergelson, et al. "Isolation of a Common Receptor for Coxsackie B Viruses and Adenoviruses 2 and 5," Science 275,1320-1323. (1997).

Louie, et al. "Severe Pneumonia Due to Adenovirus Serotype 14: A New Respiratory Threat?," Clin Infect Dis 46,421-425 (2008).

Tate, et al. "Outbreak of Severe Respiratory Disease Associated with Emergent Human Adenovirus Serotype 14 at a US Air Force Training Facility in 2007," J Infect Dis 199, 1419-1426 (2009).

Wang, et al. "Receptor usage of a newly emergent adenovirus type 14," Virology 387,436-441 (2009).

Yamamoto, et al. "Current Issues and Future Directions of Oncolytic Adenoviruses," Mol Ther 18, 243-250 (2010).

Di Guilmi, et al. "Human adenovirus serotype 3 (Ad3) and the Ad3 fiber protein bind to a 130-kDa membrane protein on HeLa cells," Virus Res 38, 71-81 (1995).

Fleischli, et al. "Species B adenovirus serotypes 3, 7, 11 and 35 share similar binding sites on the membrane cofactor protein CD46 receptor," J Gen Viro/88, 2925-2934 (2007).

Short, et al. "Adenovirus serotype 3 utilizes CD80 (B7.1) and CD86 (B7.2) as cellular attachment receptors," Virology 322,349-359 (2004).

Short, et al. "Members of adenovirus species B utilize CD80 and CD86 as cellular attachment receptors," Virus Res 122,144-153 (2006).

Sirena, et al. "The Human Membrane Cofactor CD46 Is a Receptor for Species B Adenovirus Serotype 3," J Virol78, 4454-4462 (2004).

Gaggar, et al. "The Human Membrane Cofactor CD46 Is a Receptor for Species B Adenovirus Serotype 3," Nat Med, 9,1408-1412 (2003).

Marttila, et al. "CD46 Is a Cellular Receptor for All Species B Adenoviruses except Types 3 and 7," J Virol, 79, 14429-14436 (2005).

Segerman, et al. "There Are Two Different Species B Adenovirus Receptors: sBAR, Common to Species B1 and B2 Adenoviruses, and sB2AR, Exclusively Used by Species B2 Adenoviruses," J Virol77, 1157-1162 (2003).

Gustafsson, et al. "The Arg279Glu Substitution in the Adenovirus Type 11p (Ad11p) Fiber Knob Abolishes EDTA-Resistant Binding to A549 and CHO-CD46 Cells, Converting the Phenotype to That of Ad7p," J Virol, 80, 1897-1905 (2006).

Persson, et al. "An Arginine Switch in the Species B Adenovirus Knob Determines High-Affinity Engagement of Cellular Receptor CD46," J Virol (2009).

Cowin, et al. "Unraveling the cytoplasmic interactions of the cadherin superfamily," Proc Natl Acad Sci USA 91,10759-10761 (1994).

Leopold, et al. "Intracellular trafficking of adenovirus: Many means to many ends," Adv Drug Deliv Rev 59,810-821 (2007).

Gao, et al. "Human adenovirus type 35: nucleotide sequence and vector development," Gene Ther 10,1941-1949 (2003).

Wang, et al. "In Vitro and In Vivo Properties of Adenovirus Vectors with Increased Affinity to CD46," J Virol S2, 10567-10579 (2008).

Nava, et al. "Desmoglein-2: A Novel Regulator of Apoptosis in the Intestinal Epithelium," Mol Bioi Cell 18, 4565-4578 (2007).

Kowalczyk, et al., "Structure and function of desmosomal transmembrane core and plaque molecules," Biophys Chem 50, 97-112 (1994).

Getsios, et al. "Working out the Strength and Flexibility of Desmosomes," Nat Rev Mol Cell Biol 5, 271-281 (2004).

Khatri, et al. "New Onto-Tools: Promoter-Express, nsSNPCounter and Onto-Translate," Nucleic Acids Res 34, W626-631 (2006).

Bostrom, et al. "Variants of the Antibody Herceptin That Interact with HER2 and VEGF at the Antigen Binding Site," Science 323,1610-1614 (2009).

Schlegel, et al. "Desmoglein 2-mediated adhesion is required for intetinal epithelial barrier integrity," Am J Physiol Gastrointest Liver Physiol 29S, G774-783 (2010).

Mahoney, et al. "Interspecies conservation and differential expression of mouse desmoglein gene family," Exp Dermatol 11, 115-125 (2002).

Schafer, et al. "Identificaation of the Ubiquitous Human Desmoglen, Dsg2, and the Expression of Catalogue of the Desmoglein Subfamily of Desmosomal Cadherins," Exp Cell Res 211,391-399 (1994).

Green, et al. "Disruption of Cell-Cell Adhesion Enhances Antibody-dependent Cellular Cytotoxicity: Implications for Antibody-based Therapeutics of Cancer," Cancer Res 62, 6891-6900 (2002).
Gaggar, et al. "Identifying Functional Adenovirus-Host Interactions Using Tandem Mass Spectrometry," Methods Mol Med 131, 141-155 (2007).
Seppen, et al. "Lentivirus administration to rat muscle provides efficient sustained expression of erythropoietin," Blood 98, 594-596 (2001).
Wang, et al. (2012) "A New Human DSG2-Transgenic Mouse Model for Studying the Tropism andPathology of Human Adenoviruses," J. Virol 86, 6286-6302 (2012).

(56) References Cited

OTHER PUBLICATIONS

Beyer, et al. "Controlled Extracellular Matrix Degradation in Breast Cancer Tumors Improves Therapy by Trastuzumab," Clin Cancer Res 18, 3340-3351 (2012).
Villegas-Mendez, et al., (2010) "In Vivo Delivery of Antigens by Adenovirus Dodecahedron Induces Cellular and Humoral Immune Responses to Elicit Antitumor Immunity," Molecular Therapy, 18(5):1046-1053.
PCT/US2011/040053 International Search Report, mailed Oct. 10, 2011.
Wang, et al. (2011) "Multimerization of Adenovirus Serotype 3 fiber knob domains is required for efficient binding of virus to desmoglein 2 and subsequent opening of epithelial junctions" Journal of Virology, 85(13):6390-6402.
PCTUS2011/040053, International Preliminary Report on Patentability and Written Opinion, mailed Dec. 20, 2012.
Abbod, et al. "Desmoglein-2: A Novel Regulator of Apoptosis in the Intestinal Epithelium," 2009 Expert Rev Anticancer Ther 9:867-870.
Adams, et al. "Monoclonal antibody therapy of cancer," 2005. Nat Biotechnol 23:1147-1157.
Amieva, et al. "Disruption of the Epithelial Apical-Junctional Complex by Helicobacter pylori CagA," 2003. Science 300:1430-1434.
Andarawewa, et al. "Ionizing Radiation Predisposes Nonmalignant Human Mammary Epithelial Cells to Undergo Transforming Growth Factor b-Induced Epithelial to Mesenchymal Transition," 2007 Cancer Res 67:8662-8670.
Beckhove, et al. "Specifically activated memory T cell subsets from cancer patients recognize and reject xenotransplanted autologous tumors," 2004. J. Clin Invest 114:67-76.
Beyer, et al. "Controlled Extracellular Matrix Degradation in Breast Cancer Tumors Improves Therapy by Trastuzumab," 2011. Mol Ther 19:479-489.
Biedermann, et al. "Desmoglein 2 is expressed abnormally rather than mutated in familial and sporadic gastric cancer," 2005. J Pathol 207:199-206.
Brennan, et al. "Tight Junctions: A Barrier to the Initiation and Progression of Breast Cancer?," 2010. J Biomed Biotechnol 2010:460607.
Disis, et al. "Existent T-Cell and Antibody Immunity to HER-2/neu Protein in Patients with Breast Cancer," 1994. Cancer Res 54:16-20.
Disis, et al. "Pre-existent immunity to the HER-2/neu oncogenic protein in patients with HER-2/neu overexpressing breast and ovarian cancer," 2000. Breast Cancer Res Treat 62:245-252.
Fasano, et al. "Vibrio cholerae produces a second enterotoxin, which affects intestinal tight junctions," 1991. Proc Natl Acad Sci USA 88:5242-5246.
Fender, et al. "Adenovirus dodecahedron, a new vector for human gene transfer," 1997. Nat Biotechnol 15:52-56.
Fessler, et al. "MUC1* is a determinant of trastuzumab (Herceptin) resistance in breast cancer cells," 2009 Breast Cancer Res Treat 118:113-124.
Feuerer, et al. "Therapy of human tumors in NOD/SCID mice with patientderived reactivated memory T cells from bone marrow," 2001. Nat Med 7:452-458.
Frank, et al. "Cleavage of E-cadherin: a mechanism for disruption of the intestinal epithelial barrier by Candida albicans," 2007 Transl Res 149:211-222.
Fuschiotti, et al. "Structure of the Dodecahedral Penton Particle from Human Adenovirus Type 3," 2006. J. Mol Biol 356:510-520.
Guarino, et al. "Epithelial-mesenchymal transition and tumour invasion," 2007. Int J Biochem Cell Biol 39:2153-2160.
Harada, et al. "Abnormal Desmoglein Expression by Squamous Cell Carcinoma Cells," 1996. Acta Derm Venereol 76:417-420.
Harari, et al. "Biology of Interactions: Antiepidermal Growth Factor Receptor Agents," 2007. J Clin Onco/25:4057-4065.
Hemminki, et al. "Preclinical and Clinical Data with a Fully Serotype 3 Oncolytic Adenovirus Ad3-hTERT-E1A in the Treatment of Advanced Solid Tumors," 2010. Molecular Therapy 18:S74.
Karamouzis, et al. "Therapies Directed Against Epidermal Growth Factor Receptor in Aerodigestive Carcinomas," 2007. JAMA 298:70-82.
Katz, et al. "Characterization of Porphyromonas gingivalis-Induced Degradation of Epithelial Cell Junctional Complexes," 2000. Infect Immun 68:1441-1449.
Klessner, et al. "EGFR and ADAMs Cooperate to Regulate Shedding and Endocytic Trafficking of the Desmosomal Cadherin Desmoglein 2," 2009. Mol Biol Cell 20:328-337.
Koeser, et al. "De novo formation of desmosomes in cultured cells upon transfection of genes encoding specific desmosomal components," 2003. Exp Cell Res 285:114-130.
Koski, et al. "Treatment of Cancer Patients With a Serotype 5/3 Chimeric Oncolytic Adenovirus Expressing GMCSF," 2010. Mol Ther 18:1874-1884.
Kurzen, et al. "Expression of desmosomal proteins in squamous cell carcinomas of the skin," 2003. J Cutan Patho/30:621-630.
Larsen, al. et al "Expression of desmosomal proteins in squamous cell carcinomas of the skin," 2003. Nat Rev Mol Cell Biol 4:700-711.
Lesniak, et al. "b1-Integrin Circumvents the Antiproliferative Effects of Trastuzumab in Human Epidermal Growth Factor Receptor-2-Positive Breast Cancer," 2009. Cancer Res 69:8620-8628.
Li, et al. "Toward a stem cell gene therapy for breast cancer," 2009. Blood 113:5423-5433.
Beyer, et al. "Controlled Extracellular Matrix Degradation in Breast Cancer Tumors Improves Therapy by Trastuzumab," 2011. in preparation.
Li, et al. "Xenograft Models for Liver Metastasis: Relationship between Tumor Morphology and Adenovirus Vector Transduction," 2004. Mol Ther 9:650-657.
Norrby, et al. "Separation and Characterization of Soluble Adenovirus Type 9 Components," 1967. J Viral 1:1101-1108.
Oliveras-Ferraros, et al. "Stem Cell Property Epithelial-to-Mesenchymal Transition is a Core Transcriptional Network for Predicting Cetuximab (ErbituxTM) Efficacy in KRAS Wild-Type Tumor Cells," 2011. J Cell Biochem 112:10-29.
Ramani, et al. "Desmoglein 2 is a substrate of kallikrein 7 in pancreatic cancer Vishnu C Ramani, Leah Hennings and Randy S Haun," 2008. BMC Cancer 8:373.
Sakamoto, et al. "Longitudinal Investigation of Epidemiologic Feature of Adenovirus Infections in Acute Respiratory Illnesses among Children in Yamagata, Japan (1986-1991)," 1995. Tohoku J Exp Med 175:185-193.
Schmitt, et al. "Homo- and Heterotypic Cell Contacts in Malignant Melanoma Cells and Desmoglein 2 as a Novel Solitary Surface Glycoprotein," 2007. J Invest Dermatol, 127:2191-2206.
Strauss, et al. "Analysis of Epithelial and Mesenchymal Markers in Ovarian Cancer Reveals Phenotypic Heterogeneity and Plasticity," 2011. PLoS One 6:e16186.
Strauss, et al. "Anatomical and physical barriers to tumor targeting with oncolytic adenoviruses in vivo," 2009. Curr Opin Mol Ther 11:513-522.
Strauss, et al. "Epithelial Phenotype Confers Resistance of Ovarian Cancer Cells to Oncolytic Adenoviruses," 2009. Cancer Res 69:5115-5125.
Sumida, et al. "Neutralizing Antibodies to Adenovirus Serotype 5 Vaccine Vectors Are Directed Primarily against the Adenovirus Hexon Protein1," 2005. J Immunol174:7179-7185.
Thiery, et al. "Complex networks orchestrate epithelial—mesenchymal transitions," 2006. Nat Rev Mol Cell Biol 7:131-142.
Thomas, et al. "Immunosuppression Enhances Oncolytic Adenovirus Replication and Antitumor Efficacy in the Syrian Hamster Model," 2008. Mol Ther 16:1665-1673.
Toso, et al. "MAGE-1-specific Precursor Cytotoxic T-Lymphocytes Present among Tumor-infiltrating Lymphocytes from a Patient with Breast Cancer: Characterization and Antigen-specific Activation," 1996. Cancer Res 56:16-20.
Trojan, et al. "Identification of Metastasis-associated Genes in Prostate Cancer by Genetic Profiling of Human Prostate Cancer Cell Lines," 2005. Anticancer Res 25:183-191.
Turley, et al. "Mechanisms of Disease: epithelial-mesenchymal transition—does cellular plasticity fuel neoplastic progression?," 2008. Nat Clin Pract Oneal.

(56) References Cited

OTHER PUBLICATIONS

Tuve, et al. "Combination of Tumor Site-Located CTL-Associated Antigen-4 Blockade and Systemic Regulatory T-Cell Depletion Induces Tumor-Destructive Immune Responses," 2007.Cancer Res 67:5929-5939.

Vermeer, et al. "Segregation of receptor and ligand regulates activation of epithelial growth factor receptor," 2003. Nature 422:322-326.

Wang, et al. "Desmoglein 2 is a receptor for adenovirus serotypes 3, 7, 11 and 14," 2011 Nat Med 17:96-104.

Wang, et al. "Identification of CD46 Binding Sites within the Adenovirus Serotype 35 Fiber Knob," 2007. J Virol, 81:12785-12792.

Wang, et al. "Arecombinant adenovirus type 35 fiber knob protein sensitizes lymphoma cells to rituximab therapy," 2010. Blood 115:592-600.

Signas, et al., "Adenovirus 3 Fiber Polypeptides Gene: Implications for the Structure of the Fiber Protein," Journal of Virology, Feb 1985, 53(2): 672-678.

Mei, et al., "Hemagglutination Properties and ncuelotides sequence analysis of the fiber gene of adenovirus genome types 11p and 11a," Virology, (1993) 194:453-462.

* cited by examiner

Figure 24

METHODS AND SYSTEMS FOR ADENOVIRUS INTERACTION WITH DESMOGLEIN 2 (DSG2)

CROSS REFERENCE TO RELATED APPLICATIONS

This application claims the benefit of U.S. Provisional Application No. 61/353,652, filed Jun. 10, 2010, U.S. Provisional Application No. 61/430,091, filed Jan. 5, 2011, and U.S. Provisional Application No. 61/470,663, filed Apr. 1, 2011, all of which are incorporated herein by reference in their entirety.

STATEMENT OF GOVERNMENT RIGHTS

This invention was made with U.S. Government support under R01CA080192 and RO1 HLA078836 awarded by the National Institutes of Health. The U.S. Government has certain rights in this invention.

BACKGROUND

Human adenoviruses (Ads) have been classified into six species (A to F), currently containing 51 serotypes. Most Ad serotypes utilize the coxsackie-adenovirus receptor (CAR) as a primary attachment receptor (Bergelson et al., 1997). This is, however, not the case for species B Ad serotypes. Recently, we have suggested a new grouping of species B Ads based on their receptor usage (Tuve et al., 2006). Group 1 (Ad16, 21, 35, 50) nearly exclusively utilize CD46 as a receptor; Group 2 (Ad3, Ad7, 14) share a common, unidentified receptor/s, which is not CD46 and which was tentatively named receptor X; Group 3 (Ad11) preferentially interacts with CD46, but also utilizes receptor X if CD46 is blocked.

Species B Ads are common human pathogens. Since 2005, a simultaneous emergence of diverse species B serotypes at the majority of US military training facilities was observed. This included serotypes Ad3, Ad7, and Ad14 (Metzgar et al., 2007). In 2007 a new, highly pathogenic strain and possibly more virulent strain of Ad14, Ad14a, has been discovered at several sites in the US and in Asia (Louie et al., 2008; Tate et al., 2009). We recently demonstrated that Ad14a belongs to species B group 2 Ads with regards to their receptor usage (Wang et al., 2009). Collectively, all receptor X utilizing serotypes (Ad3, Ad7, Ad14, Ad14a, and Ad11) are referred to herein as AdB-2/3.

AdB-2/3 have great relevance as gene transfer vectors, particularly with regard to tumors of epithelial origin, representing most solid tumors (Yamamoto and Curiel, 2010). Epithelial cells maintain several intercellular junctions and an apical-basal polarity. Key features of epithelial cells are conserved in epithelial cancers in situ and in cancer cell lines (Turley et al., 2008). Both CAR and CD46 are often trapped in tight and adherence junctions of epithelial cancer cells and are not accessible to Ads that use these attachment receptors (Coyne and Bergelson, 2005; Strauss et al., 2009). In contrast, AdB-2/3 efficiently infect epithelial cancer cells, which is accomplished in part through induction of processes that are reminiscent of Epithelial-to-Mesenchymal Transition (EMT) (Strauss et al., 2009). Another distinctive feature of AdB-2/3 is their ability to produce subviral dodecahedral particles during their replication, consisting of Ad fiber and penton base (Norrby et al., 1967). Penton-Dodecahedra (PtDd) cannot assemble from full-length penton base protein, but require spontaneous N-terminal truncation by proteolysis between residues 37 and 38 (Fuschiotti et al., 2006). This cleaved site is conserved in Ad3, Ad7, Ad11, and Ad14 but is not present in Ad2 and Ad5. In the case of Ad3 the PtDd are formed at a massive excess of $5.5 \times 10^6$ PtDd per infectious virus (Fender et al., 2005), and it has been suggested that PtDd enhance Ad3 infectivity by disturbing intercellular junctions, thus favoring virus spreading (Walters et al., 2002).

The first attempts to identify receptor X date back to 1995. Recently, several candidates for receptor X such as CD46, CD80 and/or CD86 were suggested (Fleischli et al., 2007; Short et al., 2004; Short et al., 2006; Sirena et al., 2004). However, no one thus far has been able to verify that these proteins can serve as the high affinity receptor for AdB-2/3 (Gaggar et al., 2003b; Gustafsson et al., 2006; Marttila et al., 2005; Persson et al., 2008; Segerman et al., 2003; Tuve et al., 2006).

SUMMARY OF THE INVENTION

In a first aspect, the present invention provides methods for enhancing therapeutic treatment, or diagnosis of a disorder associated with epithelial tissue, and/or imaging epithelial tissues, comprising administering to a subject in need thereof:
a) an amount of one or more therapeutic sufficient to treat the disorder, diagnostic sufficient to diagnose the disorder, and/or imaging agent sufficient to image the epithelial tissue; and
b) an amount of AdB-2/3 fiber multimer or functional equivalent thereof sufficient to enhance efficacy of the one or more therapeutics, diagnostics, and/or imaging agents.

The method of the invention can be used to treat and/or diagnose disorders associated with epithelial tissue, and/or image epithelial tissues, such as epithelial tissues in which such a disorder is believed present, where such disorders include but are not limited to solid tumors, irritable bowel syndrome, inflammatory bowel disorder, Crohn's disease, ulcerative colitis, constipation, gatroesophageal reflux disease, chronic obstructive pulmonary disease, asthma, bronchitis, pulmonary emphysema, cystic fibrosis, interstitial lung disease, pneumonia, primary pulmonary hypertension, pulmonary embolism, pulmonary sarcoidosis, tuberculosis, pancreatitis, pancreatic duct disorders, brain disorders (ie: any brain disorder that could benefit from improved transport of drugs through the epithelial blood-brain barrier), bile duct obstruction, cholecystitis, choledocholithiasis, infections (including but not limited to cellulitis, pneumonia, and pyelonephritis), and gallstones. In a preferred embodiment, the disorder is a solid tumor, including, but not limited to, breast tumors, lung tumors, colon tumors, rectal tumors, stomach tumors, prostate tumors, ovarian tumors, uterine tumors, cervical tumors, kidney tumors, skin tumors, melanomas, pancreatic tumors, liver tumors, endocrine tumors, brain tumors, head and neck tumors, nasopharyngeal tumors, gastric tumors, squamous cell carcinomas, adenocarcinomas, bladder tumors, and esophageal tumors.

The methods of any embodiment of the invention can utilize, for example, AdB-2/3 fiber multimers selected from the group consisting of an Ad3 fiber multimer, and Ad7 fiber multimer, an Ad11 fiber multimer, an Ad14 fiber multimer, an Ad14a fiber multimer, combinations thereof, and functional equivalents thereof. In a preferred embodiment, the AdB-2/3 fiber multimer is an Ad3 fiber multimer, or functional equivalents thereof. In further embodiments, the AdB-2/3 fiber multimer can comprise AdB-2/3 virions, AdB-2/3 capsids, AdB-2/3 dodecahedral particles (PtDd), recombinant AdB-2/3 fiber multimers, and functional equivalents thereof. In preferred embodiments, the AdB-2/3 fiber multimer comprises an Ad3 PtDd or junction opener 1 (JO-1) (SEQ ID NO:20)

Any suitable therapeutic, diagnostic, or imaging agent can be used in these methods. In embodiments where therapeutics are used, such therapeutics may include but are not limited to antibodies, immunoconjugates, vaccines, radioactive particle/radiation therapy ("radiation"), chemotherapeutics, cellular immunotherapy including adoptive T-cell therapy and dendritic cell therapy, nanoparticles, inhaled therapeutics, gene therapy constructs, and nucleic acid therapeutics or combinations thereof. In preferred embodiments, the therapeutic comprises a chemotherapeutic or an anti-tumor monoclonal antibody. Exemplary anti-tumor monoclonal antibodies that can be used in the methods of the invention include, but are not limited to trastuzumab, cetuximimab, petuzumab, apomab, conatumumab, lexatumumab, bevacizumab, bevacizumab, denosumab, zanolimumab, lintuzumab, edrecolomab, rituximab, ticilimumab, tositumomab, alemtuzumab, epratuzumab, mitumomab, gemtuzumab ozogamicin, oregovomab, pemtumomab daclizumab, panitumumab, catumaxomab, ofatumumab, and ibritumomab.

In one preferred embodiment, the disorder associated with epithelial tissue comprises a Her-2 positive tumor. Exemplary Her-2 positive tumors that can be treated under this embodiment include, but are not limited to, breast tumors, gastric tumors, colon tumors, and ovarian tumors. In this embodiment, it is further preferred that the therapeutic comprises trastuzumab; in a further preferred embodiment, the therapeutic further comprises one or more chemotherapeutics and/or radiation. In this embodiment, it is further preferred that the AdB-2/3 fiber multimer comprises an Ad3 PtDd, JO-1 (SEQ ID NO:20), or functional equivalents thereof. In another preferred embodiment, the subject to be treated has not responded to trastuzumab therapy.

In another preferred embodiment, the disorder associated with epithelial tissue comprises an EGFR-positive tumor. Exemplary EGFR-positive tumors include, but are not limited to lung tumors, colon tumors, breast tumors, rectal tumors, head and neck tumors, and pancreatic tumors. In this embodiment, it is preferred that the therapeutic comprises cetuximab; in a further preferred embodiment, the therapeutic further comprises one or more chemotherapeutics and/or radiation. In this embodiment, it is further preferred that the AdB-2/3 fiber multimer comprises an Ad3 PtDd, JO-1 (SEQ ID NO:20), or functional equivalents thereof. In another preferred embodiment, the subject to be treated has not responded to cetuximab therapy.

In another embodiment, the disorder associated with epithelial tissue comprises a solid tumor and therapeutic comprises a vascular endothelial growth factor (VEGF) inhibitor.

In a second aspect, the present invention provides methods for treating a disorder associated with epithelial tissue, comprising administering to a subject in need thereof an amount of AdB-2/3 fiber multimer or functional equivalent thereof, sufficient to treat the disorder. In this embodiment, the AdB-2/3 fiber multimer is administered as a monotherapy. In one embodiment, the method is used to treat an AdB-2/3 viral infection. In another embodiment, the disorder to be treated is a solid tumor. Exemplary solid tumors that can be treated using this aspect of the invention include but are not limited to breast tumors, lung tumors, colon tumors, rectal tumors, stomach tumors, prostate tumors, ovarian tumors, uterine tumors, cervical tumors, kidney tumors, skin cancers, melanomas, pancreatic tumors, liver tumors, endocrine tumors, brain tumors, head and neck tumors, nasopharyngeal tumors, gastric tumors, squamous cell carcinomas, adenocarcinomas, bladder tumors, and esophageal tumors. In this aspect, exemplary AdB-2/3 fiber multimers for use include, but are not limited to an Ad3 fiber multimer, and Ad7 fiber multimer, an Ad11 fiber multimer, an Ad14 fiber multimer, an Ad14a fiber multimer, combinations thereof, and functional equivalents thereof. In a preferred embodiment, the AdB-2/3 fiber multimer is an Ad3 fiber multimer, and functional equivalents thereof. In a further preferred embodiment, the AdB-2/3 fiber multimer is selected from the group consisting of AdB-2/3 virions, AdB-2/3 capsids, AdB-2/3 dodecahedral particles (PtDd), recombinant AdB-2/3 fiber multimers, and functional equivalents thereof. In various further preferred embodiments, the AdB-2/3 fiber multimer comprises an Ad3 PtDd or junction opener 1 (JO-1) (SEQ ID NO:20), In a third aspect, the present invention provides recombinant AdB-2/3 fiber polypeptides, comprising:
a) one or more AdB-2/3 fiber polypeptide shaft domains, or functional equivalents thereof;
b) an AdB-2/3 fiber polypeptide knob domain, or functional equivalent thereof. operatively linked to and located C-terminal to the one or more AdB-2/3 fiber polypeptide shaft domains; and
c) one or more non-AdB-2/3-derived dimerization domains operatively linked to and located N-terminal to the one or more AdB-2/3 fiber polypeptide shaft domains.

In one embodiment, the recombinant AdB-2/3 fiber polypeptide does not include an AdB-2/3 tail domain. In another embodiment, each shaft domain is selected from the group consisting of an Ad3 shaft domain, an Ad7 shaft domain, an Ad11 shaft domain, an Ad 14 shaft domain, an Ad14a shaft domain, combinations thereof, and functional equivalents thereof. In a further embodiment, the one or more shaft domains comprise 1-22 shaft domains. In various further embodiments, each shaft domain comprises or consists of an amino acid sequence according to SEQ ID NO:1, SEQ ID NO:2, SEQ ID NO:3, SEQ ID NO:4, SEQ ID NO:5, SEQ ID NO:11 or SEQ ID NO:12. In a further embodiment, the knob domain is selected from the group consisting of an Ad3 knob domain, an Ad7 knob domain, an Ad11 knob domain, an Ad 14 knob domain, an Ad14a knob domain, and functional equivalents thereof. In various further embodiments, the knob domain comprises or consists of an amino acid sequence according to SEQ ID NO:6, SEQ ID NO:7, SEQ ID NO:8, SEQ ID NO:9, SEQ ID NO:10, SEQ ID NO:13 or SEQ ID NO:14. In a further embodiment, the dimerization domain comprises an amino acid sequence selected from the group consisting of EVSALEK (SEQ ID NO: 22) and/or KVSALKE (SEQ ID NO: 23). In a preferred embodiment, the recombinant AdB-2/3 polypeptide comprises: (a) one or more shaft domains that each comprise or consist of an Ad3 shaft domain (SEQ ID NO: 1); and (b) a knob domain comprises or consists of an Ad3 knob domain (SEQ ID NO:6).

In a further preferred embodiment, the recombinant AdB-2/3 fiber polypeptide comprises or consists of the amino acid sequence of JO-1 (SEQ ID NO:20), In a further preferred embodiment, the AdB-2/3 fiber polypeptide is multimerized; most preferably dimerized.

In other aspects, the present invention provides isolated nucleic acids encoding the recombinant AdB-2/3 fiber polypeptides of the invention; recombinant expression vectors comprising the isolated nucleic acids of the invention; host cells comprising the recombinant expression vectors of the invention; and pharmaceutical compositions comprising AdB-2/3 multimers as described herein. In a further aspect, the present invention provides methods for improving delivery of a compound to an epithelial tissue, comprising contacting the epithelial tissue with (a) one or more compound to be delivered to the epithelial tissue; and (b) an amount of AdB-2/3 fiber multimer, or functional equivalent thereof, sufficient to enhance delivery of the one or more compounds to the epithelial tissue. The methods permit improved delivery of any compound that targets epithelial cells, including but not limited to diagnostic compounds and imaging compounds. In one preferred embodiment, the epithelial tissue comprises a solid tumor.

In a still further aspect, the present invention provides methods for improving delivery of a compound to tissue expressing desmoglein 2 (DSG2), comprising contacting the tissue expressing DSG2 with (a) one or more compound to be delivered to the tissue; and (b) an amount of AdB-2/3 fiber multimer, or functional equivalent thereof, sufficient to enhance delivery of the one or more compounds to the tissue. The methods of this aspect of the invention can be used to improve delivery of any compound of interest to a tissue expressing DSG2.

In a yet further aspect, the present invention provides methods for inducing an epithelial to mesenchymal transition (EMT) in a tissue, comprising contacting the epithelial tissue with an amount of AdB-2/3 fiber multimer, or functional equivalent thereof, sufficient to induce EMT.

In one preferred embodiment of each of these further aspects of the invention, the AdB-2/3 fiber multimer is selected from the group consisting of an Ad3 fiber multimer, and Ad7 fiber multimer, an Ad11 fiber multimer, an Ad14 fiber multimer, an Ad14a fiber multimer, combinations thereof, and functional equivalents thereof. In various further preferred embodiments, the AdB-2/3 fiber multimer is an Ad3 fiber multimer, or a functional equivalent thereof; the AdB-2/3 fiber multimer is selected from the group consisting of AdB-2/3 virions, AdB-2/3 capsids, AdB-2/3 dodecahedral particles (PtDd), recombinant AdB-2/3 fiber multimers, and functional equivalents thereof; the AdB-2/3 fiber multimer comprises an Ad3 PtDd; the AdB-2/3 fiber multimer comprises junction opener 1 (JO-1) (SEQ ID NO:20); and the AdB-2/3 fiber multimer is a dimer.

In another aspect, the present invention provides method for identifying candidate compounds for one or more of treating a disorder associated with epithelial tissue, improving delivery of a substance to an epithelial tissue, for improving delivery of a substance tissue expressing DSG2, inducing an EMT in a tissue, and/or treating an AdB-2/3 infection comprising (a) contacting an AdB-2/3 fiber multimer to DSG2 under conditions to promote multimer binding to DSG2, wherein the contacting is carried out in the presence of one or more test compounds; and (b) identifying positive test compounds that compete for binding of the AdB-2/3 fiber multimer to DSG2 compared to control; wherein the positive test compounds are candidate compounds for one or more of treating a disorder associated with epithelial tissue, improving delivery of a substance to an epithelial tissue, for improving delivery of a substance tissue expressing DSG2, inducing an EMT in a tissue, and/or treating an AdB-2/3 infection.

a) Competition of $^3$H-labeled Ad binding by recombinant DSG2. $^3$H-Ad3, Ad7, Ad14, Ad14a, Ad11, Ad5 and Ad35 virus were pre-incubated with 6 µg ml$^{-1}$ recombinant human DSG2 protein. Attachment of virus particles incubated with PBS was taken as 100%. For analysis of Ad11 attachment, cells were also incubated with 50 µml$^{-1}$ of Ad35K on ice for one hour before adding of Ad11 virus to block CD46. b) Competition of Ad transduction by recombinant DSG1, DSG2 or DSC2 proteins. c) Competition of $^3$H-Ad binding by DSG2-specific antibodies. n=5. PBS vs. 6D8: P=0.013; PBS vs. 8E5: P=0.0014. The specificity of mAbs to different DSG2 domains is as follows (for a scheme of DSG2, see FIG. 1f): 20G1 (Pro-peptide region), 7H9 (Pro/EC1), 13B11 (EC1/EC2), 10D2 (EC1/EC2), 8E5 (EC3), 6D8 (EC3/EC4). d) and e) Effect of siRNA-mediated DSG2 downregulation on Ad attachment (d) and transduction (e). Shown are mean fluorescence intensity values. n=5. Note that at 18 hours post-infection, GFP levels were comparable for Ad35-GFP and Ad5/35-GFP, which allowed us to also use the first-generation Ad5/35-GFP vector in further studies. f) Cytolysis of Ad3-GFP infected BT474 cells at day 7 after infection. siRNA transfected cells were infected at adjusted MOIs that allow for comparable initial transduction rates, i.e. MOI 1.0 pfu per cell and 0.5 pfu per cell for DSG2 siRNA and control siRNA treated cells, respectively. Seven days later, viable cells were stained with crystal violet. Despite the higher virus dose, less killing was seen in cells transfected with DSG2 siRNA, suggesting the importance of DSG2 in lateral spreading of Ad3. g) Cytolysis of Ad3-GFP infected cells at day 7 after infection. siRNA transfected small airway epithelial cells were infected at adjusted MOIs. Seven days later, cell viability was measured by WST-1 assay. Viability of PBS treated cells was taken 100%. n=3. Ad3-GFP/control siRNA vs. Ad3-GFP DSG2 siRNA: P<0.001.

Figure 4:
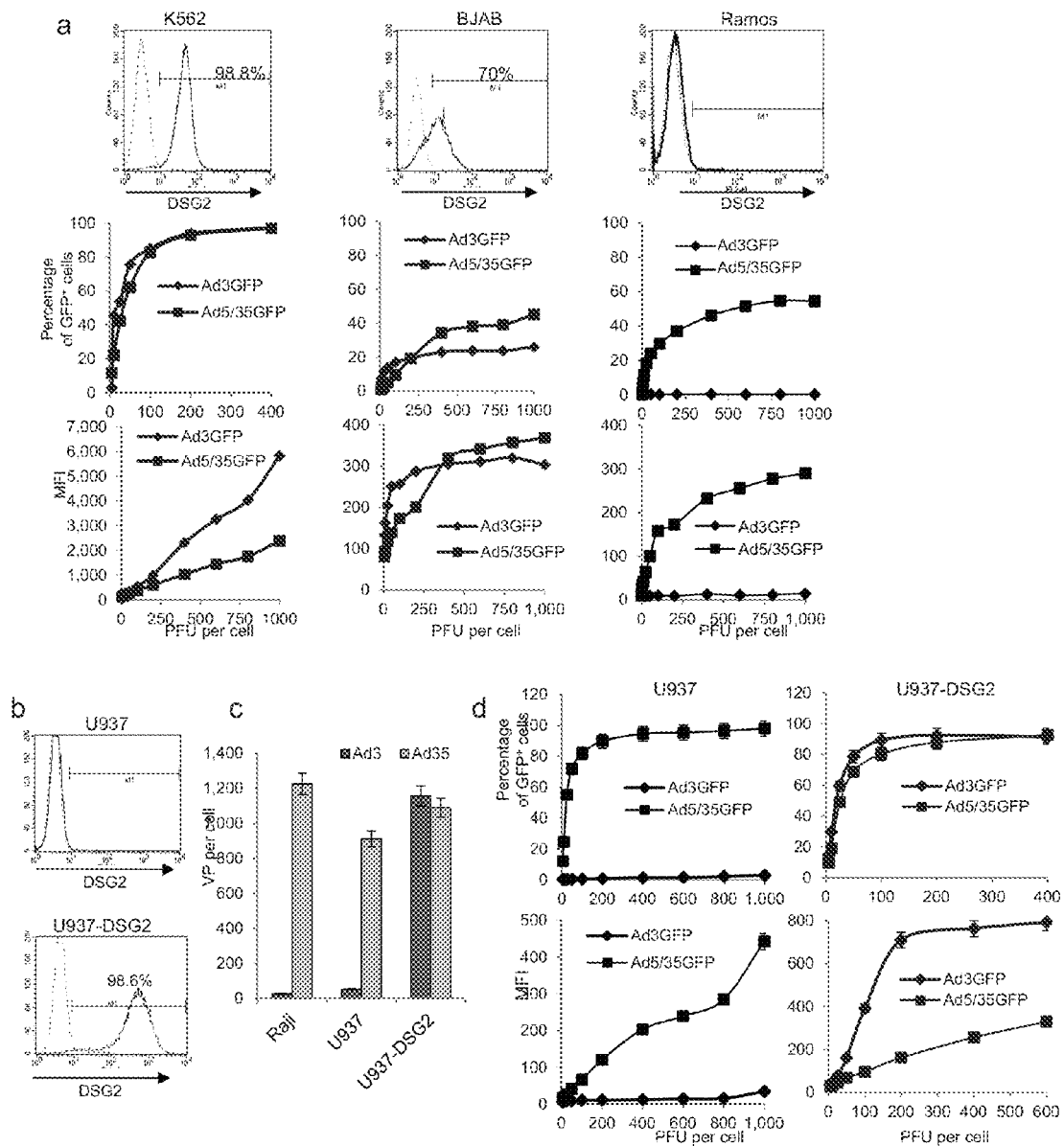

FIG. 4 Validation of DSG2 as Ad receptor. "Gain-of-function" studies.

a) Transduction of human cell lines that express different DSG2 levels. Human erythromyeloblastoid leukemia K562 cells and Burkitt's B-cell lymphoma BJAB and Ramos cells were infected with Ad3-GFP and Ad5/35-GFP at increasing MOIs and GFP expression was measured 18 hours later. N=3. Standard deviation was less than 10% for all data points. b) Ectopic DSG2 expression. Human histiocytic lymphoma U937 cells were infected with a lentivirus vector carrying the DSG2 cDNA under the control of the EF1a promoter. Stable DSG2 expression was detected in >98% of lentivirus transduced cells by flow cytometry. c) Attachment of $^3$H-Ad3 and $^3$H-Ad35 to Raji, U937 and DSG2-expressing U937 (U937-DSG2) cells. Note that Ad35 attachment is mediated through CD46 and can be blocked by soluble CD46 (data not shown). d) GFP expression after transduction of U937 and U937-DSG2 cells with Ad3-GFP and Ad5/35-GFP. n=3

Figure 5:
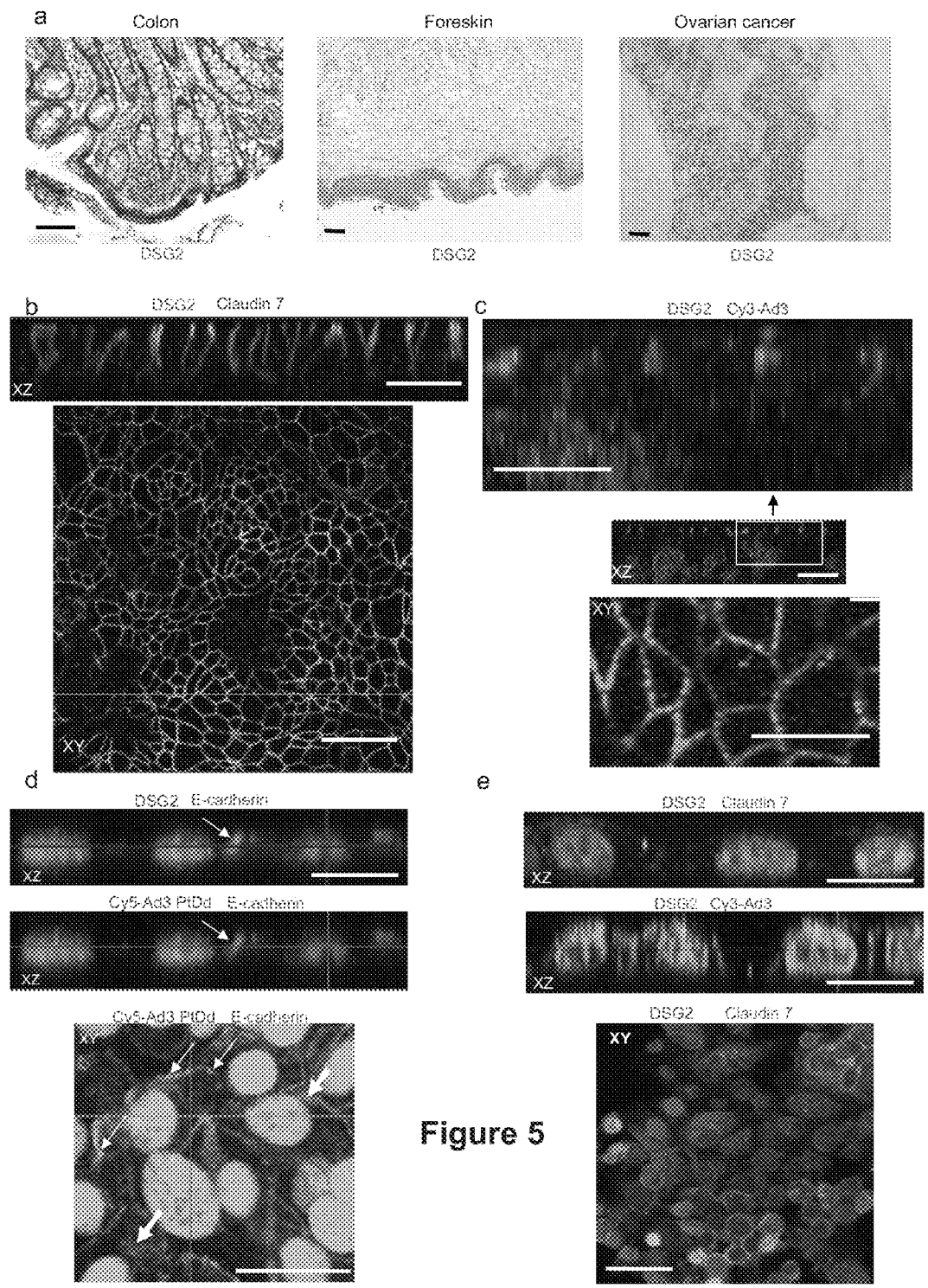

FIG. 5 DSG2 localization in human epithelial cells and interaction with Ad3.

a) Immunohistochemistry studies on human colon, foreskin and ovarian cancer paraffin sections with DSG2-specific antibodies. Positive staining appears in brown. b) Confocal microscopy immunofluorescence analysis of polarized human colon cancer T84 cells for DSG2 (green) and the intercellular junction protein Claudin 7 (red). Nuclei are blue. XY and XZ planes are shown. c) Ad3 binding to DSG2. T84 cells were incubated with Cy3-labeled Ad3 particles (red) for 15 minutes, washed, and subjected to confocal microscopy. The upper XZ image is a higher magnification. Note that at least two (green) DSG2 signals are associated with one (red) Cy3-Ad3 signal. d) Confocal microscopy of normal human small airway epithelial cells (not grown in TRANSWELL™ chambers). Cells were incubated with Cy5-labelled PtDd for 15 min and then washed with PBS. The upper XZ panel shows co-localization of DSG2 (red) and E-cadherin (green). The lower XZ panel is the same image showing purple Cy5-PtDd signals co-localized with green E-cadherin signals. The XY panel shows purple (PtDd) and green E-cadherin channels. Thin arrows mark membrane localized PtDd, thick arrows label cytoplasmic DSG2. e) Confocal microscopy immunofluorescence analysis of human cervical carcinoma HeLa cells (upper XZ and XY panels) and HeLa cells incubated for 15 min with Cy3-Ad3 (lower XZ panel). Scale bars for all confocal microphotographs are 20 µm.

Figure 6:
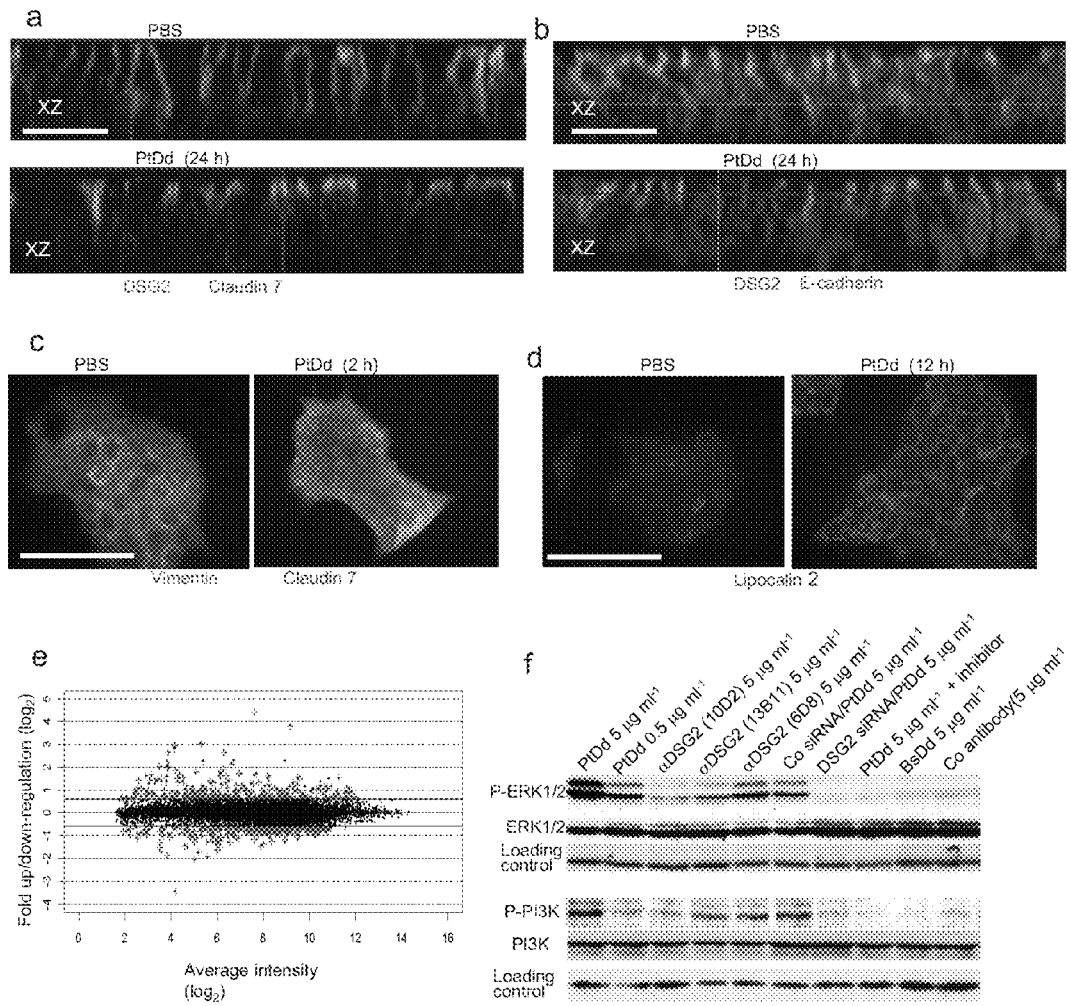

FIG. 6 Epithelial-to-mesenchymal transition signaling induced by Ad3 virions and PtDd in epithelial cells.

a-d) Phenotypic changes triggered by PtDd in breast cancer epithelial cells. 1×10$^5$ BT474 cells were incubated with 50 ng of PtDd or BsDd for the indicated time and subjected to staining with antibodies. The scale bar is 20 µm in all ZY confocal images (a, b) and 40 µm in the standard immunofluorescense studies (c, d). e) Graphic demonstration of array data for up- and down-regulated genes (PtDd vs. PBS treated cells). Each dot represents one gene. f) Western blot analysis of ERK1/2-MAPK and PI3K phosphorylation analyzed 6 hours after incubation of BT474 cells with PtDd, BsDd, DSG2-specific antibodies (10D2, 13B11, or 6D8), or control antibody (anti-GAPDH) at the indicated concentrations. For pathway inhibition, cells were treated overnight with Erk1/2 inhibitor U0126 (5 µM) or PI3K inhibitor Wortmannin (2.5 µM) before PtDd was added. The efficacy of the drugs for inhibition of the specific pathway was validated in a previous study[8]. GAPDH is used to demonstrate equal loading.

Figure 2:
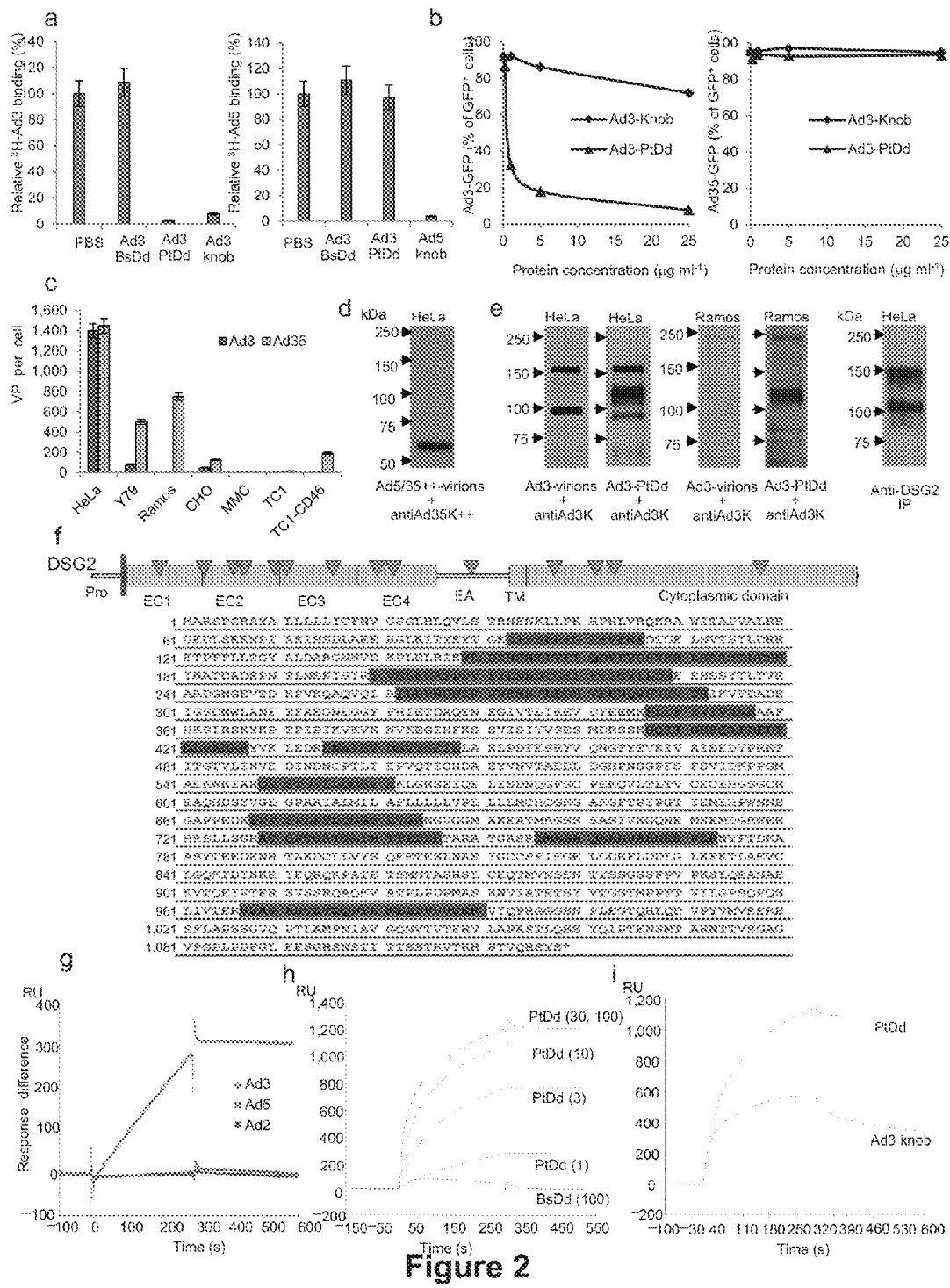
FIG. 2. Identification of receptor X using Ad3 virions and Ad3 PtDd.
a) Competition of $^3$H-labeled Ad3 and Ad5 virus attachment to HeLa cells after pre-incubation with Ad3 BsDd, PtDd, or Ad fiber knobs. Attachment in PBS-treated cells was taken as 100%. n=5. Data are represented as mean+/−SEM). Ad3-PtDd vs. Ad3 knobP=0.0033. b) Competition of Ad3-GFP and Ad35-GFP virus infection. HeLa cells were pretreated with Ad3 fiber knob or PtDd at increasing concentrations and then exposed to Ad3-GFP (left panel) or Ad35-GFP virus (right panel) at an MOI of 100 pfu/cell. GFP expression was measured 18 hours later by flow cytometry. Data are represented as mean. Standard deviation was less than 10% for all data points. c) Attachment of $^3$H-labeled Ad3 and Ad35 viruses to human and non-human cell lines. Y79 and Ramos are human retinoblastoma and lymphoma cells, respectively. CHO cells are Chinese Hamster ovary cells. MMC and TC1 cells are mouse mammary carcinoma and lung carcinoma cells, respectively. TC1-CD46 cells express human CD46. Shown are the average number of viral particels attached per cells. n=5. d and e) Identification of receptor X by affinity capture and MS/MS. Membrane protein fractions were prepared from HeLa and Ramos cells. Protein blots were hybridized with Ad5/35++ virions (d) and Ad3 virions or Ad3 PtDd (e). Binding was visualized with polyclonal antibodies against Ad35++ knob (d) or Ad3 knob (e) (see also FIGS. 1f and g). Solubilized HeLa cell membrane lysates were also immunoprecipitated with DSG2 mAb 6D8 crosslinked with protein A/G plus agarose. Western blot of immunoprecipitates was performed with DSG2 monoclonal antibody AH12.2 (see antiDSG2-IP). f) MS/MS analysis of the 160 kDa band. Upper panel: Structure of DSG2. EC: extracellular domain, EA: juxtamembrane extracellular anchor domain, TM: transmembrane domain. Lower panel: amino acid sequence of DSG2. Highlighted are the peptide sequences captured by MS/MS analysis of the 160 kDa band. The triangles in the DSG2 scheme (top panel) indicate the localization of the identified peptides with regards to the different domains. MS/MS analysis detected 14 peptides DSG2 with a high confidence factor (20.8% protein coverage and Sequest cross correlation coefficient scores ranging from 2.6 to 5.5 for individual peptides). g-i) BIACORE™ plasmon surface resonance studies with recombinant human DSG2 immobilized on sensorchips. Ad2, Ad3 and Ad5 at 5·10$^9$ vp per ml (g), different concentrations of PtDd (h) or PtDd and Ad3 fiber knob (i) were injected over the activated surface and response signals were collected over the indicated time periods.
Figure 7:
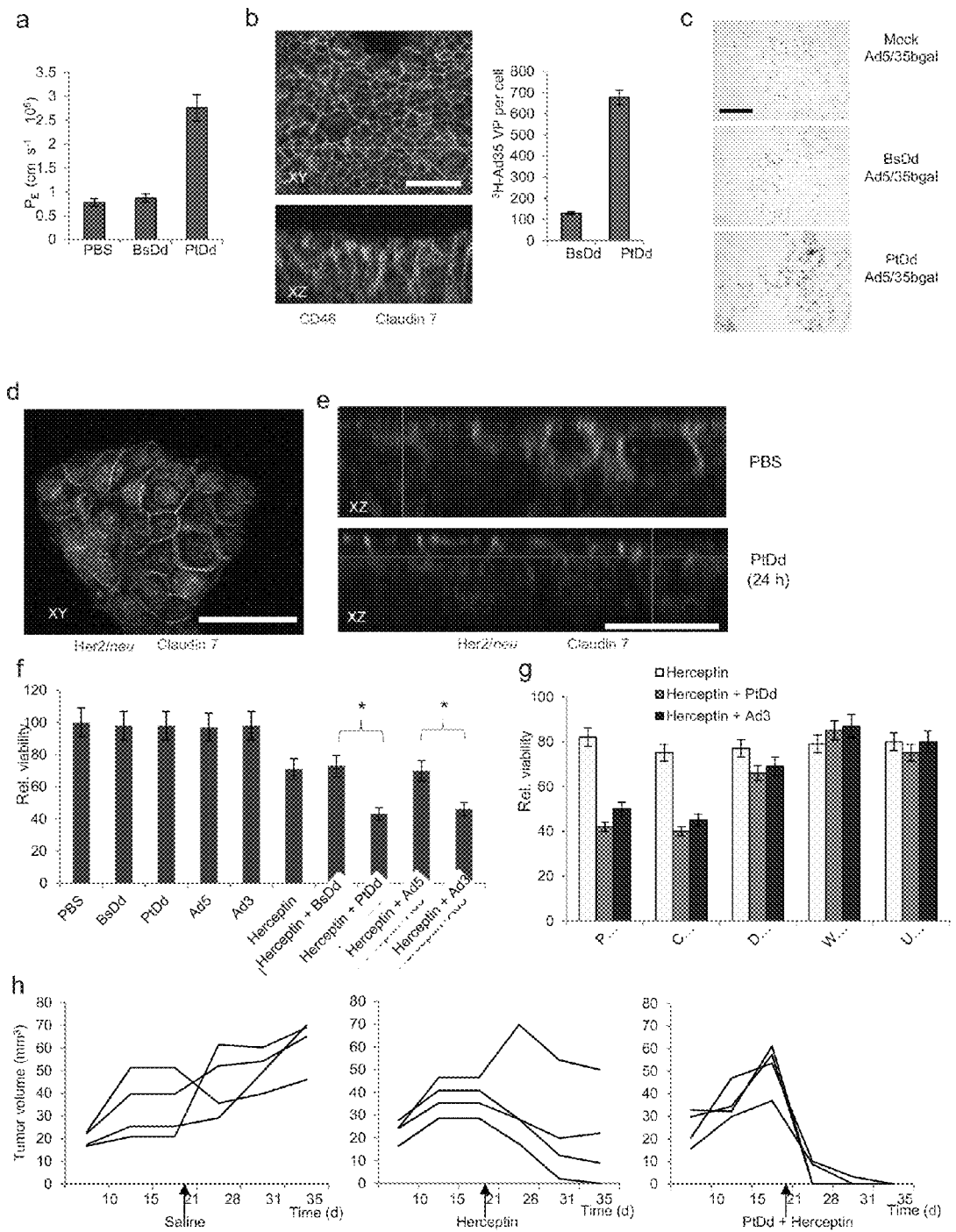

FIG. 7 Opening of intercellular junctions in epithelial breast cancer cells by interaction of Ad3 virions or PtDd with DSG2.

a) FITC-Dextran diffusion through monolayers of BT474 cells. BT474 cells cultured in transwell chamber with 0.4 µm pore size were treated with 0.5 µml$^{-1}$ BsDd, PtDd or 2×10$^8$ Ad particles per ml for 2 hours and then 4 kDa FITC-dextran was added to the apical compartment. Paracellular flux was assessed in aliquots from the apical and basal chambers. BsDd vs. PtDd: P<0.001. b) Facilitation of $^3$H-Ad35 uptake by PtDd. Left panel: Trapping of CD46 in intercellular junctions of T84 cells. Co-localization of CD46 and the intercellular junction protein Claudin 7 results in yellow signals. Right panel: $^3$H-Ad35 attachment. BT474-cells were incubated with PtDd or BsDd and $^3$H-Ad35 for 2 hours on ice, washed, and then incubated at 37° C. for 60 min. Non-internalized Ad particles were removed by trypsin digestion and cell-associated radioactivity was measured. c) Mice carrying subcutaneous ovc316 tumors were injected intravenously with 50 µg PtDd or BsDd eight hours before intravenous injection of 1×10$^9$ pfu of Ad5/35-bGal. Sections were stained with X-gal 72 hours after injection. The scale bar is 40 µm. d) Confocal microscopy for Her2/neu and Claudin 7 in the Her2/neu-positive human breast cancer cell line BT474. These cells do not form monolayers. Note that in PBS treated cells, most Her2/neu signals (green) colocalize with Claudin 7 (red) resulting in yellow signals. Upon PtDd treatment, Claudin 7 signals decrease while more Her2/neu staining appears on the cell surface. e) Confocal microscopy of BT474 cells two hours after treatment with PBS or PtDd. f) Ad3 and PtDd enhance killing of Her2/neu positive breast cancer cells by Herceptin. Viability of PBS-treated cells was taken 100%.

n=5, *P<0.05. g) Ad3 and PtDd enhancement of Herceptin therapy is mediated by DSG2 and involves ERK/MAPK and PI3K pathways. BT474 cells were transfected with control and DSG2 siRNA as described in FIGS. 2d and 48 hours later treated with Ad3 or PtDd and Herceptin as described in g). For inhibitor studies, BT474 cells were incubated with the indicated agents overnight. Cells were washed and treated with PtDd/Ad3 and Herceptin as described in above. n=5, PBS vs. Wortmannin, U0126: P<0.05. h) PtDd-mediated enhancement of Herceptin therapy in vivo. Shown is the tumor volume of individual mice at different days after BT474-M1 cell injection.

Figure 8:
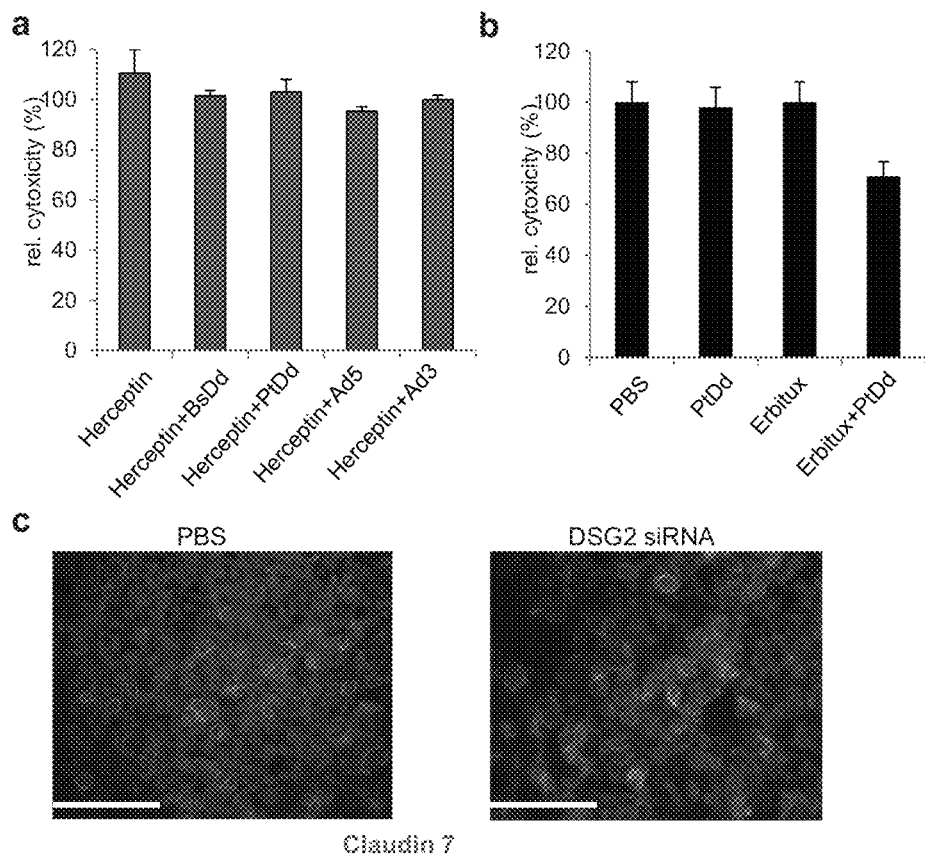

FIG. 8. Effect of PtDd on mAb therapy. a) Ad3 and PtDd do not enhance killing of Her2/neu-negative MDA-MB-231 breast cancer cells by Herceptin. MDA-MB-231 breast cancer cells were incubated with 0.5 mg/ml of BsDd or PtDd, or $2 \times 10^8$ viral particles/ml of uv-inactivated Ad5 or Ad3 for 12 hours, followed by an incubation with Herceptin (15 mg/ml) for 30 min. Cell viability was measured 2 hours later by WST-1 assay from ROCHE BIOSCIENCES™. Viability of PBS-treated cells was taken 100%. b) Ad3 and PtDd enhance killing of EGFR-positive colon cancer cells by Erbitux (anti-EGFR). LoVo cells (EGFR-positive) were incubated with 0.5 mg/ml of PtDd for 12 hours, followed by incubation with Erbitux (15 mg/ml) for 30 min. Cell viability was measured 2 hours later by WST-1 assay. Viability of PBS-treated cells was taken 100%. *p<0.05. c) Effect of DSG2 siRNA on adherence junctions of BT474 cells. Shown is claudin 7 staining of BT474 cells at day 2 after treatment with PBS or DSG2 siRNA. The scale bar is 40 mm.

Figure 9:
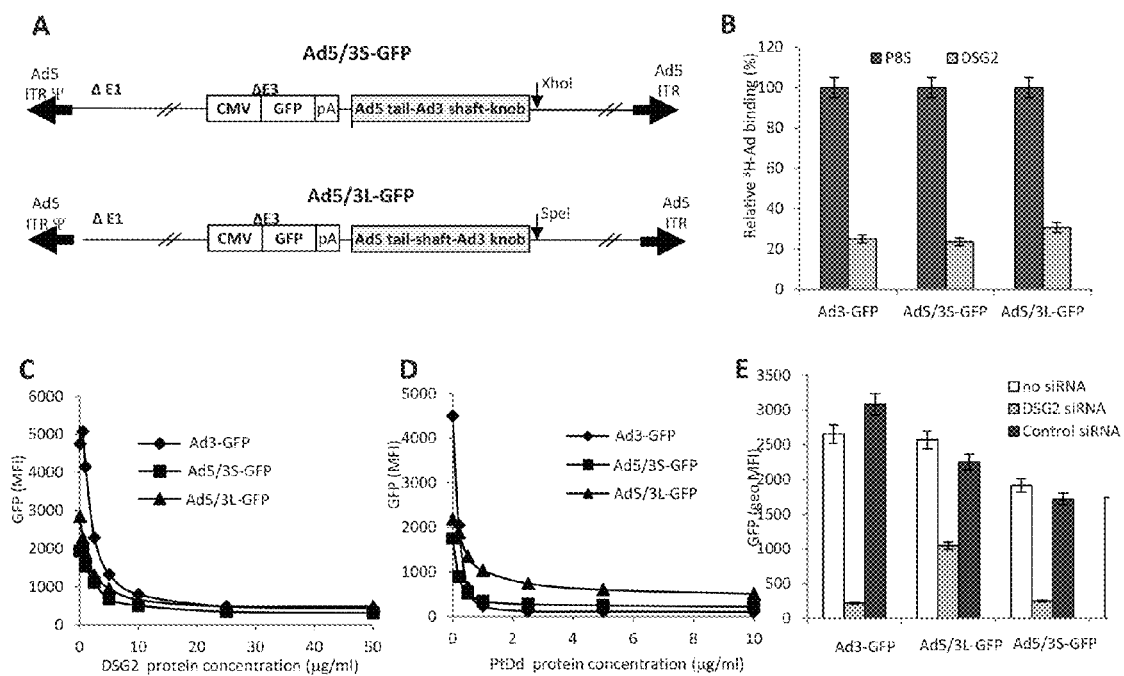

FIG. 9. Role of DSG2 in transduction of chimeric Ad5/3 vectors. A) Structure of Ad5/3 vectors. The vectors are based on Ad5 and are deleted for the E1 and E3 regions. Both vectors contain a GFP expression cassette inserted into the E3 region. In Ad5/3L-GFP, the Ad5 fiber knob domain is replaced by that from Ad3. In Ad5/3S-GFP the Ad5 shaft and knob domains were replaced by the corresponding domains from Ad3. The Ad3 shaft domain contains 6 shaft motifs, while the Ad5 shaft domain contains 22 shaft motifs. B) Blocking of Ad attachment by recombinant DSG2 protein. $H^3$-labeled Ads were incubated with 6 mg/ml of recombinant human DSG2 protein on ice for one hour and then added to HeLa cells for 1 hour on ice. Ad attachment to cells incubated with PBS instead of DSG2 was taken as 100%. n=3, i.e. three separate wells. Ad3-GFP is a vector derived from Ad3 that contains the same GFP expression cassette as the Ad5/3 vectors. C) Blocking of Ad attachment by recombinant DSG2 protein. Ad vectors were incubated with increasing concentrations of DSG2 protein at room temperature for 60 minutes. Then, HeLa cells were infected at an MOI of 100 pfu/cell for 60 min, after which the viruses were removed and new medium was added. GFP fluorescence was measured 18 hours later by flow cytometry. n=3. Shown are average values. The standard deviation was less than 10% for all samples. D) Competition of Ad infection by Ad3 PtDd. HeLa cells were incubated with increasing concentrations of PtDd for 60 minutes and then infected with Ad vectors at an MOI of 100 pfu/cell for 60 min, after which the viruses were removed and new medium added. GFP fluorescence was measured 18 hours later. N=3. Shown are average values. The standard deviation was less than 10% for all samples. E) DSG2 siRNA blocks infection of Ad5/3 vectors. A total of one microgram of siRNA was transfected onto $1 \times 10^5$ HeLa cells. Cells were collected 48 hours after transfection by Versene, and $1 \times 10^5$ cells were re-plated. The second day, cells were infected with Ad vectors at an MOI of 100 pfu/cell. GFP fluorescence was measured 18 hours later.

Figure 10:
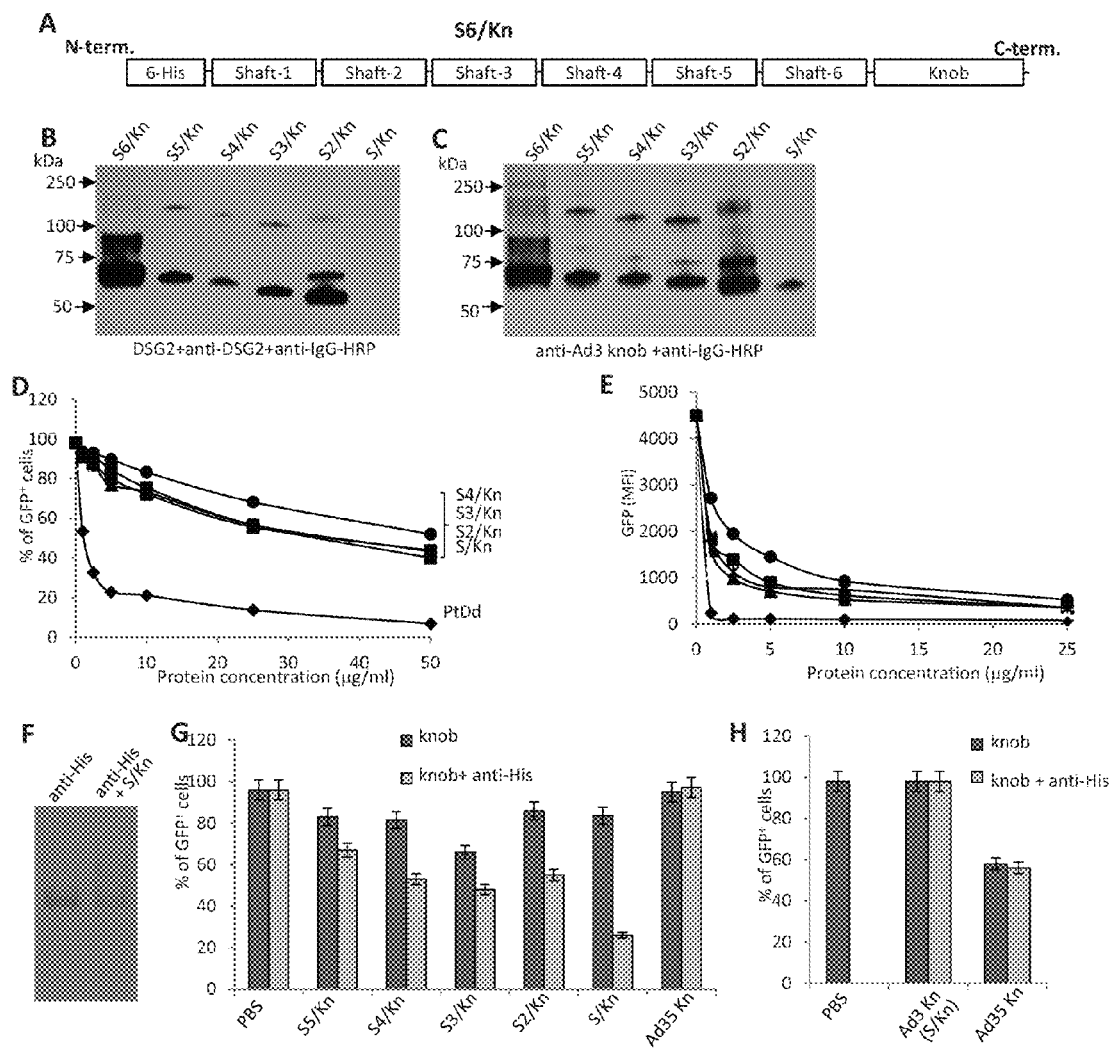

FIG. 10. Blocking of Ad3 infection requires cross-linking of Ad3 fiber knobs. A) Structure of a recombinant Ad3 fiber knobs (S6/Kn) containing an N-terminal His-tag, six shaft motifs (S6), and the knob domain (Kn). Additional fiber knob variants contained 5, 4, 3, 2, or 1 shaft motifs and were labeled S5/Kn, S4/Kn, S3/Kn, S2/Kn, and S/Kn, respectively. B) Western blot analysis of recombinant Ad3 fiber knobs. Filters were incubated with recombinant DSG2, followed by mouse monoclonal anti-DSG2 antibodies and anti-mouse IgG HRP conjugates. Visible are trimeric forms of the Ad3 fiber knobs in the range of 50 to 70 kDa. The theoretical molecular weights of (timeric) S6/Kn, S5/Kn, S4/Kn, S3/Kn, S2/Kn, and S/Kn are 93.9, 89.7, 84.3, 79.2, 74.4, and 69.3 kDa. S6/Kn and S2/Kn formed more multimers of fiber knobs (>75 kDa) than the other knobs and tended to generate inclusion bodies in E. coli. Denaturation of fiber knobs would result in 25-30 kDa monomers (not shown). C) Western blot using antibodies against the Ad3 fiber knob as a probe. D and E) Competition of Ad3-GFP transduction. HeLa cells were incubated with increasing concentrations of PtDd and different Ad3 fiber knobs for 60 minutes and then infected with Ad3-GFP at an MOI of 100 pfu/cell for 60 min, after which the viruses were removed and new medium added. GFP fluorescence was measured 18 hours later. n=3. Shown are average values of percent GFP-positive cells (D) and mean GFP fluorescence (E). The standard deviation was less than 10% for all samples. S5/Kn is not shown for clarity. F) Crosslinking of His-tagged fiber knob (S/Kn) by anti-His antibodies. Anti-His mAb was incubated with PBS or S/Kn for 15 min and run on a native polyacrylamide gel. The antibody has a molecular weight of 150 kDa. An additional band with a higher molecular weight appeared in the presence of S/Kn reflecting a complex of both proteins. The knob alone is not shown. G) Effect of cross-linking of Ad3 fiber knobs with anti-His antibodies on inhibition of Ad3-GFP transduction. 5 mg/ml of Ad3 fiber knobs were incubated with 20 mg/ml of mouse anti-His mAbs at room temperature for 60 minutes, then added onto $1 \times 10^5$ HeLa cell. After 60 minutes incubation, 100 pfu/cell of Ad3GFP virus were added and GFP was analyzed as described in D). The differences between "knob" and "knob+anti-His" were significant (P<0.005) for all Ad3 fiber knobs. For comparison, we also included Ad35 fiber knob (non-dimerizing) into this study. H) Effect of cross-linked Ad3 or Ad35 fiber knobs on Ad35-GFP transduction. Ad35-GFP is a vector derived from Ad35 containing a CMV-GFP expression cassette (33). Ad3 and Ad35 fiber knob are proteins that contain a His-tag, one shaft motif, and the corresponding knobs (31). (Ad3 knob is the same as S/Kn). The experiment was performed as described in G). The difference between "knob" and "knob+anti-His" was not significant.

Figure 11:
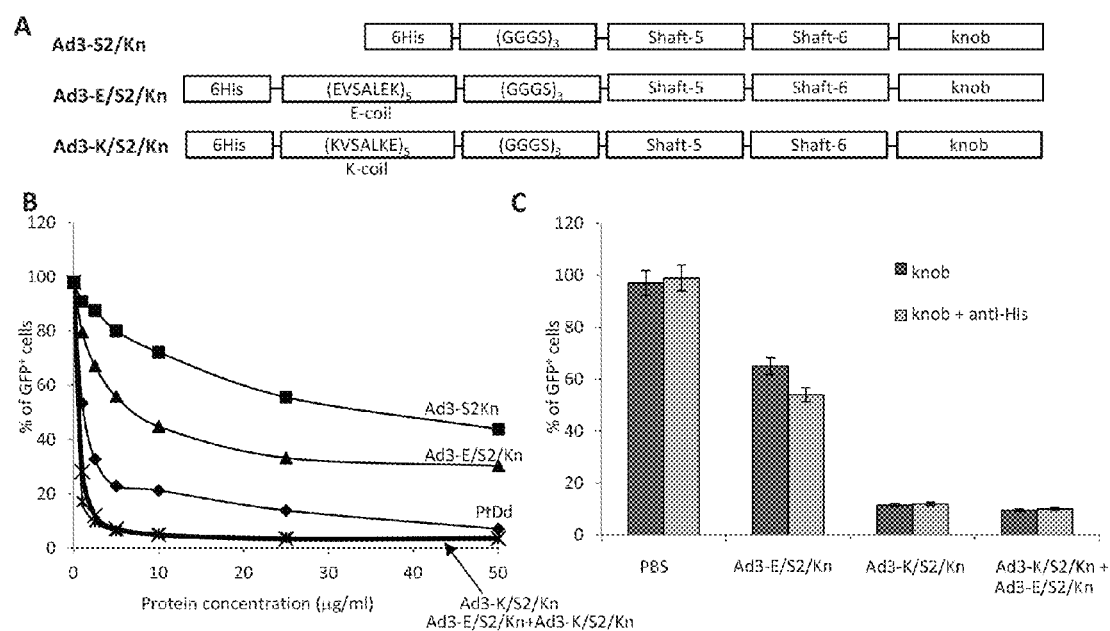

FIG. 11. Ad3 fiber knob dimerization via E-/K-coils. A) Schematic structure of recombinant Ad3 fiber knob proteins, containing an N-terminal His-tag, dimerization domains (E-coli or K-coil (37)), a flexible linker, two fiber shaft motifs ($5^{th}$ and $6^{th}$), and the Ad3 fiber knob domain. Ad3-52/Kn is a fiber that lacks the dimerization domains. B) Competition of Ad3-GFP transduction. HeLa cells were incubated with increasing concentrations of PtDd and different Ad3 fiber knobs for 60 minutes and then infected with Ad3-GFP at an MOI of 100 pfu/cell for 60 min, after which the viruses were removed and new medium added. GFP fluorescence was measured 18 hours later. n=3. Shown are average values of percent GFP-positive cells. Ad3-K/S2/Kn+Ad3-E/S2/Kn is a 1:1 mixture of both fiber knobs. PtDd vs Ad3-E/S2/Kn: p=0.074; PtDd vs Ad3-K/S2/Kn+Ad3-E/S2/Kn: P=0.03; Ad3-K/S2/Kn vs Ad3-K/S2/Kn+Ad3-E/S2/Kn: p=0.62. C) Cross-linking of Ad3 fiber knobs with anti-His antibodies. 5 mg/ml of Ad3 fiber knobs were incubated with 20 mg/ml of mouse anti-His mAbs at room temperature for 60 minutes, then added onto $1\times10^5$ HeLa cell. After 60 minutes incubation, 100 pfu/cell of Ad3-GFP virus were added and GFP was analyzed as described in B). The difference between "knob" and "knob+anti-His" is significant for Ad3-E/S2/Kn ($p<0.05$), but not for the other samples.

Figure 12:
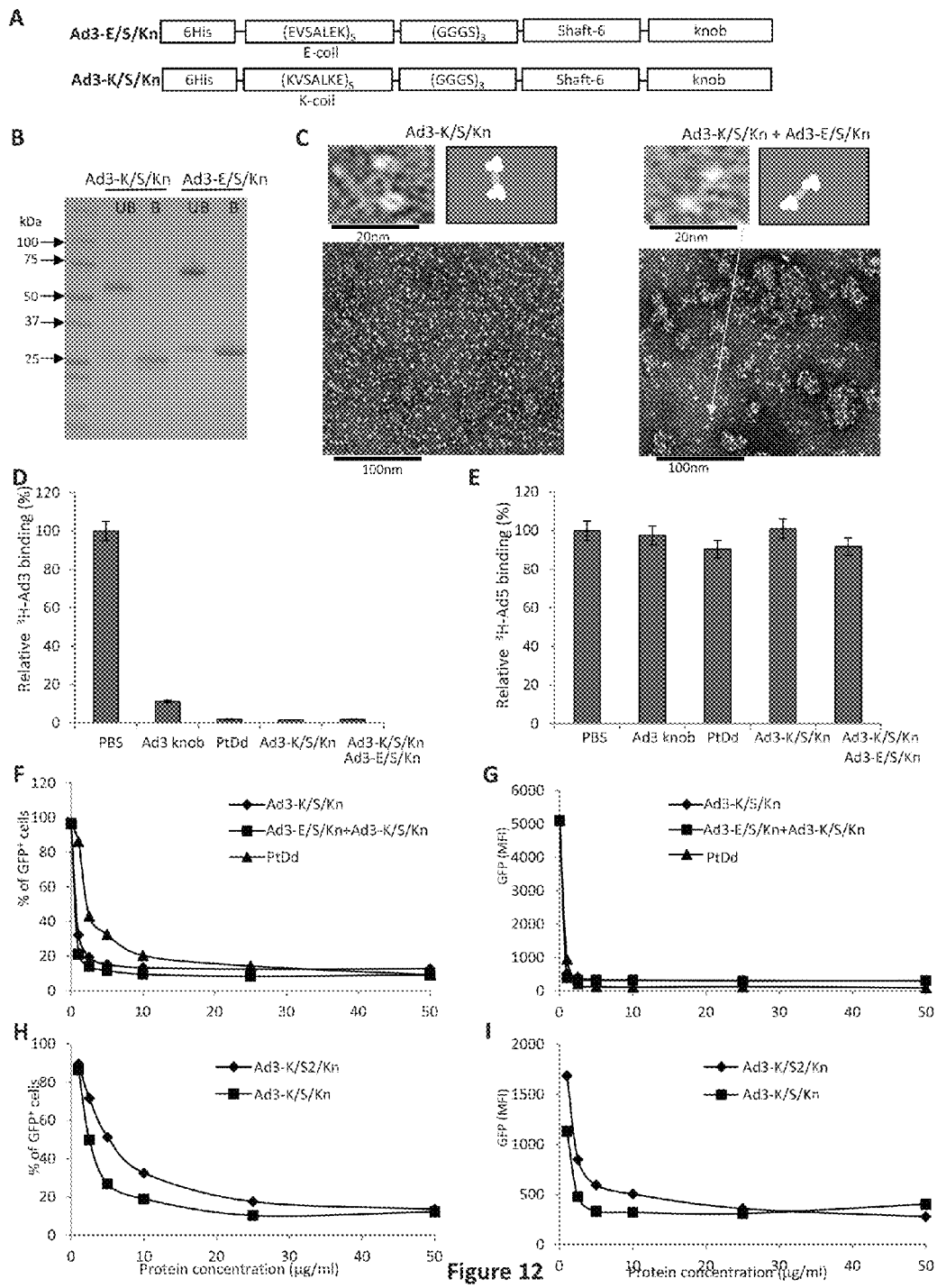

FIG. 12. Analysis of dimeric fiber knobs containing only one shaft motif. A) Schematic structure of recombinant Ad3 fiber knob proteins Ad3-K/S/Kn and Ad3-E/S/Kn. The theoretical molecular weight of each fiber knob trimer is ~60 kDa. B) Coomassie blue stained gel. Samples were run on a 4-15% gradient polyacrylamide gel in Tris/glycine/0.1% SDS buffer. UB-unboiled samples, B-boiled samples. Note that boiling in Laemmli buffer disrupts the trimeric protein structures resulting in ~25 kDa fiber knob monomers. C) Negative stain electron microscopy of purified Ad3-K/S/Kn and Ad3-K/S/Kn mixed with Ad3-E/S/Kn. The upper left image shows fiber knob dimers in both preparations. Note that the fiber knob itself is a trimer. The lower images show aggregates that contain more than two fiber knobs. The right panels show schematic drawings of the photographs. D) Blocking of $^3$H-Ad3 attachment by recombinant Ad3 fiber knobs or PtDd. Ad attachment to cells incubated with PBS was taken as 100%. N=3. E) Blocking of $^3$H-Ad5 attachment by recombinant Ad3 fiber knobs or PtDd. Ad attachment to cells incubated with PBS was taken as 100%. N=3. F and G) Competition of Ad3-GFP transduction. HeLa cells were incubated with increasing concentrations of fiber knobs or PtDd for 60 minutes and then infected with Ad3-GFP at an MOI of 100 pfu/cell for 60 min, after which the viruses were removed and new medium added. GFP fluorescence was measured 18 hours later. n=3. Shown are average values of percent GFP-positive cells (F) and mean GFP fluorescence (G). The standard deviation was less than 10% for all samples. H and I) The same study as in F and G) was performed with Ad3-K/S/Kn and the fiber knobs with two shaft motifs, Ad3-K/S2/Kn.

Figure 13:
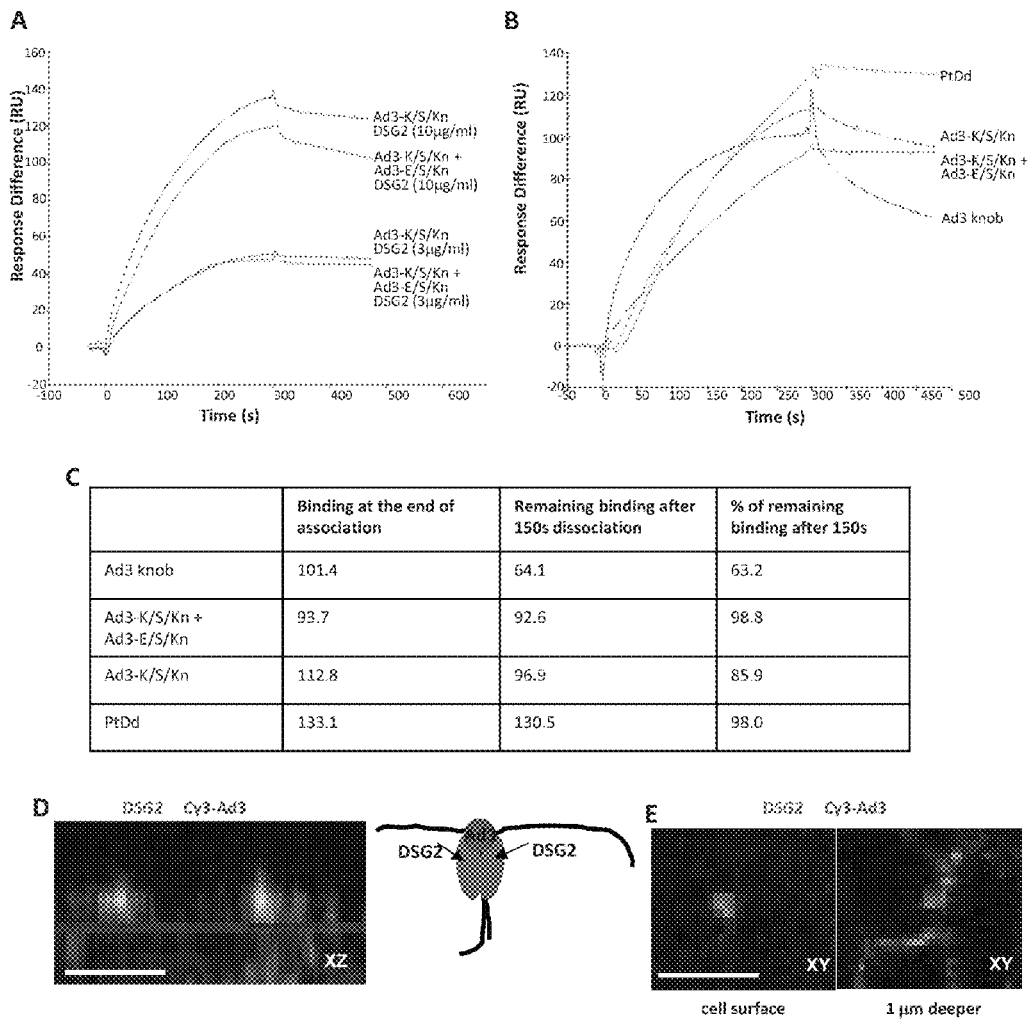

FIG. 13. SPR analysis of Ad3-K/S/Kn+Ad3-E/S/Kn and Ad3-K/S/Kn interaction with DSG2. A) Biotinylated fiber knobs were immobilized to streptavidin-linked sensorchips. DSG2 was injected at indicated concentrations (3 and 10 mg/ml). Response signals were collected over the indicated time periods with automatic background subtraction. B) DSG2 was immobilized on sensorchips and background was automatically subtracted from the control flowcell. Injection of Ad3 fiber knob (non-dimerizing), Ad3-K/S/Kn and Ad3-E/S/Kn+Ad3-K/S/Kn at 10 mg/ml, and PtDd at 3 mg/ml to normalize all the responses to about 100RU (taking into account that dodecahedron has 12 fibers and that SPR signal depends on the molecular weight of the analyte.) C) Summary of SPR data shown in B) and calculation of remaining signal 150s after the end of injection. D) Confocal immunofluorescence analysis of DSG2 and Ad3 particles on epithelial colon cancer T84 cells. Shown are cells from the lateral side, i.e. stacked XZ confocal image layers. Cells were exposed to Cy-3 labeled Ad3 particles for 15 min, washed, fixed, and stained with anti-DSG2 antibodies (green). Ad3 particles appear in red. The scale bar is 20 mm. The right panel shows a schematic drawing of the confocal image with two DSG2 units clustered by the Ad3 particle. E) XY sections of the cell surface and 1 mm deeper. The images suggest that Ad3 binds to DSG2 molecules that is exposed on the cells surface. Note that most of the DSG2 is localized, deeper, i.e. distal of tight junctions.

Figure 14:
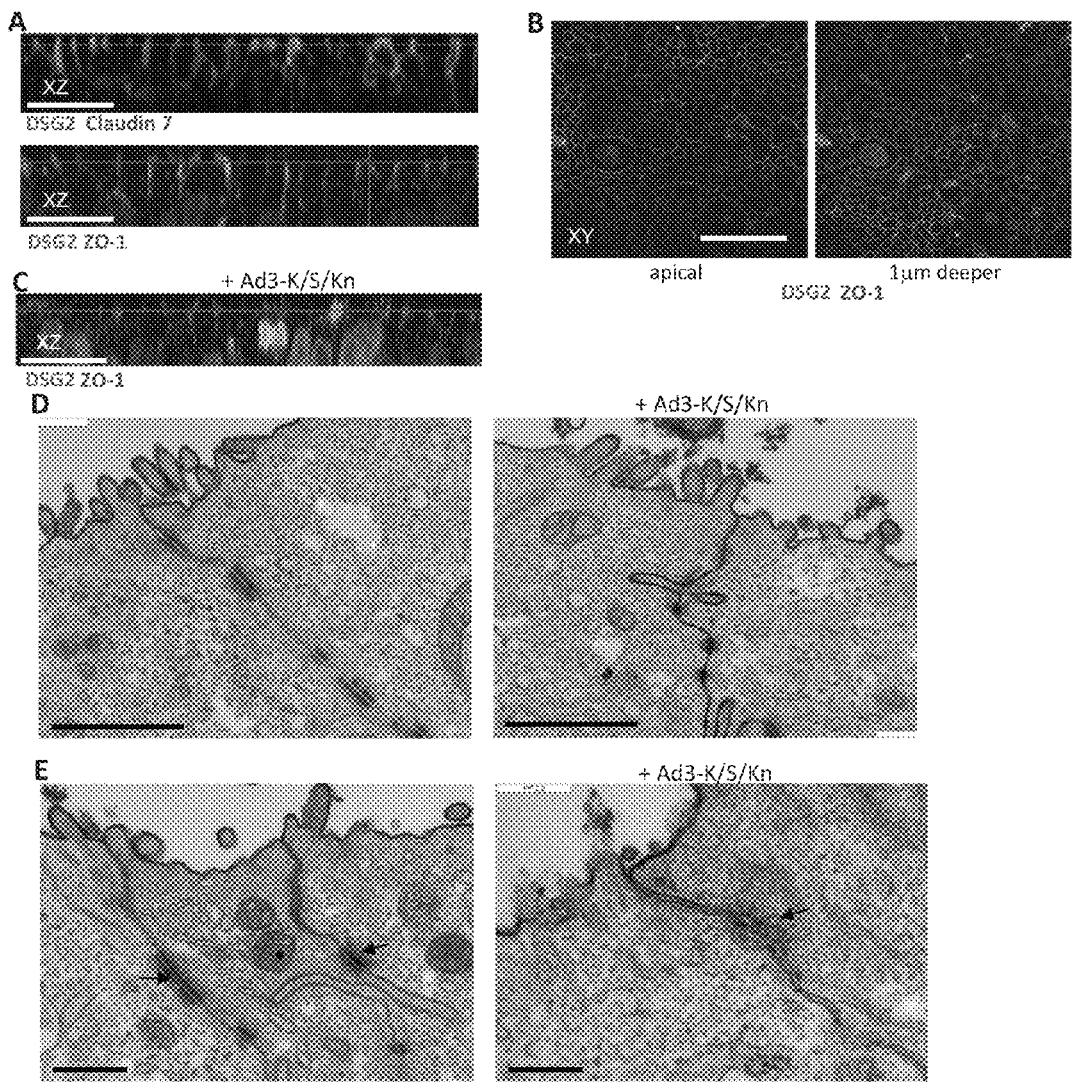

FIG. 14. Analysis of epithelial junctions. Studies were performed on polarized colon carcinoma T84 cells cultured for 20 days in TRANSWELL™ chambers. A) Confocal immunofluorescence microscopy. Shown are representative stacked XZ images. Upper panel: DSG2 (green) appears at the apical site of baso-lateral junctions marked by claudin 7 (red). Lower panel: The tight junction marker ZO-1 (red) is localized at the apical side of DSG2 (green). Claudin 7 staining masks the lower part of DSG2 "streaks" in the lateral membrane, while ZO-1 staining covers the upper part of DSG2 signals. The scale bar is 20 mm. B) Shown are XY sections from the cell surface and 1 mm deeper stained for DSG2 (green) and ZO-1 (red). C) Cells were treated with Ad3-K/S/Kn (5 mg/ml) and analyzed 12 hours later for DSG2 and ZO-1. D) Transmission electron microscopy of junctional areas of T84 cells. Cells were either treated with PBS (left panel) or Ad3-K/S/Kn (right panels) for one hour on ice, washed, and then incubated for 1 hour at 37° C. At this time, the electron-dense dye ruthenium red (1) was added together with the fixative. If tight junctions (above the desmosomes) are closed, the dye only stains the apical membrane (black line). If tight junctions are open, the dye penetrates between the cells and stains the baso-lateral membrane. The scale bar is 1 mm. Magnification is 40,000×. E) A larger magnification (100,000×) shows the disintegration of desmosomes (marked by an arrow) after Ad3-K/S/Kn treatment. The scale bar is 0.2 mm.

Figure 15:
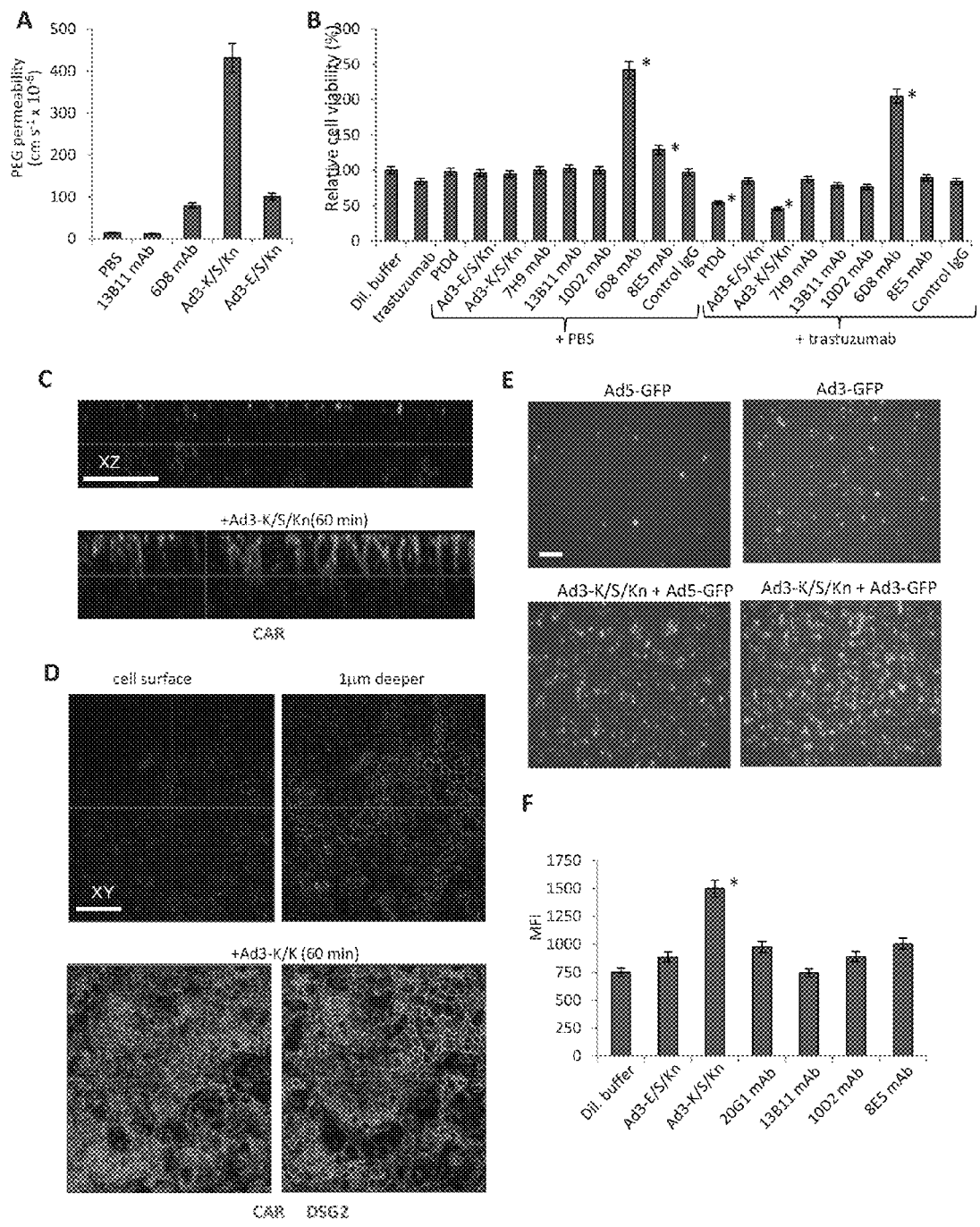

FIG. 15. Functional analyses of epithelial junction opening. A) T84 cells were grown in polyester membrane TRANSWELL™ inserts for 21 days until transepithelial resistance was constant, implying that tight intercellular junctions had formed. Shown is $^{14}$C-PEG-4,000 diffusion through polarized T84 cells cultured in TRANSWELL™ chambers. Cells were incubated with PBS or the various DSG2 ligands for 15 min, after which $^{14}$C-PEG-4,000 was added to the inner chamber. Paracellular flux was assessed in aliquots from the apical and basal chambers as described elsewhere (1). The following monoclonal antibodies against different extracellular domains (ECD) of DSG2 were used: 13B11-mAb (against the ECD 1/2) and 6D8-mAb (against the ECD 3/4). Ad3-K/S/Kn is the dimerizing form. Ad3-E/S/Kn is unable to dimerize. B) Effect of DSG2 ligands on trastuzumab killing of Her2/neu-positive breast cancer BT474-M1 cells. Cells were incubated at 100% confluence for 2 days. Ligands were added to the inner chamber for 1 hour followed by PBS or trastuzumab. Cell viability was measured two hours later (see Material and Methods). In addition to 13B11 and 6D8 mAbs, the following anti-DSG2 antibodies were used: 7H9 (against the pro-peptide domain), 10D2 (against the ECD 2), 8E5 against the ECD 3/4). Viability of dilution buffer-treated cells was taken 100%. n=5, i.e. five separate wells. *: $p<0.05$ compared to dilution buffer. C) Confocal microscopy for CAR in T84 cells treated with dilution buffer or Ad3-K/S/Kn (stacked XZ layers). T84 cells were grown in polyester membrane TRANSWELL™ inserts for 21 days. Ad3-K/S/Kn (40 mg/ml) or dilution buffers were added for 60 min, after which cells were washed and subjected to immunofluorescence analysis. CAR appears as green staining. Nuclei are blue. The scale bar is 20 mm. D) Confocal microscopy for CAR in polarized T84 cells. XY images were taken of the cell surface and at a layer 1 mm beneath the cell surface (right panels). Experimental conditions were as in C). The scale bar is 20 mm. E) Ad transduction of T84 cells. T84 cells were grown in polyester membrane TRANSWELL™ inserts for 21 days. Ad3-GFP and Ad5-GFP was added to the inner chamber at an MOI of 250 pfu/cell together with dilution buffer (upper panels) or Ad3-K/S/Kn (40 mg/ml). Three hours later, virus was removed and cells were washed. GFP expression was analyzed after 20 hours of incubation. Shown are representative images. For quantification, GFP-positive cells from 10 independent images of three independent experiments were counted. The scale bar is 20 mm. F) Flow cytometry of Ad5-GFP infected cells. T84 cells were infected with Ad5-GFP as described in E) either in the presence of dilution buffer or 40 mg/ml DSG2 ligands. n=3. *: P<0.05 compared to dilution buffer.

Figure 16:
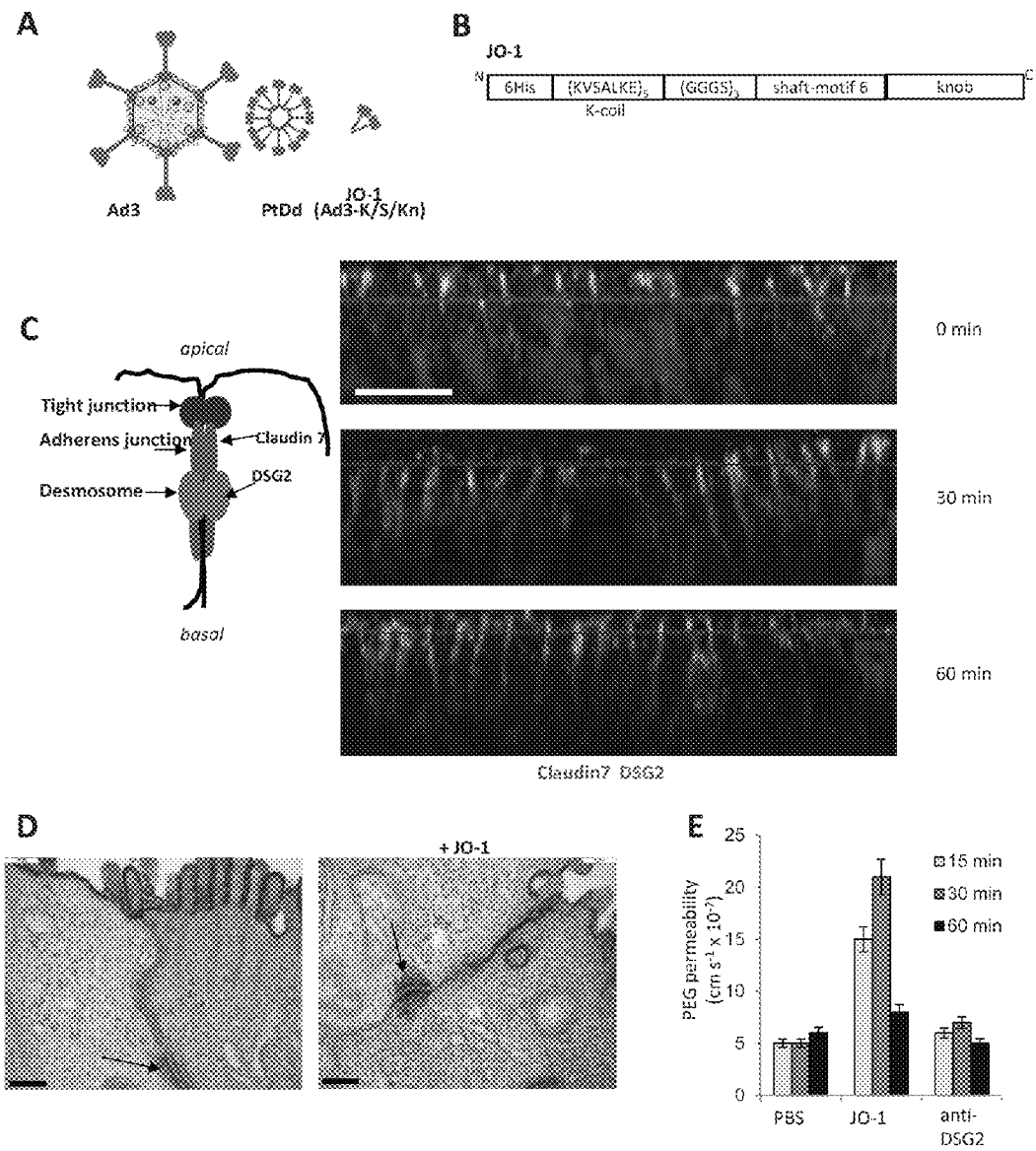

FIG. 16. Transient opening of epithelial junctions by JO-1. A) Structure of Ad3 viral particles. Left panel: complete, infectious Ad3 particle. The capsid proteins fiber and penton base are shown in green and blue, respectively. The trimeric fiber knob is shown in red. Middle panel: Ad3 pentondodecahedra (PtDd) formed by spontaneous assembly of 12 recombinant pentons (fiber+penton base). Right panel: dimeric Ad3 fiber (JO-1). B) Schematic structure of JO-1 containing an N-terminal His-tag, a dimerization domain [K-coil (Zeng et al., 2008)], a flexible linker, one fiber shaft motif, and the homotrimeric Ad3 fiber knob domain. JO-1 is produced in E-coli (at a yield of ~10 mg/l) and purified with Ni-columns. C) Left panel: simplified structure of epithelial junctions with tight junctions, desmosomes, and adherens junctions. DSG2 is a desmosomal protein. Claudin 7 is an adherens junction protein. Right panels: Confocal immunofluorescence microscopy of T84 cells. Shown are representative stacked XZ images. Cells were treated with JO-1 (5 μg/ml) for 1 h on ice. After removal of JO-1, cells were incubated at 37° C. and analyzed 0, 30, and 60 min later. Upper panel: DSG2 (green) appears at the apical site of baso-lateral junctions marked by claudin 7 (red). Middle panel: within 30 min after adding JO-1, claudin 7 staining increases and DSG2 staining becomes visible along the upper part of the lateral membrane (yellow signals). Lower panel: By 60 minutes, lateral junctions resemble those of time point "0 min". The scale bar is 40 μm. D) Transmission electron microscopy of junctional areas of polarized colon cancer T84 cells. Cells were either treated with PBS (left panel) or JO-1 (right panel) for 1 h on ice, washed, and then incubated for 1 h at 37° C. At this time, the electron-dense dye ruthenium red (Amieva et al., 2003) was added together with the fixative. If tight junctions (above the desmosomes, marked by arrows) are closed, the dye only stains the apical membrane (black line). If tight junctions are open, the dye penetrates between the cells and stains the baso-lateral membrane. The scale bar is 1 μm. Magnification is 40,000×. E) $^{14}$C-PEG-4,000 diffusion through monolayers of T84 cells at different time points after adding JO-1 or anti-DSG2 antibody (6D8, directed against ECD3/4). Cells were incubated on ice for 1 h with DSG2 ligands and washed. Fresh medium containing $^{14}$C-PEG-4,000 was then added to the inner chamber. Paracellular flux was assessed in aliquots from the apical and basal chambers as described elsewhere (Amieva et al., 2003). The experiment was repeated 3 times.

Figure 17:
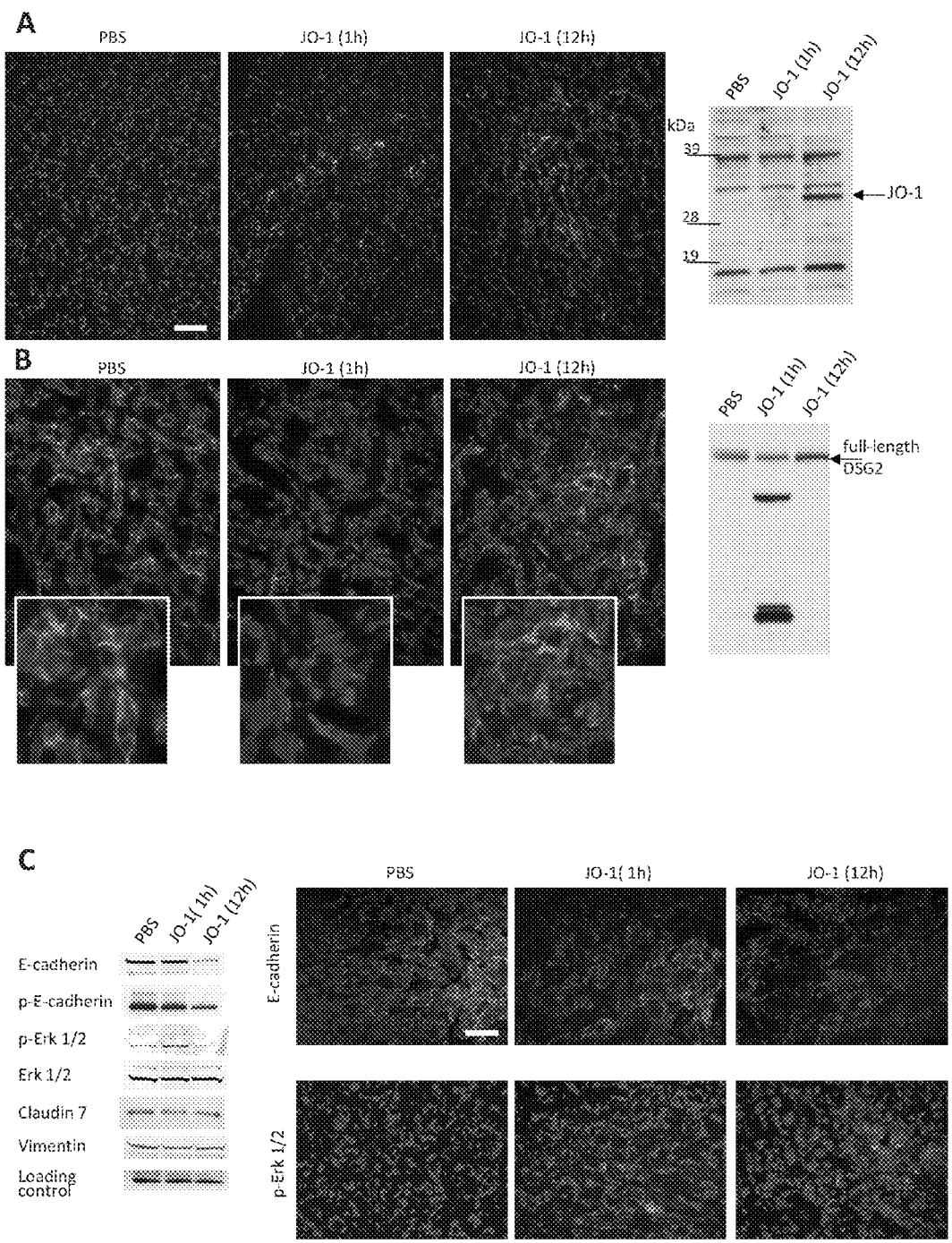

FIG. 17. Analysis of mechanism of JO-1 action in tumors in vivo. A total of 4×10$^6$ human breast cancer HCC1954 cells were injected into the mammary fat pad of CB17-SCID/beige mice. Thirty days later, when tumors reached a volume of ~200 mm$^3$, JO-1 (2 mg/kg in 200 μl PBS) was injected intravenously. Tumors were harvested either 1 or 12 h after JO-1 injection. Control mice received 200 μl PBS and tumors were collected 1 h later. A) Kinetics of JO-1 accumulation in tumors. Left panels: immunofluorescence analysis of tumor sections using anti-His tag antibodies (for visualization of JO-1). Representative sections are shown. The scale bar is 20 μm. Right panel: Western blot analysis of tumor tissue using Ad3-fiber knob specific antibodies (Wang et al., 2011b). The specific band representing JO-1 is marked by an arrow. Representative images are shown. The experiment was repeated 3 times. B) Analysis of DSG2 in tumors. Left panel: immunofluorescence analysis of tumor sections using DSG2 antibodies (mAb 6D8 against extracellular domain 3/4 of DSG2). The inserts show a higher magnification. Right panel: The same anti-DSG2 antibody was used for Western blot analysis of tumor tissue. C) Intracelluar signaling in vivo. Left panel: Western blot analysis of tumor tissue for E-cadherin and phosphorylated E-cadherin, Erk 1/2, phosphorylated Erk1/2, claudin 7, and vimentin. Antibodies against gamma-tubulin were used to assess sample loading ("loading control"). Right panels: immunofluorescence analysis using antibodies against E-cadherin and phosphorylated Erk1/2. Representative images are shown. The experiment was repeated 3 times.

Figure 18A:
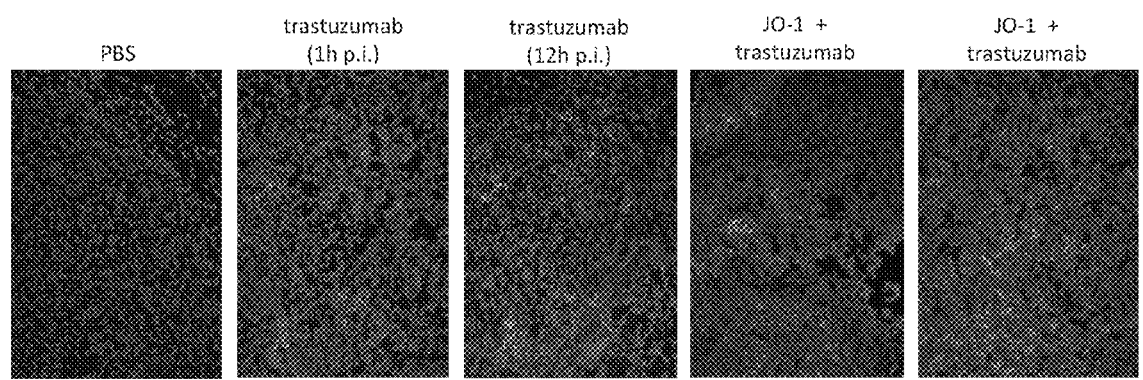
Figure 18B:
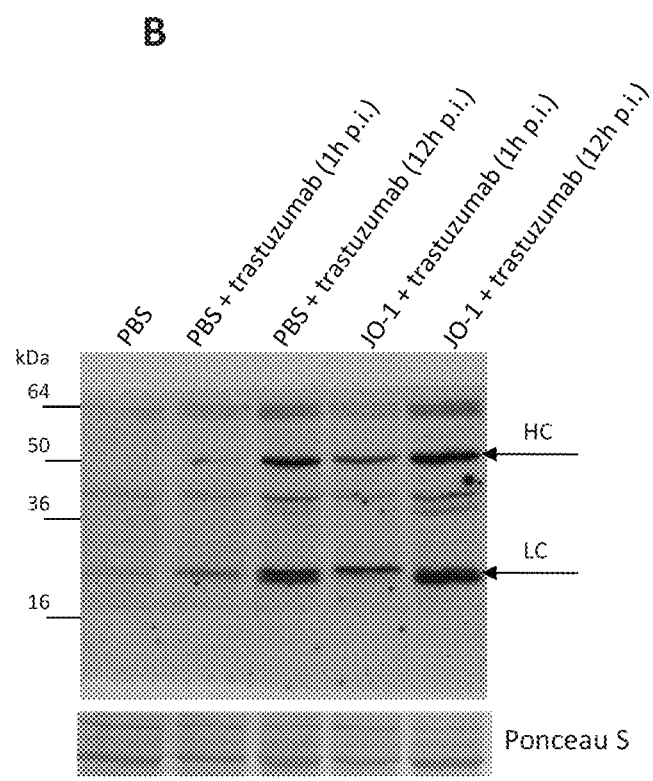

FIG. 18. JO-1 improves penetration of trastuzumab in HCC1954 breast cancer tumors in situ. Tumor bearing mice were intravenously injected with PBS or JO-1 (2 mg/kg) followed by trastuzumab 1 h later. Tumors were harvested 1 h or 12 h after trastuzumab injection. A) Sections were stained for human IgG (i.e. trastuzumab). Positive staining appears green. Representative sections are shown. The scale bar is 20 μm. B) Western blot analysis for human IgG (trastuzumab) in tumors. Heavy (HC) and light (LC) Ig chains are indicated by arrows. Ponceau S staining for total protein blotted to the membrane serves a loading control. Representative images are shown.

Figure 19:
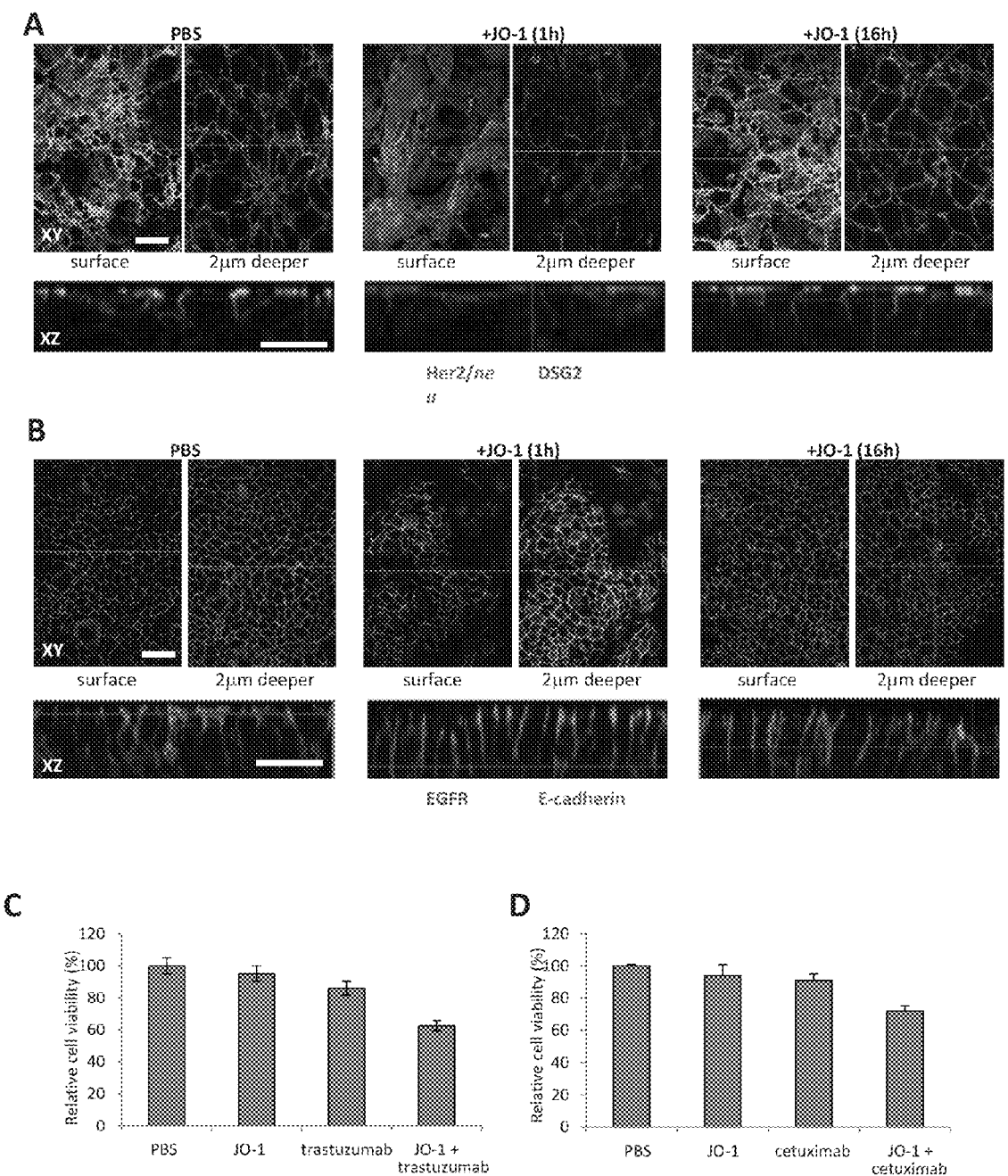

FIG. 19. JO-1 increases mAb killing of cells in which the target receptors are trapped in epithelial junctions. A) Confocal microscopy of Her2/neu (green) and DSG2 (red) staining on polarized BT474 cell cultures (XY and XZ images). Cells treated with PBS are shown in the left panel. Middle and right panels: Cells were treated with JO-1 (20 μg/ml) for 1 h on ice. After removal of JO-1, cells were incubated at 37° C. and analyzed 1 h and 16 h later. XY images show the cell surface (left) and a section 2 p below the cell surface. The scale bar is 40 μm. B) Confocal microscopy of EGFR (red) and the tight junction protein E-cadherin (green) on polarized A549 lung cancer cells. C) JO-1 enhances killing of Her2/neu-positive breast cancer cells by trastuzumab. BT474 cells were incubated with JO-1 (5 μg/ml) or PBS. Trastuzumab (15 μg/ml) was added 1 h later. Cell viability was measured after 3 h by WST-1 assays as described earlier (Wang et al., 2010). Viability of PBS-treated cells was taken as 100%. n=5, P<0.05 for trastuzumab vs. JO-1+trastuzuma b. Representative images are shown. The experiment was repeated 3 times. D) JO-1 enhances cetuximab killing of EGFR-positive A549 cells. n=5, P<0.05 for cetuximab vs. JO-1+cetuximab.

Figure 20:
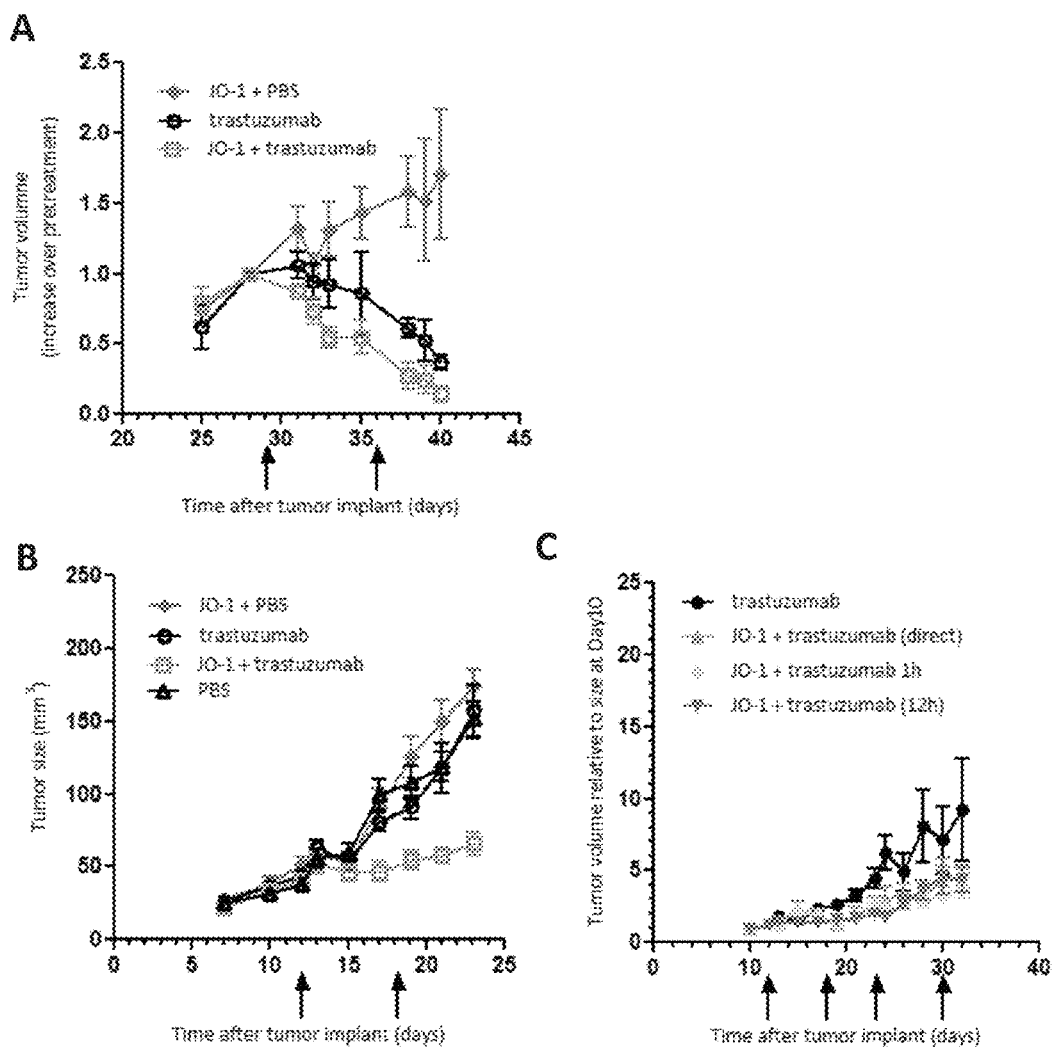

FIG. 20. JO-1 improves trastuzumab therapy in Her2/neu positive breast cancer models. A) A total of 4×10$^6$ BT474-M1 cells, (a tumorigenic subclone of BT474) were injected into the mammary fat pad of CB17-SCID/beige mice. 29 days later (when tumors reached a volume of ~100 mm$^3$), mice received an intravenous injection of 50 μg JO-1 (2 mg/kg) or PBS, followed by an intraperitoneal injection of trastuzumab (10 mg/kg)* or PBS 10 h later. A second treatment cycle was started at day 36 (marked by arrows). Shown is the increase in tumor volume (compared to pretreatment levels at day 29) in individual animals. n=5. Tumor volumes at day 40 were significantly lower in JO-1+ trastuzumab treated mice than in animals that received trastuzumab alone (P<0.01). *This dose of trastuzumab and its route of application is routinely used in mice (Beyer et al., 2011). B) A similar therapy study was performed with HCC1954 Her2/neu-positive breast cancer derived tumors. These tumors are more resistant to trastuzumab treatment. A total of 4×10$^6$ HCC1954 cells, were injected into the mammary fat pad of CB17-SCID/beige mice. Eighteen days later (when tumors reached a volume of ~100 mm$^3$), mice received an intravenous injection of 50 μg JO-1 (2 mg/kg) or PBS, followed by an intraperitoneal injection of trastuzumab or PBS 10 h later. n=5. trastuzumab vs.

JO-1+trastuzumab P<0.001. C) Effect of various time intervals between JO-1 and trastuzumab injection on therapeutic outcome. Mice bearing HCC1954 breast cancer tumors were injected with a mixture of JO-1 and trastuzumab, JO-1 followed by trastuzumab 1 h later and, JO-1 followed by trastuzumab 10 h later. Injections were repeated weekly. n=5 trastuzumab vs. JO-1+trastuzumab (10 h) P<0.001; trastuzumab vs. JO-1+trastuzumab (1 h) P<0.0058; trastuzumab vs. JO-1+trastuzumab (mixed) P<0.0074. JO-1+trastuzumab (10 h) vs. JO-1+trastuzumab (1 h) P<0.17, not significant (ns); JO-1+trastuzumab (10 h) vs. JO-1+trastuzumab (mixed) P<0.47, ns.

Figure 21:
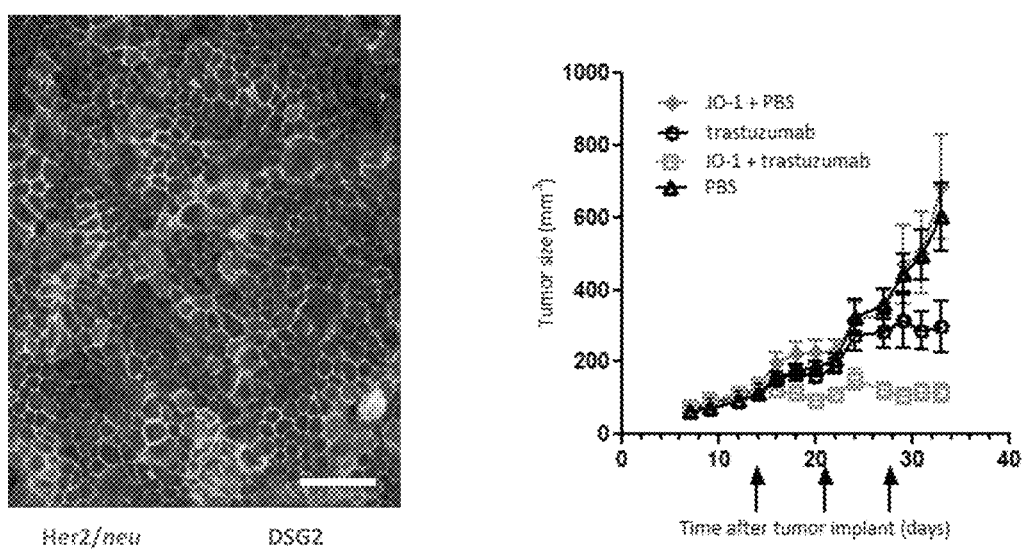

FIG. 21. JO-1 improves trastuzumab therapy in a Her2/neu-positive gastric cancer model. left panel: Immunofluorescence microscopy of Her2/neu-positive human gastric cancer cells (NCI-N87). The scale bar is 20 μm. right panel: JO-1/trastuzumab treatment of mice bearing subcutaneous human gastric cancer (NCI-N87) xenograft tumors. n=5, trastuzumab vs. JO-1+trastuzumab (days 29 and 33): P<0.05

FIG. 22. JO-1 improves cetuximab therapy in lung cancer xenograft models. A) Immunodeficient CB17-SCID/beige mice were subcutaneously injected with $1\times10^6$ A549 cells. JO-1 was injected at day 11 intravenously (2 mg/kg) or intraperitoneally (4 mg/kg) followed by an intraperitoneal injection of cetuximab or PBS 10 h later. One group received 1 mg/kg of JO-1 intravenously and 1 mg/kg intratumorally. n=5, cetuximab vs. JO-1 i.v.+i.t. plus cetuximab P<0.001; cetuximab vs. JO-1 i.v. plus cetuximab P<0.001; cetuximab vs. JO-1 i.p.+cetuximab P<0.001. The differences between the different JO-1 injection routes were not significant. B) Immunodeficient CB17-SCID/beige mice were subcutaneously injected with $1\times10^6$ A549 cells. Eleven days later (when tumors reached a volume of ~100 mm³), mice received an intravenous injection of 2 mg/kg PtDd followed by an intraperitoneal injection of cetuximab (10 mg/kg) or PBS 10 h. A second treatment cycle was started at day 15 (marked by arrows). n=5. Cetuximab vs. PtDd plus cetuximab P<0.001. C) Metastatic lung cancer model. CB17-SCID/beige mice were intravenously injected with $1\times10^6$ A549 cells. 10 days later, mice received an intravenous injection of 2 mg/kg JO-1 or PBS, followed by an intraperitoneal injection of cetuximab (10 mg/kg) or PBS 10 h later. The treatment was repeated every 3 days until day 38. n=10. Left panels: Lungs from individual mice stained with India ink. Healthy tissue appears black. Tumor tissue stains white. Right panel: representative sections of lungs stained with H&E.

Figure 23:
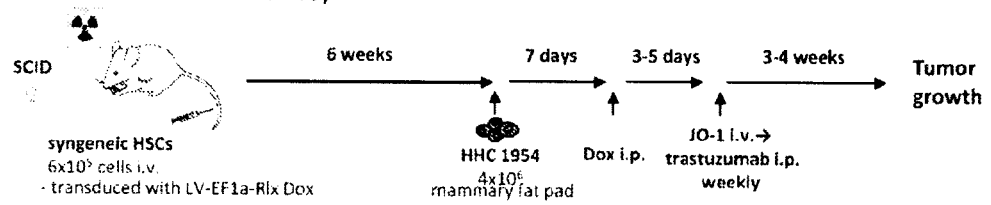
Figure 23:
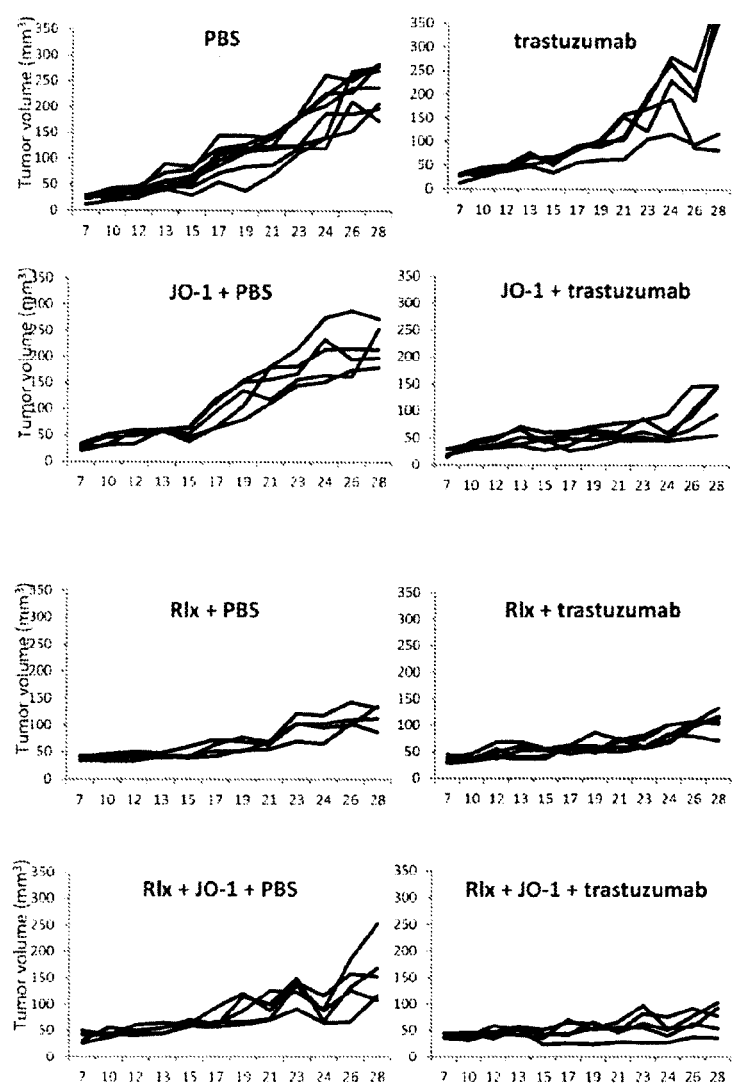

FIG. 23. Combination therapy of JO-1 and relaxin in the HCC1854 breast cancer model. A) Schematic illustration of the experiment. Lethally irradiated mice received either mock transduced or LV-EF1a/Rlx transduced Lin⁻ hematopoietic stem cell. Six weeks later, after engraftment of HSCs, mice were injected into the mammary fat pad with $4\times10^6$ HCC1954 cells. Relaxin expression was activated by Doxycyclin 7 days later. Mice were then given weekly treatment of PBS, PBS/trastuzumab or JO-1/trastuzumab and tumor volumes were measured. B) Tumor volumes of individual mice. n=5. trastuzumab vs. JO-1+trastuzumab P<0.001: Rlx JO-1+trastuzumab vs. Rlxtrastuzumab P<0.001; Rlx PBS vs. PBS P<0.001.

Figure 24:
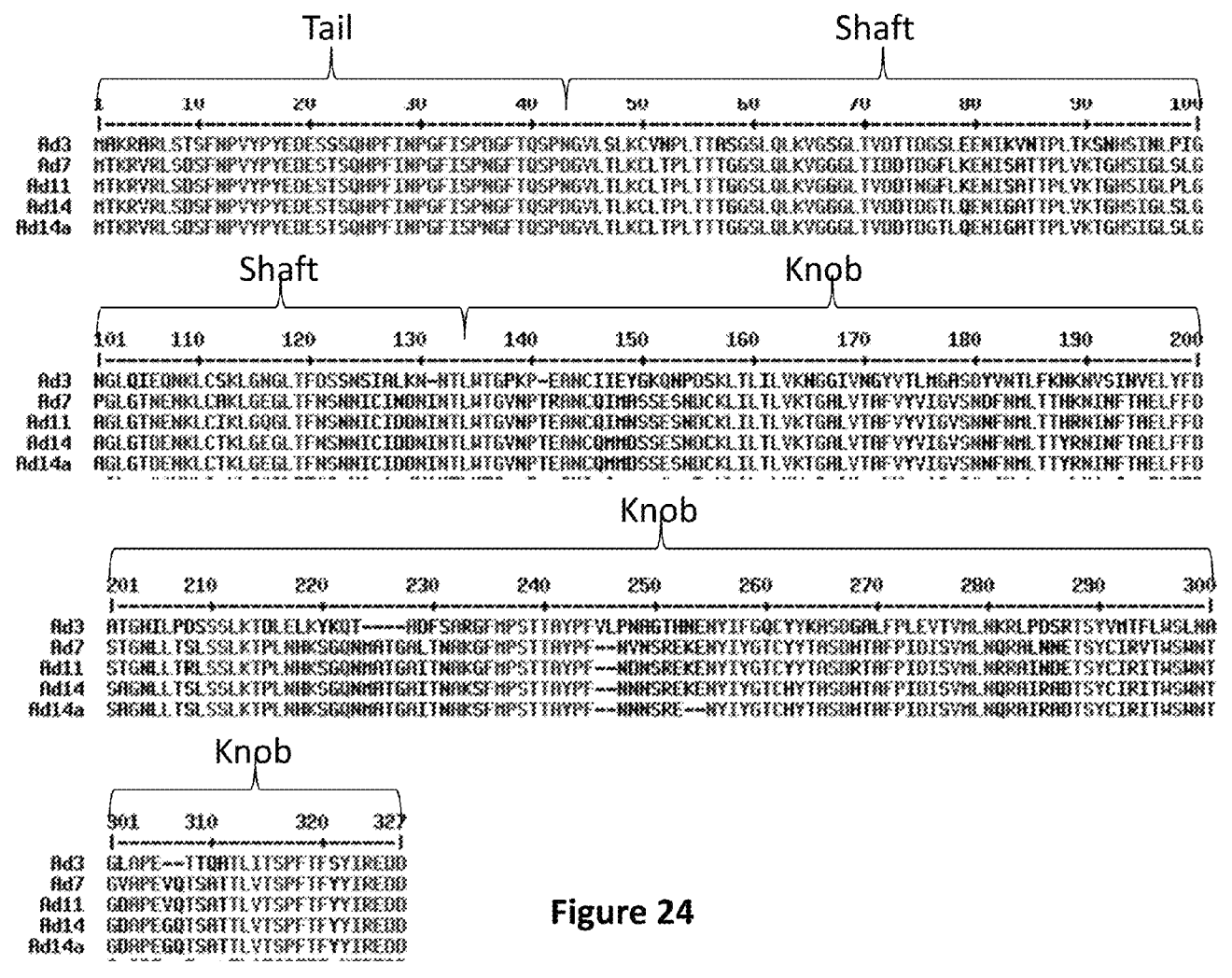

FIG. 24. Alignment of the fiber polypeptides of Ad3, Ad7, Ad11, Ad14, and Ad14a and their domain structure is noted.

DETAILED DESCRIPTION OF THE INVENTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the AMBION™ 1998 Catalog (AMBION™, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

As used herein, the abbreviation "Ad" refers to an adenovirus and is typically followed by a number indicating the serotype of the adenovirus. For example, "Ad3" refers to adenovirus serotype 3.

All embodiments of any aspect of the invention can be used in combination, unless the context clearly dictates otherwise.

In a first aspect, the invention provides methods for enhancing therapeutic treatment, diagnosis, or imaging of a disorder associated with epithelial tissue, comprising administering to a subject in need thereof (a) an amount of one or more therapeutics sufficient to treat the disorder, diagnostic sufficient to diagnose the disorder, and/or imaging agent sufficient to image the epithelial tissue; and (b) an amount of AdB-2/3 fiber multimer, or functional equivalent thereof, sufficient to enhance efficacy of the one or more therapeutics, diagnostics, and/or imaging agents.

The methods of this aspect of the invention can be used to enhancing therapeutic treatment, diagnosis, or imaging of a disorder associated with epithelial tissue by improving access for the therapeutic, diagnostic, and/or imaging agent to their target and dissemination in epithelial tissue. While not being bound by any mechanism, the inventors believe this occurs through complementary mechanisms: movement of the target receptor from the basolateral to the apical cell surface thus allowing better access to the epithelial tissue target by therapeutics, diagnostics, and/or imaging agents that target the receptor, such as monoclonal antibodies), and better penetration of the therapeutic through disruption of intercellular junctions. As disclosed in detail herein, the inventors have discovered that desmogelin-2 (DSG2) is the primary high affinity receptor for AdB-2/3. DSG2 is a calcium-binding transmembrane glycoprotein belonging to the cadherin protein family. In epithelial cells, DSG2 is a component of the cell-cell adhesion structure. Its cytoplasmic tail interacts with a series of proteins that are in direct contact with regulators of cell adhesion and intercellular junctions/cell morphology. It has been shown that DSG2 is overexpressed in a series of epithelial malignancies including gastric cancer, squamous cell carcinomas, melanoma, metastatic prostate cancer, and bladder cancer.

While not being bound by a specific mechanism of action, the inventors believe that the AdB-2/3 fiber multimer binding to DSG2 serves to trigger transient DSG2-mediated opening of intercellular junctions, which serves to improve access of therapeutics, diagnostics, imaging agents, or any other compound of interest that binds to a target in epithelial cells that would otherwise be trapped to at least some extent in intercellular junctions. Detailed examples of such activity are provided herein.

The methods of the invention have broad application for delivery of any therapeutic, diagnostic, imaging agent, or other compound to epithelial tissue comprising intercellular junctions where access to a target of interest can be limited, as DSG2 is widely expressed in epithelial cells. As used herein, a "disorder associated with epithelial tissue" is any disorder wherein therapeutic, diagnostic, or imaging agent administered to/across epithelial cells/epithelial tissue provides a clinical benefit to a patient, whether in improving therapeutic, diagnostic, and/or imaging efficacy. Such disorders include, but are not limited to, solid tumors (i.e.: any tumor with epithelial cell junctions), gastrointestinal disorders (including but not limited to irritable bowel syndrome, inflammatory bowel disorder, Crohn's disease, ulcerative colitis, constipation, gastroesophageal reflux disease, Barrett's esophagus, etc.), skin diseases (including but not limited to psoriasis and dermatitis), lung disorders (including but not limited to chronic obstructive pulmonary disease, asthma, bronchitis, pulmonary emphysema, cystic fibrosis, interstitial lung disease, pneumonia, pancreatic duct disorders, brain disorders (ie: any brain disorder that could benefit from improved transport of drugs through the blood-brain barrier), primary pulmonary hypertension, pulmonary embolism, pulmonary sarcoidosis, tuberculosis, etc.), renal disorders, (including but not limited to glomerulonephritis), liver diseases (including but not limited to hepatitis), endocrine disorders (including but not limited to diabetes and thyroid disorders), pancreatic duct disorders (including but not limited to pancreatitis), and bile duct disorders (including but not limited to bile duct obstruction, cholecystitis, choledocholithiasis, gallstones, etc.) and infections of epithelial tissues (including but not limited to cellulitis, pneumonia, hepatitis, and pyelonephritis). In one preferred embodiment, the disorder associated with epithelial tissue comprises a solid tumor, including but not limited to breast tumors, lung tumors, colon tumors, rectal tumors, skin tumors, endocrine tumors, stomach tumors, prostate tumors, ovarian tumors, uterine tumors, cervical tumors, kidney tumors, melanomas, pancreatic tumors, liver tumors, brain tumors, head and neck tumors, nasopharyngeal tumors, gastric tumors, squamous cell carcinomas, adenocarcinomas, bladder tumors, and esophageal tumors. As will be understood by those of skill in the art, such tumors include primary tumors, tumors that are locally invasive, as well as tumors that have metastasized.=

As used herein, "enhancing efficacy" means any increase in therapeutic, diagnostic, and/or imaging efficacy over what would be seen using the therapeutic, diagnostic, and/or imaging agen alone. For example, measurements of therapeutic efficacy will vary depending on the disorder being treated, but are readily identified by an attending physician. For example, such increases in efficacy include, but are not limited to increasing one or more of the following relative to treatment with the therapeutic alone: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s). In one non-limiting example, treating a solid tumor provides an ability to induce egress of tumor receptors from the basolateral side of epithelial cells to enable improved access and killing of the tumor.

For cancer, there are standards for defining tumor response and standard methods of measuring response. These include tumor response, which is determined by monitoring the change in tumor size or a serum marker of disease. A partial response is more than a 50% reduction in the tumor, while a complete response is defined as complete disappearance of the tumor. Methods used to measure tumors are well known to physicians and include physical examination, radiological testing such as CT scans, MRI, PET scans, X-rays as well as serum markers such as prostate specific antigen, which is used to monitor prostate cancer. Other measures of therapeutic efficacy of cancer treatment include measurements of time to progression, progression-free survival and overall survival.

Improved diagnostic efficacy includes any improvement in efficacy compared to administration of the diagnostic alone, including but not limited to, increasing specificity and/or sensitivity of the diagnostic test. Improved imaging efficacy includes any improvement in efficacy compared to administration of the imaging agent alone, including but not limited to specificity, sensitivity, reproducibility, contrast enhancement, detection of smaller sites of disease, more accurate delineation of disease, such as size and shape of diseases, such as tumors, abscesses, etc.

In various embodiments, the increase in efficacy is a 5%, 10%, 15%, 20%, 25%, 50%, 75%, 100%, or greater benefit compared to efficacy with the therapeutic, diagnostic, and/or imaging agent alone across a patient population.

Any suitable subject can be treated using the methods of the invention, preferably human subjects.

As used herein, "AdB-2/3" is any adenovirus serotype that uses DSG2 as an epithelial cell receptor for viral binding. To date, Ad3, Ad7, Ad11, Ad14, and Ad14a serotypes have been identified. As other Ad serotypes are identified, those of skill in the art can readily identify those that belong to the AbD-2/3 family based on DSG2 binding assays as disclosed herein. For example, surface plasmon resonance (SPR) studies using sensors containing immobilized recombinant DSG2 can be used to determine if new Ad serotypes bind to DSG2, combined with DSG2 competition studies. Further exemplary studies, such as loss and gain of function analyses, are described in detail in Example 1.

The adenovirus virion is an icosahedron characterized by a fiber located at the base of each of the 12 vertices of the capsid. The fiber on the virion is a homotrimeric structure consisting of 3 individual fiber polypeptides. Each adenovirus fiber polypeptide is an asymmetrical structure consisting of an N-terminal tail, which interacts with the penton base protein of the capsid and contains the signals necessary for transport of the protein to the cell nucleus; a shaft, which contains a number of 15-residue repeating units; and a C-terminal knob domain that contains the determinants for receptor binding (J. S. Hong and J. A. Engler, *Journal of Virology* 70:7071-7078 (1996)). All adenoviruses attach to their receptors through the knob structure on the end of the fiber.

Thus, as used herein, the term AdB-2/3 "fiber polypeptide" refers the full length fiber polypeptide expressed by AdB-2/3 (for example, SEQ ID NOS 15-19, with Ad3 fiber polypeptide as SEQ ID NO:15, Ad7 fiber polypeptide as SEQ ID NO:16, Ad11 polypeptide as SEQ ID NO:17, Ad14 fiber polypeptide as SEQ ID NO:18, and Ad14(a) fiber polypeptide as SEQ ID NO:19) that comprises an N-terminal tail domain, a shaft domain, and a C-terminal knob domain. The fiber polypeptides spontaneously assemble into homotrimers, referred to as "fibers," which are located on the outside of the adenovirus virion at the base of each of the twelve vertices of the capsid.

As used herein, an "AdB-2/3 fiber multimer" is any construct comprising a multimer (dimer, trimer, etc.) of an AdB-2/3 fiber, or functional equivalent thereof. As will be understood by those of skill in the art, the AdB-2/3 fiber comprises a homotrimeric knob. The AdB-2/3 fiber multimer is a multimer, such as a dimer, of the homotrimeric AdB-2/3 fiber. As disclosed in detail in the examples that follow, AdB-2/3 fiber multimers are required for binding to DSG2 that triggers transient DSG2-mediated opening of intercellular junctions, which serves to improve access of therapeutics to therapeutic targets that would otherwise be trapped in intercellular junctions In one embodiment, the AdB-2/3 fiber multimer is selected from the group consisting of an Ad3 fiber multimer, an Ad7 fiber multimer, an Ad11 fiber multimer, an Ad14 fiber multimer, an Ad14a fiber multimer, combinations thereof, and functional equivalents thereof. In a preferred embodiment the AdB-2/3 fiber multimer is an Ad3 fiber multimer.

Exemplary constructs comprising one or more AdB-2/3 fiber multimers (or chimeras/functional equivalents thereof) include, but are not limited to, AdB-2/3 virions (such as "killed" virions, for example UV-treated virions), AdB-2/3 capsids, AdB-2/3 dodecahedral particles (PtDd) (subviral dodecahedral particles produced by AdB-2/3 during their replication), recombinant AdB-2/3 fiber multimers (including but not limited to those disclosed in any embodiment or combination of embodiments below), and functional equivalents thereof. In a preferred embodiment, the one or more AdB-2/3 fiber multimers comprise or consist of an AdB-2/3 PtDd, such as an Ad3 PtDd. In another preferred embodiment, the one or more AdB-2/3 fiber multimers comprise or consist of any embodiment or combination of embodiments of the compositions of the invention described below. In a further preferred embodiment, the AdB-2/3 fiber multimer comprises or consists of the polypeptide referred to herein as JO-1 (junction-opener-1), (SEQ ID NO:20), or functional equivalents thereof. As shown in the examples that follow, JO-1 (described in the examples as a self-dimerizing Ad3 fiber derivative) is a multimer of a single chain, recombinant AdB-2/3 fiber polypeptide domain, wherein the polypeptide comprises a knob domain capable of homotrimerization. Thus, JO-1 is an AdB-2/3 fiber multimer according to the present invention.

Methods for preparing large quantities of AdB-2/3 virions and capsid are well known in the art, as are methods for large scale production of PtDd. Similarly, methods for recombinant production of AdB-2/3 fiber multimers (such as JO-1) by incorporating dimerization domains in the recombinant polypeptides are well within the level of skill in the art based on the teachings herein.

The methods of the invention can thus be carried out using any AdB-2/3 fiber multimer capable of binding to DSG2 and triggering transient DSG2-mediated opening of intercellular junctions. Thus, non-naturally occurring modifications (deletions, additions, substitutions, chimeras of different Ad serotype fiber proteins and domains thereof, etc.) to the AdB-2/3 fiber multimers disclosed herein are "equivalents thereof" of the AdB-2/3 fiber multimers and are within the scope of the present invention, so long as they function to bind DSG2 and are capable of multimerizing and triggering DSG2-mediated opening of intercellular junctions. Based on the teachings herein for testing binding to DSG2 and for assessing DSG2-mediated opening of intercellular junctions, it is well within the level of skill in the art to identify such functional equivalents of the AdB-2/3 fiber multimers. In one non-limiting example, assays to assess the flux of a labeled compound (such as FITC-dextran) through confluent polarized epithelial cells, in the presence of candidate AdB-2/3 fiber multimers, are demonstrated in Examples 1 and 2 below. In another non-limiting example, assays in the presence of candidate AdB-2/3 fiber multimers to assess access to proteins not normally accessible due to epithelial cell junctions (such as CD46, Claudin 7, and ZO-1) are demonstrated in Examples 1 and 2 below. Further such assays are also disclosed herein.

AdB-2/3 fiber multimerization can be determined according to methods well known to the practitioners in the art. For example, multimerization of the recombinant AdB-2/3 fiber constructs can be assessed by criteria including sedimentation in sucrose gradients, resistance to trypsin proteolysis, and electrophoretic mobility in polyacrylamide gels (Hong and Engler, *Journal of Virology* 70:7071-7078 (1996)). Regarding electrophoretic mobility, the fiber multimer is a very stable complex and will run at a molecular weight consistent with that of a multimer when the sample is not boiled prior to SDS-PAGE. Upon boiling, however, the multimeric structure is disrupted and the protein subsequently runs at a size consistent with the protein monomer. Any therapeutic, diagnostic, imaging agent, or other compound that can target epithelial tissue and whose delivery to epithelial tissue can be improved by transient opening of intercellular junctions can be used in the methods of the invention. In one embodiment, the therapeutic is selected from the group consisting of antibodies, immunoconjugates, nanoparticles, nucleic acid therapeutics, and combinations thereof, chemotherapeutics, vaccines, radioactive particle/radiation therapy ("radiation"), cellular immunotherapy including adoptive T-cell therapy and dendritic cell therapy (example: intratumoral penetration of administered T-cells), inhaled therapeutics, gene therapy constructs (including but not limited to AdB-2/3 virus as a gene therapy vector, and co-administration with an Ad5-based gene therapy vector), other nucleic acid therapeutics, and combinations thereof.

In various embodiments, the therapeutic is selected from the group consisting of alkylating agents, angiogenesis inhibitors, antibodies, antimetabolites, antimitotics, antiproliferatives, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, growth factor inhibitors, heat shock protein (HSP)-90 inhibitors, demethylating agents, histone deacetylase (HDAC) inhibitors, hormonal therapies, immunologicals, inhibitors of apoptosis proteins (IAPB) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors and the like.

Exemplary therapeutics falling within these various classes include, but are not limited to: docetaxel, doxorubicin, irinotecan, paclitaxel (Taxol®), paclitaxel albumin bound particles (Abraxane®), doxorubicin HCL liposome (Doxil®), BiTE antibodies such as adecatumumab (Micromet MT201), blinatumomab (Micromet MT103) and the like, siRNA-based therapeutics, alkylating agents including altretamine, AMD-473, AP-5280, apaziquone, bendamustine, brostallicin, busulfan, carboquone, carmustine (BCNU), chlorambucil, CLORETAZINE.® (laromustine, VNP 40101M), cyclophosphamide, dacarbazine, decitabine, 5'-azacytidine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like; angiogenesis inhibitors including endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like; antimetabolites including ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-.beta.-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, methotrexate analogs (such as trimetrexate and pralatraxate), mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, and the like; Bcl-2 protein inhibitors including AT-101 ((−) gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl) benzoyl)-4-(((1R)-3-(dimethylamino)-1-((phenylsulfanyl) methyl)propyl)amino)-3-nitrobe-nzenesulfonamide) (ABT-737), N-(4-(4-((2-(4-chlorophenyl)-5,5-dimethyl-1-cyclohex-1-en-1-yl)methyl)pip-erazin-1-yl)benzoyl)-4-(((1R)-3-(morpholin-4-yl)-1-((phenylsulfanyl)methyl-) propyl)amino)-3-((trifluoromethyl)sulfonyl)benzene-sulfonamide (ABT-263), GX-070 (obatoclax) and the like; Bcr-Abl kinase inhibitors include DASATINIB® (BMS-354825), GLEEVEC® (imatinib) and the like; CDK inhibitors including AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like; EGFR inhibitors including ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like; ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAb AR-209, mAb 2B-1 and the like; histone deacetylase inhibitors include romidepsin, LAQ-824, MS-275, trapoxin, suberoylanilide hydroxamic acid (SAHA), TSA, valproic acid and the like; HSP-90 inhibitors including 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like; activators of death receptor pathways including TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab; platinum chemotherapeutics include cisplatin, ELOXATIN® (oxaliplatin) eptaplatin, lobaplatin, nedaplatin, PARAPLATIN® (carboplatin), satraplatin, picoplatin and the like; VEGFR inhibitors including AVASTIN® (bevacizumab), ABT-869, AEE-788, axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMATHi (vandetanib, ZD-6474) and the like; dendritic cell therapy (sipuleucel-T, Provenge®); topoisomerase inhibitors including aclarubicin, 9-aminocamptothecin, amonafide, amsacrine, becatecarin, belotecan, BN-80915, CAMPTOSAR® (irinotecan hydrochloride), camptothecin, dexrazoxine, diflomotecan, edotecarin, ELLENCE® or PHARMORUBICIN® (epirubicin), etoposide, exatecan, abraxane, irenotecan,10-hydroxycamptothecin, gimatecan, lurtotecan, mitoxantrone, orathecin, pirarbucin, pixantrone, rubitecan, sobuzoxane, SN-38, tafluposide, topotecan and the like; antibodies including AVASTIN® (bevacizumab), CD40-specific antibodies, chTNT-1/B, denosumab, ERBITUX® (cetuximab), HUMAX-CD4® (zanolimumab), IGF I R-specific antibodies, lintuzumab, PANOREX® (edrecolomab), RENCAREX® (WX G250), RITUXAN® (rituximab), ticilimumab, trastuzumab and the like; hormonal therapies including ARIMIDEX® (anastrozole), AROMASIN® (exemestane), arzoxifene, CASODEX® jb nnb nb nbbv(bicalutamide), CETROTIDE® (cetrorelix), degarelix, deslorelin, DESOPAN® (trilostane), dexamethasone, DROGENIL® (flutamide), EVISTA® (raloxifene), AFEMA® (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON® (nilutamide), NOLVADEX® (tamoxifen citrate), PLENAXIS® (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like; immunologicals including interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE® (IFN-alpha), BAM-002 (oxidized glutathione), BEROMUN® (tasonermin), BEXXAR® (tositumomab), CAM PATH®(alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN®. (90Y-Ibritumomab tiuxetan) and the like; ofatumumab; biological response modifiers agents including krestin, lentinan, sizofuran, picibanil PF-3512676 (CpG-8954), ubenimex and the like; pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL® (triacetyluridine troxacitabine) and the like; purine analogs including LANVIS® (thioguanine) and PURI-NETHOL® (mercaptopurine).; antimitotic agents including batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like; and other chemotherapeutic agents such as ABRAXANE® (ABI-007), ABT-100 (farnesyl transferase inhibitor), ADVEXIN® (Ad5CMV-p53 vaccine), ALTOCOR® or MEVACOR® (lovastatin), AMPLIGE®. (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); 0: Vincristine (ONCOVIN®); P: prednisone), CYPAT® (cyproterone acetate), combrestatin A4P, DAB(389)EGF (catalytic and translocation domains of diphtheria toxin fused via a His-Ala linker to human epidermal growth factor) or TransMlD-107R® (diphtheria toxins), dacarbazine, dactinomycin, 5,6-dimethylxanthenone-4-acetic acid (DMXAA), enilouracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-.alpha., interferon-.gamma., JUNOVAN® or MEPACT® (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN® (rubitecan), OSIDEM® (antibody-based cell drug), OVAREX® MAb (murine monoclonal antibody), paclitaxel, PANDIMEX® (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio) quinazoline dihydrochloride), TNFERADE® (adenovector: DNA carrier containing the gene for tumor necrosis factor-.alpha.), TRACLEER® or ZAVESCA® (bosentan), tretinoin (Retin-A), tetrandrine, TRISENOX®. (arsenic trioxide), VIRULIZIN®, ukrain (derivative of alkaloids from the greater celandine plant), vitaxin (anti-alphavbeta3 antibody), XCYTRIN® (motexafin gadolinium), XINLAY® (atrasentan), XYOTAX® (paclitaxel poliglumex), YONDELIS® (trabectedin), ZD-6126, ZINECARD® (dexrazoxane), ZOMETA® (zolendronic acid), crizotinib, zorubicin and the like.

In another preferred embodiment, the therapeutic comprises a compound that binds to desmoglein-2; preferably a compound that binds to DSG2 and opens up tight junctions.

In other embodiments, the therapeutic comprises radioactive particles/radiation therapy. Any suitable radioactive therapy or particle can be used as deemed appropriate by an attending physician, including but not limited to cobalt-60, iodine-131, iridium-192, strontium-89, samarium 153, rhenium-186 and lead-212.

In a preferred embodiment, the therapeutic is an anti-tumor therapeutic and comprises a chemotherapeutic or anti-tumor monoclonal antibody as described herein. In a further preferred embodiment, the anti-tumor therapeutic comprises an antibody selected from the group consisting of trastuzumab, cetuximab, petuzumab, apomab, conatumumab, lexatumumab, bevacizumab, bevacizumab, denosumab, zanolimumab, lintuzumab, edrecolomab, rituximab, ticilimumab, tositumomab, alemtuzumab, epratuzumab, mitumomab, gemtuzumab ozogamicin, oregovomab, pemtumomab daclizumab, panitumumab, catumaxomab, ofatumumab, and ibritumomab. Non-limiting examples of useful anti-tumor mAb and their specific uses are listed in Table 1, and as further described in Campoli, M., et al., *Principles & Practice of Oncology* 23(1&2):1-19 (2009), incorporated herein by reference.

TABLE 1

Tumor-Antigen Specific mAbs for Cancer Treatment

| Antibody | Isotype | Target | Disease Indication |
| --- | --- | --- | --- |
| SGN-75 | humanized IgG1 | CD70 | solid tumors, including renal cell cancer, CD70 + hematologic malignancies |
| Trastuzumab | humanized IgG1 | HER2/neu | HER2/neu(+) breast cancer* |
| Cetuximab | Chimeric IgG1 | EGFR | EGFR(+) colon cancer* |
| Panitumumab | Fully human IgG2 | EGFR | EGFR(+) colon cancer* |
| Matuzumab | Humanized IgG1 | EGFR | non-squamous non-small cell lung cancer (NSCLC), head and neck squamous cell carcinoma (HNSCC), breast and pancreatic cancer, colon cancer (CC) |

TABLE 1-continued

Tumor-Antigen Specific mAbs for Cancer Treatment

| Antibody | Isotype | Target | Disease Indication |
|---|---|---|---|
| Pertuzumab | Humanized IgG1 | EGFR | NSCLC, HNSCC, CC, breast and ovarian cancer |
| Ipilimumab (MDX-010) | Humanized IgG1 | CTLA-4 | NSCLC, RCC, metastatic melanoma |
| Tremelimumab (CP-675, 206) | Humanized IgG1 | CTLA-4 | NSCLC, RCC, metastatic melanoma |
| Sibrotuzumab | Humanized IgG1 | FAP** | NSCLC, CC |
| DR-4-specific mapatumumab (TRM-1, HGS-ETR1) | Humanized IgG1 | TRAIL | NSCLC, CC, ovarian cancer, multiple myeloma, |
| DR-5-specific lexatumumab (HGS-ETR2, TRA-8) | Humanized IgG1 | TRAIL | solid tumors |
| Cantuzumab mertansine | Humanized IgG1-maytansinoid | CanAg*** | CC, pancreatic cancer |
| Bevacizumab (Avastatin) | humanized IgG1 | vascular endothelial growth factor (VEGF) | colon cancer*, non-squamous non-small cell lung cancer (NSCLC)*, metastatic breast cancer* |

The monoclonal antibody therapeutics can be any type of monoclonal antibody, including but not limited to standard monoclonal antibodies, humanized monoclonals, fully human antibodies generated from mice or other sources, chimeric monoclonals, and fragments thereof. "Humanized monoclonal antibodies" refers to monoclonal antibodies derived from a non-human monoclonal antibody, such as a mouse monoclonal antibody. Alternatively, humanized monoclonal antibodies can be derived from chimeric antibodies that retain, or substantially retain, the antigen-binding properties of the parental, non-human, monoclonal antibodies but which exhibit diminished immunogenicity as compared to the parental monoclonal antibody when administered to humans. For example, chimeric monoclonal antibodies can comprise human and murine antibody fragments, generally human constant and mouse variable regions. Humanized monoclonal antibodies can be prepared using a variety of methods known in the art, including but not limited to (1) grafting complementarity determining regions from a non-human monoclonal antibody onto a human framework and constant region ("humanizing"), and (2) transplanting the non-human monoclonal antibody variable domains, but "cloaking" them with a human-like surface by replacement of surface residues ("veneering"). These methods are disclosed, for example, in, e.g., Jones et al., Nature 321:522-525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991). Monoclonal antibodies can be fragmented using conventional techniques, and the fragments screened for utility in the same manner as for whole antibodies. For example, F(ab')$_2$ fragments can be generated by treating antibody with pepsin. The resulting F(ab')$_2$ fragment can be treated to reduce disulfide bridges to produce Fab' fragments. Fab fragments can be obtained by treating an IgG antibody with papain; F(ab') fragments can be obtained with pepsin digestion of IgG antibody. A F(ab') fragment also can be produced by binding Fab' described below via a thioether bond or a disulfide bond. A Fab' fragment is an antibody fragment obtained by cutting a disulfide bond of the hinge region of the F(ab')2. A Fab' fragment can be obtained by treating a F(ab')2 fragment with a reducing agent, such as dithiothreitol. Antibody fragment peptides can also be generated by expression of nucleic acids encoding such peptides in recombinant cells (see, e.g., Evans et al., J. Immunol. Meth. 184: 123-38 (1995)). For example, a chimeric gene encoding a portion of a F(ab')2 fragment can include DNA sequences encoding the CH I domain and hinge region of the H chain, followed by a translational stop codon to yield such a truncated antibody fragment molecule. Non-limiting examples of monoclonal antibody fragments include (i) a Fab fragment, a monovalent fragment consisting essentially of the VL, VH, CL and CH I domains; (ii) F(ab)2 and F(ab')2 fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., (1989) Nature 341:544-546), which consists essentially of a VH domain; and (vi) one or more isolated CDRs or a functional paratope.

In one preferred embodiment that can be combined with any embodiment or combination of embodiments of the invention, the disorder comprises a Her-2 positive tumor, and the method comprises co-administering the AdB-2/3 fiber multimer together with suitable monoclonal antibody therapy, alone or in combination with a chemotherapeutic, radiation, or combinations thereof. In a further preferred embodiment, the monoclonal antibody is trastuzumab. In a further preferred embodiment that can be combined with any of these embodiments, the Her-2 positive tumor is selected from the group consisting of a breast tumor, a gastric tumor, a colon tumor, and an ovarian tumor, In a most preferred embodiment, the AdB-2/3 fiber multimer comprises an Ad3 PtDd, JO-1 multimers (SEQ ID NO:20), or functional equivalents thereof. As shown in the examples that follow, AdB-2/3 fiber multimer co-administration with trastuzumab leads to improved trastuzumab access to Her-2 receptors in a breast tumor model, resulting in greatly improved trastuzumab therapeutic efficacy. In a further preferred embodiment, the method is carried out on patients who have not responded adequately to trastuzumab, such as by lack of tumor remission, by tumor relapse, or by development of resistance to trastuzumab. The methods of these embodiments can also be used to help reduce the dosage of trastuzumab required to obtain therapeutic efficacy, and can thus serve to limit side effects (such as trastuzumab-associated cardiotoxicity).

In another preferred embodiment that can be combined with any embodiment or combination of embodiments of the invention, the disorder comprises an EGFR-positive tumor, and the method comprises co-administering the AdB-2/3 fiber multimer together with suitable monoclonal antibody therapy, alone or in combination with a chemotherapeutic, radiation, or combinations thereof. In a further preferred embodiment, the monoclonal antibody is cetuximab. In a further preferred embodiment that can be combined with any of these embodiments, the EGFR-positive tumor is selected from the group consisting of a lung tumor, a colon tumor, a breast tumor, a rectal tumor, a head and neck tumor, and a pancreatic tumor. In a most preferred embodiment, the AdB-2/3 fiber multimer comprises an Ad3 PtDd, JO-1 multimers (SEQ ID NO:20), or functional equivalents thereof. As shown in the examples that follow, AdB-2/3 fiber multimer co-administration with cetuximab leads to improved cetuximab access to EGFR receptors in a lung tumor model, resulting in greatly improved cetuximab therapeutic efficacy. In a further preferred embodiment, the method is carried out on patients who have not responded adequately to cetuximab, such as by lack of tumor remission, by tumor relapse, or by development of resistance to cetuximab. The methods of these embodiments can also be used to help reduce the dosage of cetuximab required to obtain therapeutic efficacy, and can thus serve to limit side effects (such as acne-like rashes that often occur during cetuximab therapy).

In one preferred embodiment that can be combined with any embodiment or combination of embodiments of the invention, the disorder comprises an epithelial tumor, and the method comprises co-administering the AdB-2/3 fiber multimer together with a vascular endothelial growth factor (VEGF) inhibitor, alone or in combination with other chemotherapeutic, radiation, or combinations thereof. Any suitable VEGF inhibitor can be used, including but not limited to bevacizumab.

In a further embodiment that can be combined with any embodiment or combination of embodiments herein, the methods involving solid tumors further comprise administering a compound capable of degrading tumor stroma proteins. As shown in the examples that follow, such an approach (combination of compound to degrade tumor stroma protein with JO-1 multimers (SEQ ID NO:20) and trastuzumab) resulted in complete tumor eradication in a breast cancer model. Any suitable compound for degrading tumor stroma proteins can be used, including but not limited to relaxin, collagenase, trypsin, dispase, MMP(metalloproteinase)-1, and MMP8. Delivery of such compounds can be by any suitable mechanism, including gene therapy, separate administration with the AdB-2/3 fiber multimer and the therapeutic, or administration as a conjugate with the AdB-2/3 fiber or therapeutic.

In a further embodiment that can be combined with any embodiment or combination of embodiments herein, the methods further comprise administering the AdB-2/3 multimer in combination with other junction openers. As used herein, a "junction opener" is a compound capable of transiently opening intercellular junctions. Any suitable junction openers can be used. In one non-limiting embodiment, the junction opener comprises Zona occludens toxin (Zot), a Vibrio cholerae (V. cholerae)-produced toxin that possess the ability to reversibly alter intestinal epithelial junctions, allowing the passage of macromolecules through mucosal barriers (Fasano et al. (1991) Proc Natl Acad Sci USA 88: 5242-5246)]. A Zot-derived hexapeptide (AT-1001) has been developed,) In another embodiment, *Clostridium perfringens* enterotoxin removes claudins-3 and -4 from the tight junctions to facilitate bacterial invasion (Sonoda N, et al. (1999) J Cell Biol 147: 195-204.]. In a further embodiment, oncoproteins encoded by human Ad, HPV, HTLV-1 can transiently open epithelial junctions by mislocalizing the junction protein ZO-1 (Latorre L I, et al. (2005) J Cell Sci 118: 4283-4293). In other embodiments, several human viruses engage tight junction or other cell junction molecules to achieve entry into epithelial cells. Among these viruses are hepatitis C virus (Evans M J, et al. (2007) Nature 446: 801-805), reovirus (Barton E S, et al. (2001) Cell 104: 441-451), and herpes simplex virus Geraghty R J, et al. (1998) Science 280: 1618-1620).

In another embodiment, the therapeutic is an inhaled therapeutic. Any suitable inhaled therapeutic can be used in the methods of the invention. In various non-limiting embodiments, the inhaled therapeutic is selected from the group consisting of corticosteroids, bronchodilators, beta agonists, anticholinergics, albuterol (PROVENTIL®; VENOLIN®; ACCUNEB®; PROAIR®), levalbuterol (XOPENEX®), pirbutrol (MAXAIR®), ipratropium bromide (ATROVENT®), beclomethasone, budesonide, flunisolide (AEROBID®), fluticasone, triamcinolone acetonide, fluticasone (a corticosteroid) and salmeterol (ADVAIR®), formtorol (a long-acting, beta-agonist bronchodilator) and budesonide (a corticosteroid) (SYMICORT®), albuterol (a beta agonist) and ipratropium (COMBIVENT®; an anticholinergic) (budesonide (PULMICORT RESPULES®), and tiopropium (SPIRIVA®; an anticholinergic bronchodilator).

In another embodiment, the compound comprises a diagnostic or imaging agent. The methods of the invention have broad application for delivery of any diagnostic, imaging agent, or other compound to epithelial tissue comprising intercellular junctions where access to a target of interest can be limited. In various non-limiting embodiments, the imaging agents can include any chemical compound that can produce a detectable signal, either directly or indirectly. Many such imaging agents are known to those of skill in the art. Examples of imaging agents suitable for use in the disclosed methods and compositions are radioactive isotopes, fluorescent molecules, magnetic particles (including nanoparticles), metal particles (including nanoparticles), phosphorescent molecules, enzymes, antibodies, ligands, and combinations thereof, while diagnostic agents may comprise a compound that is a diagnostic marker for a particular epithelial disorder bound to the such an imaging agent. Methods for detecting and measuring signals generated by imaging agents are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. In one preferred embodiment, the imaging agent and/or diagnostic is one that can be used to detect a tumor, whether by direct tumor binding, or by coupling of the imaging or diagnostic agent with a compound that can bind the tumor.

In one example, the imaging agents can comprise a fluorescent imaging agent, while diagnostic agents may comprise a compound that is a diagnostic marker for a particular epithelial disorder bound to the fluorescent imaging agent. A fluorescent imaging agent is any chemical moiety that has a detectable fluorescence signal. This imaging agent can be used alone or in combination with other imaging agents. Examples of suitable fluorescent agents that can be used in the compositions and methods disclosed herein include, but are not limited to, fluorescein (FITC), 5-carboxyfluorescein-N-hydroxysuccinimide ester, 5,6-carboxymethyl fluorescein, nitrobenz-2-oxa-1,3-diazol-4-yl (NBD), fluorescamine, OPA, NDA, indocyanine green dye, the cyanine dyes (e.g., Cy3, Cy3.5, Cy5, Cy5.5 and Cy7), 4-acetamido-4'-isothiocyanatostilbene-2,2' disulfonic acid, acridine, acridine isothiocyanate, 5-(2'-aminoethyl)aminonaphthalene-1-sulfonic acid (EDANS), 4-amino-N-[3-vinylsulfonyl)phenylinaphthalimide-3,5 disulfonate, N-(4-anilino-1-naphthyl)maleimide, anthranilamide, BODIPY, Brilliant Yellow, coumarin, 7-amino-4-methylcoumarin (AMC, Coumarin 120), 7-amino-4-trifluoromethylcoumarin (Coumaran 151), cyanosine, 4',6-diaminidino-2-phenylindole (DAPI), 5',5"-dibromopyrogallol-sulfonaphthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino] naphthalene-1-sulfonyl chloride (DNS, dansylchloride), 4-(4'-dimethylaminophenylazo)benzoic acid (DABCYL), 4-dimethylaminophenylazophenyl-4'-isothiocyanate (DABITC), eosin, eosin isothiocyanate, erythrosin B, erythrosine, isothiocyanate, ethidium bromide, ethidium, 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein isothiocyanate, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron[R] Brilliant Red 3B-A), 6-carboxy-X-rhodamine (ROX), 6-carboxyrhodamine (R6G), lissamine rhodamine B sulfonyl chloride rhodamine (Rhod), 5,6-tetramethyl rhodamine, rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, rosolic acid, coumarin-6, and the like, including combinations thereof. These fluorescent imaging moieties can be obtained from a variety of commercial sources, including MOLECULAR PROBES™, Eugene, Oreg. and RESEARCH ORGANICS™ Cleveland, Ohio, or can be synthesized by those of ordinary skill in the art.

In another example, the imaging agents can comprise a Magnetic Resonance Imaging (MRI) agent, while diagnostic agents may comprise a compound that is a diagnostic marker for a particular epithelial disorder bound to the MRI agent. A MRI agent is any chemical moiety that has a detectable magnetic resonance signal or that can influence (e.g., increase or shift) the magnetic resonance signal of another agent. This type of imaging agent can be used alone or in combination with other imaging agent. In still another example, a gadolinium-based MRI agent can serve as an imaging agent. An example of a suitable MRI agent that can be incorporated into the disclosed imaging agents is para-amino-benzyl diethylenetriaminepentaacetic acid (p-NH$_2$-Bz-DTPA, Compound 7), a conjugable form of diethylenetriaminepentaacetic acid (DTPA), which is known to strongly bind gadolinium and is approved for clinical use as a magnetic resonance contrast agent. Incorporation of an MRI agent on a large macromolecule such as a dendrimeric substrate as disclosed herein can allow large T1 relaxation (high contrast) and multiple copies of agent on a single molecule, which can increase signal. By combining an MRI imaging agent and, for example, a fluorescent imaging agent, the resulting agent can be detected, imaged, and followed in real-time via MR I. Other imaging agents include PET agents that can be prepared by incorporating an 18F or a chelator for 64Cu or 68Ga. Also, addition of a radionuclide can be used to facilitate SPECT imaging or delivery of a radiation dose, while diagnostic agents may comprise a compound that is a diagnostic marker for a particular epithelial disorder bound to the PET agent.

In some embodiments, the diagnostic agent is a diagnostic imaging agent, including but not limited to position emission tomography (PET) agents, computerized tomography (CT) agents, magnetic resonance imaging (MRI) agents, nuclear magnetic imaging agents (NMI), fluoroscopy agents and ultrasound contrast agents. Such diagnostic agents include radioisotopes of such elements as iodine (I), including $^{123}$I, $^{125}$I, $^{131}$I, etc. barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{14}$C, or the like, fluorescently labeled compounds, or their complexes, chelates, adducts and conjugates. Any suitable PET agents can be used, including but not limited to carbon-11, nitrogen-13, oxygen-15, fluorine-18,11C-metomidate, and glucose analogues thereof, including but not limited to fludeoxyglucose (a glucose analog labeled with fluorine-18.

In other embodiments, the diagnostic agent is a marker gene that encode proteins that are readily detectable when expressed in a cell (including, but not limited to, beta-galactosidase, green fluorescent protein, luciferase, and the like) and labeled nucleic acid probes (e.g., radiolabeled or fluorescently labeled probes). In some embodiments, covalent conjugation of diagnostics agents to the AdB-2/3 multimers provided herein is achieved according to a variety of conjugation processes. In other embodiments, the diagnostic agent is non-covalently associated with AdB-2/3 multimers provided In a further aspect, the present invention provides methods for improving delivery of a substance to an epithelial tissue, comprising contacting the epithelial tissue with (a) one or more compound to be delivered to the epithelial tissue; and (b) an amount of AdB-2/3 fiber multimer, or functional equivalent thereof, sufficient to enhance delivery of the one or more compounds to the epithelial tissue. In this aspect, the compounds may be any suitable compound such as those described in detail above. In a preferred embodiment, the one or more compounds comprise an imaging agent. In a further preferred embodiment the epithelial tissue comprises a solid tumor, including any of those disclosed in the present application. In various non-limiting embodiments, the solid tumor is selected from the group consisting of breast tumors, lung tumors, colon tumors, rectal tumors, stomach tumors, prostate tumors, ovarian tumors, uterine tumors, skin tumors, endocrine tumors, cervical tumors, kidney tumors, melanomas, pancreatic tumors, liver tumors, brain tumors, head and neck tumors, nasopharyngeal tumors, gastric tumors, squamous cell carcinomas, adenocarcinomas, bladder tumors, and esophageal tumors.

In a still further aspect, the present invention provides methods for improving delivery of a substance cell or tissue expressing desmoglein 2 (DSG2), comprising contacting the cell or tissue expressing DSG2 with (a) one or more compound to be delivered to the cell or tissue; and (b) an amount of AdB-2/3 fiber multimer, or functional equivalent thereof, sufficient to enhance delivery of the one or more compounds to the tissue. Exemplary tissue types expressing DSG2 include, but are not limited to epithelial cells/tissue (such as those disclosed herein), human platelets and granulocytes. As shown in the examples that follow, DSG2 also acts as receptor in non-polarized cells. Thus, these methods find application not only in epithelial cells and tissue, but also are relevant, for example, in AdB-2/3 pathogenesis and the intravascular application of AdB-2/3 vectors for gene therapy purposes.

In a still further aspect, the present invention provides methods for inducing an epithelial to mesenchymal transition (EMT) in a tissue, comprising contacting the epithelial tissue with an amount of AdB-2/3 fiber multimer, or functional equivalent thereof, sufficient to induce EMT. EMT is a cellular transdifferentiation program where epithelial cells lose characteristics such as intercellular junctions and gain properties of mesenchymal cells. EMT is characterized by increased expression of mesenchymal markers, increased expression of extracellular matrix compounds, decreased expression of epithelial markers, altered location of transcription factors, and activation of kinases, and disassociation of intercellular junctions.

In each of these further aspects, any embodiment of the compounds and AdB-2/3 fiber multimers described herein can be used. In one non-limiting embodiment, the AdB-2/3 fiber multimer is selected from the group consisting of an Ad3 fiber multimer, an Ad7 fiber multimer, an Ad11 fiber multimer, an Ad14 fiber multimer, an Ad14a fiber multimer, combinations thereof, and functional equivalents thereof. In another embodiment, the AdB-2/3 fiber multimer is an Ad3 fiber multimer, or a functional equivalent thereof. In another embodiment, the AdB-2/3 fiber multimer is selected from the group consisting of AdB-2/3 virions, AdB-2/3 capsids, AdB-2/3 dodecahedral particles (PtDd), recombinant AdB-2/3 fiber multimers, and functional equivalents thereof. In various preferred embodiments, the AdB-2/3 fiber multimer comprises an Ad3 PtDd or a junction opener 1 (JO-1) (SEQ ID NO:20) multimer (such as a dimer), or functional equivalent thereof. In a further preferred embodiment that can be combined with each of these embodiments, the AdB-2/3 fiber multimer is a dimer. While not being bound by any specific mechanism of action, it is believed that these further aspects each take advantage of the AdB-2/3 fiber multimer serving to disrupt intercellular junctions.

In all of the aspects and embodiments of the methods of the invention, the therapeutic, diagnostic, and/or imaging agent can be administered together with the AdB-2/3 multimer or may be administered together. In one embodiment, the therapeutic and AdB-2/3 multimer are attached, via any suitable covalent or non-covalent binding. In one non-limiting embodiment, an AbB-2/3 multimer can attached to a toxin or other drug to kill solid tumor cells.

The AdB-2/3 fiber multimer and/or therapeutic can be administered in any way deemed suitable by an attending physician, depending on whether a local or systemic mode of administration is most appropriate for the condition being treated. As used herein, the terms "systemic delivery" and "systemic administration" are intended to include, but are not limited to, oral and parenteral routes including intramuscular (IM), subcutaneous, intravenous (IV), intra-arterial, inhalational, sublingual, buccal, topical, transdermal, nasal, rectal, vaginal, and other routes of administration that effectively result in dispersement of the delivered agent to a single or multiple sites of intended therapeutic action. Preferred routes of systemic delivery for the present compositions include intravenous, intramuscular, subcutaneous, and inhalational. In one preferred embodiment, intravenous administration is used, such as for treatment of disseminated tumors (and for monoclonal antibody delivery). In another embodiment, oral delivery may be preferred, for example, for treating gastrointestinal (GI) epithelial disorders. In another embodiment, nasal or aerosol delivery may be preferred for delivery to the lungs, such as for lung epithelial disorders.

The AdB-2/3 fiber multimer may be introduced in association with another molecule, such as a lipid or liposome to protect the polypeptides from enzymatic degradation. For example, the covalent attachment of polymers, especially polyethylene glycol (PEG), has been used to protect certain proteins from enzymatic hydrolysis in the body and thus prolong half-life.

The AdB-2/3 fiber multimer and/or therapeutic may be systemically administered on a periodic basis at intervals determined to maintain a desired level of therapeutic effect. For example, administration by intravenous injection may be once per day, once per week, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for AdB-2/3 fiber multimer and/or therapeutic will vary as a function of the multimer and/or therapeutic being administered, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s). Dosage ranges of AdB-2/3 fiber multimers will generally range between 0.01 and 250 mg/kg, preferably between 0.1 and 10 mg/kg, and more preferably between 0.10 to 0.5 mg/kg. Dosages of approved therapeutics are readily identifiable by medical practitioners. The therapeutic may also be able to be administered at a reduced dose due to enhanced penetration into epithelial tissues, such as cancers.

The AdB-2/3 fiber multimer may be administered to the subject before, simultaneously, or after administration of the therapeutic. In a preferred embodiment, administration of the therapeutic and the AdB-2/3 fiber multimer are carried out at the same time. The timing of administrations of the therapeutic relative to the AdB-2/3 fiber multimer can be varied to achieve the greatest therapeutic effect. Preferably, the therapeutic is administered at a time to ensure its contact with the transient opening of the intercellular junction caused by AdB-2/3 fiber multimer binding to DSG2. For example, the therapeutic can be administered prior to, simultaneously with, after each administration of the AdB-2/3 fiber multimer. In other preferred embodiments, the therapeutic can be administered after the administration of the AdB-2/3 fiber multimer, for example up to 5 minutes, 10 minutes, 15 minutes, 30 minutes, 45 minutes, 1 hour, 2 hours, 3 hours, 4 hours, 5 hours, 6 hours, 8 hours, 10 hours, 12 hours, 18 hours, 24 hours, 30 hours, 36 hours, 40 hours, 42 hours, 48 hours, 54 hours, 60 hours, 66 hours, 72 hours, 78 hours, 84 hours, 90 hours, or even up to 96 hours after the administration of the AdB-2/3 fiber multimer.

In another aspect, the present invention provides methods for treating a disorder associated with epithelial tissue, comprising administering to a subject in need thereof an amount of AdB-2/3 fiber multimer, or functional equivalent thereof, sufficient to treat the disorder. In this embodiment, no other therapeutic is delivered. In non-limiting embodiments, the monotherapy is used to treat a disorder selected from the group consisting of an AdB-2/3 viral infection, a solid tumor, or a disorder that can be treated using an AdB-2/3-based gene delivery vector. For example, in treating solid tumors, the method comprises improving access of immune system cells to the site of the disorder, such as by penetration (such as intratumoral penetration of pre-existing natural killer cells, T-cells or dendritic cells). The method can also be used to treat any of the disorders associated with epithelial cells discussed above that can benefit from improved access of cells of the immune system to the target epithelial cells. In one preferred embodiment, the disorder is a solid tumor, and the method comprises improving immune system attack of the tumor. The method can be used with any of the solid tumors discussed above. All embodiments and combinations of embodiments of the first aspect of the invention can be used in this second aspect as well, unless the context clearly dictates otherwise.

Thus, in various embodiments of this second aspect, the AdB-2/3 fiber multimer is selected from the group consisting of an Ad3 fiber multimer, an Ad7 fiber multimer, an Ad11 fiber multimer, an Ad14 fiber multimer, and an Ad14a fiber multimer. Similarly, exemplary constructs comprising one or more AdB-2/3 fiber multimers (or chimeras/functional equivalents thereof) for use in this aspect of the invention include, but are not limited to, AdB-2/3 virions, AdB-2/3 capsids, AdB-2/3 dodecahedral particles (PtDd) (subviral dodecahedral particles produced by AdB-2/3 during their replication), recombinant AdB-2/3 fiber multimers (including but not limited to those disclosed in any embodiment or combination of embodiments below, such as a JO-1 multimer, such as a JO-1 dimer), and functional equivalents thereof. In a preferred embodiment, the one or more AdB-2/3 fiber multimers comprise or consist of an AdB-2/3 PtDd, such as an Ad3 PtDd. In another preferred embodiment, the one or more AdB-2/3 fiber multimers comprise or consist of any embodiment or combination of embodiments of the compositions of the invention described below, such as a JO-1 dimer. Further, the methods of this aspect of the invention can be carried out using any AdB-2/3 fiber multimer capable of binding to DSG2 and triggering transient DSG2-mediated opening of intercellular junctions. Thus, non-naturally occurring modifications (deletions, additions, substitutions, chimeras of different Ad serotype fiber proteins and domains thereof, etc.) to the AdB-2/3 fiber multimers disclosed herein are within the scope of the present invention, so long as they function to bind DSG2 and trigger DSG2-mediated opening of intercellular junctions. Based on the teachings herein for testing binding to DSG2 and for assessing DSG2-mediated opening of intercellular junctions, it is well within the level of skill in the art to identify such functional equivalents of the AdB-2/3 fiber multimers.

In another aspect, the present invention provides recombinant AdB-2/3 fiber polypeptides, comprising: (a) one or more AdB-2/3 fiber polypeptide shaft domains, or functional equivalents thereof; (b) an AdB-2/3 fiber polypeptide knob domain, or functional equivalent thereof, operatively linked to and located C-terminal to the one or more AdB-2/3 fiber protein shaft domains; and (c) one or more non-AdB-2/3-derived dimerization domains operatively linked to and located N-terminal to the one or more AdB-2/3 fiber polypeptide shaft domains.

In a preferred embodiment, the recombinant polypeptides do not include a tail domain from an Ad fiber polypeptide. As is disclosed in detail below, the inventors have localized the required sites for fiber polypeptide multimerization and binding to DSG2 to the shaft and knob domains of the AdB-2/3 proteins. The polypeptides of this aspect of the invention can thus be used, for example, to form AdB-2/3 fiber multimers for use in the various methods of the invention discussed above. In this aspect, the recombinant polypeptides can include shaft and knob domains from any AdB-2/3 virus, or any mutants (substitutions, additions, deletions, chimeras, etc.) to such shaft and knob domains that retain or improve binding affinity to DSG2, and are capable of forming multimers (such as dimers) via the dimerization domain (functional equivalents). It is well within the level of skill in the art to generate such mutants, and testing of such mutants for DSG2 binding and resulting suitability for use in the recombinant polypeptides of the invention is also within the level of skill in the art based on the teachings herein. For example, surface plasmon resonance (SPR) studies using sensors containing immobilized recombinant DSG2 can be used to determine if recombinant polypeptides being assessed bind to DSG2, combined with DSG2 competition studies. In one non-limiting embodiment, the polypeptide may be modified or mutated to reduce its immunogenicity by changing its amino acid sequence using techniques well known to those skilled in the art. Further exemplary studies, such as loss and gain of function analyses, are described in detail in Example 1.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

As used herein, the term "operatively linked" refers to an arrangement of elements wherein the domains are configured so that they function as a unit for their intended purpose. The term does not require that the domains are immediately adjacent on the polypeptide, as spacer/linker sequences may be present between the domains, the lengths of which can be quite variable. In one non-limiting embodiment, the spacer length between any two domains of the recombinant AdB-2/3 fiber polypeptides can be between about 0 amino acids and about 20 amino acids. In various other non-limiting embodiments, the spacer length can be 0-20, 0-19, 0-18, 0-17, 0-16, 0-15, 0-14, 0-13, 0-12, 0-11, 0-10, 0-9, 0-8, 0-7, 0-6, 0-5, 0-4, 0-3, 0-2, 0-1, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20, 5-19, 5-18, 5-17, 5-16, 5-15, 5-14, 5-13, 5-12, 5-11, 5-10, 5-9, 5-8, 5-7, 5-6, 6-20, 6-19, 6-18, 6-17, 6-16, 6-15, 6-14, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-14, 11-13, 11-12, 12-20, 12-19, 12-18, 12-17, 12-16, 12-15, 12-14, 12-13, 13-20, 13-19, 13-18, 13-17, 13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, 19-20, 20, 19, 18, 17, 16, 15, 14, 13, 12, 11, 10, 9, 8, 7, 6, 5, 4, 3, 2, 1, or 0 amino acids in length.

As used herein, "recombinant polypeptide" means a non-naturally occurring protein product, wherein the domains of the recombinant polypeptide are derived from one or more other proteins or artificially derived sequences. For example, each domain can be derived from a different naturally occurring protein sequence (ex: shaft sequence from one AdB-2/3 serotype; knob domain from a different AdB-2/3 serotype; etc.). The recombinant polypeptide may be constructed by a variety of mechanisms including, but not limited to, standard DNA manipulation techniques and chemical assembly via subunit parts of the recombinant polypeptide. The chemical assembly may lead to an equivalent form as the molecular genetic form or alternative associations with equivalent function. In a preferred embodiment, the recombinant polypeptide is produced by standard recombinant DNA techniques. Techniques for such recombinant production and isolation of the recombinant polypeptides of the invention are well within the level of skill in the art based on the teaching herein.

In one embodiment, each shaft domain is selected from the group consisting of an Ad3 shaft domain, an Ad7 shaft domain, an Ad11 shaft domain, an Ad 14 shaft domain, an Ad14a shaft domain, combinations thereof, and functional equivalents thereof. The shaft domain is required for fiber knob dimerization, which is required for binding to DSG2 and resulting transient opening of intercellular junctions. Thus, functional equivalents of the shaft domains of these Ad virus serotypes can be readily determined by those of skill in the art, based on the examples provided below. For example, surface plasmon resonance (SPR) studies using sensors containing immobilized recombinant DSG2 can be used to determine if recombinant polypeptides being assessed bind to DSG2, combined with DSG2 competition studies. Further exemplary studies, such as loss and gain of function analyses, are described in detail in Example 1.

The recombinant polypeptides may comprise between 1 and 22 AdB-2/3 fiber polypeptide shaft domains. Thus, in various embodiments to polypeptides comprise 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5, 3-4, 4-22, 4-21, 4-20, 4-19, 4-18, 4-17, 4-16, 4-15, 4-14, 4-13, 4-12, 4-11, 4-10, 4-9, 4-8, 4-7, 4-6, 4-5, 5-22, 5-21, 5-20, 5-19, 5-18, 5-17, 5- 16, 5-15, 5-14, 5-13, 5-12, 5-11, 5-10, 5-9, 5-8, 5-7, 5-6, 6-22, 6-21, 6-20, 6-19, 6-18, 6-17, 6-16, 6-15, 6- 14, 6-13, 6-12, 6-11, 6-10, 6-9, 6-8, 6-7, 7-22, 7-21, 7-20, 7-19, 7-18, 7-17, 7-16, 7-15, 7-14, 7-13, 7-12, 7-11, 7-10, 7-9, 7-8, 8-22, 8-21, 8-20, 8-19, 8-18, 8-17, 8-16, 8-15, 8-14, 8-13, 8-12, 8-11, 8-10, 8-9, 9-22, 9-21, 9-20, 9-19, 9-18, 9-17, 9-16, 9-15, 9-14, 9-13, 9-12, 9-11, 9-10, 10-22, 10-21, 10-20, 10-19, 10-18, 10-17, 10-16, 10-15, 10-14, 10-13, 10-12, 10-11, 11-22, 11-21, 11-20, 11-19, 11-18, 11-17, 11-16, 11-15, 11-14, 11-13, 11-12, 12-22, 12-21, 12-20, 12-19, 12-18, 12-17, 12-16, 12-15, 12-14, 12-13, 13-22, 13-21, 13-20, 13-19, 13-18, 13-17, 13-16, 13-15, 13-14, 14-22, 14-21, 14-20, 14-19, 14-18, 14-17, 14-16, 14-15, 15-22, 15-21, 15-20, 15-19, 15-18, 15-17, 15-16, 16-22, 16-21, 16-20, 16-19, 16-18, 16-17, 17-22, 17-21, 17-20, 17-19, 17-18, 18-22, 18-21, 18-20, 18-19, 19-22, 19-21, 19-20, 20-22, 20-21, 21-22, 1, 2, 3, 4, 5, 6, 7, 8, 9, 10, 11, 12, 13, 14, 15, 16, 17, 18, 19, 20, 21, or 22 AdB-2/3 fiber protein shaft domains. Where more than 1 AdB-2/3 fiber protein shaft domain is present, each shaft domain can be identical, or one or more copies of the shaft domain may differ in a single recombinant polypeptide. In a preferred embodiment, the recombinant AdB-2/3 fiber polypeptide has a single shaft domain.

In another embodiment, one or more (or all) shaft domains in the recombinant polypeptide comprise or consist of an amino acid sequence according to SEQ ID NO 11:

GVL(T/S)LKC(L/V)(T/N)PLTT(T/A)(G/S)GSLQLKVG(G/S)GL

TVD(D/T)T(D/N)G(T/F/S)L(Q/K/E)ENI(G/S/K)(A/V)(T/N)

TPL(V/T)K(T/S)(G/N)HSI(G/N)L(S/P)(L/I)G(A/P/N)GL (G/Q)(T/I)(D/E)(E/Q)NKLC(T/S/A)KLG(E/Q/N)GLTF(N/D)

S(N/S)N(I/S)(C/I)(I/A)(D/N/L)(D/K)N(I/--)NTL.

In this sequence and other variable sequences shown herein, the variable residues are noted within parentheses, and a "-" indicates that the residue may be absent.

In another embodiment, one or more (or all) shaft domains in the recombinant polypeptide comprise or consist of an amino acid sequence according to SEQ ID NO 12:

GVLTLKCLTPLTTTGGSLQLKVGGGLT(V/I)DDTDG(T/F)L(Q/K)EN

I(G/S)ATTPLVKTGHSIGL(S/P)LG(A/P)GLGT(D/N)ENKLC(T/A)

KLG(E/Q)GLTFNSNNICI(D/N)DNINTL

In a still further embodiment, one or more (or all) shaft domains in the recombinant polypeptide comprise or consist of an amino acid sequence selected from the group consisting of SEQ ID NO:1 (Ad3), SEQ ID NO:2 (Ad7), SEQ ID NO:3 (Ad11), SEID NO:4 (Ad14), and SEQ ID NO:5 (Ad14(a). See FIG. 24 for an alignment of the AdB-2/3 fiber polypeptides and their domain structures. In one embodiment, the knob domain in the recombinant polypeptide is selected from the group consisting of an Ad3 knob domain, an Ad7 knob domain, an Ad11 knob domain, an Ad 14 knob domain, an Ad14a knob domain, and functional equivalents thereof. The knob domain is required for binding to DSG2. Thus, functional equivalents of the knob domains of these Ad virus serotypes can be readily determined by those of skill in the art, based on the teachings herein of various assays for assessing binding to DSG2. For example, surface plasmon resonance (SPR) studies using sensors containing immobilized recombinant DSG2 can be used to determine if recombinant polypeptides being assessed bind to DSG2, combined with DSG2 competition studies. Further exemplary studies, such as loss and gain of function analyses, are described in detail in Example 1.

In another embodiment, the knob domain comprises or consists of an amino acid sequence according to SEQ ID NO 13:

WTG(V/P)(N/K)P(T/)(E/R)ANC(Q/I)(M/I)(M/E)(Y/A/N/D)

(S/K)(S/K)(E/Q)(S/N)(N/P)D(C/S)KL(I/T)L(I/T)LVK(T/

N)G(A/I)(L/I)V(T/N)(A/G)(F/Y)V(Y/T)(V/L)(I/M)G(V/

A)S(N/D)(N/D/Y)(F/V)N(M/T)L(T/F)(T/K)(Y/H/N)(R/K)

N(I/V)(N/S)(F/I)(T/N)(A/V)EL(F/Y)FD(S/A)(A/T)G(N/

H)(L/I)L(T/P)(S/R/D)(L/S)SSLKT(P/D)L(N/E)(H/L)K(S/

Y)(G/K)Q(N/T)(M/--)(A/--)(T/--)(G/--)A(I/L/D)(T/F)

-continued (N/S)A(K/R)(S/G)FMPSTTAYPF(--/V)(--/L)(N/P)(N/D/V)

(N/A)(S/G)(R/T)(E/H)(N/K/--)(--/E)NYI(Y/F)G(T/Q)C (H/Y)Y(T/K)ASD(H/G)(T/A)(A/L)FP(I/L)(D/E)(I/V)(S/T)

VMLN(Q/R/K)R(A/L)(I/L/P)(R/N/D)(A/D/N/S)(D/E/R)TSY (C/V)(I/M)(R/T)(I/V/F)(T/L)WS(W/L)N(T/A)G(D/L/V)A

PE(G/V/--)(Q/--)T(S/T)(A/Q)(T/A)TL(V/I)TSPFTF(Y/S)

YIREDD.

In a further embodiment, the knob domain comprises or consists of an amino acid sequence according to SEQ ID NO:14:

WTGVNPT(E/R)ANCQ(M/I)(M/I)(D/N/A)SSESNDCKLILTLVKTG

ALVTAFVYVIGVSN(N/D)FNMLTT(Y/H)(R/K)NINFTAELFFDS(A/

T)GNLLT(S/R)LSSLKTPLNHKSGQNMATGA(I/L)TNAK(S/G)FMP

STTAYPFN(N/D/V)NSRE(--/K)(-/E)NYIYGTC(H/Y)YTASD(H/

R)TAFPIDISVMLN(Q/R)RA(I/L)(R/N)(A/D/N)(D/E)TSYCIR (I/V)TWSWNTG(D/V)APE(G/V)QTSATTLVTSPFTFYYIREDD

In a still further embodiment, the knob domain comprises or consists of an amino acid sequence selected from the group consisting of SEQ ID NO:6 (Ad3), SEQ ID NO:7 (Ad7), SEQ ID NO:8 (Ad11), SEQ ID NO:9 (Ad14), and SEQ ID NO:10 (Ad14a). See FIG. 24 for an alignment of the AdB-2/3 fiber polypeptides and their domain structures.

As used herein a "dimerization domain" is a peptide sequence that promotes dimerization in the recombinant polypeptide that contains it. Any suitable non-AdB-2/3-derived dimerization domain can be used in the recombinant polypeptide of the invention, so long as it permits dimerization of the recombinant polypeptide and thus binding to DSG2. The dimerization domain is non-AdB-2/3-derived, in that it is not a naturally occurring domain in an AdB-2/3 fiber polypeptide.

Non-limiting examples of the numerous dimerization domains known to those of skill in the art and suitable for use in the present invention include, but are not limited to peptide helices containing at least one helix, or a structure formed by a helix, a coil and another helix, etc., coiled coil structures, dimerization domains within, for example, many cell surface signaling receptors, Fc regions or hinge regions of an antibody, leucine zippers, the STAT protein N terminal domain, FK506 binding protein, the LexA protein C-terminal domain, nuclear receptors, the FkpA N-terminal domain, orange carotenoid protein from A. maxima, M1 matrix protein from influenza, neuraminidase from influenza virus, *E. coli* fuculose aldolase; and the like. (see, e.g., O'Shea, Science. 254: 539 (1991), Barahmand-Pour et al., Curr. Top. Microbiol. Immunol. 211: 121-128 (1996); Klemm et al., Annu. Rev. Immunol. 16: 569-592 (1998); Klemm et al., Annu. Rev. Immunol. 16: 569-592 (1998); Ho et al., Nature. 382: 822-826 (1996); and Pomeranz et al., Biochem. 37: 965 (1998)). Further examples include residues 325 to 410 in the bovine papillomavirus E2 protein, (Dostatni, N., et al., EMBO J. 7 (1988) 3807-3816; Haugen, T., et al. EMBO J. 7 (1988) 4245-4253; McBride, A., et al., EMBO J. 7 (1988) 533-539; McBride, A., et al., Proc Natl Acad Sci USA 86 (1989) 510-514), Type I deodinase (D1): DFLVIYIEEAHASDGW (SEQ ID NO: 24) or ADFL-YI-EAH-DGW (SEQ ID NO: 25); HIV-1 Capsid Protein: QGPKEPFRDYVDRFYKTLRA (SEQ ID NO: 26); leucine zipper dimerization motif of yeast GCN4: HMKQL D VEEL S NYHL N VARL K VGER (SEQ ID NO: 27); leucine zipper in *Escherichia coli* transcriptional antiterminator protein; and BglG: GVTQLMREMLQLIKFQFSLNYQEESLSYQRLVT (SEQ ID NO: 28). In preferred embodiments, the dimerization domain comprises one or more copies of EVSALEK (SEQ ID NO:22) and/or KVSALKE (SEQ ID NO: 23).

It is well within the level of skill in the art to identify appropriate peptide sequences that can serve as dimerization domains, and mutants thereof, in the recombinant polypeptides of the present invention, based on the teachings herein, such as those disclosed below in Example 2. For example, dimerization of the recombinant AdB-2/3 fiber polypeptides can be assessed by criteria including sedimentation in sucrose gradients, resistance to trypsin proteolysis, and electrophoretic mobility in polyacrylamide gels (Hong and Engler, *Journal of Virology* 70:7071-7078 (1996)).

The recombinant polypeptides may comprise one or more non-AdB-2/3-derived dimerization domains. Thus, in various embodiments, the recombinant polypeptide comprises 1, 2, 3, 4, 5, 6, 7, 8, 9, 10, or more non-AdB-2/3-derived dimerization domains. Where multiple domains are present in a polypeptide, it is preferred that each dimerization domain is the same.

In a preferred embodiment a spacer peptide is located between the dimerization domain and the one or more shaft domains. In a further preferred embodiment, the spacer peptide is a peptide with structural flexibility. Virtually any peptide with structural flexibility can be used. As an example, the flexible peptide may comprise repetitions of amino acid residues, such as Gly-Gly-Gly-Ser (SEQ ID NO: 62), or any other suitable repetition of amino acid residues. In another embodiment, the hinge region of an antibody can be used. The spacer can be any suitable length that maintains the ability of the recombinant polypeptide to dimerize and to maintain binding of the recombinant polypeptide to DSG2.

In one preferred embodiment, the recombinant AdB-2/3 polypeptide comprises:

(a) one or more shaft domains that each comprise or consist of an Ad3 shaft domain (SEQ ID NO:1); and (b) a knob domain comprises or consists of an Ad3 knob domain (SEQ ID NO:6).

This preferred embodiment can be used with any embodiment or combination of embodiments described herein. For example, any suitable dimerization domain can be used, including but not limited to one or more copies of EVSALEK (SEQ ID NO:22) and/or KVSALKE (SEQ ID NO: 23). Similarly any suitable spacer peptides can be used between the dimerization domain and the shaft domain and/or between the shaft domain and the knob domain. In a most preferred embodiment, the recombinant AdB-2/3 polypeptide comprises or consists of JO-1 (SEQ ID NO:20), or a multimer thereof (such as a dimer).

The recombinant polypeptides may comprise further domains, such as a domain for isolation of the polypeptide and/or a detection domain, see, for example, JO-1 with a His Tag in the examples and in SEQ ID NO:21). An isolation domain can be added to facilitate purification/isolation of the polypeptide following, for example, recombinant polypeptide production. Any suitable isolation domain can be used, including but not limited to HIS, CBP, CYD (covalent yet dissociable NorpD peptide), Strep II, FLAG, HPC (heavy chain of protein C) peptide tags, GST and MBP affinity tags. As used herein, “detection domain” means one or more amino acid sequence that can be detected. Any suitable detection domain can be used, including but not limited to, inherently fluorescent proteins (e.g. Green Fluorescent Proteins and fluorescent proteins from nonbioluminescent *Anthozoa* species), cofactor-requiring fluorescent or luminescent proteins (e.g. phycobiliproteins or luciferases), and epitopes recognizable by specific antibodies or other specific natural or unnatural binding probes, including, but not limited to, dyes, enzyme cofactors and engineered binding molecules, which are fluorescently or luminescently labeled.

In another embodiment, the recombinant polypeptides are in a multimeric form, such as a dimer, trimer, etc. In a preferred embodiment, a JO-1 (SEQ ID NO:20) multimer comprises a JO-1 dimer formed by dimerization through the dimerization domains in each JO-1 homotrimer (ie: a JO-1 polypeptide is a homotrimer through trimerization of the knob domain) In multimeric form (such as a dimer), the recombinant polypeptides comprise AdB-2/3 fiber multimers, and can be used in the various methods of the invention discussed above. As will be understood by those of skill in the art, such multimers may comprise multimers of identical recombinant polypeptide of the invention, or may comprise multimers of different recombinant polypeptides of the invention. In one embodiment, the dimerization domains are the same in each recombinant polypeptide forming part of the multimer. In another embodiment, the dimerization domains are different in each recombinant polypeptide forming part of the multimer. In another embodiment, the shaft and/or knob domains are the same in each recombinant polypeptide forming part of the multimer. In another embodiment, the shaft and/or knob domains are different in each recombinant polypeptide forming part of the multimer.

AdB-2/3 fiber multimerization can be determined according to methods well known to the practitioners in the art. For example, multimerization of the recombinant AdB-2/3 fiber constructs can be assessed by criteria including sedimentation in sucrose gradients, resistance to trypsin proteolysis, and electrophoretic mobility in polyacrylamide gels (Hong and Engler, *Journal of Virology* 70:7071-7078 (1996)). Regarding electrophoretic mobility, the fiber multimer is a very stable complex and will run at a molecular weight consistent with that of a multimer when the sample is not boiled prior to SDS-PAGE. Upon boiling, however, the multimeric structure is disrupted and the protein subsequently runs at a size consistent with the protein monomer.

The recombinant polypeptides, or multimeric versions thereof, may be stored in solution or frozen.

In another embodiment, the recombinant polypeptides of the invention are combined with (such as conjugated to) one or more therapeutics for a disorder associated with epithelial tissue. Such conjugates can be used, for example, in the therapeutic methods of the invention. Methods for conjugating the polypeptides of the invention to a therapeutic of interest, such as by covalent binding or chemical cross-linking, are well known to those of skill in the art. Any suitable therapeutic can be used to form a conjugate according to this embodiment of the invention, including but not limited to those disclosed above, as well as tumor stroma degrading compounds, such as relaxin. In a preferred embodiment, the therapeutic is an anti-tumor therapeutic and comprises a chemotherapeutic or anti-tumor monoclonal antibody as described herein. In a further preferred embodiment, the anti-tumor therapeutic comprises an antibody selected from the group consisting of trastuzumab, cetuximimab, petuzumab, Apomab, conatumumab, lexatumumab, bevacizumab, bevacizumab, denosumab, zanolimumab, lintuzumab, edrecolomab, rituximab, ticilimumab, tositumomab, alemtuzumab, epratuzumab, mitumomab, gemtuzumab ozogamicin, oregovomab, pemtumomab daclizumab, panitumumab, catumaxomab, ofatumumab, and ibritumomab.

In another aspect, the present invention provides nucleic acids encoding the polypeptide or any embodiment of the invention. The nucleic acids may comprise RNA or DNA, and can be prepared and isolated using standard molecular biological techniques, based on the teachings herein. The nucleic acids may comprise additional domains useful for promoting expression and/or purification of the encoded protein, including but not limited to polyA sequences, modified Kozak sequences, and sequences encoding epitope tags, export signals, and secretory signals, nuclear localization signals, and plasma membrane localization signals.

In a further aspect, the present invention provides recombinant expression vectors comprising the nucleic acid of any aspect of the invention operatively linked to a promoter. "Recombinant expression vector" includes vectors that operatively link a nucleic acid coding region or gene to any promoter capable of effecting expression of the gene product. The promoter sequence used to drive expression of the disclosed nucleic acids in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the AMBION™ 1998 Catalog (AMBION™, Austin, Tex.). The expression vector must be replicable in the host organisms either as an episome or by integration into host chromosomal DNA, and may comprise any other components as deemed appropriate for a given use, including but not limited to selection markers such as an antibiotic-resistance gene.

In a still further aspect, the present invention provides host cells comprising the recombinant expression vectors disclosed herein, and progeny thereof, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). Techniques utilizing cultured cells transfected with expression vectors to produce quantities of polypeptides are well known in the art.

In another aspect, the present invention provides pharmaceutical compositions, comprising (a) an AdB-2/3 fiber multimer, or functional equivalent thereof; and (b) a pharmaceutically acceptable carrier.

The AdB-2/3 fiber multimer can be any such multimer as described herein according to any aspect, embodiment, or combination of embodiments of the invention. In various preferred embodiments, the AsB-2/3 fiber multimer comprises an AdB-2/3 virion, an AdB-2/3 capsid, an AdB-2/3 PtDd, or a recombinant AdB-2/3 fiber multimer of the invention, or functional equivalents thereof. In various other preferred embodiments, the AdB-2/3 fiber multimer is selected from the group consisting of an Ad3 fiber multimer, an Ad7 fiber multimer, an Ad11 fiber multimer, an Ad14 fiber multimer, an Ad14a fiber multimer, and combinations or chimeras thereof. In a preferred embodiment, the one or more AdB-2/3 fiber multimers comprise or consist of an AdB-2/3 PtDd (such as Ad3 PtDd). In another preferred embodiment, the one or more AdB-2/3 fiber multimers comprise or consist of any embodiment or combination of embodiments of the compositions of the invention described herein, such as a JO-1 (SEQ ID NO:20) dimer.

The pharmaceutical composition may further comprise one or more therapeutic for treating a disorder associated with epithelial tissue, including but not limited to those disclosed above. In a preferred embodiment, the therapeutic is an anti-tumor therapeutic and comprises a chemotherapeutic or anti-tumor monoclonal antibody as described herein. In a further preferred embodiment, the anti-tumor therapeutic comprises an antibody selected from the group consisting of trastuzumab, cetumiximab, petuzumab, Apomab, conatumumab, lexatumumab, bevacizumab, bevacizumab, denosumab, zanolimumab, lintuzumab, edrecolomab, rituximab, ticilimumab, tositumomab, alemtuzumab, epratuzumab, mitumomab, gemtuzumab ozogamicin, oregovomab, pemtumomab daclizumab, panitumumab, catumaxomab, ofatumumab, and ibritumomab.

The pharmaceutically acceptable carrier is non-toxic, biocompatible and is selected so as not to detrimentally affect the biological activity of the multimers (and any other therapeutic agents combined therewith). Exemplary pharmaceutically acceptable carriers for peptides are described in U.S. Pat. No. 5,211,657 to Yamada. The compositions may be formulated into preparations in solid, semi-solid, gel, liquid or gaseous forms such as tablets, capsules, powders, granules, ointments, solutions, suppositories, inhalants, and injections, allowing for oral, parenteral, or surgical administration. Suitable carriers for parenteral delivery via injectable, infusion, or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids, such as oleic acid, find use in the preparation of injectables. The carrier and agent may be compounded as a liquid, suspension, polymerizable or non-polymerizable gel, paste or salve. The carrier may also comprise a delivery vehicle to sustain (i.e., extend, delay, or regulate) the delivery of the agent(s) or to enhance the delivery, uptake, stability, or pharmacokinetics of the therapeutic agent(s). Such a delivery vehicle may include, by way of non-limiting example, microparticles, microspheres, nanospheres, or nanoparticles composed of proteins, liposomes, carbohydrates, synthetic organic compounds, inorganic compounds, polymeric or copolymeric hydrogels, and polymeric micelles. Suitable hydrogel and micelle delivery systems include the PEO:PHB:PEO copolymers and copolymer/cyclodextrin complexes disclosed in International Publication No. WO 2004/009664 A2, and the PEO and PEO/cyclodextrin complexes disclosed in U.S. Publication No. 2002/0019369 A1. Such hydrogels may be injected locally at the site of intended action, or subcutaneously or intramuscularly to form a sustained release depot.

For intrathecal (IT) or intracerebroventricular (ICV) delivery, appropriately sterile delivery systems (e.g., liquids; gels; suspensions, etc.) can be used to administer the compositions.

For oral administration of non-peptidergic agents, the compositions may be carried in an inert filler or diluent such as sucrose, cornstarch, or cellulose.

The compositions of the present invention may also include biocompatible excipients, such as dispersing or wetting agents, suspending agents, diluents, buffers, penetration enhancers, emulsifiers, binders, thickeners, flavoring agents (for oral administration). Exemplary formulations can be parenterally administered as injectable dosages of a solution or suspension of the multimer in a physiologically acceptable diluent with a pharmaceutical carrier that can be a sterile liquid such as water, oils, saline, glycerol, or ethanol. Additionally, auxiliary substances such as wetting or emulsifying agents, surfactants, pH buffering substances and the like can be present in compositions comprising modified polypeptides. Additional components of pharmaceutical compositions include petroleum (such as of animal, vegetable, or synthetic origin), for example, soybean oil and mineral oil. In general, glycols such as propylene glycol or polyethylene glycol are preferred liquid carriers for injectable solutions.

The pharmaceutical composition can also be administered in the form of a depot injection or implant preparation that can be formulated in such a manner as to permit a sustained or pulsatile release of the multimers and other therapeutic (if present).

The pharmaceutical composition may comprise in addition to the polypeptide of the invention (a) a lyoprotectant; (b) a surfactant; (c) a bulking agent; (d) a tonicity adjusting agent; (e) a stabilizer; (f) a preservative and/or (g) a buffer. in some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic: acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan rnonopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The pharmaceutical composition can be packaged in any suitable manner. In one embodiment, the pharmaceutical composition is packaged as a kit containing a container (such as a vial) of the AdB-2/3 fiber multimer. In a preferred embodiment, the kit further comprises, in the same or a separate container (such as a vial), a therapeutic, diagnostic, or imaging agent to be administered to a subject, together with the AdB-2/3 fiber multimer. Any suitable AdB-2/3 fiber multimer can be used in the kits; in a most preferred embodiment AdB-2/3 fiber multimer is a mulitmer (such as a dimer) of JO-1.

In a further aspect, the present invention provides kits comprising (a) one or more recombinant polypeptides/AdB-2/3 fiber multimers, isolated nucleic acids, recombinant expression vectors, and/or host cells of the invention; and (b) instructions for its/their use in treating a disorder associated with epithelial tissue. The kits may further comprise a therapeutic for use in the methods of the present invention.

In another aspect, the present invention provides method for identifying candidate compounds for one or more of treating a disorder associated with epithelial tissue, improving delivery of a substance to an epithelial tissue, for improving delivery of a substance tissue expressing DSG2, inducing an EMT in a tissue, and/or treating an AdB-2/3 infection comprising (a) contacting an AdB-2/3 fiber multimer to DSG2 under conditions to promote multimer binding to DSG2, wherein the contacting is carried out in the presence of one or more test compounds; and (b) identifying positive test compounds that compete with the AdB-2/3 fiber multimer for binding to DSG2 compared to control; wherein the positive test compounds are candidate compounds for one or more of treating a disorder associated with epithelial tissue, improving delivery of a substance to an epithelial tissue, for improving delivery of a substance tissue expressing DSG2, inducing an EMT in a tissue, and/or treating an AdB-2/3 infection.

Positive test compounds that compete with the AdB-2/3 fiber multimer for binding to DSG2 are candidate compounds for transiently opening intracellular junctions through their interaction with DSG2. Follow-up assays to verify the ability of the compounds to transiently open intracellular junctions through their interaction with DSG2 can be carried out by any suitable methods, including but not limited to studies disclosed in the examples that follow. Compounds so identified for treating a disorder associated with epithelial tissue, improving delivery of a substance to an epithelial tissue, improving delivery of a substance tissue expressing DSG2, or inducing an EMT in a tissue, can be used as substitutes for the AdB-2/3 multimer in any of the methods of the present invention. Furthermore, AdB-2/3 represent important human pathogens causing respiratory tract infections (some sever) and pharyngoconjunctival fever. Thus compounds that can treat AdB-2/3 infection would be useful. As disclosed herein, DSG2 as the primary high-affinity receptor used by AdB-2/3, and thus compounds that can diminish AdB-2/3 binding to DSG2 are candidate compounds for treating or limiting development of AdB-2/3 infection.

In this aspect, the AdB-2/3 multimer can be any AdB-2/3 multimer disclosed in any embodiment or combination of embodiments. Thus, in various non-limiting embodiments, the AdB-2/3 multimer can be AdB-2/3 virions, AdB-2/3 capsids, AdB-2/3 dodecahedral particles (PtDd) (subviral dodecahedral particles produced by AdB-2/3 during their replication), recombinant AdB-2/3 fiber multimers (including but not limited to those disclosed in any embodiment or combination of embodiments below), and functional equivalents thereof. In a preferred embodiment, the one or more AdB-2/3 fiber multimers comprise or consist of an AdB-2/3 PtDd, such as an Ad3 PtDd. In another preferred embodiment, the one or more AdB-2/3 fiber multimers comprise or consist of any embodiment or combination of embodiments of the compositions of the invention described below. In a further preferred embodiment, the AdB-2/3 fiber multimer comprises or consists of the a JO-1 (SEQ ID NO:20) dimer, or functional equivalents thereof.

Any suitable control can be used, including but not limited to an AdB-2/3 multimer binding to DSG2 in the absence of test compounds, In one embodiment, the DSG comprises recombinant DSG2. In another embodiment, the methods use cells expressing DSG2 (endogenously or recombinantly) on the cell surface.

In one non-limiting embodiment, surface plasmon resonance (SPR) studies using sensors containing immobilized recombinant DSG2 can be used to identify candidate compounds that AdB-2/3 fiber multimer binding to DSG2, combined with DSG2 competition studies. Further exemplary studies, such as loss and gain of function analyses, are described in detail in Example 1.

In another embodiment, the identifying comprises transduction studies, where the ability of test compounds to diminish binding is detected as a decrease in the ability of functional AdB-2/3 virions to transduce DSG2-expressing epithelial cells, such as disclosed in Example 1.

In another embodiment, DSG2-expressing cell extract is electrophoretically separated and Western blotted, and labeled AdB-2/3 fiber multimer is used to probe the Western blot in the presence of the test compounds. In a further embodiment, dot-blot assays can be used, such as those described in Wang et al., J. Virology (2007) 81:12785-12792; and Wang et al. (2008) 82:10567-10579.

Further examples of techniques for identifying candidate compounds for treating an AdB-2/3 infection are provided in the examples that follow.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Na-amino protected Na-t-butyloxycarbonyl) amino acid resin with standard deprotecting, neutralization, coupling and wash protocols, or standard base-labile Na-amino protected 9-fluorenyl-methoxycarbonyl (Fmoc) amino acids. Both Fmoc and Boc Na-amino protected amino acids can be obtained from SIGMA™, Cambridge Research Biochemical, or other chemical companies familiar to those skilled in the art. In addition, the polypeptides can be synthesized with other Na-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be chemically synthesized or recombinantly expressed as well. Recombinant expression techniques are well known to those in the art (See, for example, Sambrook, et al., 1989, supra). The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other than polypeptides, antibodies, or nucleic acids, such compounds can be made by any of the variety of methods in the art for conducting organic chemical synthesis.

Example 1

Desmoglein 2 is a Receptor for Adenovirus Serotypes 3, 7, 11, and 14

Abstract

We have identified desmoglein 2 (DSG2) as the primary high-affinity receptor used by adenovirus (Ad) serotypes Ad3, Ad7, Ad11, and Ad14. These serotypes represent important human pathogens causing respiratory tract infections. In epithelial cells, adenovirus binding to DSG2 triggers events reminiscent of epithelial-to-mesenchymal transition, leading to transient opening of intercellular junctions. This improves access to receptors, e.g. CD46 and Her2/neu, which are trapped in intercellular junctions. In addition to complete virions, dodecahedral particles (PtDd), formed by viral penton and fiber in excess during viral replication, can trigger DSG2-mediated opening of intercellular junctions as shown by studies with recombinant Ad3 PtDd. Our findings shed light on adenovirus biology and pathogenesis and have implications for cancer therapy.

Introduction

Human adenoviruses (Ads) have been classified into six species (A to F) currently containing 55 serotypes. Most Ad serotypes utilize the coxsackie-adenovirus-receptor (CAR) as a primary attachment receptor[1]. This is, however, not the case for species B Ad serotypes. Recently, we have suggested a new grouping of species B Ads based on their receptor usage[2]. Group 1 (Ad16, 21, 35, 50) nearly exclusively utilize CD46 as a receptor; Group 2 (Ad3, Ad7, 14) share a common, unidentified receptor/s, which is not CD46 and which was tentatively named receptor X; Group 3 (Ad11) preferentially interacts with CD46, but also utilizes receptor X if CD46 is blocked.

Species B Ads are common human pathogens. Since 2005, a simultaneous emergence of diverse species B serotypes, including serotypes Ad3, Ad7, and Ad14, was observed. In 2007, a new, highly pathogenic and possibly more virulent strain of Ad14, Ad14a, has been discovered at several sites in the US and in Asia[3-4]. We recently demonstrated that Ad14a belongs to species B group 2 Ads with regards to their receptor usage[5]. Collectively, we will refer to all receptor X-utilizing serotypes (Ad3, Ad7, Ad14, Ad14a, and Ad11) as AdB-2/3.

AdB-2/3 have potential as gene transfer vectors, particularly with regard to tumors of epithelial origin[6]. Epithelial cells maintain several intercellular junctions (tight junctions, adherens junctions, gap junctions, and desmosomes), a feature which is often conserved in epithelial cancers in situ and in cancer cell lines[7]. Both CAR and CD46 are trapped in intercellular junctions of epithelial cancer cells and are not accessible to Ads that use these attachment receptors[8-9]. In contrast, AdB-2/3 efficiently infect epithelial cancer cells, which is accomplished in part through induction of processes that are reminiscent of Epithelial-to-Mesenchymal Transition (EMT)[8], a cellular transdifferentiation program in which epithelial cells lose characteristics, such as intercellular junctions, and gain properties of mesenchymal cells[10]. Another distinctive feature of AdB-2/3 is their ability to produce subviral dodecahedral particles during their replication, consisting of Ad fiber and penton base[11]. Penton-Dodecahedra (PtDd) cannot assemble from full-length penton base protein, but require spontaneous N-terminal truncation by proteolysis between residues 37 and 38[12]. This cleaved site is conserved in Ad3, Ad7, Ad11, and Ad14 but is not present in Ad2 and Ad5 (FIG. 1a). In the case of Ad3, PtDd are formed at a massive excess (5.5×10[6] PtDd per infectious virus) and it has been hypothesized that PtDd contribute to virus escape and spreading[13].

The first attempts to identify receptor X date back to 1995. These initial studies indicated the interaction of Ad3 with a ~130 kDa HeLa cell protein[14]. Recently, several candidates for receptor X such as CD46, CD80 and/or CD86 were suggested[15-18]. However, we and others have thus far been unable to verify that these proteins can serve as the high affinity receptor for AdB-2/3[2,19-23].

In the present study, using Ad3 virions and recombinant Ad3 PtDd as a probe for receptor X, we identified desmoglein 2 (DSG2) as a high affinity receptor for AdB-2/3 serotypes. DSG2 is a calcium-binding transmembrane glycoprotein belonging to the cadherin protein family. In epithelial cells, DSG2 is a component of the cell-cell adhesion structure[24]. Its cytoplasmic tail interacts with a series of proteins that are in direct contact with regulators of cell adhesion and intercellular junctions/cell morphology[25]. It has been shown that DSG2 is overexpressed in a series of epithelial malignancies including gastric cancer[26], squamous cell carcinomas[27], melanoma[28], metastatic prostate cancer[29], and bladder cancer[30].

Results

DSG2 is a Receptor for AdB-2/3 Viruses.

Our previous studies showed that Ad3 binds at nanomolar affinity to a high-density cellular receptor[2]. Ad3 binding was sensitive to trypsin and could be blocked by EDTA, implying that binding required divalent cations. First we sought to identify the Ad3 capsid protein that mediates high-affinity binding to cells, which we would later use to search for the high-affinity receptor X. Notably, high-affinity binding of Ad5 to CAR and Ad35 binding to CD46, respectively, is mediated by the corresponding fiber knob[31]. Our previous studies, however, revealed that a single recombinant, timeric Ad3 knob could not completely block Ad3 virus binding even when very high concentrations were used, indicating that other or additional capsid moieties are involved in Ad3 binding[32]. Consequently, we utilized recombinant Ad3 dodecahedra composed of Ad3 penton bases (BsDd) or Ad3 penton bases and fibers (PtDd) (FIG. 1b)[33] to compete for Ad3 binding. We showed that PtDd but not BsDd blocked attachment of Ad3 to cells (FIG. 2a). PtDd also blocked binding of other AdB-2/3, e.g. Ad14, Ad14a, as well as Ad11, if CD46 is also blocked. PtDd did, however, not inhibit binding of Ad5 and only partially blocked Ad35 binding (FIG. 2a, FIG. 1c). Preincubation of cells with PtDd resulted in better Ad3 binding inhibition than Ad3 knob mixed with BsDd (FIG. 1d). The ability of PtDd to compete with Ad3 was also confirmed in transduction studies, where PtDd efficiently blocked an Ad3 vector (Ad3-GFP) but not the transduction of an Ad35 vector (Ad35-GFP (that uses CD46 as a receptor) (FIG. 2b). Ad3-GFP (FIG. 1e) and Ad35-GFP[34] are wild-type Ad3- and Ad35-based vectors containing a CMV-GFP expression cassette inserted into the E3 region.

To select an optimal cell line for receptor X identification, we compared Ad3 virus binding to several human and animal cell lines (FIG. 2c). Ad3 did not bind to rodent cells suggesting that receptor X was not expressed or not accessible to Ad3 in these cells. Of the 10 human cell lines initially tested (HeLa, K562, SKOV3, 293, HT29, SKHep1, Saos, Y79, Ramos), Ad3 binding was absent only on Ramos (human Burkitt' lymphoma) cells.

To identify Ad receptor candidates, HeLa cell membrane proteins were solubilized, separated on polyacrylamide gels, and blotted. Blots were hybridized with viral particles and binding was visualized with virus fiber knob specific antibodies. Specific gel bands were excised and analyzed by tandem mass-spectroscopy (MS/MS). First, we tested whether this assay can detect a known Ad receptor, CD46. When filters were incubated with CD46-targeting Ad5/35++virions[35], a single band was found that matched CD46 (FIG. 2d). Incubation of filters with Ad3 virions revealed two bands with molecular weights of 160 kDa and 90 kDa (FIG. 2e). In addition to these two bands, Ad3 PtDd also reacted with HeLa proteins in the range of 130 kDa. Both 160 and 90 kDa bands were absent in Ramos cells, i.e. cells that do not bind Ad3. The ~130 kDa PtDd-binding band appeared in both HeLa and Ramos cells suggesting that it is not an Ad3 virus receptor. MS/MS-analysis of the 160 kDa band identified 14 peptides matching human desmoglein 2 (DSG2) (FIG. 2f). IP/Western analyses of HeLa membrane proteins demonstrated that both the 160 and 90 kDa bands were recognized by DSG2-specific antibodies (FIG. 2e, right panel). This is in aggreement with previous Western blot studies showing that the 160 kDa band represents full size DSG2, and that the 90 kDa band is a DSG2 variant that lacks the intracellular domain, the transmembrane domain, and the juxtamembrane extracellular anchor domain[36-37].

BIACORE™ surface plasmon resonance (SPR) studies with sensors containing immobilized recombinant human DSG2 demonstrated that Ad3, but not Ad2 or Ad5, virions interact with DSG2 (FIG. 2g). Recombinant PtDd but not BsDd particles bound to DSG2 (FIG. 2h). The $K_D$ (equilibrium dissociation constant) of PtDd-DSG2 interaction was 2.5 nM. PtDd binding to immobilized DSG2 was specific as demonstrated by the fact that soluble DSG2 competed with it (data not shown). SPR analysis of binding kinetics also showed that Ad3 fiber knob dissociates faster from DSG2, which suggests the existence of additional DSG2 binding site(s) within the fiber shaft and/or the requirement of fiber multimerization for high affinity binding to DSG2 (FIG. 2i, also see FIG. 1d).

Figure 3:
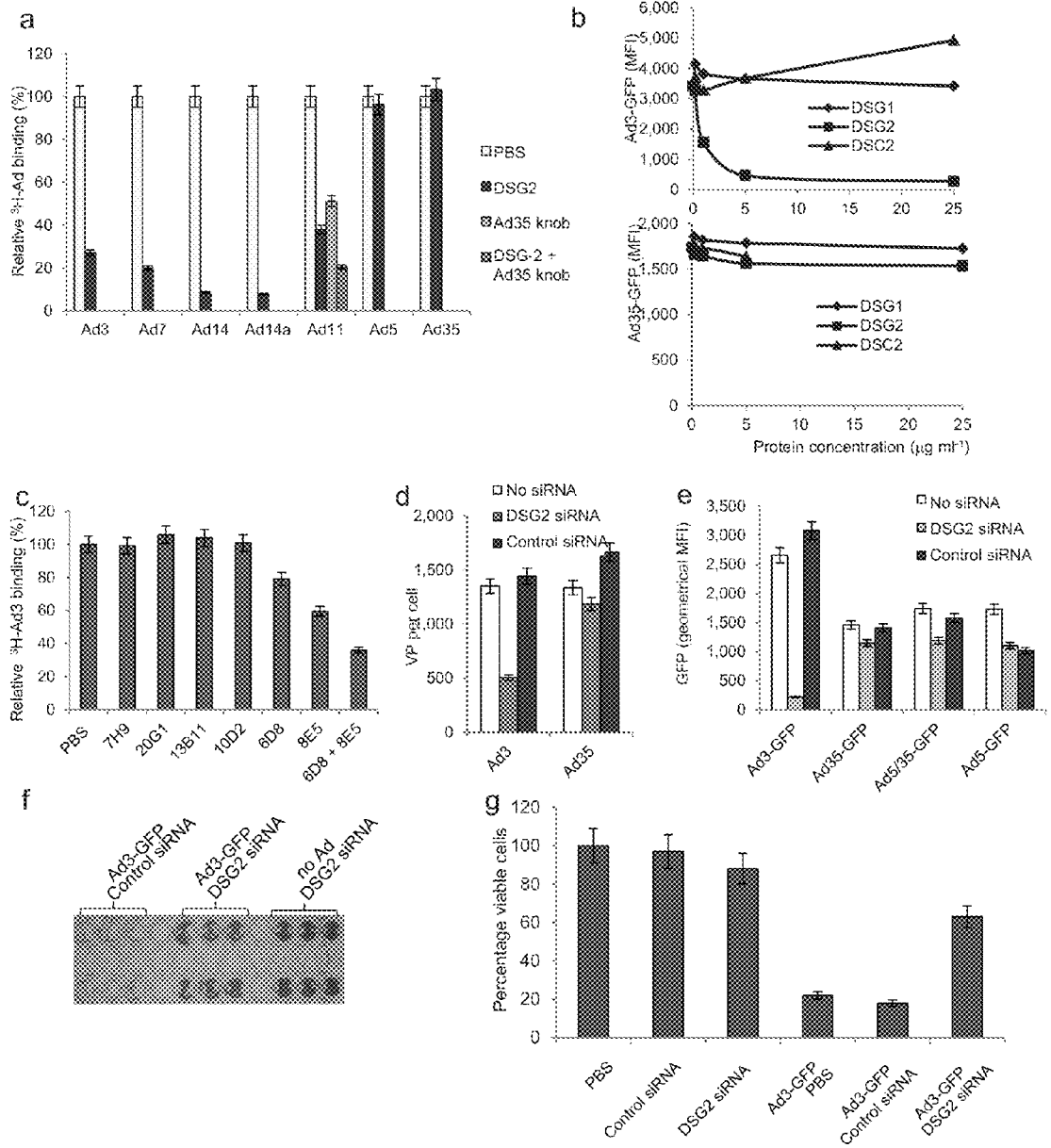
FIG. 3 Validation of DSG2 as Ad receptor. "Loss-of-function" studies.

Loss- and gain-of-function studies were performed on cell lines to validate DSG2 as a critical receptor for AdB-2/3 binding/infection. Recombinant DSG2 protein blocked the binding of Ad3 as well as other AdB2/3 Ads, i.e. Ad7, Ad14, Ad14a, and Ad11 to HeLa cells, but not the binding of Ad5 and Ad35 (FIG. 3a). Ad3-GFP infection was efficiently inhibited by DSG2 protein but not by other structurally related members of the cadherin superfamily (desmoglein 1-DSG1 and desmocollin 1-DSC1)[38] (FIG. 3b). This study also showed that DSG2 protein had no effect on transduction by the CD46-targeting vector (Ad35-GFP). Significant inhibition of Ad3 attachment was observed with monoclonal antibodies (mAbs) against extracellular domains 3 and 4 (FIG. 3c) (for a scheme of DSG2, see FIG. 2f). Transfection of HeLa cells with a pool of DSG2-specific siRNAs resulted in ~7-fold downregulation of surface DSG2 levels (data not shown). Ad3 attachment was 3 fold lower in DSG2-siRNA treated HeLa cells compared to control siRNA-treated cells (p<0.001) (FIG. 3d). GFP expression levels after infection with Ad3-GFP were 13.9-fold lower in DSG2-siRNA transfected cells than in control siRNA transfected cells (FIG. 3e). DSG2-specific siRNA did not affect transduction with the CAR-targeting vector Ad5-GFP. However, DSG2-siRNA transfection also decreased binding and transduction with the CD46-specific vectors Ad35-GFP and Ad5/35-GFP. DSG2-siRNA did not decrease CD46 levels in HeLa cells. At this point we cannot explain this phenomenon. It appears, however, to be specific to HeLa cells. No decrease in Ad35-GFP or Ad5/35-GFP transduction was detected in 293 cells or breast cancer BT474 cells that were transfected with DSG2-siRNA (data not shown).

siRNA mediated DSG2 downregulation also decreased viral cytolysis and spread in cells that were infected at 100% confluence at an MOI of one Ad3-GFP pfu per cell. Using adjusted multiplicities of infection (MOIs) (to achieve comparable percentages of GFP expression at 16 hours post-infection), we followed viral cytolysis over time and found larger lytic plaques in control siRNA than in DSG2 siRNA-transfected cells at day 7 p.i. This is reflected in crystal violet staining of viable cells that remained attached to tissue culture wells, i.e. cells that did not develop cytopathic effects due to virus infection (FIG. 3f). Quantitative analysis of cell viability showed significantly less cell killing in cells in which DSG2 was downregulated by siRNA compared to control siRNA treated cells (FIG. 3g).

For gain-of-function studies, we selected a series of cell lines with different DSG2 expression levels and measured Ad3-GFP transduction (FIG. 4a). All cell lines that lacked DSG2 expression (lymphoma Ramos, Raji, Mino, and HH cells) were refractory to Ad3-GFP transduction, but could be transduced by the CD46 targeting Ad5/35-GFP vector (because CD46 is expressed on these cells[39]). DSG2-positive K562 cells, on the other hand, could be efficiently transduced with Ad3-GFP. About 70% of BJAB cells were DSG2 positive and, correspondingly, the percentage of GFP-positive cells reached a plateau at about 50%. To conclusively prove the critical role of DSG2 in Ad3 infection, we ectopically expressed DSG2 via lentivirus vector gene transfer in the histiocytic lymphoma cell line U937, which is refractory to Ad3-GFP transduction (FIG. 4b). Ectopic DSG2 expression in U937-DSG2 cells conferred efficient Ad3 attachment and transduction, whereas Ad35 attachment and Ad5/35-GFP transduction was unaffected in these cells (FIGS. 4c and d).

DSG2 Localization in Human Cells:

As expected, we found DSG2 in cell membranes of normal epithelial tissues (foreskin and colon) and epithelial cancers (breast and ovarian cancer) (FIG. 5a). Confocal immunofluorescence microscopy studies of polarized colon cancer T84 and CaCo-2 cells demonstrated colocalization of DSG2 and the intercellular junction protein Claudin 7 (FIG. 5b). In stacked XZ image sections (FIG. 5b) {or XY sections taken at different depth of the cell layer (data not shown), DSG2 appears at the distal end of intercellular junctions. DSG2 also colocalized with the adherens junction protein E-cadherin in epithelial cells ( ). Fifteen minutes after adding Cy3-labelled Ad3 to polarized cells, viral particles were detectable in association with junction-localized DSG2 (FIG. 5c). Similar results were obtained with normal small airway epithelial cells incubated with PtDd for 15 min as shown by triple labeling of Cy5-PtDd, DSG2, and E-cadherin (FIG. 5d, upper panel). PtDd signals were on cell membranes (FIG. 5d, lower panel, thin arrows) and in the cytoplasm (thick arrows), most likely reflecting internalized particles.

In contrast to polarized epithelial cell lines, in non-polarized cells, such as HeLa cells, intercellular junctions (i.e.

membrane-localized Claudin 7 and E-cadherin signals) were absent. DSG2 and Ad3 were found dispersed over the cell surface (FIG. 5e).

Our studies on Ad3 infection of HeLa cells (FIGS. 2 and 3) indicate that DSG2 also acts as receptor in non-polarized cells. In this context, it is noteworthy that we detected DSG2 and Ad3 binding/transduction in human platelets and granulocytes (data not shown). Although these findings are relevant for Ad3 pathogenesis and the intravascular application of Ad3 vectors for gene therapy purposes, we focused in this study on analyzing the consequences of Ad3-DSG2 interaction in polarized epithelial cells.

Ad3 interaction with DSG2 triggers EMT.

Recently, we found that AdB-2/3 interaction with epithelial ovarian cancer cells triggered EMT. EMT is characterized by increased expression of mesenchymal markers, increased expression of extracellular matrix compounds, decreased expression of epithelial markers, altered location of transcription factors, and activation of kinases[7]. Here, we attempted to prove that Ad3 interaction with DSG2 triggers EMT-like events. To avoid potential side effects of viral gene expression on cell morphology, the studies utilized ultraviolet light (UV)-inactivated Ad particles and recombinant Ad3 PtDd. Overall, the results with both types of particles were similar. Incubation of epithelial cancer cells with PtDd (FIG. 6) or UV-inactivated Ad3 (not shown) caused remodeling of junctions as reflected by the decrease in of membrane/junction-localized Claudin 7 (FIG. 6a) or E-cadherin signals (FIG. 6b). Furthermore, after PtDd treatment we found stronger immunofluorescence signals of the mesenchymal markers Vimentin and Lipocalin 2 (FIGS. 6c and d). To identify intracellular signaling pathways triggered by PtDd interaction with DSG2, we studied mRNA expression profiles. Twelve hours after incubation of polarized BT474 cells with PBS, BsDd, or PtDd, mRNA was analyzed using Affymetrix human ST gene arrays. We found that PtDd treatment resulted in >1.5-fold upregulation of 430 genes and >1.5-fold down-regulation of 352 genes when compared to PBS-treated cells (FIG. 6e). The list of altered genes was further processed by Pathway-Express software[40]. This computation suggested that PtDd mediated marked activation of a number of signaling pathways involved in EMT, including phosphatidylinositol (PI), mitogen activated protein kinase (MAPK aka ERK), Wnt, adherens junctions, focal adhesion, and regulation of actin cytoskeleton signaling pathways.

Western blot analysis using phosphorylation-specific antibodies showed that PtDd, but not BsDd, triggered the activation of PI3K and MAPK/ERK1/2, i.e. key kinases involved in EMT (FIG. 6f). Activation of these pathways was also triggered by DSG2-specific mAbs (6D8, and to a lesser degree 10D2, and 13B11,) but not with mAbs directed against CD46. PtDd activation of pathways was mediated by DSG2, because MAPK/ERK1/2 and PI3K phosphorylation was decreased in cells transfected with DSG2 siRNA, but not in control siRNA treated cells. Finally, PtDd-triggered phosphorylation of kinases was absent when cells were pretreated with the ERK1/2 inhibitor U0126 (upper panel) or the PI3K inhibitor Wortmannin (lower panel). Taken together, our data suggest that Ad3 or Ad3PtDd binding to DSG2 triggers EMT in epithelial cells.

Ad3 and PtDd Increase Access to Receptors that are Trapped in Intercellular Junctions.

To test whether Ad3 virion- or Ad3 PtDd-triggered EMT also results in opening of intercellular junctions, we studied barrier properties in monolayers of epithelial cells. First we measured the flux of 4 kDa FITC-dextran through confluent polarized BT474 cells cultured in TRANSWELL™ chambers (FIG. 7a). We found that PtDd but not BsDd incubation significantly increased the permeability coefficient compared to phosphate buffered saline (PBS). We then tested whether Ad3 or PtDd-triggered EMT and transient junction-opening would increase access to proteins that are normally not accessible due to epithelial cell junctions. An example for such a junction-localized receptor is CD46, the high-affinity receptor for Ad35 and Ad5/35[8]. We confirmed that a large number of CD46 molecules localizes to junctions of BT474 cells (FIG. 7b, left panels). PtDd pre-treatment significantly increased the attachment of $^3$H-Ad35 to BT474 cells when compared to BsDd treatment (FIG. 7b, right panel). An enhancing effect of PtDd on transduction of CD46-targeting Ad vectors was also demonstrated in vivo in subcutaneous epithelial tumors (FIG. 7c). Intravenous injection of PtDd eight hours before application of Ad5/35-bGal increased viral transduction. Beta-galactosidase activity, measured in tumor lysates 3 days after Ad injection, was $2.3(+/-0.2) \times 10^5$ rlu/g protein, $2.7(+/-0.6) \times 10^5$ rlu/g, and $38(+/-3.5)_{x10}{}^5$ rlu/g for mice that were mock-injected, BsDd-coinjected, and PtDd-coinjected, respectively.

In another line of experiments in breast cancer cell cultures, we found that Her2/neu, the receptor for the widely used monoclonal antibody Herceptin (trastuzumab) co-stained with the intercellular junction protein Claudin 7 (FIG. 7d). This suggests that not all Her2/neu molecules are accessible to Herceptin. Incubation of the Her2/neu-positive breast cancer cell line BT474 with PtDd triggered relocalization of Her2/neu to the cell surface (FIG. 7e). To consolidate this observation, we tested whether Ad3 or Ad3PtDd would improve BT474 cell killing by Herceptin. In agreement with earlier studies[41], Herceptin caused death of approximately 25% of BT474 cells cells (FIG. 7f). Pre-incubation of BT474 cells with UV-inactivated Ad3 particles or PtDd increased Herceptin cytotoxicity by more than 2-fold. Incubation with UV-inactivated Ad5 particles or BsDd had no effect on Herceptin killing. In addition, Herceptin and PtDd/Herceptin had no cytotoxic effect on the Her2/neu-negative breast cancer cell line MDA-MB-231 (FIG. 8a). The enhancing effect of PtDd and Ad3 on Herceptin killing of BT474 cells was mediated by DSG2, as downregulation of DSG2 in BT474 cells by DSG2 siRNA abolished this effect (FIG. 7g). We also studied whether inhibition of key pathways involved in EMT affects the enhancing effect of PtDd on Herceptin cytotoxicity. These studies showed that inhibtion of PI3K by Wortmannin, as well as inhibition of MAPK/ERK by U0126 counteracted PtDd enhancement of Herceptin therapy (FIG. 7g). Importantly, intravenous injection of PtDd (2 mg/kg) into BT474-M1-tumor-bearing mice before Herceptin treatment resulted in elimination of tumors, an outcome that could not be achieved with Herceptin injection alone (FIG. 7h). PtDd pretreatment also allowed the unfolding of the therapeutic effect of the EGFR-specific mAb Erbitux (cetuximab) as it increased killing of EGFR-positive colon cancer LoVo cells with this antibody in vitro (FIG. 8b).

Discussion

In this study we describe two major findings: i) DSG2 is a receptor crucial for infection of a series of human adenoviruses that are common pathogens and important biomedical tools. ii) Ad interaction with DSG2 results in the opening of intercellular junctions, thus increasing access to receptors trapped therein.

DSG2 is an Ad Attachment Receptor.

The use of complete Ad3 particles or PtDd as a receptor probe was instrumental in the identification of DSG2 as the attachment receptor for Ad3, Ad7, Ad11, and Ad14. Previous attempts with Ad3 fiber knob domains as a bait did not yield meaningful receptor candidates[32]. Our competition and surface plasmon resonance studies shown in FIG. 2, indicate that the DSG2 interacting domain(s) within Ad3 are formed by the fiber only in the spatial constellation that is present in viral particles. This clearly widens our understanding of Ad attachment mechanisms, which, so far, were thought to involve only a high affinity interaction between the fiber knob and the cellular receptor, i.e. CAR or CD46.

Role of Ad3 and PtDd Interaction with DSG2 in Viral Dissemination.

During replication of Ad5, excess production of fiber results in the disruption of epithelial junctions either by interfering with CAR dimerization (which is critical for maintenance of junctions) or by triggering intracellular signaling that leads to reorganization of intercellular junctions[42-43]. Both mechanisms could also be involved in Ad3 virion/DSG2- and Ad3 PtDd/DSG2-mediated intercellular junction opening. We have experimental support for intracellular signaling triggered by Ad3 and PtDd binding to DSG2 in epithelial cells. Immunofluorescence, PI3K/MAPK phosphorylation, mRNA expression array, and metabolic pathway inhibition data suggest that Ad3 and PtDd trigger EMT in epithelial cells resulting in transient opening of intercellular junctions. Intercellular junction opening mediated by interaction of Ad3 particles or recombinant PtDd with DSG2 is further supported by increased cell permeability and access to receptors that are trapped in intercellular junctions (CD46 and Her2/neu). Along this line, a recent study showed that antibodies against the extracellular domain of DSG2 resulted in the opening of intercellular junctions in CaCo-2 cell monolayers[44].

Ad3 virion- and PtDd-triggered EMT, i.e. the dissociation of the intercellular junctions, appears to have an important biological role. We speculate that, specifically the massive overproduction of PtDd during viral infection and its interaction with DSG2, facilitate the lateral viral spread in epithelial cells and, potentially, the penetration of Ad into subepithelial cell layers and the blood stream.

Implications for Ad Pathogenesis.

Our findings that DSG2 is an attachment receptor that facilitates further viral spread, sheds light on the Ad3 infection mechanism of the respiratory tract epithelium. Furthermore, the observation that Ad3 binds to DSG2 on platelet and granulocytes has potential implications on systemic spread of this virus once it has entered the blood stream. Although mouse DSG2 shares 76% homology with human DSG2[45], our data, showing that mouse cells are refractory to Ad3-GFP infection, indicate that mouse DSG2 cannot function as an Ad3 receptor. To study pathogenesis of AdB-2/3 serotypes, transgenic mice that express human DSG2 under the control of adequate endogenous regulatory elements resulting in DSG2 expression in a pattern and at levels similar to humans, would be a critical tool.

Implications for Cancer Therapy.

DSG2 has been proposed as a marker for epithelial tumors[46]. The epithelial phenotype of cancer cells and the ability to form physical barriers represent a mechanism that restricts access of drugs, antibodies, oncolytic viruses, or immune cells to the sites of tumors, thus diminishing the efficacy of such therapeutic modalities[47]. We demonstrated here, in three examples (Ad5/35 vectors, Herceptin, and Erbitux), that this important problem in cancer therapy can perhaps be addressed by the use of DSG2-interacting Ad3 components.

In conclusion, we report the discovery of the high affinity receptor for a series of common human Ads. Our study contributes to the understanding of how Ads induce cellular processes in order to gain access to epithelial tissue. Our findings have implications for improving cancer therapies.

Methods

Proteins and Antibodies.

The knob domains of Ad3, Ad5, and Ad35 fibers were produced in E. coli as described elsewhere[48]. Recombinant Ad3 penton-dodecahedra (PtDd) and base dodecahedra (BsDd) were produced in insect cells and purified as described previously[33]. Polyclonal rabbit antibodies against purified recombinant Ad3 and Ad35K++ knob were produced by PickCell Laboratories B.V. (Amsterdam, The Netherlands). DSG2-specific monoclonal antibodies 20G1, 7H9, 13B11, 10D2 and 8E5[49] were purified from hybridoma culture supernatant.

Cell Lines.

Cells were cultured as described in the SI. BT474 is a Her2/neu-positive breast cancer cell line with epithelial cell features. To achieve cell polarization, $1.4 \times 10^5$ BT474, T84 and CaCo2 cells were cultured in collagen-coated 6.5 mm TRANSWELL™ inserts (0.4 µm pore size) (Costar TRANSWELL™ Clears) for 10 days until transepithelial resistance was stable.

Adenoviruses.

Wild-type Ad3 (GB strain), Ad7p (Gomen stain), Ad11p (Slobitski strain), Ad14 (DeWit strain), and Ad35 (Holden strain) were obtained from the ATCC. Ad14a is new genomic variant of Ad14[5]. Propagation, methyl-$^3$H thymidine labeling, purification and titering of Ads was performed as described elsewhere[2]. Ad5/35-GFP and Ad5-GFP are Ad5 vectors containing Ad35 and Ad5 fibers and a CMV-GFP expression cassette[50]. Ad3-GFP and Ad35-GFP are wild-type Ad3- and Ad35-based vectors containing a CMV-GFP expression cassette inserted into the E3 region. Construction of Ad3-GFP is described in SI. Ad35-GFP has been described previously[34]. For transduction studies, cells were exposed to Ad vectors at the indicated MOIs for one hour, washed, and GFP expression was measured by flow cytometry 18 hours later.

Membrane Protein Preparation.

HeLa cell membrane proteins were prepared as described earlier[51]. Briefly, HeLa cell pellets were re-suspended in ice-cold homogenization buffer (20 mM Hepes, 1.5 mM $MgCl_2$, 5 mM KCl, 150 mM NaCl, 15% glycerol, 0.25 M sucrose, 0.1 mM EDTA, 2 mM-mercaptoethanol, 1 mM PMSF). After disruption with a 3 ml syringe and 21G needle, the lysate was centrifuged at 400×g for 15 minutes. The supernatant was diluted with 2 times volume of PBS and centrifuged at 35,000 rpm for 1 hour in an ultracentrifuge. The membrane protein pellet was resuspended in solubilization buffer (50 mM Hepes, 5 mM $MgCl_2$, 5 mM KCl, 150 mM NaCl, 15% glycerol, 0.25 M sucrose, 0.1 mM EDTA, 2 mM-mercaptoethanol, 1 mM PMSF, 0.5% Brij 96V(FLUKA™, St Louis, Mo.). The use of Brij96V as a detergent was intrumental as desmosomal proteins are highly insoluble.

Western Blot with Ad3 and PtDd.

Technical details for mass-spectroscopy analysis are described elsewhere[51]. To immunoprecipitate DSG2 from soluble crude membrane protein preparations, DSG2-specific mAb 6D8, and the Pierce Crosslink Immunoprecipitation Kit (Pierce Biotechnology, Rockford, Ill.) were used. Crude membrane proteins from HeLa cells were solubilized with 0.5% detergent Brij 96V, pre-incubated with control resin for 3 hours at 4° C. to reduce nonspecific binding, and then incubated with DSG2 antibody crosslinked proteinA/G agarose overnight at 4° C. Bound protein were eluted per manufacturer's instruction.

Surface Plasmon Resonance (SPR) Analyses.

Acquisitions were done on a BIACORE™ 3000 instrument. HBS-N (GE-HEALTHCARE™, Pittsburgh, Pa.) supplemented with 2 mM $CaCl_2$ was used as running buffer in all experiments at a flow rate of 5 l min$^{-1}$. Immobilisation on CM4 sensorchip (BIACORE™) was performed using DSG2 (LENICO TECHNOLOGY™, Inc.) at 0.1 mg ml$^{-1}$ diluted in 10 mM sodium acetate buffer pH4.2 injected for 10 minutes on EDC-NHS activated flow-cell. A control flow-cell was activated by EDC-NHS and inactivated by ethanolamine. Different concentration of PtDd, BsDd, Ad3 fiber knob were injected for 5 minutes followed by 3 minutes dissociation time and the signal was automatically subtracted from the background of the ethanolamine deactivated EDC-NHS flow cell. For the adenovirus binding experiments, a similar protocol was used with the injection of wild-type Ad2, Ad3 and Ad5 at 5·10$^9$ vp per ml.

siRNA Studies.

A set of DSG2 specific siRNA was synthesized by DHARMACON™ (THERMO SCIENTIFIC™). The target sequences were CAAUAUACCUGUAGUAGAA (SEQ ID NO: 29), GAGAGGAUCUGUCCAAGAA (SEQ ID NO: 30), CCUUAGAGCUACGCAUUAA (SEQ ID NO: 31) and CCAGUGUUCUACCUAAAUA (SEQ ID NO: 32). Control siRNA was purchased from QIAGEN™, Valencia, Calif. siRNA transfection was performed using HyperFect transfection reagent (QIAGEN™)

DSG2 Expressing U937 Cells.

DSG2 cDNA (accession No. BC099657) from Capital Biosciences (Rockville, Md.) was cloned into the lentivirus vector pRRL-SIN[52] under the control of the EF1 promoter. VSVG-pseudotyped lentivirus vectors were produced and titered as described earlier[53].

Animal Studies:

All experiments involving animals were conducted in accordance with the institutional guidelines set forth by the University of Washington. Mice were housed in specific-pathogen-free facilities. Breast cancer xenografts were established by injecting cancer cells in matrigel (1:1 vol/vol) into the mammary fat pad of CB17 SCID-beige mice. Herceptin was injected intraperitoneally at a dose of 10 mg/kg. PtDd was given intravenously at a dose of 2 mg/kg. Tumor volumes were measured as described previously[54].

REFERENCES FOR EXAMPLE 1

1. Bergelson, J. M., et al. Isolation of a common receptor for Coxsackie B viruses and adenoviruses 2 and 5. *Science* 275, 1320-1323. (1997).
2. Tuve, S., et al. A new group B adenovirus receptor is expressed at high levels on human stem and tumor cells. *J Virol* 80, 12109-12120 (2006).
3. Louie, J. K., et al. Severe pneumonia due to adenovirus serotype 14: a new respiratory threat? *Clin Infect Dis* 46, 421-425 (2008).
4. Tate, J. E., et al. Outbreak of severe respiratory disease associated with emergent human adenovirus serotype 14 at a US air force training facility in 2007. *J Infect Dis* 199, 1419-1426 (2009).
5. Wang, H., Tuve, S., Erdman, D. D. & Lieber, A. Receptor usage of a newly emergent adenovirus type 14. Virology 387, 436-441 (2009).
6. Yamamoto, M. & Curiel, D. T. Current issues and future directions of oncolytic adenoviruses. *Mol Ther* 18, 243-250 (2010).
7. Turley, E. A., Veiseh, M., Radisky, D. C. & Bissell, M. J. Mechanisms of Disease: epithelial-mesenchymal transition-does cellular plasticity fuel neoplastic progression? *Nat Clin Pract Oncol* (2008).
8. Strauss, R., et al. Epithelial phenotype of ovarian cancer mediates resistance to oncolytic adenoviruses. Cancer Research 15, 5115-5125 (2009).
9. Coyne, C. B. & Bergelson, J. M. CAR: a virus receptor within the tight junction. *Adv Drug Deliv Rev* 57, 869-882 (2005).
10. Thiery, J. P. & Sleeman, J. P. Complex networks orchestrate epithelial-mesenchymal transitions. *Nat Rev Mol Cell Biol* 7, 131-142 (2006).
11. Norrby, E., Nyberg, B., Skaaret, P. & Lengyel, A. Separation and characterization of soluble adenovirus type 9 components. *J Virol* 1, 1101-1108 (1967).
12. Fuschiotti, P., et al. Structure of the dodecahedral penton particle from human adenovirus type 3. *J Mol Biol* 356, 510-520 (2006).
13. Fender, P., Boussaid, A., Mezin, P. & Chroboczek, J. Synthesis, cellular localization, and quantification of penton-dodecahedron in serotype 3 adenovirus-infected cells. *Virology* 340, 167-173 (2005).
14. Di Guilmi, A. M., Barge, A., Kitts, P., Gout, E. & Chroboczek, J. Human adenovirus serotype 3 (Ad3) and the Ad3 fiber protein bind to a 130-kDa membrane protein on HeLa cells. *Virus Res* 38, 71-81 (1995).
15. Fleischli, C., et al. Species B adenovirus serotypes 3, 7, 11 and 35 share similar binding sites on the membrane cofactor protein CD46 receptor. *J Gen Virol* 88, 2925-2934 (2007).
16. Short, J. J., et al. Adenovirus serotype 3 utilizes CD80 (B7.1) and CD86 (B7.2) as cellular attachment receptors. *Virology* 322, 349-359 (2004).
17. Short, J. J., Vasu, C., Holterman, M. J., Curiel, D. T. & Pereboev, A. Members of adenovirus species B utilize CD80 and CD86 as cellular attachment receptors. *Virus Res* 122, 144-153 (2006).
18. Sirena, D., et al. The human membrane cofactor CD46 is a receptor for species B adenovirus serotype 3. *J Virol* 78, 4454-4462 (2004).
19. Gaggar, A., Shayakhmetov, D. M. & Lieber, A. CD46 is a cellular receptor for group B adenoviruses. *Nat Med* 9, 1408-1412 (2003).
20. Marttila, M., et al. CD46 is a cellular receptor for all species B adenoviruses except types 3 and 7. *J Virol* 79, 14429-14436 (2005).
21. Segerman, A., Arnberg, N., Erikson, A., Lindman, K. & Wadell, G. There are two different species B adenovirus receptors: sBAR, common to species B1 and B2 adenoviruses, and sB2AR, exclusively used by species B2 adenoviruses. *J Virol* 77, 1157-1162 (2003).
22. Gustafsson, D. J., Segerman, A., Lindman, K., Mei, Y. F. & Wadell, G. The Arg279Gln [corrected] substitution in the adenovirus type 11p (Ad11p) fiber knob abolishes EDTA-resistant binding to A549 and CHO-CD46 cells, converting the phenotype to that of Ad7p. *J Virol* 80, 1897-1905 (2006).
23. Persson, B. D., et al. An arginine switch in the species B adenovirus knob determines high-affinity engagement of the cellular receptor CD46. *J Virol* (2008).
24. Chitaev, N. A. & Troyanovsky, S. M. Direct Ca2+-dependent heterophilic interaction between desmosomal cadherins, desmoglein and desmocollin, contributes to cell-cell adhesion. *J Cell Biol* 138, 193-201 (1997).
25. Cowin, P. Unraveling the cytoplasmic interactions of the cadherin superfamily. *Proc Natl Acad Sci USA* 91, 10759-10761 (1994).

26. Biedermann, K., et al. Desmoglein 2 is expressed abnormally rather than mutated in familial and sporadic gastric cancer. *J Pathol* 207, 199-206 (2005).
27. Harada, H., Iwatsuki, K., Ohtsuka, M., Han, G. W. & Kaneko, F. Abnormal desmoglein expression by squamous cell carcinoma cells. *Acta Derm Venereol* 76, 417-420 (1996).
28. Schmitt, C. J., et al. Homo- and heterotypic cell contacts in malignant melanoma cells and desmoglein 2 as a novel solitary surface glycoprotein. *J Invest Dermatol* 127, 2191-2206 (2007).
29. Trojan, L., et al. Identification of metastasis-associated genes in prostate cancer by genetic profiling of human prostate cancer cell lines. *Anticancer Res* 25, 183-191 (2005).
30. Abbod, M. F., Hamdy, F. C., Linkens, D. A. & Catto, J. W. Predictive modeling in cancer: where systems biology meets the stock market. *Expert Rev Anticancer Ther* 9, 867-870 (2009).
31. Leopold, P. L. & Crystal, R. G. Intracellular trafficking of adenovirus: many means to many ends. *Adv Drug Deliv Rev* 59, 810-821 (2007).
32. Tuve, S., et al. Role of cellular heparan sulfate proteoglycans in infection of human adenovirus serotype 3 and 35. *PLoS Pathog* 4, e1000189 (2008).
33. Fender, P., Ruigrok, R. W., Gout, E., Buffet, S. & Chroboczek, J. Adenovirus dodecahedron, a new vector for human gene transfer. *Nat Biotechnol* 15, 52-56 (1997).
34. Gao, W., Robbins, P. D. & Gambotto, A. Human adenovirus type 35: nucleotide sequence and vector development. *Gene Ther* 10, 1941-1949 (2003).
35. Wang, H., et al. In vitro and in vivo properties of adenovirus vectors with increased affinity to CD46. *J Virol* 82, 10567-10579 (2008).
36. Nava, P., et al. Desmoglein-2: a novel regulator of apoptosis in the intestinal epithelium. *Mol Biol Cell* 18, 4565-4578 (2007).
37. Kowalczyk, A. P., et al. Structure and function of desmosomal transmembrane core and plaque molecules. *Biophys Chem* 50, 97-112 (1994).
38. Getsios, S., Huen, A. C. & Green, K. J. Working out the strength and flexibility of desmosomes. *Nat Rev Mol Cell Bio*l5, 271-281 (2004).
39. Wang, H., et al. A recombinant adenovirus type 35 fiber knob protein sensitizes lymphoma cells to rituximab therapy. *Blood* 115, 592-600 (2010).
40. Khatri, P., et al. New Onto-Tools: Promoter-Express, nsSNPCounter and Onto-Translate. *Nucleic Acids Res* 34, W626-631 (2006).
41. Bostrom, J., et al. Variants of the antibody herceptin that interact with HER2 and VEGF at the antigen binding site. *Science* 323, 1610-1614 (2009).
42. Walters, R. W., et al. Adenovirus fiber disrupts CAR-mediated intercellular adhesion allowing virus escape. *Cell* 110, 789-799 (2002).
43. Coyne, C. B., Shen, L., Turner, J. R. & Bergelson, J. M. Coxsackievirus entry across epithelial tight junctions requires occludin and the small GTPases Rab34 and RabS. *Cell Host Microbe* 2, 181-192 (2007).
44. Schlegel, N., et al. Desmoglein 2-mediated adhesion is required for intestinal epithelial barrier integrity. *Am J Physiol Gastrointest Liver Physio*/298, G774-783 (2010).
45. Mahoney, M. G., Simpson, A., Aho, S., Uitto, J. & Pulkkinen, L. Interspecies conservation and differential expression of mouse desmoglein gene family. *Exp Dermatol* 11, 115-125 (2002).
46. Schafer, S., Koch, P. J. & Franke, W. W. Identification of the ubiquitous human desmoglein, Dsg2, and the expression catalogue of the desmoglein subfamily of desmosomal cadherins. *Exp Cell Res* 211, 391-399 (1994).
47. Green, S. K., Karlsson, M. C., Ravetch, J. V. & Kerbel, R. S. Disruption of cell-cell adhesion enhances antibody-dependent cellular cytotoxicity: implications for antibody-based therapeutics of cancer. *Cancer Res* 62, 6891-6900 (2002).
48. Wang, H., et al. Identification of CD46 binding sites within the adenovirus serotype 35 fiber knob. *J Virol* 81, 12785-12792 (2007).
49. Keim, S. A., Johnson, K. R., Wheelock, M. J. & Wahl, J. K., 3rd. Generation and characterization of monoclonal antibodies against the proregion of human desmoglein-2. *Hybridoma (Larchmt)* 27, 249-258 (2008).
50. Shayakhmetov, D. M., Papayannopoulou, T., Stamatoyannopoulos, G. & Lieber, A. Efficient gene transfer into human CD34(+) cells by a retargeted adenovirus vector. *J Virol* 74, 2567-2583 (2000).
51. Gaggar, A., Shayakhmetov, D. & Lieber, A. Identifying functional adenovirus-host interactions using tandem mass spectrometry. Methods Mol Med 131, 141-155 (2007).
52. Seppen, J., Barry, S. C., Harder, B. & Osborne, W. R. Lentivirus administration to rat muscle provides efficient sustained expression of erythropoietin. *Blood* 98, 594-596 (2001).
53. Li, Z., et al. Toward a stem cell gene therapy for breast cancer. Blood 113, 5423-5433 (2009).
54. Tuve, S., et al. Combination of tumor site-located CTL-associated antigen-4 blockade and systemic regulatory T-cell depletion induces tumor-destructive immune responses. *Cancer Res* 67, 5929-5939 (2007).

Example 2

Multimerization of Adenovirus Serotype 3 Fiber Knob Domains is Required for Efficient Binding of Virus to Desmoglein 2 and Subsequent Opening of Epithelial Junctions Abstract In Example 1, we identified desmoglein 2 (DSG2) as the main receptor for a group of species B adenoviruses (Ads), including Ad3, a serotype that is widely distributed in the human population. In this example, we have attempted to delineate structural details of Ad3 interaction with DSG2. For CAR- and CD46-interacting Ad serotypes, attachment to cells can be completely blocked by an excess of recombinant fiber knob protein, while soluble Ad3 fiber knob only inefficiently blocks Ad3 infection. We found that the DSG2 interacting domain(s) within Ad3 are formed by several fiber knob domains that have to be in the spatial constellation that is present in viral particles. Based on this finding, we generated a small recombinant, self-dimerizing protein containing the Ad3 fiber knob (Ad3-K/S/Kn). Ad3-K/S/Kn bound to DSG2 with high affinity and blocked Ad3 infection. We demonstrated by confocal immunofluorescence and transmission electron microscopy analyses that Ad3-K/S/Kn, through its binding to DSG2, triggered transient opening of intercellular junctions in epithelial cells. Pretreatment of epithelial cells with Ad3-K/S/Kn resulted in increased access to receptors that are localized in or masked by epithelial junctions, e.g. CAR or Her2/neu. Ad3-K/S/Kn treatment released CAR from tight junctions and thus increased transduction of epithelial cells by a serotype Ad5-based vector. Furthermore, pretreatment of Her2/neu-positive breast cancer cells with Ad3-K/S/Kn increased killing of cancer cells by the Her2/neu-targeting monoclonal antibody trastuzumab (Herceptin). This study widens our understanding of how Ads achieve high avidity to their receptors and infection of epithelial tissue. The small recombinant protein Ad3-K/S/Kn has practical implications for the therapy of epithelial cancer and gene/drug delivery to normal epithelial tissues.

Introduction

The protruding fiber is the moiety within the Ad capsid that mediates a high affinity binding to the primary attachment receptor. Each Ad capsid has 12 fibers linked to penton bases. Each fiber consists of a tail domain that is anchored within the penton base, a shaft domain consisting of repeats of up to 14 amino acids that form β-sheets (with the number of repeats ranging from 6 to 23 in different serotypes), and the C-terminal homo-trimeric knob domain. For CAR- and CD46-interacting Ads, the knob domain binds with high affinity to the receptor and soluble fiber knobs completely block infection. In this study, we have attempted to delineate structural details of Ad3 interaction with DSG2. We report that multimers of (trimeric) Ad3 fiber knobs are required for high affinity DSG2 binding. This is clearly different from the strategy of CAR- and CD46-interacting Ad serotypes to achieve infection. This specific mode of Ad3-DSG2 interaction is functionally crucial for Ad3, because it allows opening of epithelial junctions.

Material and Methods

Proteins and Antibodies.

Recombinant human DSG2 protein was from Leinco Technologies, Inc. (St. Louis, Mo.). The recombinant Ad3 fibers were produced in *E. coli* with N-terminal 6-His tags, using the pQE30 expression vector (QIAGEN™, Valencia, Calif.) and purified by Ni-NTA agarose chromatography as described elsewhere (34). Recombinant Ad3 penton-dodecahedra (Pt-Dds) was produced in insect cells and purified as described previously (8).

The following antibodies were used for immunofluorescence studies: polyclonal goat anti-DSG2 (R&D Systems, Inc., Minneapolis, Minn.), mouse mAb anti-DSG2 (clone 6D8) (CELL SCIENCES™, Canton, Mass.), rabbit anti-Claudin 7 (ABCAM™, Cambridge, Mass.), FITC conjugated goat anti-adenovirus (MILLIPORE™ Billerica, Mass.), monoclonal anti-6×His (Serotec, MCA1396), rabbit anti-20-1 antibody (CELL SIGNALING TECHNOLOGY™ Inc., Beverly, Mass.). Polyclonal rabbit antibodies against purified recombinant Ad3 knob were produced by PICKCELL LABORITORIES™ B.V. (Amsterdam, The Netherlands). Monoclonal anti-DSG2 antibodies 20G1, 7H9, 13B11, 10D2 and 8E5 (12) were purified from hybridoma culture supernatants.

Recombinant Ad3 Fiber Knobs.

The recombinant Ad3 fiber knobs S/Kn, S2/Kn, S3/Kn, S4/Kn, S5/Kn, and S6/Kn were generated by PCR using Ad3 genomic DNA as a template. The PCR products were then cloned into the *E. coli* expression vector pQE30 as BclI/HindIII or BamHI/HindIII fragments. The following primers were used:

S6/Kn-forward:
(SEQ ID NO: 33)
5'-CTGATGAATTCTTGATCAGGGGTTTTAAGTCTTAAATGTGTTAAT

CC-3'

S5/Kn-forward:
(SEQ ID NO: 34)
5'-TTACTGATGAATTCTTGATCA GGCTCCCTCCAACTTAAAGTG

GGAAGTGGT-3'

S4/Kn-forward:
(SEQ ID NO: 35)
5'-TTACTGATGAATTCTGGATCC TTAGAAGAAAACATCAAAGTT

AACAC-3'

S3/Kn-forward:
(SEQ ID NO: 36)
5'-TTACTGATGAATTCTGGATCC CATTCTATAAATTTACCAATA

GGAAACGGT-3'

S2/Kn-forward:
(SEQ ID NO: 37)
5'-TTACTGATGAATTCTGGATCC AACAAACTTTGCAGTAAACTC

GGAAATGG-3'

S/Kn-forward:
(SEQ ID NO: 38)
5'-ACCATCACGGATCCAATTCTATTGCACTGAA-3' reverse for all constructs:
(SEQ ID NO: 39)
5'-AGCTAATTAAGCTTAGTCATCTTCTCTAATATAGG-3'

For generating the K- or E-coil containing Ad3 fiber knobs the following oligonucleotides were annealed and cloned into pQE30 as BamHI fragments.

for pQE30-Kcoil:
(SEQ ID NO: 40)
5'ATCAAAGGTAAGCGCTTTAAAGGAGAAAGTTTCAGCACTTAAAGAAAA

GGTATCCGCTTTAAAGGAGAAAGTTTCAGCACTTAAAGAAAAGTGTCCG

CTCTGAAAGAAG-3'
and (SEQ ID NO: 41)
5'GATCCTTCTTTCAGAGCGGACACTTTTTCTTTAAGTGCTGAAACTTTC

TCCTTTAAAGCGGATACCTTTTCTTTAAGTGCTGAAACTTTCTCCTTTAA

AGCGCTTACCTTT-3' for pQE30-Ecoil
(SEQ ID NO: 42)
5'ATCAGAGGTAAGCGCTTTAGAGAAAGAAGTTTCAGCACTTGAGAAGGA

GGTATCCGCTTTAGAGAAAGAAGTTTCAGCACTTGAGAAGGAAGTGTCCG

CTCTGGAAAAAG-3'
and (SEQ ID NO: 43)
5'GATCCTTTTTCCAGAGCGGACACTTCCTTCTCAAGTGCTGAAACTTCT

TTCTCTAAAGCGGATACCTCCTTCTCAAGTGCTGAAACTTCTTTCTCTAA

AGCGCTTACCTCT-3'

To generate Ad3-E/S2/Kn and Ad3-K/S2/Kn, the following primers were used:

Forward:
(SEQ ID NO: 44)
5'ATCTAGGATCCGGTGGCGGTTCTGGCGGTGGCTCCGGTGGCGGTTCTA

ACAAACTTTGCAGTAAACTCGGAAATGGTCTTACATTTGACT-3'

Reverse:
(SEQ ID NO: 45)
5'AGCTAATTAAGCTTAGTCATCTTCTCTAATATAGG-3'

The PCR products were then cloned into the BamHI/HindIII site of pQE30-Kcoil and pQE30-E. coli. To generate Ad3-E/S/Kn and Ad3-K/S/Kn, the following primers were used:

Forward:
(SEQ ID NO: 46)
5'TTATTGCTACTGGATCCGGTGGCGGTTCTGGCGGTGGCTCCGGTGGCG

GTTCTAATTCTATTGCACTGAAAAATAACAC-3'

Reverse:
(SEQ ID NO: 47)
5'AGCTAATTAAGCTTAGTCATCTTCTCTAATATAGG-3'

The PCR products were than cloned into the BamHI/HindIII site of pQE30-Kcoil and pQE30-Ecoil. Cell lines. 293 (MICROBIX™, Toronto, Ontario, Canada), HeLa (American Type Culture Collection, ATTC) were cultured in Dulbecco modified Eagle medium (DMEM) supplemented with 10% fetal calf serum (FCS), 2 mmol/L L-glutamine (Glu), 100 units/mL penicillin, and 100 µg/mL streptomycin (P/S). BT474-M1 cells (16) were cultured in DMEM/F:12 with 10% FBS, 1% Pen/Strep and L-Glutamine. Colon cancer T84 cells (ATCC CCL-248)) were cultured in a 1:1 mixture of Ham's F12 medium and DMEM, 10% FBS, Glu and P/S. To achieve cell polarization, $1.4 \times 10^5$ T84 cells were cultured in 6.5 mm TRANSWELL™ inserts (0.4 µm pore size) (Costar TRANSWELL™ Clears) for more than 20 days until transepithelial resistance was stable.

Adenoviruses.

Propagation, methyl-$^3$H thymidine labeling, purification and titering of Ads was performed as described elsewhere (31). Ad5/35-GFP and Ad5-GFP are Ad5 vectors containing Ad35 and Ad5 fibers and a CMV-GFP expression cassette (24). Ad3-GFP is a wild-type Ad3-based vector containing a CMV-GFP expression cassette inserted into the E3 region (33). Ad5/3L-GFP and Ad5/3S-GFP are E1/E3 deleted, Ad5-based vectors, containing the same CMV-GFP expression cassette inserted into the E3 region. The construction of chimeric Ad vectors followed the protocol described earlier (23). The primer sequences used to construct the chimeric fiber genes were as follows:

for Ad5/3L-GFP,
SF
(SEQ ID NO: 48)
(5'-GACACGGAAACCGGTCCTCCAACTGTGCCTTTTCTTACTCC-3'),

SR
(SEQ ID NO: 49)
(5'-GCAGTTGGCTTCTGGTTTTGGACCTGTCCACAAAGTTAGCTTATCA

TTATTTTGTTTCC-3'),

KF
(SEQ ID NO: 50)
(5'-GGAAACAAAATAATGATAAGCTAACTTTGTGGACAGGTCCAAAAC

CAGAAGCCAACTGC-3'),

KR
(SEQ ID NO: 51)
(5'-TGAAAAATAAACACGTTGAAACATAACACAACTAGTTCTTTATTCT

TGGGCATTTTAGTCATCTTCTCTAATATAGGAAAAGGTAAATG-3'),

R1
(SEQ ID NO: 52)
(5'-CATTTACCTTTTCCTATATTAGAGAAGATGACTAAAATGCCCAAGA

ATAAAGAACTAGTTGTGTTATGTTTCAACGTGTTTATTTTTCA-3')
and

R2
(SEQ ID NO: 53)
(5'-ATACTTAGGGTACCAATCGATATGGCCACGTGGGTTCTGTGGTCC

C-3').

For Ad5/3S-GFP,
SF
(SEQ ID NO: 54)
(5'-ACGGAAACCGGTCCTCCAACTGTGCCTTTTCTTACTCCTCCCTTTG

TATCCCCCAATGGGTTTCAAGAGAGTCCCCCTGGGGTTTTAAGTCTTAAA

TGTG-3'),

KR
(SEQ ID NO: 55)
(5'-GAAAAATAAACACGTTGAAACATAACACACTCGAGTCTTTATTCTT

GGGCATTTTAGTCATCTTCTCTAATATAGGAAAAGGTAAATG-3'),

R1
(SEQ ID NO: 56)
(5'-CATTTACCTTTTCCTATATTAGAGAAGATGACTAAAATGCCCAAGA

ATAAAGACTCGAGTGTGTTATGTTTCAACGTGTTTATTTTTC-3')
and

R2
(SEQ ID NO: 57)
(5'-ATACTTAGGGTACCAATCGATATGGCCACGTGGGTTCTGTGGTC

CC-3').

SpeI or XhoI restriction sites were introduced after the fiber stop codon for Ad5/3L-GFP or Ad5/3S-GFP, respectively. To generate full-length E1/E3-deleted vector genomes, the corresponding shuttle plasmid containing chimeric fiber genes and GFP expression cassette were inserted in pAdHM4 by homologous recombination in E. coli strain BJ1583. The resulting plasmids pAd5/3L-GFP and pAd5/3S-GFP were analyzed by restriction analysis and sequencing. To produce the corresponding viruses, pAd5/3L-GFP and pAd5/3S-GFP were digested with PacI to release the viral genomes and transfected into 293 cells as described before. Recombinant viruses were propagated in 293 cells and purified by standard methods. Ad particle (viral particle, VP) concentrations were determined spectrophotometrically by measuring the optical density at 260 nm ($OD_{260}$) and plaque titering (plaque forming units, pfu) was performed using 293 cells as described elsewhere (24). The VP to pfu ratio was 20:1 for all virus preparations.

Attachment and Transduction Assays.

Adherent cells were detached from culture dishes by incubation with Versene and washed with PBS. A total of $1.8 \times 10^5$ cells/tube was resuspended in 100 µl of ice-cold adhesion buffer containing $^3$H-labeled Ad at a multiplicity of infection (M01) of 8,000 VP per cell. After 1 h of incubation at 4° C., cells were pelleted and washed twice with 0.5 ml of ice-cold wash-buffer (PBS, 1% FBS). After the last wash, the supernatant was removed, and the cell-associated radioactivity was determined with a scintillation counter. The number of viral particles (VP) bound per cell was calculated by using the virion specific radioactivity and the number of cells. For competition studies, 4.5 µg of competitor (PtDds, fiber knobs, antibodies) were allowed to attach for 60 min at 4° C. in adhesion buffer and non-bound competitor removed by washing cells twice with PBS before cells were resuspended in attachment buffer containing $^3$H-labeled Ad. For transduction studies, cells were exposed to Ad vectors at the indicated MOIs for one hour, washed, and GFP expression in 20,000 cells was measured by flow cytometry 18 hours later.

Ad5 Infection Studies.

In all transduction studies of HeLa, we have used conditions (MOI, virus concentration, exposure time) that have been optimized previously to be within the linear range of transduction (33).

Western Blot:

Mini-PROTEAN precast gels (BIO-RAD, Hercules, Calif.) with 4-15% gradient polyacrylamide were used. For the studies shown in FIG. 2B, a total of 0.5 μg protein was mixed with 2× loading buffer (10 mM Tris-HCl, pH6.8, 200 mM DTT, 4% SDS, 20% glycerol, 0.2% bromophenol blue). Samples were either boiled (B) for 5 min or loaded unboiled (UB). The following running buffer was used: 25 mM Tris, 0.192 M glycine, 0.1% SDS, pH8.3. After electrophoresis, proteins were transferred to nitrocellulose and incubated with anti-DSG2 antibodies or anti-Ad3knob antibodies as described previously (33).

Native Polyacrylamide Gel Electrophoresis:

For the study shown in FIG. 2F, a total of 0.4 μg proteins were mixed in 2× sample buffer (62.5 mM Tris-HCl, pH6.8, 40% glycerol, 0.01% bromophenol blue), not boiled, and run in 25 mM Tris, pH 8.3, 0.192 M glycine. Permeability assay. A total of $5\times10^5$ T84 cells were seeded in 12 mm TRANSWELL™ inserts (PET membrane, with 0.4 μm pore size (CORNING™, NY) and cultured for >20 days until transepithelial resistance was stable. Culture medium was changed every 2-3 days. The cells were exposed to DSG2 ligands (20 m/ml) in adhesion medium (DMEM, 1% FBS, 2 mM $MgCl_2$, 20 mM HEPES) for 15 min at room temperature. Then, 1 mCi of $[^{14}C]$ polyethylene glycol-4000 (PEG-4000); (PERKIN ELMER™, Covina Calif.) diluted with DMEM/K12 medium was added into the inner chamber. Medium aliquots were harvested from the inner and outer chamber at 15 and 30 min and measured by a scintillation counter. Permeability was calculated as described elsewhere (36).

Trastuzumab Cytotoxicity Assay.

$5\times10^4$ BT474-M1 cells/well were plated in triplicate in 96 well plates and grown to confluence. Ad3 fiber knobs or monoclonal antibodies (5 μg/ml) were added to the inner chamber. One hour later, trastuzumab (GENENTECH™, San Francisco, Calif.) (15 m/ml) was added and cell viability was measured 2 hours later by WST-1 assay (ROCHE™, San Francisco, Calif.). Three independent studies were performed.

Immunofluorescence Analyses.

Cells were cultured in 8 chamber glass slides (BD Falcon), washed twice with ice-cold PBS and then fixed with methanol/aceton (1:1 vol/vol) for 15 min at 4° C. or with 4% paraformaldehyde for 30 min at 4° C. After fixation, cells were washed with PBS twice and blocked with 500 μl PBS/2% dry-milk powder for 20 min at room temperature. Antibody staining was performed in 100 μl PBS for 90 min at 37° C. or 4° C. overnight. If needed, secondary antibodies directed against the appropriate host, were applied after 3 washes with PBS for 45 min at room temperature. After 3 washes with PBS, glass slides were mounted using VECTASHIELD with DAPI (VECTOR LABS™). Photographs were taken with a Leica DFC300FX digital camera. Confocal images were taken on a ZEISS™ META confocal microscope using 40× or 100× oil lenses and ZEISS™ 510 software (ZEISS™ MicroImaging, Thornwood, N.Y.).

Electron Microscopy.

Polarized cells in TRANSWELL™ chambers were fixed with half-strength Karnovsky's fixative (2% paraformaldehyde, 2.5% glutaraldehyde, 0.2 M Cacodylate buffer) for one hour at room temperature. The fixative in the inner chamber contained 0.2% ruthenium red. The ruthenium red (Ruthenium(III)chloride oxide, ammoniated), was purchased from Alfa Aesar (Ward Hill, Mass.). Post-fixation was performed with 1% $OsO_4$-phosphate buffer. The membranes were then cut out from the TRANSWELL™ chambers and embedded in Medcast (Ted Pella, Redding, Calif.). Ultrathin sections were stained with uranyl acetate and lead citrate. Processed grids were evaluated with a JEOL JEM1200EXII transmission electron microscope. Images were acquired with an Olympus SIS Morada Digital CCD camera using iTEM software for image processing.

siRNA Studies.

A set of DSG2 specific siRNA was synthesized by DHARMACON™ (THERMO SCIENTIFIC™). The target sequences were CAAUAUACCUGUAGUAGAA (SEQ ID NO: 29), GAGAGGAUCUGUCCAAGAA(SEQ ID NO: 30), CCUUAGAGCUACGCAUUAA (SEQ ID NO: 31) and CCAGUGUUCUACCUAAAUA (SEQ ID NO: 32). Control siRNA was purchased from QIAGEN™, Valencia, Calif. siRNA transfection was performed using HyperFect transfection reagent (QIAGEN™). A total of $1\times10^5$ HeLa were transfected with 1 ug DSG2 siRNA or control siRNA. Forty eight hours after siRNA transfection, cells were collected with versene, and the attachment of $^3$H-Ad3 or $^3$H-Ad35 virus was analyzed as described above. Forty eight hours after siRNA transfection, cells were infected with Ad vectors at an MOI of 50 pfu/cells, and GFP expression was analyzed 18 hours later.

Surface Plasmon Resonance (SPR) Analyses.

Acquisitions were done on a BIACORE™ X instrument. HBS-N (GE-HEALTHCARE™, Pittsburgh, Pa.) supplemented with 2 mM $CaCl_2$ was used as running buffer in all experiments at a flow rate of 5 μl/min. Immobilization on CM4 sensorchip (BIACORE™) was performed using DSG2 (LENICO TECHNOLOGY™, Inc.) at 0.1 μg/ml diluted in 10 mM sodium acetate buffer pH4.2 injected for 10 minutes on EDC-NHS activated flow-cell. A control flow-cell was activated by ethyl(dimethylaminopropyl) carbodiimide (EDC)/N-Hydroxysuccinimide (NHS) and inactivated by ethanolamine. Different concentration of Ad3 fiber knobs or PtDds were injected for 5 minutes association followed by 3 minutes dissociation time, and the signal was automatically subtracted from the background of the ethanolamine deactivated EDC-NHS flow cell.

For experiments using biotinylated ligands, two flow cells of a CM4 sensorchips were activated as described above and then coated by injection of streptavidin (0.1 μg/ml in acetate buffer pH4.1) for 5 minutes. Biotinylated ligands were then injected at 0.1 μg/ml in running buffer for 5 minutes on one of these two flow cells, the other being used for background subtraction during the run. Different concentrations of soluble DSG2 were then injected in running buffer on these flowcells and background was automatically subtracted.

Negative Stain Electron Microscopy.

Recombinant fiber knob proteins were visualized by negative-stain EM to assess their assembly status. The standard mica/carbone preparation was used with protein at 0.1 mg/ml. Samples were stained using 1% (w/v) sodium silicotungstate (pH 7.0) and visualized on Philips CM12 electron microscope at 100 kV.

Statistical Analysis:

All results are expressed as mean+/−SD. Wilcoxon signed-rank test was applied when applicable. A p-value <0.05 was considered significant.

Results

Chimeric Ad5 Vectors Containing Ad3 Fibers use DSG2 as a Receptor.

Our preliminary studies indicated that DSG2 interacting domain(s) within Ad3 are formed by the fiber or fiber/penton only in the spatial constellation that is present in viral particles, i.e. Ad3 virions or PtDds. To assess a potential role of Ad3 penton (which is present in PtDds) in binding to DSG2, we generated an Ad vector that contained Ad3 fibers (Ad5/3S-GFP), but had all other capsid proteins (including the penton) derived from Ad5. To evaluate whether the Ad3 fiber shaft had a cucial role in Ad3-DSG2 interaction, e.g., contained DSG2 additional binding sites, we also generated a chimeric Ad5/3 vector that had the Ad3 shaft substituted by the Ad5 shaft (Ad5/3L-GFP) (FIG. 9A). Notably, while the Ad3 fiber shaft contains 6 shaft repeat motifs, the Ad5 shaft is longer and contains 22 shaft motifs. For comparison, we used an Ad3 vector (Ad3-GFP) containing the same GFP expression cassette as the Ad5/3 vectors (33). We analyzed whether Ad5/3S-GFP and Ad5/3L-GFP vectors use DSG2 for infection. Attachment of $^3$H-labeled Ad vectors to HeLa cells was blocked by recombinant DSG2 protein to the same degree for Ad3-GFP, Ad5/3S-GFP, and Ad3/5L-GFP (FIG. 9B). As expected, recombinant DSG2 also blocked transduction of all three vectors as measured based on GFP intentsity 18 hours after infection of HeLa cells (FIG. 9C). PtDd, used as a competitor for DSG2 interaction domains within the Ad virions, blocked Ad3-GFP, Ad5/3S-GFP, and Ad3/5L-GFP transduction to similar levels (FIG. 9D). To prove the crucial role of DSG2 in the infection of Ad3 and Ad5/3 vectors, we transfected HeLa cells with siRNA specific to DSG2 mRNA or control siRNA. The mean fluorescence DSG2 intensity at 48 hours after transfection of siRNA was 22.1 and 195 for DSG2 siRNA and control siRNA transfected HeLa cells, respectively, indicating efficient inhibition of DSG2 expression by DSG2 siRNA. DSG2 mRNA knockdown significantly decreased Ad3-GFP, Ad5/3S-GFP, and Ad3/5L-GFP transduction ($p<0.001$) (FIG. 9E). Interestingly, the knockdown of DSG2 decreased Ad5/3L-GFP transduction to a lesser degree ($p<0.01$) than the transduction of the vectors containing Ad3 fibers (Ad3-GFP and Ad5/3S-GFP). We speculate that Ad5/3L-GFP can use receptors other than DSG2. Taken together, these studies show: i) Ad5/3 vectors use DSG2 as a receptor. This has relevance for clincal studies because Ad5/3 vectors are used in patients (14, 35) and ii) the DSG2 interacting domains of Ad3 are located within the fiber. It appears that the Ad pentons (within PtDds or Ad5 and Ad3 virions) merely provides a scaffold for the correct spatial constellation of Ad3 fiber knobs for interaction with DSG2.

Crosslinking of Ad3 Fiber Knobs is Required for Efficient Binding to DSG2.

We then focused our attention on the Ad3 fiber. We produced in *E. coli* a series of recombinant Ad3 fiber knob proteins, containing the fiber knob and increasing numbers of Ad3 shaft repeats (from one to six repeats) (FIG. 10A). Western blot analyses using DSG2 or antiAd3 fiber knob antibodies showed that all recombinant fiber knobs formed trimers (FIGS. 10 B,C). As observed previously (33), the Ad3 fiber knob plus one shaft domain (S/Kn) did not bind DSG2 in Western blot analyses, indicating a potential steric influence of the shaft motif on the Ad3 knob conformation. The protein containing 6 shaft motifs (S6/Kn) tended to form aggregates and was therefore not used in further studies. When used in competition studies, all recombinant fiber knob proteins inhibited Ad3-GFP transduction significantly less than PtDds (FIG. 10 D,E). We then attempted to test whether Ad3 fiber knob dimerization would increase DSG2 binding. Because all recombinant fiber knobs contained an N-terminal His tag (used for protein purification), we mixed Ad3 fiber knobs with antibodies against the His tag to achieve their crosslinking. Formation of complexes between anti-His tag antibodies and fiber knob was demonstrated by electrophoresis in native polyacrylamide gels (FIG. 10F). When anti-His antibodies crosslinked fiber knobs were used as competitors, a significant inhibition of Ad3-GFP transduction (compared to fiber knobs mixed with control IgG) was observed (FIG. 10G), suggesting that dimers of Ad3 fiber knobs are required for DSG2 binding. This appeared to be a new Ad binding strategy unique to Ad3, because anti-His antibody crosslinking of the Ad35 fiber knobs had no effect on infection by the CD46-interacting vector Ad35-GFP (FIG. 10H).

Ad3 Fiber Knob Dimers Block Ad3 Infection.

Crosslinking with antibodies enhanced the blocking effect of Ad3 fiber knobs containing fewer shaft motifs than the wild-type Ad3 fiber knob. For a potential therapeutic application of Ad3 fiber knobs as junction openers, we focused our further studies on decreasing the size of the molecule by evaluating fiber knob variants with the minimum number of shaft motifs, i.e. S2/Kn. Based on the finding that fiber knob cross-linking increased binding to DSG2, we generated dimers of S2/Kn by incorporating dimerization domains. To avoid the spontaneous fiber knob dimerization and potential formation of inclusion bodies during production in *E. coli*, we utilized a hetero-dimeric system consisting of E-coil and K-coil peptides, which interact with each other with high affinity (17). Two fiber knob variants containing five repeats of EVSALEK (SEQ ID NO:22) (K-coil) and KVSALKE (SEQ ID NO:23) (E-coil) respectively, a G/S rich-flexibility domain followed by two shaft motifs and the homotrimeric fiber knob domain were generated (FIG. 11A). Ad3-K/S2/Kn and Ad3-E/S2/Kn were produced separately in *E. coli* and purified by affinity chromatography. For dimerization, both purified proteins were mixed at a 1:1 concentration ratio. The mixture of Ad3-K/S2/Kn and Ad3-E/S2/Kn blocked Ad3 infection as efficiently as PtDd (FIG. 11B). Interestingly, Ad3-K/S2/Kn alone had the same competing strength as the mixture of both peptides, while Ad3-E/S2/Kn alone only inefficiently blocked infection. This suggests that Ad3-K/S2/Kn is able to homodimerize, while Ad3-E/S2/Kn is not. In support of this, we found that further crosslinking with anti-His antibodies increased the blocking effect of Ad3-E/S2/Kn ($p<0.05$), but not that of Ad3-K/S2/Kn (FIG. 11C).

Binding of a Minimal Dimeric Ad3 Fiber Knob Protein to DSG2.

We then attempted to produce the smallest Ad3 fiber knob dimer, containing the K-coil or E-coil dimerization domain, only one shaft motif, and the homotrimeric Ad3 fiber knob (Ad3-K/S/Kn and Ad3-E/S/Kn) (FIG. 12A). Because of their smaller size, such proteins have potential therapeutic advantages in egress from blood vessels, tissue penetration and, theoretically, also contain fewer immunogenic epitopes. Ad3-K/S/Kn and Ad3-E/S/Kn were produced in *E. coli* and purified by affinity chromatography. Analysis by polyacrylamide gel electrophoresis showed that the vast majority of Ad3-K/S/Kn and Ad3-E/S/Kn were present as trimers (~65-70 kDa) (FIG. 12B). Ad3-K/S/Kn alone and in combination with Ad3-E/S/Kn were analyzed by negative stain electron microscopy to assess their assembly status (FIG. 12C). Dimers of fiber knobs and aggregates thereof were found for both Ad3-K/S/Kn and Ad3-K/S/Kn+Ad3-E/S/Kn, but larger aggregates were less abundant in Ad3-K/S/Kn preparations. Both Ad3-K/S/Kn and Ad3-K/S/Kn+Ad3-E/S/Kn blocked Ad3 attachment to HeLa cells at a level comparable to PtDd (FIG. 12D). Pre-incubation of HeLa cells with Ad3-K/S/Kn and Ad3-K/

S/Kn+Ad3-E/S/Kn did not affect Ad5 attachment (FIG. 12E). As expected, Ad3-K/S/Kn and Ad3-K/S/Kn+Ad3-E/S/Kn also efficiently inhibited Ad3 infection (FIGS. 12F,G). A side-by-side comparison of the fiber knobs with two and one shaft motif did not reveal significant differences in their ability to block Ad3 infection (FIGS. 12H,I).

SPR Analysis of Dimeric Ad3 Fiber Knob Binding to DSG2.

To study the interaction of Ad3-K/S/Kn and Ad3-K/S/Kn+Ad3-E/S/Kn with DSG2 in more detail, we performed surface plasmon resonance (SPR) studies. We initially designed binding experiments, in which DSG2 molecules were allowed to bind to immobilized fiber knobs (FIG. 13A). For immobilization, fiber knobs were biotinylated and linked via streptavidin to sensorchips. Kinetics analyses showed that both Ad3-K/S/Kn and Ad3-K/S/Kn+Ad3-E/S/Kn similarly recognized DSG2 with a low dissociation at the end of injection. Clearly, the binding of soluble DSG2 to fibers only poorly mimics the physiological interaction between a cell surface and the virus. We therefore immobilized the receptor, DSG2, at the sensorchip surface and injected Ad3-K/S/Kn and Ad3-K/S/Kn+Ad3-E/S/Kn, and, for comparison, PtDd and (monomeric) Ad3 fiber knob at concentrations that give a similar SPR response (FIG. 13B). The outcome of these studies should depend on the valence of the fiber knobs, which is trimeric for Ad3 fiber knob (monomer), 2× trimeric for Ad3-K/S/Kn and Ad3-K/S/Kn+Ad3-E/S/Kn, 12× trimeric for PtDd. It is further complicated by the fact that within PtDd not all fibers can simultaneously interact with DSG2. While the association of the fiber knob dimers was similar (FIG. 13C "Binding at the end of association"), there were clear differences in the dissociation behavior. Ad3 fiber knob (non-dimerizing, described previously (33)) ("Ad3 knob") dissociated faster than the other three ligands. Almost no dissociation was seen for PtDd and Ad3-K/S/Kn+Ad3-E/S/Kn. Ad3-K/S/Kn dissociation was between that of Ad3 fiber knob and Ad3-K/S/Kn+Ad3-E/S/Kn. Although complex, these data clearly show that dimeric Ad3-K/S/Kn and Ad3-K/S/Kn+Ad3-E/S/Kn dissociate slower from DSG2 than does Ad3 fiber knob. This can be explained by an avidity mechanism, implying that Ad3-K/S/Kn and Ad3-K/S/Kn+Ad3-E/S/Kn bind to several DSG2 molecules; a mechanism that allows achieving an overall low dissociation rate and highly stable attachment. Notably, although it is possible that all dimers in Ad3-K/S/Kn+Ad3-E/S/Kn are formed by Ad3-K/S/Kn, differences in dissociation rates argue against it. Further studies are required to prove this in detail.

Interaction of Ad3 with several DSG2 molecules is supported by immunofluorescence analyses of epithelial cells (FIGS. 13D and E). These studies, using Cy3-labelled Ad3 virions, suggest that one virion clusters several DSG2 proteins around itself. As outlined later, we hypothesize that this specific clustering of receptors has functional consequences with regards to triggering intracellular signaling and opening of epithelial junctions. Notably, in Example 1 we showed that PtDd binding to DSG2 triggers an epithelial-to-mesenchymal transition (EMT) in epithelial cells resulting in transient opening of intercellular junctions.

Multimeric DSG2 Ligands (Ad3 Virions, PtDds, Ad3-K/S/Kn) Trigger Opening of Epithelial Junctions Epithelial cells maintain several intercellular junctions (tight junctions, adherens junctions, gap junctions, and desmosomes), a feature which is often conserved in epithelial cancers in situ and in cancer cell lines (29). FIG. 14A shows confocal immunofluorescence microscopy images of polarized colon carcinoma T84 cells. Shown are the cells from the lateral side, i.e. stacked XZ-layers. Intercellular junctions are visible as long vertical streaks marked by the adhesion junction protein Claudin 7 and the desmosomal protein DSG2. DSG2 (green) is localized at the apical end of Claudin 7 signals. The tight junction protein ZO-1 can be found further apical of DSG2 (lower panel). The latter is also visualized in XY images, which show a "chicken-wire" network of tight junctions marked by ZO-1 at the apical cell surface, whereas a section 1 μm deeper shows DSG2 staining (FIG. 14B). Importantly, exposure of T84 cells to Ad3-K/S/Kn triggered partial dissolution of epithelial junctions, reflected in decreased staining for DSG2 and ZO-1 (FIG. 14C), in comparison to untreated cells (FIG. 14A, lower panel).

Opening of epithelial junctions by Ad3-K/S/Kn was further confirmed by electron microscopy (EM) studies. EM images of untreated epithelial cells show intact tight and desmosomal junctions as judged by the exclusion of the apically applied dye ruthenium red from basolateral space (FIG. 14D, left panel). The dye appears as an electron-dense line along the cell membrane surface. Incubation of epithelial cells with Ad3-K/S/Kn resulted in leakage of ruthenium red deep into the lateral space within 1 hour of Ad3-K/S/Kn addition (FIG. 14D right panel). Partial disassembly of desmosomes (marked by arrows) in Ad3-K/S/Kn treated cells is clearly visible in FIG. 14E. In addition to Ad3-K/S/Kn, opening of epithelial junctions was observed in confocal immunofluorescence and EM studies with Ad3 virions, PtDd, and Ad3-K/S/Kn+Ad3-E/S/Kn (data not shown). Exposure of cells to Ad3 fiber knob (non-dimerizing) or Ad3-E/S/Kn, i.e. DSG2 ligands that are unable to multimerize, had no effect on epithelial junctions (data not shown). These studies indicate that opening of epithelial junctions requires dimers or multimers of Ad3 fiber knobs.

In addition to leakage studies with ruthenium red, we used three functional assays to demonstrate opening of epithelial junctions by Ad3-K/S/Kn: i) Exposure of polarized epithelial cells to Ad3-K/S/Kn increased the transepithelial permeability within 30 minutes, as shown by $^{14}$C-PEG-4000 transflux studies (FIG. 15A). Importantly, permeability after incubation with non-dimerizing Ad3-E/S/Kn fiber knobs or mAbs against different regions of the extracellular domain of DSG2 was >5-fold lower than after incubation with Ad3-K/S/Kn. ii) Previous studies showed that in polarized breast cancer BT474-M1 cells, Her2/neu, the target for Herceptin/trastuzumab, is trapped in epithelial junctions, and that incubation of BT474-M1 cells with Ad3 PtDd increases access to Her2/neu and increases trastuzumab killing of cancer cells (33). Here we used this assay to study the effect of additional DSG2 ligands on trastuzumab cytotoxicity (FIG. 15B). We found that Ad3-K/S/Kn significantly increased killing of BT474-M1 cells by trastuzumab. In contrast, DSG2 ligands that are not able to dimerize, i.e. Ad3-E/S/Kn and a series of anti-DSG2 antibodies, had no significant effect on trastuzumab killing. Notably, one of the anti-DSG2 antibodies against the extracellular domains 3/4 (mAb 6D8), appeared to stimulate tumor cell proliferation. iii) CAR, the receptor for Ad5, is localized in tight junctions of polarized T84 epithelial cells (3). This is shown by confocal immunofluorescence microscopy in T84 cells (FIG. 15C, upper panel and FIG. 15D, upper panel). Incubation of these cells with Ad3-K/S/Kn greatly increased CAR staining, which now appeared along the lateral membranes (FIG. 15C, lower panel) and at the cell surface (FIG. 15D, lower panel). We speculated that this is the result of disassembly of tight junctions and better accessibility of CAR to anti-CAR antibodies that were applied to the apical side of T84 cells. Another potential assay for disruption of tight junctions and CAR accessibility is transduction with a CAR-targeting Ad vector. Infection of polarized T84 cells (apical side) with Ad5-GFP at an MOI of 250 pfu/cell resulted in transduction of 8(+/−2) % of cells (based on GFP-positive cells counted 20 hours after infection) (FIG. 15E). Ad5-GFP infection in the presence of Ad3-K/S/Kn yielded 38(+/−9) % of GFP-positive cells. Ad3-GFP in the presence of dilution buffer or Ad3-K/S/Kn transduced 17(+/−6) % or 68(+/−17) % of T84 cells, respectively. The latter in agreement with an earlier study, showing that Ad3 infects polarized epithelial cells more efficiently than Ad5 (28). This is most likely due to its ability to bind to DSG2 and trigger junction opening. Ad3-K/S/Kn increased Ad3-GFP transduction. We speculate that the relatively small Ad3-K/S/Kn protein and it high concentration initially reaches more DSG2 receptors than Ad3 virions and thus enhances opening of tight junctions. In all settings shown in FIG. 15E, most cells at the periphery of the monolayers (i.e. cells that are in contact with the walls of the inner chamber, without tight junctions) were GFP-positive. Therefore, we counted GFP-positive cells in fields at the center of TRANSWELL™. The latter has to be considered in the interpretation of flow cytometry analysis of GFP expression after Ad5-GFP infection in the presence of dilution buffer or Ad3-K/S/Kn (FIG. 15F). Although background GFP fluorescence levels were relatively high, the presence of Ad3-K/S/Kn, but not the presence of Ad3-E/S/Kn or anti-DSG2 mAbs significantly increased GFP expression levels after Ad5-GFP infection.

Overall, our functional studies showed that Ad3-K/S/Kn can trigger opening of epithelial junctions, while ligands that are unable to multimerize had no effect on junctions.

Discussion

In this study, we describe two findings: i) multimerization of Ad3 fiber knob is required to achieve high-affinity and stable binding to DSG2 and ii) the multimeric mode of Ad3-fiber knob/DSG2 interaction triggers opening of epithelial junctions.

Most Ad infections, including infection by the CAR-interacting Ad5, the DSG2-interacting Ad3, and the CD46-interacting Ad35 (22) target the airway epithelium. Achieving a high avidity binding to receptors with a low dissociation rate appears to be crucial for Ad infection in order to maintain contact between virus and target cells, and more importantly, to trigger subsequent events that allow the virus to disrupt the epithelial barrier, enter the target cells, and spread within the target tissue. For CAR- and CD46-binding Ads, high avidity binding is achieved through interaction between the trimeric fiber knob and three receptor units. Furthermore, as shown for the interaction between Ad11 and CD46, initial Ad binding to the receptor can trigger conformational changes in the receptor to stabilize the binding (21); although it remains to be shown that the latter mechanism is used by Ads other than Ad11. For CAR— and CD46-interacting Ads, attachment involves the fiber knob and the receptor, and it can be completely blocked by an excess of soluble fiber knob. This is not the case for the DSG2-binding Ad3. We have shown that complete inhibition of Ad3 binding and infection requires the physical linkage and, most likely, a specific spatial constellation of at least two fiber knobs. This is achieved with Ad virions, Ad3 PtDds or dimeric Ad3-K/S/Kn. These ligands appear to achieve simultaneous binding to several DSG2 molecules, which, on the one hand, provides a high avidity and, on the other hand, is functionally relevant for opening of epithelial junctions. We are currently conducting crystal structure and mutagenesis studies to further support our findings on Ad3-DSG2 interaction.

In order to initiate infection, many pathogens have evolved mechanisms to disrupt junctional integrity. *Vibrio cholera* strains produce *Zona occludens* toxin (Zot), which possess the ability to reversibly alter intestinal epithelial junctions, allowing the passage of macromolecules through mucosal barriers (6). *Clostridium perfringens* enterotoxin removes claudins-3 and -4 from the tight junctions to facilitate bacterial invasion (25). Furthermore, oncoproteins encoded by human Ad, HPV, HTLV-1 can transiently open epithelial junctions by mislocalizing the junction protein ZO-1 (15). The latter mechanisms used by viruses appear to play a role in lateral viral spread. However, for an efficient initial infection, attachment of virus must be linked with triggering the opening of epithelial junctions.

In Example 1, using immunofluorescence, PI3K/MAPK phosphorylation, mRNA expression array, and metabolic pathway inhibition approaches, we reported that binding of DSG2 by Ad3 virions and Ad3 PtDds triggers an epithelial-to-mesenchymal transition in epithelial cells, resulting in transient opening of intercellular junctions. Intercellular junction opening mediated by interaction of Ad3 particles or recombinant PtDds with DSG2 was further supported by increased epithelial cell permeability and access to receptors that are trapped in intercellular junctions (e.g. Her2/neu). In the present study, we provide morphological (confocal immunofluorescence, EM) and functional (permeability, trastuzumab killing, Ad5 infection) data showing that Ad3-K/S/Kn also triggers junction opening. Importantly, other DSG2 ligands that are not able to multimerize and cluster DSG2 such as monomeric Ad3-E/S/Kn or monoclonal antibodies against different regions of DSG2 were unable to efficiently open junctions. It remains, however, the question how Ad3 can pass the tight junctions that are located at the apical side of DSG2/desmosomes. We speculate that efficient infection occurs through a positive feed-forward mechanism because the Ad-DSG2 mediated junction opening occurs within minutes thereby exposing DSG2 trapped in junctions to viral particles that are present at the site of infection. In the discussion of Ad3 infection mechanisms, it is also noteworthy that, during Ad3 replication, PtDds are formed at a massive excess of $5.5 \times 10^6$ PtDds per infectious virus (7). This suggests that PtDd formation is functionally important for Ad3, i.e. advantageous in spread or persistence of Ad3. A similar mechanism appears to take place in infection of epithelial cells by Ad5. During replication of Ad5, excess production of fiber results in the disruption of epithelial junctions either by interfering with CAR dimerization or by triggering intracellular signaling that leads to reorganization of intercellular junctions (4, 32). Recently, it has been suggested (based on in vitro studies) that CD46 is exposed apically on polarized epithelial respiratory cells and is therefore more likely to function as an Ad receptor for initial infection in vivo (9). We could not confirm this in human CD46 transgenic mice, where the CD46 expression pattern did not correlate with Ad transduction (19). Moreover, in polarized epithelial cancer cultures, we found CD46 trapped in intercellular junctions and not accessible to Ad35 applied to the cell surface (33). At this point, we believe that the question of how CD46-binding Ads disrupt the epithelial barrier remains to be answered.

The finding that Ad3-K/S/Kn triggers junction opening has practical implications because intercellular junctions represent physical obstacles for access and intratumoral dissemination of anti-cancer therapeutics (26-27). An epithelial junction opener would be relevant for cancer therapies with monoclonal antibodies directed against tumor-associated antigens that are trapped in epithelial junctions (e.g. Her2/neu or EGFR1) (33). A junction opener might also improve the efficacy of adoptive T-cell therapy (5) or treatment with liposomal chemotherapy drugs (10). Finally, Ad3-K/S/Kn might increase that efficacy of transduction of normal or malignant tissues by Ad5-based gene therapy vectors. The biotechnological applicability of Ad3-K/S/Kn is further underscored by the ease of its production and purification and by the fact that it spontaneously homodimerizes.

In conclusion, our study sheds light on the mechanisms of Ad3 infection of epithelial cells. The finding that Ad3-K/S/Kn, a small recombinant protein, triggers opening of epithelial junctions has implications for cancer therapy and drug delivery into epithelial tissues.

REFERENCES FOR EXAMPLE 2

1. Arnberg, N. 2009. Adenovirus receptors: implications for tropism, treatment and targeting. Rev Med Virol 19:165-178.
2. Chitaev, N. A., and S. M. Troyanovsky. 1997. Direct Ca2+-dependent heterophilic interaction between desmosomal cadherins, desmoglein and desmocollin, contributes to cell-cell adhesion. Cell Biol 138:193-201.
3. Coyne, C. B., and J. M. Bergelson. 2005. CAR: a virus receptor within the tight junction. Adv Drug Deliv Rev 57:869-882.
4. Coyne, C. B., L. Shen, J. R. Turner, and J. M. Bergelson. 2007. Coxsackievirus entry across epithelial tight junctions requires occludin and the small GTPases Rab34 and RabS. Cell Host Microbe 2:181-192.
5. Disis, M. L. 2009. Enhancing cancer vaccine efficacy via modulation of the tumor microenvironment. Clin Cancer Res 15:6476-6478.
6. Fasano, A., B. Baudry, D. W. Pumplin, S. S. Wasserman, B. D. Tall, J. M. Ketley, and J. B. Kaper. 1991. *Vibrio cholerae* produces a second enterotoxin, which affects intestinal tight junctions. Proc Natl Acad Sci USA 88:5242-5246.
7. Fender, P., A. Boussaid, P. Mezin, and J. Chroboczek. 2005. Synthesis, cellular localization, and quantification of penton-dodecahedron in serotype 3 adenovirus-infected cells. Virology 340:167-173.
8. Fender, P., R. W. Ruigrok, E. Gout, S. Buffet, and J. Chroboczek. 1997. Adenovirus dodecahedron, a new vector for human gene transfer. Nat Biotechnol 15:52-56.
9. Granio, O., K. J. Ashbourne Excoffon, P. Henning, P. Melin, C. Norez, G. Gonzalez, P. H. Karp, M. K. Magnusson, N. Habib, L. Lindholm, F. Becq, P. Boulanger, J. Zabner, and S. S. Hong. 2010. Adenovirus 5-fiber 35 chimeric vector mediates efficient apical correction of the cystic fibrosis transmembrane conductance regulator defect in cystic fibrosis primary airway epithelia. Hum Gene Ther 21:251-269.
10. Harper, B. W., A. M. Krause-Heuer, M. P. Grant, M. Manohar, K. B. Garbutcheon-Singh, and J. R. Aldrich-Wright. 2010. Advances in platinum chemotherapeutics. Chemistry 16:7064-7077.
11. Kalin, S., B. Amstutz, M. Gastaldelli, N. Wolfrum, K. Boucke, M. Havenga, F. DiGennaro, N. Liska, S. Hemmi, and U. F. Greber. 2010. Macropinocytotic uptake and infection of human epithelial cells with species B2 adenovirus type 35. J Virol 84:5336-5350.
12. Keim, S. A., K. R. Johnson, M. J. Wheelock, and J. K. Wahl, 3rd. 2008. Generation and characterization of monoclonal antibodies against the proregion of human desmoglein-2. Hybridoma (Larchmt) 27:249-258.
13. Kirby, I., E. Davison, A. J. Beavil, C. P. Soh, T. J. Wickham, P. W. Roelvink, I. Kovesdi, B. J. Sutton, and G. Santis. 2000. Identification of contact residues and definition of the CAR-binding site of adenovirus type 5 fiber protein. J Virol 74:2804-2813.
14. Koski, A., L. Kangasniemi, S. Escutenaire, S. Pesonen, V. Cerullo, I. Diaconu, P. Nokisalmi, M. Raki, M. Rajecki, K. Guse, T. Ranki, M. Oksanen, S. L. Holm, E. Haavisto, A. Karioja-Kallio, L. Laasonen, K. Partanen, M. Ugolini, A. Helminen, E. Karli, P. Hannuksela, T. Joensuu, A. Kanerva, and A. Hemminki. 2010. Treatment of cancer patients with a serotype 5/3 chimeric oncolytic adenovirus expressing GMCSF. Mol Ther 18:1874-1884.
15. Latorre, I. J., M. H. Roh, K. K. Frese, R. S. Weiss, B. Margolis, and R. T. Javier. 2005. Viral oncoprotein-induced mislocalization of select PDZ proteins disrupts tight junctions and causes polarity defects in epithelial cells. J Cell Sci 118:4283-4293.
16. Lee, C., J. Dhillon, M. Y. Wang, Y. Gao, K. Hu, E. Park, A. Astanehe, M. C. Hung, P. Eirew, C. J. Eaves, and S. E. Dunn. 2008. Targeting YB-1 in HER-2 overexpressing breast cancer cells induces apoptosis via the mTOR/STAT3 pathway and suppresses tumor growth in mice. Cancer Res 68:8661-8666.
17. Litowski, J. R., and R. S. Hodges. 2002. Designing heterodimeric two-stranded alpha-helical coiled-coils. Effects of hydrophobicity and alpha-helical propensity on protein folding, stability, and specificity. J Biol Chem 277:37272-37279.
18. Lortat-Jacob, H., E. Chouin, S. Cusack, and M. J. van Raaij. 2001. Kinetic analysis of adenovirus fiber binding to its receptor reveals an avidity mechanism for trimeric receptor-ligand interactions. J Biol Chem 276:9009-9015.
19. Ni, S., A. Gaggar, N. Di Paolo, Z. Y. Li, Y. Liu, R. Strauss, P. Soya, J. Morihara, Q. Feng, N. Kiviat, P. Toure, P. S. Sow, and A. Lieber. 2006. Evaluation of adenovirus vectors containing serotype 35 fibers for tumor targeting. Cancer Gene Ther 13:1072-1081.
20. Norrby, E., B. Nyberg, P. Skaaret, and A. Lengyel. 1967. Separation and characterization of soluble adenovirus type 9 components. J Virol 1:1101-1108.
21. Persson, B. D., D. M. Reiter, M. Marttila, Y. F. Mei, J. M. Casasnovas, N. Arnberg, and T. Stehle. 2007. Adenovirus type 11 binding alters the conformation of its receptor CD46. Nat Struct Mol Biol 14:164-166.
22. Sanchez, M. P., D. D. Erdman, T. J. Torok, C. J. Freeman, and B. T. Matyas. 1997. Outbreak of adenovirus 35 pneumonia among adult residents and staff of a chronic care psychiatric facility. J Infect Dis 176:760-763.
23. Shayakhmetov, D. M., and A. Lieber. 2000. Dependence of adenovirus infectivity on length of the fiber shaft domain. J Virol 74:10274-10286.
24. Shayakhmetov, D. M., T. Papayannopoulou, G. Stamatoyannopoulos, and A. Lieber. 2000. Efficient gene transfer into human CD34(+) cells by a retargeted adenovirus vector. J Virol 74:2567-2583.
25. Sonoda, N., M. Furuse, H. Sasaki, S. Yonemura, J. Katahira, Y. Horiguchi, and S. Tsukita. 1999. *Clostridium perfringens* enterotoxin fragment removes specific claudins from tight junction strands: Evidence for direct involvement of claudins in tight junction barrier. J Cell Biol 147:195-204.
26. Strauss, R., and A. Lieber. 2009. Anatomical and physical barriers to tumor targeting with oncolytic adenoviruses in vivo. Curr Opin Mol Ther 11:513-522.
27. Strauss, R., P. Soya, Y. Liu, Z.-Y. Li, S. Tuve, D. Pritchard, P. Brinkkoetter, T. Moller, O. Wildner, S. Pesonen, A. Hemminki, N. Urban, C. Drescher, and A. Lieber. 2009. Epithelial phenotype of ovarian cancer mediates resistance to oncolytic adenoviruses. Cancer Research 15:5115-5125.
28. Strauss, R., P. Soya, Y. Liu, Z. Y. Li, S. Tuve, D. Pritchard, P. Brinkkoetter, T. Moller, O. Wildner, S. Pesonen, A. Hemminki, N. Urban, C. Drescher, and A. Lieber. 2009. Epithelial phenotype confers resistance of ovarian cancer cells to oncolytic adenoviruses. Cancer Res 69:5115-5125.
29. Turley, E. A., M. Veiseh, D. C. Radisky, and M. J. Bissell. 2008. Mechanisms of Disease: epithelial-mesenchymal transition-does cellular plasticity fuel neoplastic progression? Nat Clin Pract Oncol.
30. Tuve, S., H. Wang, J. D. Jacobs, R. C. Yumul, D. F. Smith, and A. Lieber. 2008. Role of cellular heparan sulfate proteoglycans in infection of human adenovirus serotype 3 and 35. PLoS Pathog 4:e1000189.
31. Tuve, S., H. Wang, C. Ware, Y. Liu, A. Gaggar, K. Bernt, D. Shayakhmetov, Z. Li, R. Strauss, D. Stone, and A. Lieber. 2006. A new group B adenovirus receptor is expressed at high levels on human stem and tumor cells. J Virol 80:12109-12120.
32. Walters, R. W., P. Freimuth, T. O. Moninger, I. Ganske, J. Zabner, and M. J. Welsh. 2002. Adenovirus fiber disrupts CAR-mediated intercellular adhesion allowing virus escape. Cell 110:789-799.
33. Wang, H., Z. Y. Li, Y. Liu, J. Persson, I. Beyer, T. Moller, D. Koyuncu, M. R. Drescher, R. Strauss, X. B. Zhang, J. K. Wahl, 3rd, N. Urban, C. Drescher, A. Hemminki, P. Fender, and A. Lieber. 2011. Desmoglein 2 is a receptor for adenovirus serotypes 3, 7, 11 and 14. Nat Med 17:96-104.
34. Wang, H., Y. C. Liaw, D. Stone, O. Kalyuzhniy, I. Amiraslanov, S. Tuve, C. L. Verlinde, D. Shayakhmetov, T. Stehle, S. Roffler, and A. Lieber. 2007. Identification of CD46 binding sites within the adenovirus serotype 35 fiber knob. J Virol 81:12785-12792.
35. Yang, S. W., J. J. Cody, A. A. Rivera, R. Waehler, M. Wang, K. J. Kimball, R. A. Alvarez, G. P. Siegal, J. T. Douglas, and S. Ponnazhagan. 2011. Conditionally Replicating Adenovirus Expressing TIMP2 for Ovarian Cancer Therapy. Clin Cancer Res 17:538-549.
36. Yang, Z., M. Horn, J. Wang, D. D. Shen, and R. J. Ho. 2004. Development and characterization of a recombinant madin-darby canine kidney cell line that expresses rat multidrug resistance-associated protein 1 (rMRP1). AAPS J 6:77-85.

Example 3

A Recombinant Epithelial Junction Opener Improves Monoclonal Antibody Therapy of Cancer Abstract The therapeutic efficacy of monoclonal antibodies (mAbs) for cancer treatment is limited by intercellular junctions that tightly link epithelial tumor cells to one another. We generated a small, recombinant adenovirus serotype 3 derived protein, junction opener 1 (JO-1), which binds to the epithelial junction protein desmoglein 2 (DSG2). We demonstrate in mouse models with tumors derived from Her2/neu- and EGFR-positive human cancer cell lines that within one hour after intravenous injection, JO-1 mediates the cleavage of DSG2 dimers in intercellular junctions as well as the activation of intracellular signaling pathways that lead to a decrease in the level of the tight junction protein E-cadherin. JO-1-triggered changes in epithelial junctions enabled better intratumoral penetration of the anti-Her2/neu mAb trastuzumab (Herceptin) as well as for improved access to its target receptor, Her2/neu, which is partly trapped in junctions. This directly translated in a better therapeutic efficacy of trastuzumab in xenograft models using Her2/neu-positive breast, gastric, and ovarian cancer cells. Furthermore, the combination of JO-1 with the EGFR-targeting mAb cetuximab (Erbitux) greatly improved the therapeutic outcome in a model of metastatic EGFR-positive lung cancer. A combination of JO-1/trastuzumab treatment with an additional approach that allows for the transient degradation of tumor stroma proteins resulted in complete tumor eradication. In addition to its clinical relevance for cancer treatment, this study also sheds light on the mechanism of adenovirus serotype 3 infection of epithelial cells.

Introduction

Monoclonal antibodies (mAbs) have emerged as a class of novel oncology therapeutics. To date, there are 21 marketed therapeutic mAbs for the treatment of cancer, with hundreds of more currently in clinical development. Among the marketed mAbs are trastuzumab (Herceptin) and cetuximab (Erbitux). Trastuzumab targets the human epidermal growth factor receptor 2 (Her2/ErbB-2). The receptor for cetuximab is the human epidermal growth factor receptor 1 (Her1/ErbB-1). Both receptors belong to the family of tyrosine kinase receptors and initiate signaling through several pathways which promote cell survival and proliferation (Harari et al., 2007). Trastuzumab is used as a first line therapy in Her2/neu positive breast cancer patients and has also been approved for metastatic Her2/neu positive gastric cancer. Current FDA-approved indications for cetuximab include colorectal, head and neck, lung, and pancreatic cancer (Wheeler et al., 2010). Most patients with early stage breast or colon cancer have a measurable tumor response to trastuzumab and cetuximab therapy. However, in patients with advanced or recurrent disease, the response rate to these mAbs is only 8% to 10% (Adams and Weiner, 2005).

The mechanisms of trastuzumab and cetuximab action include the activation of antibody-dependent or complement-dependent cytotoxicity, and interference with tyrosine kinase receptor signaling that is required for tumor cell survival (Wheeler et al., 2010). A unifying aspect among these mechanisms is that tumor cell growth inhibition is dependent on the binding of mAbs to their corresponding receptors. Therefore, molecules that prevent access and binding to the receptor, either by physically inhibiting intratumoral transport from blood vessels to malignant cells or masking of receptors, are predicted to block trastuzumab and cetuximab activity (Lesniak et al., 2009). Among these molecules are tumor stroma proteins such as collagen or laminin (Li et al., 2004). In a recent study, we demonstrated that transient degradation of these stroma proteins significantly improved trastuzumab therapy (Beyer et al., 2011).

In addition to obstacles formed by tumor stroma proteins, the epithelial phenotype of cancer cells also creates physical barriers to cancer therapy (Strauss and Lieber, 2009; Strauss et al., 2009). Several studies demonstrated that the expression or upregulation of epithelial proteins correlated with increased resistance to trastuzumab (Fessler et al., 2009) and cetuximab (Oliveras-Ferraros et al., 2011) therapy of breast and colorectal cancer, respectively. Epithelial cells maintain several intercellular junctions (tight junctions, adherens junctions, gap junctions, and desmosomes), a feature which is often conserved in epithelial cancers in situ and in cancer cell lines (Turley et al., 2008). Epithelial junctions are composed of adhesive dimers consisting of cadherin molecules derived from two neighboring cells (Koeser et al., 2003). Desmogleins 1, 2, and 3 (DSG1-3) and desmocollins 1, 2, and 3 ($DSC_{1-3}$) are subclasses of cadherins. DSC2 and DSG2 are widely expressed and are found together in desmosomes of the basal layer of epithelial cells. The cytoplasmic tails of the desmosomal cadherins link the plasma membrane to the cytoskeleton through a complex of proteins, which include plakoglobin, desmoplakin, and plakophilins. Desmoglein 2

Figure 1:
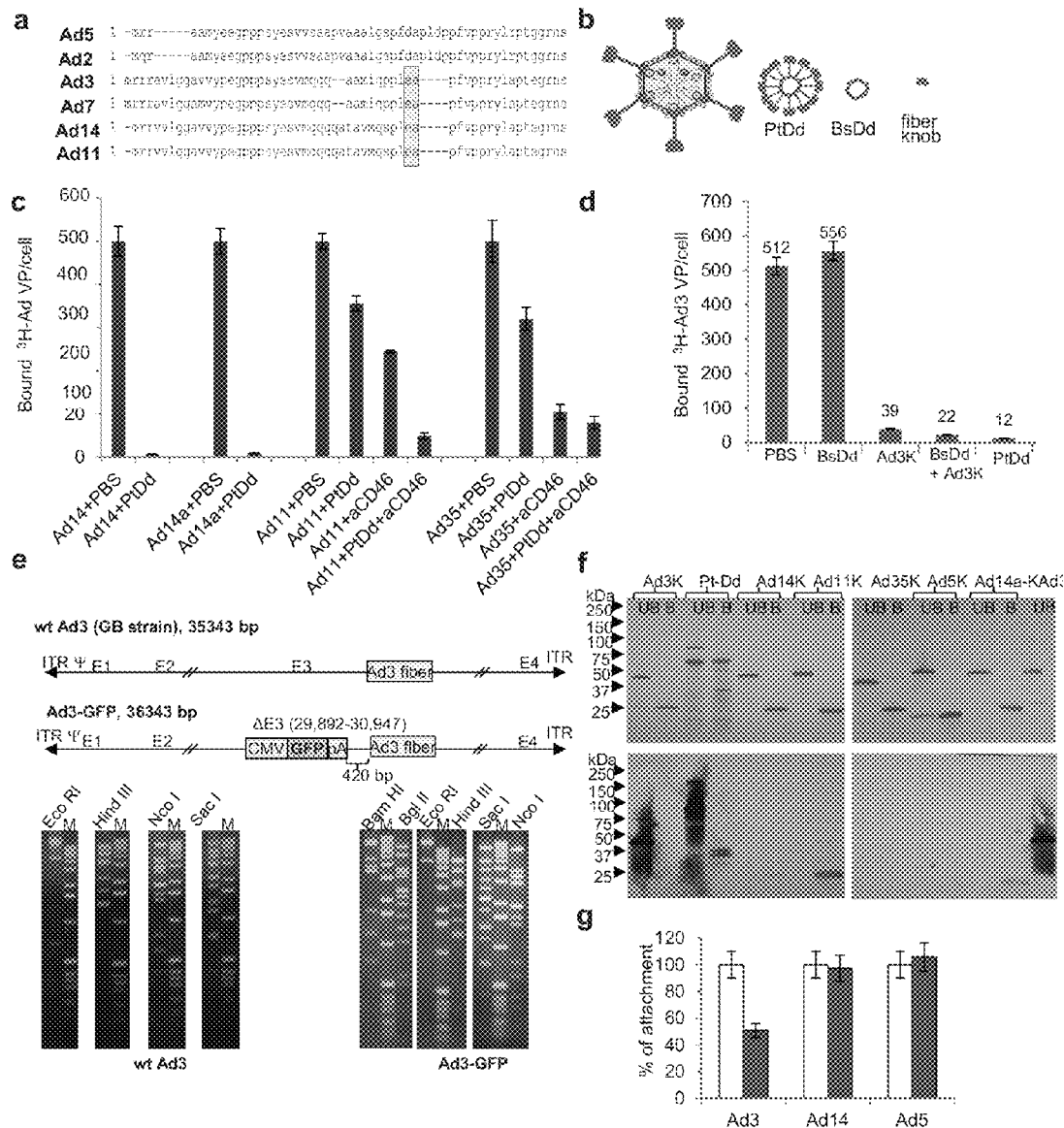
FIG. 1. Tools for Ad receptor identification and competition studies for Ad attachment.
a) Amino acid alignment of N-termini of Ad pentons. The protease cleavage site at aa 37/38 is marked in orange. b) Scheme of viral particles and particle components used in this study. PtDd possess 12 units containing penton base and trimeric fiber. BsDd only contain penton base. c) Competition of $^3$H-labeled Ad14, Ad14a, Ad11 and Ad35 virus attachment to HeLa cells after pre-incubation with Ad3 BsDd, PtDd, or antiCD46 antibodies (aCD46). Attachment in PBS-treated cells was taken as 100%. n=5. Notably, the finding that PtDd partially blocks Ad35 could be due to the physical proximity of DSG2 and CD46 in HeLa cells. d) Ad3 attachment studies as in c) after preincubation with both Ad3 fiber knob and BsDd (BsDd+Ad3K). The molar concentration of Ad3K was equal that of fiber knob within PtDd used for competition. e) Scheme of Ad3-GFP vector. The vector is based on wild-type Ad deleted for nt 29,892-30,947 to accommodate the CMV-GFP-polyA expression cassette. The lower panel shows restriction enzyme analyses of wt Ad3 and Ad3-GFP with the expected fragments. M: DNA size marker. f and g) Validation of polyclonal rabbit antibody against recombinant Ad3 fiber knob. f) Western blot. Ad knobs (Ad3K, Ad5K, 14K, 14aK, Ad11K, Ad35K) or PtDd were separated in PAG cells with (B) and without (UB) sample denaturation. Filters were incubated with antiAd3K antiserum and anti-rabbit-HRP antibodies. g) Inhibition of Ad attachment: $^3$H-labeled Ad3, Ad14 and Ad5 virus were incubated with PBS (white bars) or rabbit anti-Ad3K serum (grey bars) for one hour on ice, then added to HeLa cells for attachment studies.

(DSG2) is overexpressed in a series of epithelial malignancies, including breast cancer (Wang et al., 2011b) (Suppl. FIG. 1), ovarian cancer (Wang et al., 2011b) (Suppl. FIG. 1), lung cancer (Wang et al., 2011b), gastric cancer (Biedermann et al., 2005), squamous cell carcinomas (Harada et al., 1996), melanoma (Schmitt et al., 2007), metastatic prostate cancer (Trojan et al., 2005), and bladder cancer (Abbod et al., 2009).

In Example 1, we demonstrated that a group of human adenoviruses (Ads) (Ad serotype 3, 7, 11, and 14) use DSG2 as a primary attachment receptor for the infection of cells. Importantly, in epithelial cells, Ad3 binding to DSG2 triggered activation of signaling pathways resulting in the transient opening of epithelial junctions. The opening of junctions was reflected by an increased transepithelial permeability and by the unmasking of proteins that are trapped in tight junctions, e.g., the coxsackie-adenovirus receptor or the zonula occludens-1 protein. The opening of the epithelial junctions was also achieved with recombinant subviral particles, such as the penton-dodecahedra (PtDd), consisting of 12 Ad3 fibers linked to their penton bases (Fuschiotti et al., 2006; Norrby et al., 1967). We subsequently generated a minimal Ad3-derived DSG2 ligand formed by two fiber knob domains. This protein, with a molecular weight of approximately 50 kDa, is produced in *E. coli* and can be easily purified. In a series of functional studies we demonstrated that this protein efficiently triggers the opening of the junction. In the following study, we therefore refer to this protein as junction opener-1 (JO-1).

In this study, we have partially delineated the in vivo mechanism of JO-1-mediated junction opening. We show that Her2/neu and EGFR are trapped in the intercellular junctions in xenograft tumors. JO-1 treatment greatly increased the permeation of mAbs in tumors and significantly increased the efficacy of trastuzumab and cetuximab therapy in a series of xenograft tumor models.

Results

JO-1 Triggers Opening of Epithelial Junctions.

In the examples above, we showed that Ad3 particles or recombinant Ad3 penton-dodecahedra (PtDd) (FIG. 16A) bind to DSG2 and trigger the transient opening of epithelial junctions, which, in turn, increases the killing of Her2/neu positive BT474 breast cancer cells by trastuzumab. As the large size of Ad3 or PtDd particles can affect their egress from blood vessels and tissue penetration, we generated smaller Ad3-derived DSG2 ligands that are functionally active as epithelial junction openers. We found that high-affinity binding to DSG2 and subsequent junction opening requires Ad3 fiber dimers. Based on this finding, we designed a small, self-dimerizing Ad3 fiber derivative, called junction-opener 1 (JO-1) (FIGS. 16A, B). JO-1 has a molecular weight of ~50 kDa and is produced in *E. coli* prior to purification by affinity chromatography.

The functional activity of JO-1 was tested on polarized colon cancer T84 cells. This demonstrated that incubation of cells with JO-1 triggered remodeling of epithelial junctions, as shown by confocal microscopy for Claudin 7 and DSG2 (FIG. 16C). The desmosomal protein DSG2 is overlaps with adherens junctions marked by Claudin 7. Within 30 min after JO-1 binding to DSG2 Claudin 7 staining increases, which is most likely the result of better accessibility of antibodies to Claudin 7 (which are applied to the inner chamber of TRANSWELL™ cultures, i.e. the apical side of polarized epithelial cells). Opening of the tight junctions, which are localized apical to the desmosomal and adherence junctions, is illustrated by electron microscopy (FIG. 16D). Microphotographs of untreated epithelial cells show intact tight junctions as judged by the exclusion of the apically applied dye ruthenium red from basolateral space. Incubation of epithelial cells with JO-1 for 1 hour resulted in the disassembly of tight junctions and leakage of ruthenium red into the basolateral space (FIG. 16D, right panel). Exposure of polarized epithelial cells to JO-1 also increased the transepithelial permeability, as shown by transflux of $^{14}$C-PEG-4000 with a molecular weight of 4000 Da (FIG. 16E). Importantly, monoclonal antibodies against different regions of the extracellular domain of DSG2 did not significantly increase transepithelial permeability. We speculate that the ligation of several DSG2 molecules is required to trigger the opening of the junctions. Microscopy and permeability studies show that JO-1 triggers the opening of junctions within minutes. The effect of JO-1 is transient as is illustrated by the fact that 60 min subsequent to the removal of a JO-1 pulse treatment, junction structure and permeability is restored to normal morphology. When JO-1 was left on cells, the morphological changes in epithelial junctions could still be seen at 24 hours after the initial addition of JO-1 (data not shown).

JO-1 Triggers Intracellular Signaling and Increases Penetration of mAb in Epithelial Tumors In Vivo.

A breast cancer xenograft model was used to study the effect of JO-1 on epithelial junctions in vivo. Human breast cancer HCC1954 cells were injected into the mammary fat pad of CB17-SCID/beige mice. The resulting tumors resembled the histology of breast cancer in humans (Li et al., 2004), i.e. tumors were vascularized and contained nests of epithelial cells glued together by epithelial junctions and surrounded by extracellular matrixes). When tumors reached a volume of ~200 mm$^3$, JO-1 was injected intravenously. JO-1 could be detected in the tumors by immunofluorescence microscopy as early as 1 hour post-injection. JO-1 accumulated in the tumors as is indicated by the increased immunofluorescence at 12 hours post injection (FIG. 17A, left three panels). This is also confirmed by Western blot analysis of tumor lysates (FIG. 17A, right panel). Analysis of DSG2 on tumor sections by immunofluorescence microscopy in PBS treated animals showed membrane localized signals (FIG. 17B, left panel). One hour subsequent to JO-1 injection, DSG2 molecules were mostly found in the cytoplasm of the tumor cells (second panel). By 12 hours, membrane localization of DSG2 appeared to be partly restored (third panel). Western blot analysis using anti-DSG2 antibodies against the extracellular domain of DSG2 revealed smaller fragments of the DSG2 extracellular domain (ECD), probably produced by proteolytic cleavage, at the 1 hour time point (FIG. 17B, right panel). Taken together these data suggest that JO-1 triggers cleavage within the DSG2 ECD and DSG2 internalization. We speculate that this disrupts DSG2 dimers between two neighboring epithelial tumor cells and contributes to remodeling of lateral junctions. No toxic side effects or changes in histology of normal epithelial tissues of the gastrointestinal or respiratory tracts were observed in JO-1 treated animals.

In the examples above, it was found in in vitro studies that Ad3 binding to DSG2 of epithelial cells triggered intracellular signaling including pathways that are involved in epithelial-to-mesenchymal transition (EMT). EMT is a reprogramming process involved in embryonal development, but also in tumor metastasis. Among the feature that characterize EMT are decreased expression of epithelial markers, altered location of transcription factors, and activation of Erk1/2 (MAPK) (Turley et al., 2008). In our studies with xenograft tumors, we found less non-phosphorylated and phosphorylated forms of E-cadherin in tumors 12 hours after intravenous injection of JO-1 (FIG. 17C, left panel). Preceding the changes in E-cadherin, was an increase in phosphorylated Erk1/2 (FIG. 17C, compare pErk1/2 PBS vs. JO-1 (1 h)). It is well established that ERK1/2 activation results in a decrease of E-cadherin expression and phosphorylation during EMT (Andarawewa et al., 2007; Larsen et al., 2003; Turley et al., 2008). The decrease in E-cadherin and an increase in signals for phosphorylated Erk1/2 upon JO-1 injection were also observed by immunofluorescence microscopy (FIG. 17C, right panels).

Overall, these studies indicate that JO-1 triggers activation of Erk1/2 pathways in vivo, in HCC1954 tumors. Based on this, we hypothesize that opening of epithelial junctions by binding of JO-1 to DSG2 involves at least two mechanisms: i) cleavage of the DSG2 ECD, and disruption of DSG2 dimers with subsequent internalization; and ii) induction of EMT-like events through the activation of Erk1/2. Next, we tested whether JO-1-triggered opening of epithelial junctions in tumors would increase the penetration of monoclonal antibodies into xenograft tumors. Trastuzumab, which is a humanized IgG1 mAb, was initially utilized for this study. As in previous studies, trastuzumab was injected intraperitoneally at a dose of 10 mg/kg. Trastuzumab was visualized in tumors with antibodies specific to human IgG. In tumor sections and Western blot analyses, trastuzumab was detectable 1 hour post-injection and at higher levels 12 hours after injection (FIG. 18). Intravenous injection of JO-1 one hour prior to the administration of trastuzumab, visibly increased the amount of trastuzumab in the tumors, indicating either better egress from blood vessels, better intratumoral penetration, and/or longer intratumoral half-life.

mAb Targets are Trapped in Epithelial Junctions.

In breast cancer xenograft sections and in cultured breast cancer cells, we found co-staining of Her2/neu and the adherens junction protein Claudin 7 (FIG. 19A,). Confocal microscopy of breast cancer BT474 cells confirmed the trapping of Her2/neu in lateral junctions. This is in agreement with an earlier study, demonstrating that Her2/neu is a basolateral protein that becomes accessible from the apical surface only when the tight junctions are disrupted (Vermeer et al., 2003). Incubation of the Her2/neu positive breast cancer cell lines BT474 (FIG. 19) or HCC1954 (not shown) with JO-1 changed the composition of the lateral epithelial junctions within 1 hour. As a result of this, Her2/neu staining at the cells surface became more intense, while it faded in areas distal to the cell surface. This suggests that JO-1 mediated junction opening triggered a translocation of Her2/neu from lateral membranes to the cell surface. The effect of JO-1 on lateral junctions was transient and cellular morphology returned to that of control cells by 16 hour after JO-1 pulse treatment. Being trapped in epithelial junctions also appears to be a problem for other cancer therapy targets such as EGFR1 (the target for cetuximab/Erbitux) as co-staining for EGFR and the tight junction protein E-cadherin suggests (FIG. 19B). In our studies with cetuximab we focused on a lung cancer model (A549 cells), as most colon cancer cell lines have mutations in K-ras, which confers resistance to cetuximab (Karamouzis et al., 2007). Similar to what we observed for Her2/neu, incubation of A549 cells with JO-1 resulted in a translocation of EGFR to the cell surface.

Release of mAb receptors from trapping is supported by the enhanced killing of cancer cells by trastuzumab and cetuximab. In vitro killing of BT474 breast cancer and A549 lung cancer cells by trastuzumab and cetuximab, respectively, was inefficient (FIGS. 19C and D). Pretreatment of these cells with JO-1 significantly increased in vitro cytotoxicity of both antibodies in the corresponding cell lines. Overall, these studies indicate that JO-1 mediates junction opening thereby allowing for a better intratumoral penetration of mAbs, as well as improving the access to their target receptors that otherwise are trapped in the junctions. Based on this we performed a series of in vivo studies to investigate whether JO-1 pre-treatment can improve the therapeutic efficacy of mAbs in xenograft models.

JO-1 Improves Trastuzumab Therapy In Vivo.

JO-1's potential enhancement of trastuzumab therapy was first tested in an orthotopic breast cancer model based on Her2/neu positive BT474-M1 cells. JO-1 injection alone had no significant effect on tumor growth (FIG. 20A). BT474-M1 tumors initially responded well to trastuzumab; however, pre-injection of JO-1 significantly enhanced the therapeutic efficacy of trastuzumab (FIG. 20A). These findings are in agreement with our studies with PtDd in this model. The enhancing effect of JO-1 pretreatment becomes more apparent when treated mice were followed long-term, i.e. for 136 days. While 60% of the animals that received trastuzumab monotherapy relapsed around day 100, none of the animals treated with JO-1+trastuzumab showed tumor re-growth (data not shown).

A second breast cancer model involved HCC1954 cells. Tumors derived from these cells are more resistant to trastuzmab (FIG. 20B). As seen in the BT474-M1 model, JO-1 pretreatment significantly improved trastuzumab therapy and stalled tumor growth. The enhancing effect of JO-1 was comparable to that of PtDd (data not shown). Based on our study with PtDd, we chose a time interval of 10 hours between JO-1 and trastuzumab injections. This regimen is supported by the kinetics of JO-1 accumulation in tumors and the kinetics of E-cadherin decrease (see FIGS. 17A and C). On the other hand, events that appear to be linked to junction opening, i.e. DSG2 cleavage or Erk1/2 activation, occur already within 1 hour after JO-1 injections. We therefore investigated how simultaneous JO-1/trastuzumab injection and injection of trastuzumab 1 hour after JO-1 application influenced the therapeutic outcome (FIG. 20C). In this study no significant difference was found when compared to the treatment approach used initially (trastuzumab 10 hours after JO-1). We speculate that this is due to the relative slow accumulation of the protein in the tumors.

To further consolidate the clinical relevance of JO-1 as a co-therapeutic for trastuzumab, we performed efficacy studies in a Her2/neu-positive gastric cancer (NCI-N87) model (FIG. 21). Similar to the breast cancer model, we found co-staining of Her2/neu and Claudin 7 in NCI-N87 cultures and xenograft tumors, suggesting trapping of Her2/neu in epithelial junctions. To establish the gastric cancer xenograft model, NCI-N87 cells were injected subcutaneously. Pre-treatment of tumor-bearing mice with JO-1 significantly improved trastuzumab therapy as reflected by delayed tumor growth.

JO-1 Improves Cetuximab Therapy In Vivo.

Figure 22A:
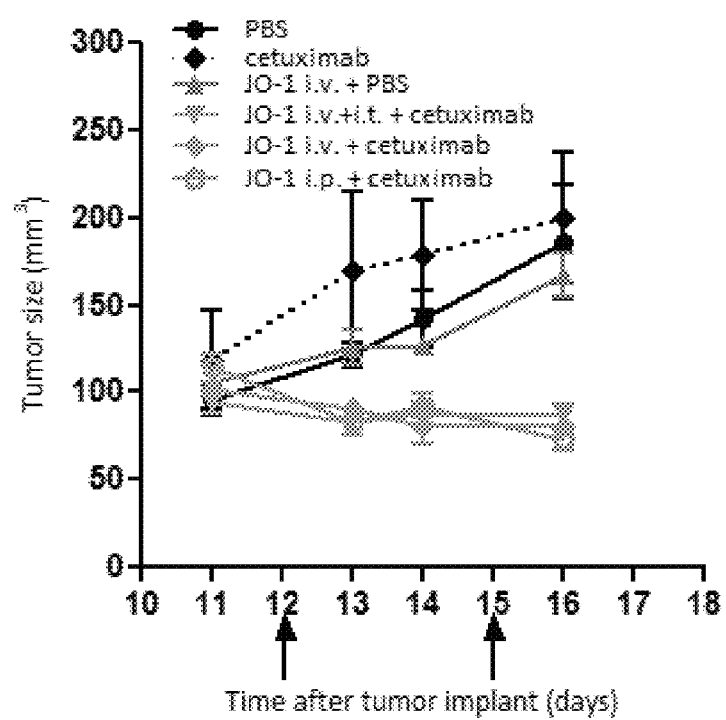
Figure 22B:
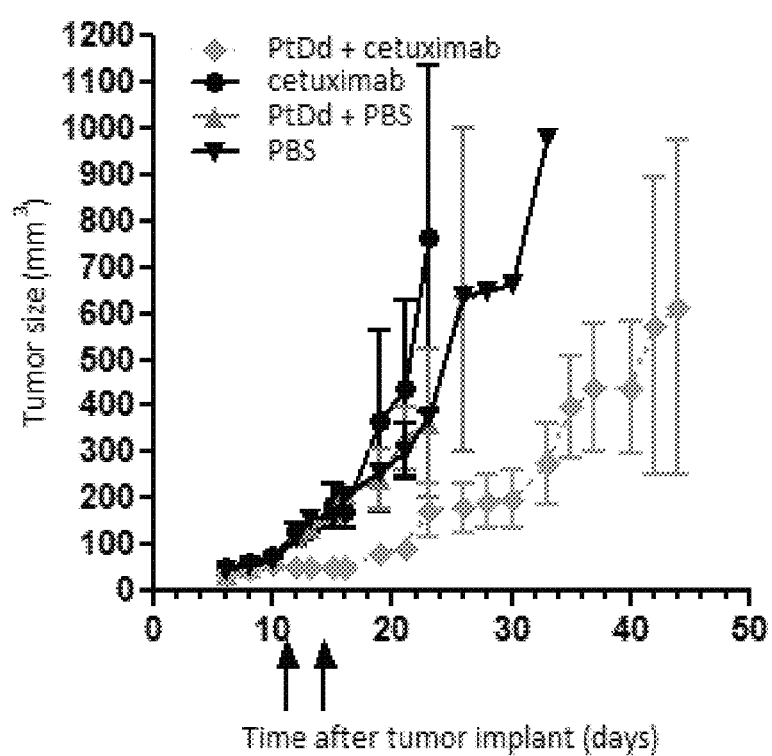

A xenograft model with subcutaneous tumors derived from A549 lung cancer cells was initially utilized. Cetuximab treatment of mice with pre-established A549 tumors did not result in a significant delay of tumor growth when compared to treatment with PBS. JO-1 was injected intravenously or intraperitoneally followed by cetuximab 12 hours later. Both treatment approaches had a significant therapeutic effect and resulted in a decrease of tumor volumes (FIG. 22A). An additional combination of intravenously injected JO-1 with an intratumoral application of the junction opener did not further increase the therapeutic efficacy. As seen in the breast cancer model, JO-1 treatment alone did not exert a significant anti-tumor effect. JO-1 pretreatment enhanced cetuximab therapy to a similar degree as seen with PtDd (FIG. 22B).

Figure 22C:
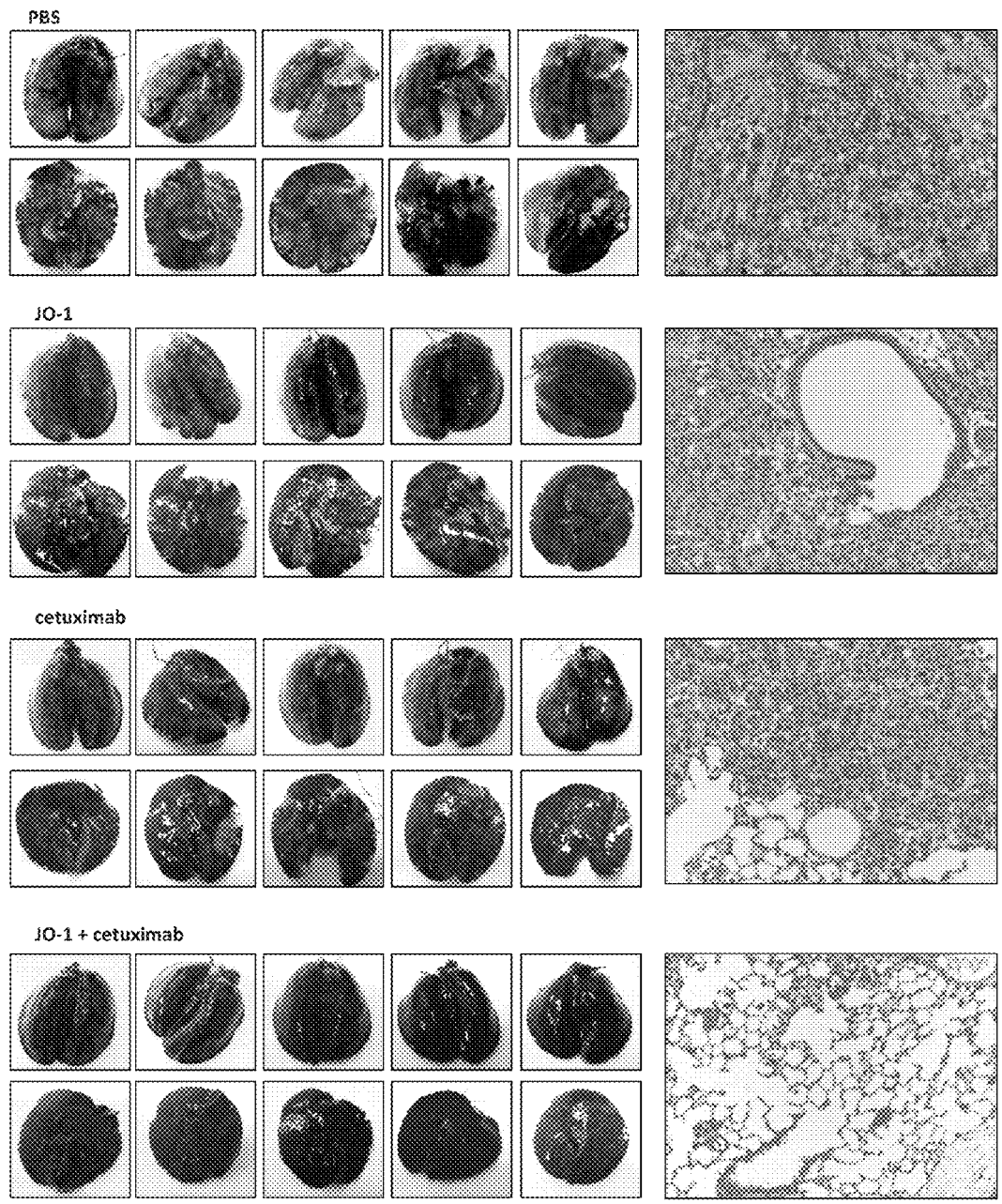

Next, the co-therapy approach was tested in an orthotopic lung cancer model. To establish this model, A549 cells were injected intravenously. In this model, mice became morbid within 37 days of tumor cell transplantation with predominant tumor localization to the lung (FIG. 22C, "PBS" group). Treatment of mice was started at day 10, i.e. 27 days before the animals in the control group reached the endpoint of the study. All animals were sacrificed at day 40. While lung metastases were clearly visible in the control group, JO-1 group, as well as the cetuximab treated animals, 80% of the lungs in the JO-1+cetuximab-treated animals were free of tumor when inspected macroscopically. Microscopy of lung sections showed that in PBS treated animals, tumor cells almost completely replaced normal lung tissue and also filled the bronchioli. (FIG. 22C, right panels). Invasion into the bronchioli was less pronounced in cetuximab injected animals. Importantly, while cetuximab treated animals had considerable, infiltrating tumor growth, the majority of JO-1+ cetuximab injected animals showed only micrometastases.

Combined Tumor Stroma Protein Degradation and Junction Opening.

We have recently shown in immunohistochemical studies of tumor sections from cancer patients and xenografts that the extracellular matrix proteins forming the tumor stroma tightly surround nests of malignant breast and colon cancer cells (Li et al., 2009). Transient degradation of tumor stroma proteins by intratumoral expression of the peptide hormone relaxin significantly enhanced trastuzumab therapy (Beyer et al., 2011). Here, we utilized the HCC1954 model to test whether additional transient tumor stroma protein degradation, would further increase the effect of JO-1 on trastuzumab therapy (FIG. 23A). To deliver the relaxin gene to the tumor we employed an approach based on hematopoietic stem cells (HSCs) (Li et al., 2009). This approach capitalizes on the observation that tumor cells secrete a number of chemokines that actively mobilize myeloid progenitors from the bone marrow and recruit them to the tumor stroma, where they differentiate into tumor-associated macrophages (TAMs). TAMs are critical for tumor survival as they produce factors that trigger/support tumor growth, neo-angiogenesis, immune escape and stroma development. The approach involved the ex vivo transduction of bone marrow derived HSCs with lentivirus vectors expressing the transgene under control of a Doxycycline (Dox)-inducible transcription cassette, and the transplantation of these cells into myelo-conditioned recipients, where they engraft in the bone marrow and provide a long-term source of genetically modified cells that will home into tumors. This study (FIG. 23B) showed that relaxin expression alone significantly delayed tumor growth and increased trastuzumab therapy. The combination of relaxin expression and JO-1 treatment stopped tumor growth. Tumors did not re-grow when treatment was terminated, in contrast to groups that received either relaxin+trastuzmab or JO-1+trastuzumab therapy. Histological analyses of residual masses in the JO-1/relaxin/trastuzumab group at the end of the observation period, showed only connective tissue. In contrast, explanted tumors from the other groups contained tumor cells, which could be cultured in vitro upon protease digestion of tumors. Notably, no adverse side effects were observed in mice that received the triple combination (JO-1/relaxin/trastuzumab) treatment. Our data underscore that physical obstacles in tumors are involved in mediating resistance to trastuzumab therapy.

Effect in the Presence of Antibodies Against JO-1 on In Vitro Cytotoxicity Assays.

Ad3 is a widely distributed pathogen. As such, JO-1 is a viral protein, which can potentially be immunogenic, and can interfere with its therapeutic activity after repeated administration. Ten out of 30 serum samples from breast cancer patients tested positive for neutralizing Ad3 antibodies (data not shown). This is in agreement with reports that the serum prevalence for neutralizing anti-Ad3 antibodies in humans (by age 10) is ~40% (Sakamoto et al., 1995). We show, however, that the anti-Ad3 antibody-positive human sera did not react with JO-1 (data not shown). This is not surprising as most neutralizing antibodies are directed against the Ad hexon (Sumida et al., 2005). To obtain anti-JO-1 positive serum, mice were vaccinated with JO-1 (data not shown). In in vitro cytotoxicity studies, no interference was found of the anti-JO-1 antibodies with the enhancing effect of JO-1 on trastuzumab killing of Her2/neu-positive BT474 cells (data not shown). Along this line, pooled human serum from healthy volunteers or breast cancer patients also did not interfere with the function of JO-1.

Discussion

JO-1 as New Co-Therapeutic.

Despite their success in many areas, the therapeutic efficacy of mAbs are limited, with only a minority of patients responding to these agents as monotherapies. The action of many anti-cancer mAbs, including trastuzumab and cetuximab, involve binding to the corresponding target receptors on tumor cells. Target receptor masking or preventing intratumoral dissemination of mAbs is a potential shielding and escape mechanism for cancer cells (Lesniak et al., 2009). In addition to the barriers formed by tumor stroma proteins, such as collagen or laminin, the epithelial phenotype of epithelial cancer also creates obstacles to mAb therapy. A recent study reported that the expression of epithelial features such as mucin 1 correlated with trastuzumab resistance (Fessler et al., 2009). Furthermore, the upregulation of E-cadherin contributed to resistance to cetuximab therapy of colorectal cancer (Oliveras-Ferraros et al., 2011).

While it has long been known that tumor invasion and metastasis is accompanied by EMT, recent studies have shown that this process can be reversed by a mesenchymal-to-epithelial transition (MET) (Thiery and Sleeman, 2006). Regaining epithelial features, including epithelial junctions, appears to represent a protection mechanism for the tumor that also shields it from anti-cancer treatment (Brennan et al., 2010; Strauss et al., 2009; Thiery and Sleeman, 2006). In this context, we found in studies on primary ovarian cancer cells that acquisition of chemoresistance and the formation of putative cancer stem cells involved processes reminiscent of MET (Strauss et al., 2011).

We hypothesized that an approach that allows for a transient dissolution of epithelial junctions could improve the therapeutic efficacy of mAbs such as trastuzumab and cetuximab. In the context of basic adenovirological studies, we designed the small recombinant protein JO-1. JO-1 binding to DSG2 resulted in the transient opening of tight junctions. This increased the penetration of trastuzumab in the tumor and allowed for better access to mAb target receptors, which, in turn, facilitated mAb therapy in a series of xenograft models involving human epithelial tumor cells. Potentially, the combination of JO-1 with trastuzumab and cetuximab might allow the reduction of the effective dose of these mAbs, thereby reducing critical side effects, i.e. trastuzumab-associated cardiotoxicity and acne-like rashes that often occur during cetuximab therapy.

JO-1 is an attractive therapeutic for development because it can be produced in high yields in E. coli. Notably, DSG2 ligands that are not able to cluster DSG2, such as monoclonal antibodies against DSG2, are inefficient in junction opening in the tumor models used in this study. To our knowledge, there is no other therapy in development that binds to DSG2, and is able to sensitize tumors to mAbs. A series of pathogens have evolved mechanisms to disrupt junction integrity. For example, *Vibrio cholerae* strains produce *Zona occludens* toxin (Zot), which possesses the ability to reversibly alter intestinal epithelial junctions, allowing the passage of macromolecules through mucosal barriers (Fasano et al., 1991). A Zot-derived hexapeptide (AT-1001) has been developed, however clinical testing in patients with coeliac disease was recently stopped due to safety concerns and the lack of efficacy.

Mechanisms of Action.

Our data suggest that JO-1 triggers junction opening in epithelial tumors through two, potentially connected mechanisms: the disruption of DSG2 dimers in intercellular junctions and/or intracellular signaling that leads to a decrease of E-cadherin and potentially other junction proteins. Because cadherins form dimers between neighboring cells, a number of pathogens have evolved mechanism to trigger cleavage within the extracellular domain of cadherins. *Candida albicans*, an organism able to invade the bloodstream via the gastrointestinal tract, binds to E-cadherin and triggers cleavage of both intra- and extracellular domains of E-cadherin, thereby destabilizing the homotypic interactions between adjacent epithelial cells (Frank and Hostetter, 2007). Furthermore, *Bacteroides fragilis* enterotoxin and *Porphyromonas gingivalis* gingipains have been associated with the degradation of E-cadherin (Katz et al., 2000; Wu et al., 1998). Both of these studies attributed the cleavage of E-cadherin to a specific bacterial protease. Our data suggest that Ad3 uses a similar mechanism to breach the epithelial barrier in the respiratory tract. We are currently studying the mechanisms of DSG2 cleavage. In ongoing studies, we are attempting to determine whether JO-1 binding triggers conformational changes within DSG2. Dissolution of DSG2 dimers might in turn destabilize more apically localized tight junctions as discussed recently (Koeser et al., 2003).

Based on in vitro studies above, Ad3 binding to DSG2 triggers the activation of Erk1/2 and other pathways involved in EMT. This study shows that Erk1/2 is activated in tumors within 1 hour after intravenous JO-1 injection. Our finding is in agreement with previous reports showing that cadherins engage in bidirectional signaling with the receptor tyrosine kinases to regulate intercellular junctions (Klessner et al., 2009). We are currently generating various DSG2 knockout models and truncated/mutated DSG2 variants to better delineated the role of DSG2 in maintaining epithelial junctions.

Side Effects on Normal Epithelial Tissues.

In humans and non-human primates, DSG2 is expressed in the gastro-intestinal and respiratory tracts (Li et al., 2011). As the mouse orthologue of DSG2 is not recognized by Ad3 or JO-1 (Wang et al., 2011b), safety studies in normal mice are relatively inadequate. We have therefore generated transgenic mice containing the human DSG2 locus. The expression pattern and level of human DSG2 in these animals were similar to those found in humans. Furthermore, we showed that JO-1 binding to human DSG2 in transgenic mouse epithelial cells triggered junction opening to a degree similar to data observed in human cells. In preliminary studies with DSG2-transgenic mice we did not find critical side effects of intravenous JO-1 injection (2 mg/kg) (Li et al., 2011). We speculate that DSG2 in normal epithelial cells is not readily accessible to intravenously applied JO-1. On the other hand, greater leakage of tumor-associated blood vessels and the lack of strict cell polarization might make epithelial tumors more responsive to JO-1. Lack of toxicity after intravenous injection of JO-1 ligands is also underscored by studies with adenoviruses containing Ad3 fibers. These viruses bind to DSG2 and act on junctions the same way as JO-1. Intravenous injection of Ad5/3 or Ad3 oncolytic vectors into humans was found to be safe (Hemminki et al., 2010; Koski et al., 2010). We are currently conducting detailed toxicity studies in non-human primates and DSG2-transgenic mice to validate the potential of JO-1 as a safe therapeutic.

JO-1 Immunogenicity.

As JO-1 is a viral protein, adaptive immune responses might develop in humans, particularly after repeated injection. This might, however, not be a clinical problem. The first-line treatment of Her2/neu-positive metastatic breast cancer is trastuzumab in combination with chemotherapeutic drugs (doxorubicin, cyclophosphamide, paclitaxel, or docetaxel). Also, cetuximab is used in combination with chemo-therapeutics (vinorelbine plus cisplatin) in non-small cell lung cancer patients. It is likely that the immunosuppressive chemotherapy prevents immune responses against JO-1. Again, this expectation is supported by studies with oncolytic adenovirus vectors. In these studies, immunosuppression allowed for repeated vector application (Thomas et al., 2008). On the other hand, it would be beneficial if JO-1 could be used in immunocompetent cancer patients. For example, JO-1 can theoretically act as an immunostimulatory monotherapy by increasing the access and intratumoral penetration of pre-existing or transplanted anti-tumor T-cells. Tumor-specific T-cells are frequently found in untreated breast cancer patients, even at late stages of disease, and transfer of these cells into mice has been shown to reject xenotransplanted autologous tumors (Beckhove et al., 2004; Disis et al., 1994; Disis et al., 2000; Feuerer et al., 2001; Toso et al., 1996). Therefore, we started to investigate in more detail JO-1 immunogenicity. Despite the fact that approximately one third of humans have neutralizing antibodies against Ad3, our studies showed these antibodies did not interact with JO-1 (Suppl. FIG. 5). Furthermore, anti-JO-1 antibodies generated by vaccination of mice did not affect the enhancing effect of JO-1 on trastuzumab killing in vitro. This is most likely due to the high affinity of the JO-1-DSG2 interaction (Wang et al., 2011a). We are currently establishing syngeneic tumors in hu-DSG2-transgenic mice to investigate how anti-JO-1 immune responses affect its efficacy. Potential Risk to Enhance Tumor Invasion and Metastasis.

In agreement with other studies (Wang et al., 2011b), (Biedermann et al., 2005), (Harada et al., 1996), (Schmitt et al., 2007), (Trojan et al., 2005), (Abbod et al., 2009), we found a higher DSG2 expression in malignant tissues than in the surrounding normal epithelial tissue. Furthermore, a recent study on squamous cell cervical cancer demonstrated that in contrast to all other desmosomal proteins, DSG2 was up-regulated in invasive cancer (Kurzen et al., 2003). There are, however, also studies reporting a reduction in the amounts of DSG2 in invasive pancreatic or gastric cancer (Ramani et al., 2008; Yashiro et al., 2006). The latter, as well as the finding that JO-1 triggers EMT-like signaling, might raise the question of whether JO-1 would facilitate metastasis. Notably, in all models used in this study, we did not see stimulation of tumor growth or macroscopic/microscopic signs of metastasis in animals treated with JO-1 alone. Tumor invasion and metastasis requires more than transient activation of EMT pathways. Detachment from epithelial cancers and migration of tumor cells is only possible after long-term crosstalk between malignant cells and the tumor microenvironment, resulting in changes in the tumor stroma and phenotypic reprogramming of epithelial cells into mesenchymal cells (Guarino, 2007).

In summary, the epithelial junction opener JO-1 has the potential to improve mAb therapies of cancer both in term of efficacy and safety, i.e. by allowing lower therapeutic mAbs doses. This study also sheds light on the mechanisms of Ad3 infection of epithelial cells.

Material and Methods

Proteins and Antibodies.

The generation of JO-1 (also known as Ad3-K/S/Kn) has been described previously (Wang et al., 2011a). JO-1 was produced in *E. coli* using the pQE30 expression vector (QIAGEN™, Valencia, Calif.) and purified by Ni-NTA agarose chromatography as described elsewhere (Wang et al., 2007). Recombinant Ad3 penton-dodecahedral (PtDd) protein complexes were produced in insect cells and purified as described elsewhere (Fender et al., 1997).

The following antibodies were used for immunofluorescence studies or Western blot: polyclonal goat anti-DSG2 (R&D Systems, Inc., Minneapolis, Minn.), mouse mAb anti-DSG2 (clone 6D8) (Cell Sciences, Canton, Mass.), rabbit anti-Claudin 7 (ABCAM™, Cambridge, Mass.), anti-human IgG-FITC (Santa Cruz), rabbit anti-EGFR (ABCAM™), mouse anti-Her2/neu (ABCAM™), mouse anti-E-cadherin (Cell Signaling), mouse anti-human IgG Fc (R&D Systems), mouse mAb against phospho-p44/42 MAPK (Erk1/2) (Thr202/Tyr204) (Cell Signaling), mouse anti-Erk1/2 (Cell Signaling), mouse anti-phospho-E-cadherin (pS838/840) (Epitomics, Inc.), mouse anti-6-His (QIAGEN™)

Cell Lines.

BT474-M1 cells were cultured in DMEM/F12 with 10% FBS, 1% Pen/Strep and 2 mM L-Glutamine. HCC1954 breast cancer, A549 lung cancer and NCI-N87 cells were cultured in RMPI with 10% FBS and 1% Pen/Strep. SKOV3-ip1 cells were cultured in MEBM medium. Colon cancer T84 cells were cultured in a 1:1 mixture of Ham's F12 medium and DMEM, with the addition of 10% FBS, Glu and Pen/Strep. To achieve cell polarization, $1.4 \times 10^5$ T84 cells were cultured in collagen-coated 6.5 mm TRANSWELL™ inserts (0.4 µm pore size) (Costar TRANSWELL™ Clears) for a period of 14 to 20 days until transepithelial resistance was stable (Wang et al., 2011b).

Immunofluorescence Analyses.

Cells were cultured in chamber glass slides (BD Falcon), washed twice with ice-cold PBS and then fixed with methanol/acetone (1:1 vol/vol) for 15 min at 4° C., or with 4% paraformaldehyde for 30 min at 4° C. Cells were washed twice with PBS after fixation and subsequently blocked with PBS containing 2% dry-milk powder (BIORAD™) for 20 min at room temperature. Antibodies were diluted in PBS (Claudin7 1:100, DSG2 1:100, Her2/neu 1:50, EGFR 1:50, E-cadherin 1:100, Human IgG 1:400, phospho-p44/42 MAPK 1:400, Penta-His 1:500) and cells were stained for 90 min at room temperature or at 4° C. overnight. When required, suitably directed secondary antibodies directed were applied after 3 washes with PBS for a period of 30 min at room temperature. Glass slides were mounted using VECTASHIELD with DAPI (VECTOR LABS™). Photographs were obtained with a Leica DFC300FX digital camera. Confocal images were taken on a ZEISS™ META Confocal Microscope using 40× or 100× oil lenses and ZEISS™ 510 software (ZEISS™ MicroImaging, Thornwood, N.Y.).

Tissues.

Paraffin sections of human breast cancers were deparaffinized and rehydrated. Antigen retrieval was performed with Vector Antigen Unmasking solutions pH 6.0 (VECTOR LABORATORIES™, Inc., Burlingame, Calif.). Mouse anti-DGS2 antibody (3G132) (ABCAM™) was diluted 1:10. Immunohistochemistry was performed using the Polink-2 HRP Broad Kit (Golden Bridge International, Inc. Mukilteo, Wash.) and DAB as a substrate.

Western Blot.

Xenograft tumor tissue was dissected, manually homogenized (tissue disruptor) and incubated for 30 min in protein lysis buffer [20 mM Hepes (pH 7.5), 2 mM EGTA, 10% glycine, 1% TritonX100, 150 mM NaCl (all from SIGMA-ALDRICH™), and protease/phosphatase inhibitors (Complete Protease Inhibitor Cocktail and PhosSTOP, Roche)] on ice. Confluent cultured cells were washed twice with ice-cold PBS and then lysed for 30 min in protein lysis buffer on ice. Samples were pelleted (10 min, 4° C., 15,000 RPM, and the protein containing supernatant stored at −80° C. A total of 80 µg of total protein was used for the Western blot procedure. Protein samples were boiled (5 min at 95° C.) and separated by polyacrylamide gel electrophoresis (PAGE) using 10% Bis-Tris gels and MOPS buffer (Novex, INVITROGEN™), followed by transfer onto nitrocellulose membranes according to the supplier's protocol (iBlot, INVITROGEN™). Membranes were blocked in PBS containing 0.1% Tween20 (PBS-T, Sigma) and 5% dry milk powder. Incubation times for primary and secondary antibodies were 16 h at 4° C. and 1 h at room temperature, respectively. Antibodies were diluted [Human IgG 1:1000, DSG2 1:500, Ad3-K serum 1:2000, p-E-cadherin 1:2000, E-cadherin 1:1000, Claudin7 1:500, Vimentin 1:2000, phospho-p44/42 MAPK (Erk1/2) 1:2000, Erk1/2 1:2000] in PBS-T and 5% dry-milk powder. Membranes were washed 5 times in PBS-T between antibody incubations, and films were developed using ECL plus (AMERSHAM™) or the Odyssey system (LI-COR BIOSCIENCES™)

DSG2 mRNA PCR:

Reverse transcription was performed on 1 µg of total RNA using the Quantitect Reverse Transcription Kit (QIAGEN™) to evaluate the expression levels of DSG2 in breast cancer. The expression of the housekeeping gene GAPDH was used as reference. The quantitative PCR (qPCR) was run in triplicates using the SensiMix SYBR Kit (Quantace) on a 7900HT Fast Real-Time PCR System (APPLIED BIOSYSTEMS™/LIFE TECHNOLOGIES™). The following primers were used:

```
DSG2 QT-PCR fw
5'-ATG ACG GCT AGG AAC ACC AC-3'     (SEQ ID NO: 58)

DSG2 QT-PCR rev
5'-TCA GGT ACA TTG GAA ACA TGA AA-3' (SEQ ID NO: 59)

GAPDH QT-PCR fw
5'-TGC ACC ACC AAC TGC TTA GC-3'     (SEQ ID NO: 60)

GAPDH QT-PCR rev
5'-GGC ATG GAC TGT GGT CAT GAG-3'    (SEQ ID NO: 61)
```

The qPCR was performed under the following conditions: after an initial 10 min enzyme activation step at 95° C., 40 amplification cycles were run, each consisting of 95° C. for 15 s and 60° C. for 1 min. Lastly, a final elongation step was performed for two minutes at 60° C.

Permeability Assay.

A total of $5 \times 10^5$ T84 cells were seeded on 12 mm TRANSWELL™ inserts [PET membrane, with 0.4 m pore size (Corning, N.Y.)] and cultured for 14-20 days until transepithelial resistance was stable. Culture medium was changed every 2-3 days. The cells were exposed to DSG2 ligands (20 g/ml) in adhesion medium (DMEM, 1% FBS, 2 mM $MgCl_2$, 20 mM HEPES) for 15 min at room temperature. Subsequently, 1 mCi of [$^{14}$C] polyethylene glycol-4000 (PEG-4000) (PERKIN ELMER™, Covina Calif.) diluted with DMEM/F12 medium, was added to the inner chamber.

Medium aliquots were harvested from the inner and outer chambers at 15 and 30 min and measured by a scintillation counter. Permeability was calculated as described elsewhere (Yang et al., 2004).

Trastuzumab and Cetuximab Cytotoxicity Assay.

BT474 or A549 cells were plated at a density of $5\times10^4$ cells/well in triplicate in 96-well plates and grown to confluence. JO-1 (500 ng/ml) was added to the medium. 12 h later, trastuzumab or cetuximab (15 g/ml) were added and cell viability was measured 2 h later by WST-1 assay (ROCHE™, San Francisco, Calif.). Three independent studies were performed.

Electron Microscopy.

Polarized cells in the TRANSWELL™ chambers were fixed with half-strength Karnovsky's fixative (2% paraformaldehyde, 2.5% glutaraldehyde, and 0.2 M Cacodylate buffer) for 1 h at room temperature. The fixative in the inner chamber contained 0.2% ruthenium red. The ruthenium red [Ruthenium(III)chloride oxide, ammoniated], was purchased from Alfa Aesar (Ward Hill, Mass.). Post-fixation was performed with 1% $OsO_4$-phosphate buffer. The membranes were cut out from the TRANSWELL™ chambers and embedded in Medcast (Ted Pella, Redding, Calif.). Ultra-thin sections were stained with uranyl acetate and lead citrate. Processed grids were evaluated with a JEOL JEM1200EXII transmission electron microscope. Images were acquired with an Olympus SIS Morada Digital CCD camera using iTEM software for image processing.

Animal Studies:

All experiments involving animals were conducted in accordance with the institutional guidelines set forth by the University of Washington. Mice were housed in specific-pathogen-free facilities. Breast cancer xenografts were established by injecting $4\times10^6$ cancer cells into the mammary fat pad of CB17 SCID-beige mice. Trastuzumab was injected intraperitoneally (i.p.) at a dose of 10 mg/kg. PtDd or JO-1 was given intravenously (i.v.) at a dose of 2 mg/kg. Tumor volumes were measured as described previously (Tuve et al., 2007). Mice were sacrificed when the tumor volume reached 1,000 $mm^3$ or ulcerated. Lung cancer xenografts were established by injecting $4\times10^6$ A549 subcutaneously (s.c.) into the right flank of CB17 SCID beige mice. Cetuximab was injected at 10 mg/kg i.p. 10 h after JO-1 i.v. injection at day 12 and repeated after 3 days. For the disseminated lung tumor model, eight week old male CB17 SCID-beige mice were intravenously injected with $2\times10^6$ A549 cells on day 1. The treatment with JO-1 (2 mg/kg i.v) and cetuximab (10 mg/kg i.p.) was started at day 10 and repeated every three days. Animals were monitored for weight loss and signs of dyspnea. Animals were sacrificed when the first mouse of the non-treatment group was moribund. India ink (15% in PBS) was injected intratracheally prior to the removal of the lungs. Metastases appeared unstained (white) against the black normal tissue. To produce anti-JO-1 antibodies, mice were injected subdermally with JO-1 mixed with Freund's adjuvant as described elsewhere (Li et al., 2009).

HSC-based Relaxin Expression:

The protocol has been described elsewhere (Beyer et al., 2011). Briefly, transplant recipients were 6- to 10-week old, female CB17 SCID-beige mice, sublethally irradiated with 350 cGy immediately before tail vein injection with $6\times10^5$ lentivirus vector-transduced bone marrow cells from 5-FU-treated mice. After engraftment of cells in the recipients' bone marrow was confirmed, a total of $4\times10^6$ HCC1954 were injected into the mammary fat pad. The lentivirus vector expressing relaxin under the control of doxycycline (Dox) has been described previously (Beyer et al., 2011).

Neutralizing Antibody Assay:

Serum samples from cancer patients were taken before patients underwent chemotherapy. Briefly, 293 cells were plated in 96-well plates at $4\times10^4$ cells per well and incubated at 37° C. The following day, serum samples were heat inactivated at 56° C. for 30 min and serially diluted from 1:2 to 1:1,204 in MEM containing 2% FCS. A total of 20 plaque forming units (PFU) per cell of wild-type Ad5 or Ad11 in 10 μl of MEM, was incubated with 100 μl of each serum dilution for 1 h at 37° C. Medium was removed from cells plated the previous day, and 55 μl of virus-containing serum was added to the cells along with 45 μl of 293 growth medium. A further 100 μl of 293 growth medium was added to the cells at 3 and 6 days postinfection. At 8 days postinfection, cells were analyzed for the presence of cytopathic effect (CPE), and serum samples were scored positive for the presence of neutralizing antibodies if no CPE was seen at a dilution of 1:2 or higher.

Statistical Analysis:

All results are expressed as mean+/−SD. Student's t-test or 2-Way ANOVA for multiple testing, were applied when applicable. A p-value <0.05 was considered significant.

REFERENCES FOR EXAMPLE 3

Abbod, M. F., F. C. Hamdy, D. A. Linkens, and J. W. Catto. 2009. Predictive modeling in cancer: where systems biology meets the stock market. *Expert Rev Anticancer Ther* 9:867-870.

Adams, G. P., and L. M. Weiner. 2005. Monoclonal antibody therapy of cancer. *Nat Biotechnol* 23:1147-1157.

Amieva, M. R., R. Vogelmann, A. Covacci, L. S. Tompkins, W. J. Nelson, and S. Falkow. 2003. Disruption of the epithelial apical-junctional complex by Helicobacter pylori CagA. *Science* 300:1430-1434.

Andarawewa, K. L., A. C. Erickson, W. S. Chou, S. V. Costes, P. Gascard, J. D. Mott, M. J. Bissell, and M. H. Barcellos-Hoff. 2007. Ionizing radiation predisposes nonmalignant human mammary epithelial cells to undergo transforming growth factor beta induced epithelial to mesenchymal transition. *Cancer Res* 67:8662-8670.

Beckhove, P., M. Feuerer, M. Dolenc, F. Schuetz, C. Choi, N. Sommerfeldt, J. Schwendemann, K. Ehlert, P. Altevogt, G. Bastert, V. Schirrmacher, and V. Umansky. 2004. Specifically activated memory T cell subsets from cancer patients recognize and reject xenotransplanted autologous tumors. *J Clin Invest* 114:67-76.

Beyer, I., Z. Li, J. Persson, Y. Liu, R. van Rensburg, R. Yumul, X. B. Zhang, M. C. Hung, and A. Lieber. 2011. Controlled extracellular matrix degradation in breast cancer tumors improves therapy by trastuzumab. *Mol Ther* 19:479-489.

Biedermann, K., H. Vogelsang, I. Becker, S. Plaschke, J. R. Siewert, H. Hofler, and G. Keller. 2005. Desmoglein 2 is expressed abnormally rather than mutated in familial and sporadic gastric cancer. *J Pathol* 207:199-206.

Brennan, K., G. Offiah, E. A. McSherry, and A. M. Hopkins. 2010. Tight junctions: a barrier to the initiation and progression of breast cancer? *J Biomed Biotechnol* 2010:460607.

Disis, M. L., E. Calenoff, G. McLaughlin, A. E. Murphy, W. Chen, B. Groner, M. Jeschke, N. Lydon, E. McGlynn, R. B. Livingston, and et al. 1994. Existent T-cell and antibody immunity to HER-2/neu protein in patients with breast cancer. *Cancer Res* 54:16-20.

Disis, M. L., K. L. Knutson, K. Schiffman, K. Rinn, and D. G. McNeel. 2000. Pre-existent immunity to the HER-2/neu oncogenic protein in patients with HER-2/neu overexpressing breast and ovarian cancer. *Breast Cancer Res Treat* 62:245-252.

Fasano, A., B. Baudry, D. W. Pumplin, S. S. Wasserman, B. D. Tall, J. M. Ketley, and J. B. Kaper. 1991. *Vibrio cholerae* produces a second enterotoxin, which affects intestinal tight junctions. *Proc Natl Acad Sci USA* 88:5242-5246.

Fender, P., R. W. Ruigrok, E. Gout, S. Buffet, and J. Chroboczek. 1997. Adenovirus dodecahedron, a new vector for human gene transfer. *Nat Biotechnol* 15:52-56.

Fessler, S. P., M. T. Wotkowicz, S. K. Mahanta, and C. Bamdad. 2009. MUC1* is a determinant of trastuzumab (Herceptin) resistance in breast cancer cells. *Breast Cancer Res Treat* 118:113-124.

Feuerer, M., P. Beckhove, L. Bai, E. F. Solomayer, G. Bastert, I. J. Diel, C. Pedain, M. Oberniedermayr, V. Schirrmacher, and V. Umansky. 2001. Therapy of human tumors in NOD/SCID mice with patient-derived reactivated memory T cells from bone marrow. *Nat Med* 7:452-458.

Frank, C. F., and M. K. Hostetter. 2007. Cleavage of E-cadherin: a mechanism for disruption of the intestinal epithelial barrier by *Candida albicans*. *Transl Res* 149:211-222.

Fuschiotti, P., G. Schoehn, P. Fender, C. M. Fabry, E. A. Hewat, J. Chroboczek, R. W. Ruigrok, and J. F. Conway. 2006. Structure of the dodecahedral penton particle from human adenovirus type 3. *J Mol Biol* 356:510-520.

Guarino, M. 2007. Epithelial-mesenchymal transition and tumour invasion. *Int J Biochem Cell Biol* 39:2153-2160.

Harada, H., K. Iwatsuki, M. Ohtsuka, G. W. Han, and F. Kaneko. 1996. Abnormal desmoglein expression by squamous cell carcinoma cells. *Acta Derm Venereol* 76:417-420.

Harari, P. M., G. W. Allen, and J. A. Bonner. 2007. Biology of interactions: antiepidermal growth factor receptor agents. *J Clin Oncol* 25:4057-4065.

Hemminki, O., G. Bauerschmitz, S. Hemmi, A. Kanerva, V. Cerullo, S. Pesonen, and A. Hemminki. 2010. Preclinical and clinical data with a fully serotype 3 oncolytic adenovirus Ad3-hTERT-E1A in the treatment of advanced solid tumors. *Molecular Therapy* 18:S74.

Karamouzis, M. V., J. R. Grandis, and A. Argiris. 2007. Therapies directed against epidermal growth factor receptor in aerodigestive carcinomas. *JAMA* 298:70-82.

Katz, J., V. Sambandam, J. H. Wu, S. M. Michalek, and D. F. Balkovetz. 2000. Characterization of *Porphyromonas gingivalis*-induced degradation of epithelial cell junctional complexes. *Infect Immun* 68:1441-1449.

Klessner, J. L., B. V. Desai, E. V. Amargo, S. Getsios, and K. J. Green. 2009. EGFR and ADAMs cooperate to regulate shedding and endocytic trafficking of the desmosomal cadherin desmoglein 2. *Mol Biol Cell* 20:328-337.

Koeser, J., S. M. Troyanovsky, C. Grund, and W. W. Franke. 2003. De novo formation of desmosomes in cultured cells upon transfection of genes encoding specific desmosomal components. *Exp Cell Res* 285:114-130.

Koski, A., L. Kangasniemi, S. Escutenaire, S. Pesonen, V. Cerullo, I. Diaconu, P. Nokisalmi, M. Raki, M. Rajecki, K. Guse, T. Ranki, M. Oksanen, S. L. Holm, E. Haavisto, A. Karioja-Kallio, L. Laasonen, K. Partanen, M. Ugolini, A. Helminen, E. Karli, P. Hannuksela, T. Joensuu, A. Kanerva, and A. Hemminki. 2010. Treatment of Cancer Patients With a Serotype 5/3 Chimeric Oncolytic Adenovirus Expressing GMCSF. *Mol Ther*

Kurzen, H., I. Munzing, and W. Hartschuh. 2003. Expression of desmosomal proteins in squamous cell carcinomas of the skin. *J Cutan Pathol* 30:621-630.

Larsen, M., M. L. Tremblay, and K. M. Yamada. 2003. Phosphatases in cell-matrix adhesion and migration. *Nat Rev Mol Cell Biol* 4:700-711.

Lesniak, D., Y. Xu, J. Deschenes, R. Lai, J. Thoms, D. Murray, S. Gosh, J. R. Mackey, S. Sabri, and B. Abdulkarim. 2009. Beta1-integrin circumvents the antiproliferative effects of trastuzumab in human epidermal growth factor receptor-2-positive breast cancer. *Cancer Res* 69:8620-8628.

Li, Z., Y. Liu, S. Tuve, Y. Xun, X. Fan, L. Min, Q. Feng, N. Kiviat, H. P. Kiem, M. L. Disis, and A. Lieber. 2009. Toward a stem cell gene therapy for breast cancer. *Blood* 113:5423-5433.

Li, Z., J. Persson, H. Wang, H. Song, I. Beyer, R. Yumul, and A. Lieber. 2011. Biodistribution of DSG2 in humans, macaques, and DSG2 transgenic mice. *in preparation*

Li, Z. Y., S, Ni, X. Yang, N. Kiviat, and A. Lieber. 2004. Xenograft models for liver metastasis: Relationship between tumor morphology and adenovirus vector transduction. *Mol Ther* 9:650-657.

Norrby, E., B. Nyberg, P. Skaaret, and A. Lengyel. 1967. Separation and characterization of soluble adenovirus type 9 components. *J Virol* 1:1101-1108.

Oliveras-Ferraros, C., A. Vazquez-Martin, S. Cufi, B. Queralt, L. Baez, R. Guardeno, X. Hernandez-Yague, B. Martin-Castillo, J. Brunet, and J. A. Menendez. 2011. Stem cell property epithelial-to-mesenchymal transition is a core transcriptional network for predicting cetuximab (Erbitux) efficacy in KRAS wild-type tumor cells. *J Cell Biochem* 112:10-29.

Ramani, V. C., L. Hennings, and R. S. Haun. 2008. Desmoglein 2 is a substrate of kallikrein 7 in pancreatic cancer. *BMC Cancer* 8:373.

Sakamoto, M., N. Yazaki, N. Katsushima, K. Mizuta, H. Suzuki, and Y. Numazaki. 1995. Longitudinal investigation of epidemiologic feature of adenovirus infections in acute respiratory illnesses among children in Yamagata, Japan (1986-1991). *Tohoku J Exp Med* 175:185-193.

Schmitt, C. J., W. W. Franke, S. Goerdt, B. Falkowska-Hansen, S. Rickelt, and W. K. Peitsch. 2007. Homo- and heterotypic cell contacts in malignant melanoma cells and desmoglein 2 as a novel solitary surface glycoprotein. *J Invest Dermatol* 127:2191-2206.

Strauss, R., Z. Y. Li, Y. Liu, I. Beyer, J. Persson, P. Soya, T. Moller, S. Pesonen, A. Hemminki, P. Hamerlik, C. Drescher, N. Urban, J. Bartek, and A. Lieber. 2011. Analysis of epithelial and mesenchymal markers in ovarian cancer reveals phenotypic heterogeneity and plasticity. *PLoS One* 6:e16186.

Strauss, R., and A. Lieber. 2009. Anatomical and physical barriers to tumor targeting with oncolytic adenoviruses in vivo. *Curr Opin Mol Ther* 11:513-522.

Strauss, R., P. Soya, Y. Liu, Z. Y. Li, S. Tuve, D. Pritchard, P. Brinkkoetter, T. Moller, O. Wildner, S. Pesonen, A. Hemminki, N. Urban, C. Drescher, and A. Lieber. 2009. Epithelial phenotype confers resistance of ovarian cancer cells to oncolytic adenoviruses. *Cancer Res* 69:5115-5125.

Sumida, S. M., D. M. Truitt, A. A. Lemckert, R. Vogels, J. H. Custers, M. M. Addo, S. Lockman, T. Peter, F. W. Peyerl, M. G. Kishko, S. S. Jackson, D. A. Gorgone, M. A. Lifton, M. Essex, B. D. Walker, J. Goudsmit, M. J. Havenga, and D. H. Barouch. 2005. Neutralizing antibodies to adenovirus serotype 5 vaccine vectors are directed primarily against the adenovirus hexon protein. *J Immunol* 174:7179-7185.

Thiery, J. P., and J. P. Sleeman. 2006. Complex networks orchestrate epithelial-mesenchymal transitions. *Nat Rev Mol Cell Biol* 7:131-142.

Thomas, M. A., J. F. Spencer, K. Toth, J. E. Sagartz, N. J. Phillips, and W. S. Wold. 2008. Immunosuppression enhances oncolytic adenovirus replication and antitumor efficacy in the Syrian hamster model. *Mol Ther* 16:1665-1673.

Toso, J. F., C. Oei, F. Oshidari, J. Tartaglia, E. Paoletti, H. K. Lyerly, S. Talib, and K. J. Weinhold. 1996. MAGE-1-specific precursor cytotoxic T-lymphocytes present among tumor-infiltrating lymphocytes from a patient with breast cancer: characterization and antigen-specific activation. *Cancer Res* 56:16-20.

Trojan, L., A. Schaaf, A. Steidler, M. Haak, G. Thalmann, T. Knoll, N. Gretz, P. Aiken, and M. S. Michel. 2005. Identification of metastasis-associated genes in prostate cancer by genetic profiling of human prostate cancer cell lines. *Anticancer Res* 25:183-191.

Turley, E. A., M. Veiseh, D. C. Radisky, and M. J. Bissell. 2008. Mechanisms of Disease: epithelial-mesenchymal transition-does cellular plasticity fuel neoplastic progression? *Nat Clin Pract Oncol*

Tuve, S., B. M. Chen, Y. Liu, T. L. Cheng, P. Toure, P. S. Sow, Q. Feng, N. Kiviat, R. Strauss, S, Ni, Z. Y. Li, S. R. Roffler, and A. Lieber. 2007. Combination of tumor site-located CTL-associated antigen-4 blockade and systemic regulatory T-cell depletion induces tumor-destructive immune responses. *Cancer Res* 67:5929-5939.

Vermeer, P. D., L. A. Einwalter, T. O. Moninger, T. Rokhlina, J. A. Kern, J. Zabner, and M. J. Welsh. 2003. Segregation of receptor and ligand regulates activation of epithelial growth factor receptor. *Nature* 422:322-326.

Wang, H., Z. Li, R. Yumul, S. Lara, A. Hemminki, P. Fender, and A. Lieber. 2011a. Multimerization of adenovirus serotype 3 fiber knob domains is required for efficient binding of virus to desmoglein 2 and subsequent opening of epithelial junctions. *J Virol*

Wang, H., Z. Y. Li, Y. Liu, J. Persson, I. Beyer, T. Moller, D. Koyuncu, M. R. Drescher, R. Strauss, X. B. Zhang, J. K. Wahl, 3rd, N. Urban, C. Drescher, A. Hemminki, P. Fender, and A. Lieber. 2011b. Desmoglein 2 is a receptor for adenovirus serotypes 3, 7, 11 and 14. *Nat Med* 17:96-104.

Wang, H., Y. C. Liaw, D. Stone, O. Kalyuzhniy, I. Amiraslanov, S. Tuve, C. L. Verlinde, D. Shayakhmetov, T. Stehle, S. Roffler, and A. Lieber. 2007. Identification of CD46 binding sites within the adenovirus serotype 35 fiber knob. *J Virol* 81:12785-12792.

Wang, H., Y. Liu, Z. Y. Li, X. Fan, A. Hemminki, and A. Lieber. 2010. A recombinant adenovirus type 35 fiber knob protein sensitizes lymphoma cells to rituximab therapy. *Blood* 115:592-600.

Wheeler, D. L., E. F. Dunn, and P. M. Harari. 2010. Understanding resistance to EGFR inhibitors-impact on future treatment strategies. *Nat Rev Clin Oncol* 7:493-507.

Wu, S., K. C. Lim, J. Huang, R. F. Saidi, and C. L. Sears. 1998. *Bacteroides fragilis* enterotoxin cleaves the zonula adherens protein, E-cadherin. *Proc Natl Acad Sci USA* 95:14979-14984.

Yang, Z., M. Horn, J. Wang, D. D. Shen, and R. J. Ho. 2004. Development and characterization of a recombinant madin-darby canine kidney cell line that expresses rat multidrug resistance-associated protein 1 (rMRP1). *AAPS J* 6:77-85.

Yashiro, M., N. Nishioka, and K. Hirakawa. 2006. Decreased expression of the adhesion molecule desmoglein-2 is associated with diffuse-type gastric carcinoma. *Eur J Cancer* 42:2397-2403.

Zeng, Y., M. Pinard, J. Jaime, L. Bourget, P. Uyen Le, M. D. O'Connor-McCourt, R. Gilbert, and B. Massie. 2008. A ligand-pseudoreceptor system based on de novo designed peptides for the generation of adenoviral vectors with altered tropism. *J Gene Med* 10:355-367.

We claim:

1. A recombinant AdB-2/3 fiber polypeptide comprising the amino acid sequence of junction opener-1 (JO-1) (SEQ ID NO:20).

2. The recombinant AdB-2/3 fiber polypeptide of claim 1, wherein the AdB-2/3 fiber polypeptide is multimerized.

3. A composition, comprising (a) the recombinant AdB-2/3 fiber polypeptide of claim 1, and (b) one or more compounds selected from the group consisting of therapeutics, diagnostics, and imaging agents.

4. A recombinant AdB-2/3 fiber polypeptide, comprising:
   a) one or more AdB-2/3 fiber polypeptide shaft domains; and
   b) an AdB-2/3 fiber polypeptide knob domain, operatively linked to and located C-terminal to the one or more AdB-2/3 fiber polypeptide shaft domains;
      wherein the recombinant AdB-2/3 fiber polypeptide is multimerized, and is capable of binding to desmoglein 2 (DSG2) on epithelial cells,
      wherein the AdB-2/3 fiber polypeptide does not include an AdB-2/3 fiber polypeptide tail domain.

5. The recombinant AdB-2/3 fiber polypeptide of claim 4, wherein each shaft domain is selected from the group consisting of an Ad3 fiber polypeptide shaft domain, an Ad7 fiber polypeptide shaft domain, an Ad11 fiber polypeptide shaft domain, an Ad 14 fiber polypeptide shaft domain, an Ad14a fiber polypeptide shaft domain, and combinations thereof.

6. The recombinant AdB-2/3 fiber polypeptide of claim 4, wherein the one or more shaft domains comprise 1-22 shaft domains.

7. The recombinant AdB-2/3 fiber polypeptide of claim 4, wherein each shaft domain comprises an amino acid sequence according to SEQ ID NO: 11.

8. The recombinant AdB-2/3 fiber polypeptide of claim 4, wherein each shaft domain comprises an amino acid sequence according to SEQ ID NO: 12.

9. The recombinant AdB-2/3 fiber polypeptide of any claim 4, wherein each shaft domain comprises an amino acid sequence selected from the group consisting of SEQ ID NO:1, SEQ ID NO:2, SEQ ID NO:3, SEQ ID NO:4, and SEQ ID NO:5.

10. The recombinant AdB-2/3 fiber polypeptide of claim 4, wherein the knob domain is selected from the group consisting of an Ad3 fiber polypeptide knob domain, an Ad7 fiber polypeptide knob domain, an Ad11 fiber polypeptide knob domain, an Ad 14 fiber polypeptide knob domain, an Ad14a fiber polypeptide knob domain.

11. The recombinant AdB-2/3 fiber polypeptide of claim 4, wherein the knob domain comprises an amino acid sequence according to SEQ ID NO 13.

12. The recombinant AdB-2/3 fiber polypeptide of claim 4, wherein the knob domain comprises an amino acid sequence according to SEQ ID NO 14.

13. The recombinant AdB-2/3 fiber polypeptide of claim 4, wherein the knob domain comprises an amino acid sequence selected from the group consisting of SEQ ID NO:6, SEQ ID NO:7, SEQ ID NO:8, SEQ ID NO:4, and SEQ ID NO:10.

14. The recombinant AdB-2/3 fiber polypeptide of claim 4, wherein the AdB-2/3 fiber polypeptide further comprises a dimerization domain comprising an amino acid sequence selected from the group consisting of EVSALEK (SEQ ID NO:22) and/or KVSALKE (SEQ ID NO: 23).

15. The recombinant AdB-2/3 fiber polypeptide of claim 4, wherein the recombinant AdB-2/3 polypeptide comprises:
   a) one or more shaft domains that each comprise an Ad3 shaft domain (SEQ ID NO:1); and
   b) a knob domain that comprises an Ad3 knob domain (SEQ ID NO:6).

16. The recombinant AdB-2/3 fiber polypeptide of claim 4, wherein the AdB-2/3 fiber polypeptide contains a single AdB-2/3 fiber polypeptide shaft domain.

17. The recombinant AdB-2/3 fiber polypeptide of claim 4, wherein the AdB-2/3 fiber polypeptide is dimerized.

18. A composition, comprising (a) the recombinant AdB-2/3 fiber polypeptide of claim 4, and (b) one or more compounds selected from the group consisting of therapeutics, diagnostics, and imaging agents.

19. The composition of claim 18, wherein the one or more compounds comprise at least one therapeutic, wherein the therapeutic is selected from the group consisting of antibodies, immunoconjugates, nanoparticles, chemotherapeutics, radioactive particles, viruses, vaccines, cellular immunotherapy therapeutics, gene therapy constructs, nucleic acid therapeutics, and combinations thereof.

* * * * *

SEQUENCE LISTING

```
<160> NUMBER OF SEQ ID NOS: 62

<210> SEQ ID NO 1
<211> LENGTH: 91
<212> TYPE: PRT
<213> ORGANISM: Homo sapiens

<400> SEQUENCE: 1

Asn Gly Val Leu Ser Leu Lys Cys Val Asn Pro Leu Thr Thr Ala Ser
1               5                   10                  15

Gly Ser Leu Gln Leu Lys Val Gly Ser Gly Leu Thr Val Asp Thr Thr
            20                  25                  30

Asp Gly Ser Leu Glu Glu Asn Ile Lys Val Asn Thr Pro Leu Thr Lys
        35                  40                  45

Ser Asn His Ser Ile Asn Leu Pro Ile Gly Asn Gly Leu Gln Ile Glu
    50                  55                  60

Gln Asn Lys Leu Cys Ser Lys Leu Gly Asn Gly Leu Thr Phe Asp Ser
65                  70                  75                  80

Ser Asn Ser Ile Ala Leu Lys Asn Asn Thr Leu
                85                  90

<210> SEQ ID NO 2
<211> LENGTH: 92
<212> TYPE: PRT
<213> ORGANISM: Homo sapiens
```

```
<400> SEQUENCE: 2

Asp Gly Val Leu Thr Leu Lys Cys Leu Thr Pro Leu Thr Thr Thr Gly
1               5                   10                  15

Gly Ser Leu Gln Leu Lys Val Gly Gly Gly Leu Thr Ile Asp Asp Thr
                20                  25                  30

Asp Gly Phe Leu Lys Glu Asn Ile Ser Ala Thr Thr Pro Leu Val Lys
            35                  40                  45

Thr Gly His Ser Ile Gly Leu Ser Leu Gly Pro Gly Leu Gly Thr Asn
        50                  55                  60

Glu Asn Lys Leu Cys Ala Lys Leu Gly Glu Gly Leu Thr Phe Asn Ser
65                  70                  75                  80

Asn Asn Ile Cys Ile Asn Asp Asn Ile Asn Thr Leu
                85                  90

<210> SEQ ID NO 3
<211> LENGTH: 92
<212> TYPE: PRT
<213> ORGANISM: Homo sapiens

<400> SEQUENCE: 3

Asn Gly Val Leu Thr Leu Lys Cys Leu Thr Pro Leu Thr Thr Thr Gly
1               5                   10                  15

Gly Ser Leu Gln Leu Lys Val Gly Gly Gly Leu Thr Val Asp Asp Thr
                20                  25                  30

Asn Gly Phe Leu Lys Glu Asn Ile Ser Ala Thr Thr Pro Leu Val Lys
            35                  40                  45

Thr Gly His Ser Ile Gly Leu Pro Leu Gly Ala Gly Leu Gly Thr Asn
        50                  55                  60

Glu Asn Lys Leu Cys Ile Lys Leu Gly Gln Gly Leu Thr Phe Asn Ser
65                  70                  75                  80

Asn Asn Ile Cys Ile Asp Asp Asn Ile Asn Thr Leu
                85                  90

<210> SEQ ID NO 4
<211> LENGTH: 92
<212> TYPE: PRT
<213> ORGANISM: Homo sapiens

<400> SEQUENCE: 4

Asp Gly Val Leu Thr Leu Lys Cys Leu Thr Pro Leu Thr Thr Thr Gly
1               5                   10                  15

Gly Ser Leu Gln Leu Lys Val Gly Gly Gly Leu Thr Val Asp Asp Thr
                20                  25                  30

Asp Gly Thr Leu Gln Glu Asn Ile Gly Ala Thr Thr Pro Leu Val Lys
            35                  40                  45

Thr Gly His Ser Ile Gly Leu Ser Leu Gly Ala Gly Leu Gly Thr Asp
        50                  55                  60

Glu Asn Lys Leu Cys Thr Lys Leu Gly Glu Gly Leu Thr Phe Asn Ser
65                  70                  75                  80

Asn Asn Ile Cys Ile Asp Asp Asn Ile Asn Thr Leu
                85                  90

<210> SEQ ID NO 5
<211> LENGTH: 92
<212> TYPE: PRT
<213> ORGANISM: Homo sapiens

<400> SEQUENCE: 5
```

```
Asp Gly Val Leu Thr Leu Lys Cys Leu Thr Pro Leu Thr Thr Thr Gly
1               5                   10                  15

Gly Ser Leu Gln Leu Lys Val Gly Gly Leu Thr Val Asp Asp Thr
            20                  25                  30

Asp Gly Thr Leu Gln Glu Asn Ile Gly Ala Thr Thr Pro Leu Val Lys
            35                  40                  45

Thr Gly His Ser Ile Gly Leu Ser Leu Gly Ala Gly Leu Gly Thr Asp
            50                  55                  60

Glu Asn Lys Leu Cys Thr Lys Leu Gly Glu Gly Leu Thr Phe Asn Ser
65              70                  75                  80

Asn Asn Ile Cys Ile Asp Asp Asn Ile Asn Thr Leu
                85                  90
```

<210> SEQ ID NO 6
<211> LENGTH: 186
<212> TYPE: PRT
<213> ORGANISM: Homo sapiens

<400> SEQUENCE: 6

```
Trp Thr Gly Pro Lys Pro Glu Ala Asn Cys Ile Ile Glu Tyr Gly Lys
1               5                   10                  15

Gln Asn Pro Asp Ser Lys Leu Thr Leu Ile Leu Val Lys Asn Gly Gly
            20                  25                  30

Ile Val Asn Gly Tyr Val Thr Leu Met Gly Ala Ser Asp Tyr Val Asn
            35                  40                  45

Thr Leu Phe Lys Asn Lys Asn Val Ser Ile Asn Val Glu Leu Tyr Phe
            50                  55                  60

Asp Ala Thr Gly His Ile Leu Pro Asp Ser Ser Ser Leu Lys Thr Asp
65              70                  75                  80

Leu Glu Leu Lys Tyr Lys Gln Thr Ala Asp Phe Ser Ala Arg Gly Phe
                85                  90                  95

Met Pro Ser Thr Thr Ala Tyr Pro Phe Val Leu Pro Asn Ala Gly Thr
                100                 105                 110

His Asn Glu Asn Tyr Ile Phe Gly Gln Cys Tyr Tyr Lys Ala Ser Asp
            115                 120                 125

Gly Ala Leu Phe Pro Leu Glu Val Thr Val Met Leu Asn Lys Arg Leu
            130                 135                 140

Pro Asp Ser Arg Thr Ser Tyr Val Met Thr Phe Leu Trp Ser Leu Asn
145                 150                 155                 160

Ala Gly Leu Ala Pro Glu Thr Thr Gln Ala Thr Leu Ile Thr Ser Pro
                165                 170                 175

Phe Thr Phe Ser Tyr Ile Arg Glu Asp Asp
                180                 185
```

<210> SEQ ID NO 7
<211> LENGTH: 191
<212> TYPE: PRT
<213> ORGANISM: Homo sapiens

<400> SEQUENCE: 7

```
Trp Thr Gly Val Asn Pro Thr Arg Ala Asn Cys Gln Ile Met Ala Ser
1               5                   10                  15

Ser Glu Ser Asn Asp Cys Lys Leu Ile Leu Thr Leu Val Lys Thr Gly
            20                  25                  30

Ala Leu Val Thr Ala Phe Val Tyr Val Ile Gly Val Ser Asn Asp Phe
            35                  40                  45
```

```
Asn Met Leu Thr Thr His Lys Asn Ile Asn Phe Thr Ala Glu Leu Phe
        50                  55                  60

Phe Asp Ser Thr Gly Asn Leu Leu Thr Ser Leu Ser Leu Lys Thr
 65              70                  75                  80

Pro Leu Asn His Lys Ser Gly Gln Asn Met Ala Thr Gly Ala Leu Thr
                85                  90                  95

Asn Ala Lys Gly Phe Met Pro Ser Thr Thr Ala Tyr Pro Phe Asn Val
            100                 105                 110

Asn Ser Arg Glu Lys Glu Asn Tyr Ile Tyr Gly Thr Cys Tyr Tyr Thr
            115                 120                 125

Ala Ser Asp His Thr Ala Phe Pro Ile Asp Ile Ser Val Met Leu Asn
            130                 135                 140

Gln Arg Ala Leu Asn Asn Glu Thr Ser Tyr Cys Ile Arg Val Thr Trp
145                 150                 155                 160

Ser Trp Asn Thr Gly Val Ala Pro Glu Val Gln Thr Ser Ala Thr Thr
                165                 170                 175

Leu Val Thr Ser Pro Phe Thr Phe Tyr Tyr Ile Arg Glu Asp Asp
                180                 185                 190

<210> SEQ ID NO 8
<211> LENGTH: 191
<212> TYPE: PRT
<213> ORGANISM: Homo sapiens

<400> SEQUENCE: 8

Trp Thr Gly Val Asn Pro Thr Glu Ala Asn Cys Gln Ile Met Asn Ser
 1               5                  10                  15

Ser Glu Ser Asn Asp Cys Lys Leu Ile Leu Thr Leu Val Lys Thr Gly
                20                  25                  30

Ala Leu Val Thr Ala Phe Val Tyr Val Ile Gly Val Ser Asn Asn Phe
            35                  40                  45

Asn Met Leu Thr Thr His Arg Asn Ile Asn Phe Thr Ala Glu Leu Phe
        50                  55                  60

Phe Asp Ser Thr Gly Asn Leu Leu Thr Arg Leu Ser Ser Leu Lys Thr
 65              70                  75                  80

Pro Leu Asn His Lys Ser Gly Gln Asn Met Ala Thr Gly Ala Ile Thr
                85                  90                  95

Asn Ala Lys Gly Phe Met Pro Ser Thr Thr Ala Tyr Pro Phe Asn Asp
            100                 105                 110

Asn Ser Arg Glu Lys Glu Asn Tyr Ile Tyr Gly Thr Cys Tyr Tyr Thr
            115                 120                 125

Ala Ser Asp Arg Thr Ala Phe Pro Ile Asp Ile Ser Val Met Leu Asn
            130                 135                 140

Arg Arg Ala Ile Asn Asp Glu Thr Ser Tyr Cys Ile Arg Ile Thr Trp
145                 150                 155                 160

Ser Trp Asn Thr Gly Asp Ala Pro Glu Val Gln Thr Ser Ala Thr Thr
                165                 170                 175

Leu Val Thr Ser Pro Phe Thr Phe Tyr Tyr Ile Arg Glu Asp Asp
                180                 185                 190

<210> SEQ ID NO 9
<211> LENGTH: 191
<212> TYPE: PRT
<213> ORGANISM: Homo sapiens

<400> SEQUENCE: 9
```

```
Trp Thr Gly Val Asn Pro Thr Glu Ala Asn Cys Gln Met Met Asp Ser
1               5                   10                  15

Ser Glu Ser Asn Asp Cys Lys Leu Ile Leu Thr Leu Val Lys Thr Gly
            20                  25                  30

Ala Leu Val Thr Ala Phe Val Tyr Val Ile Gly Val Ser Asn Asn Phe
            35                  40                  45

Asn Met Leu Thr Thr Tyr Arg Asn Ile Asn Phe Thr Ala Glu Leu Phe
        50                  55                  60

Phe Asp Ser Ala Gly Asn Leu Leu Thr Ser Leu Ser Leu Lys Thr
65                  70                  75                  80

Pro Leu Asn His Lys Ser Gly Gln Asn Met Ala Thr Gly Ala Ile Thr
                85                  90                  95

Asn Ala Lys Ser Phe Met Pro Ser Thr Thr Ala Tyr Pro Phe Asn Asn
                100                 105                 110

Asn Ser Arg Glu Lys Glu Asn Tyr Ile Tyr Gly Thr Cys His Tyr Thr
            115                 120                 125

Ala Ser Asp His Thr Ala Phe Pro Ile Asp Ile Ser Val Met Leu Asn
130                 135                 140

Gln Arg Ala Ile Arg Ala Asp Thr Ser Tyr Cys Ile Arg Ile Thr Trp
145                 150                 155                 160

Ser Trp Asn Thr Gly Asp Ala Pro Glu Gly Gln Thr Ser Ala Thr Thr
                165                 170                 175

Leu Val Thr Ser Pro Phe Thr Phe Tyr Tyr Ile Arg Glu Asp Asp
                180                 185                 190
```

<210> SEQ ID NO 10
<211> LENGTH: 189
<212> TYPE: PRT
<213> ORGANISM: Homo sapiens

<400> SEQUENCE: 10

```
Trp Thr Gly Val Asn Pro Thr Glu Ala Asn Cys Gln Met Met Asp Ser
1               5                   10                  15

Ser Glu Ser Asn Asp Cys Lys Leu Ile Leu Thr Leu Val Lys Thr Gly
            20                  25                  30

Ala Leu Val Thr Ala Phe Val Tyr Val Ile Gly Val Ser Asn Asn Phe
            35                  40                  45

Asn Met Leu Thr Thr Tyr Arg Asn Ile Asn Phe Thr Ala Glu Leu Phe
        50                  55                  60

Phe Asp Ser Ala Gly Asn Leu Leu Thr Ser Leu Ser Leu Lys Thr
65                  70                  75                  80

Pro Leu Asn His Lys Ser Gly Gln Asn Met Ala Thr Gly Ala Ile Thr
                85                  90                  95

Asn Ala Lys Ser Phe Met Pro Ser Thr Thr Ala Tyr Pro Phe Asn Asn
                100                 105                 110

Asn Ser Arg Glu Asn Tyr Ile Tyr Gly Thr Cys His Tyr Thr Ala Ser
            115                 120                 125

Asp His Thr Ala Phe Pro Ile Asp Ile Ser Val Met Leu Asn Gln Arg
130                 135                 140

Ala Ile Arg Ala Asp Thr Ser Tyr Cys Ile Arg Ile Thr Trp Ser Trp
145                 150                 155                 160

Asn Thr Gly Asp Ala Pro Glu Gly Gln Thr Ser Ala Thr Thr Leu Val
                165                 170                 175

Thr Ser Pro Phe Thr Phe Tyr Tyr Ile Arg Glu Asp Asp
```

180       185

```
<210> SEQ ID NO 11
<211> LENGTH: 91
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X is T or S
<220> FEATURE:
<221> NAME/KEY: MISC_FEATURE
<222> LOCATION: (8)..(8)
<223> OTHER INFORMATION: X is L or V
<220> FEATURE:
<221> NAME/KEY: MISC_FEATURE
<222> LOCATION: (9)..(9)
<223> OTHER INFORMATION: X is T or N
<220> FEATURE:
<221> NAME/KEY: MISC_FEATURE
<222> LOCATION: (14)..(14)
<223> OTHER INFORMATION: X is T or A
<220> FEATURE:
<221> NAME/KEY: MISC_FEATURE
<222> LOCATION: (15)..(15)
<223> OTHER INFORMATION: X is G or S
<220> FEATURE:
<221> NAME/KEY: MISC_FEATURE
<222> LOCATION: (24)..(24)
<223> OTHER INFORMATION: X is G or S
<220> FEATURE:
<221> NAME/KEY: MISC_FEATURE
<222> LOCATION: (30)..(30)
<223> OTHER INFORMATION: X is D or T
<220> FEATURE:
<221> NAME/KEY: MISC_FEATURE
<222> LOCATION: (32)..(32)
<223> OTHER INFORMATION: X is D or N
<220> FEATURE:
<221> NAME/KEY: MISC_FEATURE
<222> LOCATION: (34)..(34)
<223> OTHER INFORMATION: X is T, F or S
<220> FEATURE:
<221> NAME/KEY: MISC_FEATURE
<222> LOCATION: (36)..(36)
<223> OTHER INFORMATION: X is Q, K or E
<220> FEATURE:
<221> NAME/KEY: MISC_FEATURE
<222> LOCATION: (40)..(40)
<223> OTHER INFORMATION: X is G, S or K
<220> FEATURE:
<221> NAME/KEY: MISC_FEATURE
<222> LOCATION: (41)..(41)
<223> OTHER INFORMATION: X is A or V
<220> FEATURE:
<221> NAME/KEY: MISC_FEATURE
<222> LOCATION: (42)..(42)
<223> OTHER INFORMATION: X is T or N
<220> FEATURE:
<221> NAME/KEY: MISC_FEATURE
<222> LOCATION: (46)..(46)
<223> OTHER INFORMATION: X is V or T
<220> FEATURE:
<221> NAME/KEY: MISC_FEATURE
<222> LOCATION: (48)..(48)
<223> OTHER INFORMATION: X is T or S
<220> FEATURE:
<221> NAME/KEY: MISC_FEATURE
<222> LOCATION: (49)..(49)
<223> OTHER INFORMATION: X is G or N
<220> FEATURE:
<221> NAME/KEY: MISC_FEATURE
<222> LOCATION: (53)..(53)
<223> OTHER INFORMATION: X is G or N
<220> FEATURE:
<221> NAME/KEY: MISC_FEATURE
<222> LOCATION: (55)..(55)
<223> OTHER INFORMATION: X is S or P
```

```
<220> FEATURE:
<221> NAME/KEY: MISC_FEATURE
<222> LOCATION: (56)..(56)
<223> OTHER INFORMATION: X is L or I
<220> FEATURE:
<221> NAME/KEY: MISC_FEATURE
<222> LOCATION: (58)..(58)
<223> OTHER INFORMATION: X is A, P or N
<220> FEATURE:
<221> NAME/KEY: MISC_FEATURE
<222> LOCATION: (61)..(61)
<223> OTHER INFORMATION: X is G or Q
<220> FEATURE:
<221> NAME/KEY: MISC_FEATURE
<222> LOCATION: (62)..(62)
<223> OTHER INFORMATION: X is T or I
<220> FEATURE:
<221> NAME/KEY: MISC_FEATURE
<222> LOCATION: (63)..(63)
<223> OTHER INFORMATION: X is D or E
<220> FEATURE:
<221> NAME/KEY: MISC_FEATURE
<222> LOCATION: (64)..(64)
<223> OTHER INFORMATION: X is E or Q
<220> FEATURE:
<221> NAME/KEY: MISC_FEATURE
<222> LOCATION: (69)..(69)
<223> OTHER INFORMATION: X is T, S, or A
<220> FEATURE:
<221> NAME/KEY: MISC_FEATURE
<222> LOCATION: (73)..(73)
<223> OTHER INFORMATION: X is E, Q, or N
<220> FEATURE:
<221> NAME/KEY: MISC_FEATURE
<222> LOCATION: (78)..(78)
<223> OTHER INFORMATION: X is N or D
<220> FEATURE:
<221> NAME/KEY: MISC_FEATURE
<222> LOCATION: (80)..(80)
<223> OTHER INFORMATION: X is N or S
<220> FEATURE:
<221> NAME/KEY: MISC_FEATURE
<222> LOCATION: (82)..(82)
<223> OTHER INFORMATION: X is I or S
<220> FEATURE:
<221> NAME/KEY: MISC_FEATURE
<222> LOCATION: (83)..(83)
<223> OTHER INFORMATION: X is C or I
<220> FEATURE:
<221> NAME/KEY: MISC_FEATURE
<222> LOCATION: (84)..(84)
<223> OTHER INFORMATION: X is I or A
<220> FEATURE:
<221> NAME/KEY: MISC_FEATURE
<222> LOCATION: (85)..(85)
<223> OTHER INFORMATION: X is D, N or L
<220> FEATURE:
<221> NAME/KEY: MISC_FEATURE
<222> LOCATION: (86)..(86)
<223> OTHER INFORMATION: X is D or K
<220> FEATURE:
<221> NAME/KEY: MISC_FEATURE
<222> LOCATION: (88)..(88)
<223> OTHER INFORMATION: X is I  or is absent

<400> SEQUENCE: 11

Gly Val Leu Xaa Leu Lys Cys Xaa Xaa Pro Leu Thr Thr Xaa Xaa Gly
1               5                   10                  15

Ser Leu Gln Leu Lys Val Gly Xaa Gly Leu Thr Val Asp Xaa Thr Xaa
            20                  25                  30

Gly Xaa Leu Xaa Glu Asn Ile Xaa Xaa Xaa Thr Pro Leu Xaa Lys Xaa
        35                  40                  45

Xaa His Ser Ile Xaa Leu Xaa Xaa Gly Xaa Gly Leu Xaa Xaa Xaa Xaa
    50                  55                  60
```

```
Asn Lys Leu Cys Xaa Lys Leu Gly Xaa Gly Leu Thr Phe Xaa Ser Xaa
 65                  70                  75                  80

Asn Xaa Xaa Xaa Xaa Xaa Asn Xaa Asn Thr Leu
                 85                  90

<210> SEQ ID NO 12
<211> LENGTH: 91
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: X is V or I
<220> FEATURE:
<221> NAME/KEY: MISC_FEATURE
<222> LOCATION: (34)..(34)
<223> OTHER INFORMATION: X is T or F
<220> FEATURE:
<221> NAME/KEY: MISC_FEATURE
<222> LOCATION: (36)..(36)
<223> OTHER INFORMATION: X is Q or K
<220> FEATURE:
<221> NAME/KEY: MISC_FEATURE
<222> LOCATION: (40)..(40)
<223> OTHER INFORMATION: X is G or S
<220> FEATURE:
<221> NAME/KEY: MISC_FEATURE
<222> LOCATION: (55)..(55)
<223> OTHER INFORMATION: X is S or P
<220> FEATURE:
<221> NAME/KEY: MISC_FEATURE
<222> LOCATION: (58)..(58)
<223> OTHER INFORMATION: X is A or P
<220> FEATURE:
<221> NAME/KEY: MISC_FEATURE
<222> LOCATION: (63)..(63)
<223> OTHER INFORMATION: X is D or N
<220> FEATURE:
<221> NAME/KEY: MISC_FEATURE
<222> LOCATION: (69)..(69)
<223> OTHER INFORMATION: X is T or A
<220> FEATURE:
<221> NAME/KEY: MISC_FEATURE
<222> LOCATION: (73)..(73)
<223> OTHER INFORMATION: X is E or Q
<220> FEATURE:
<221> NAME/KEY: MISC_FEATURE
<222> LOCATION: (85)..(85)
<223> OTHER INFORMATION: X is D or N

<400> SEQUENCE: 12

Gly Val Leu Thr Leu Lys Cys Leu Thr Pro Leu Thr Thr Thr Gly Gly
 1               5                  10                  15

Ser Leu Gln Leu Lys Val Gly Gly Leu Thr Xaa Asp Asp Thr Asp
                 20                  25                  30

Gly Xaa Leu Xaa Glu Asn Ile Xaa Ala Thr Thr Pro Leu Val Lys Thr
                 35                  40                  45

Gly His Ser Ile Gly Leu Xaa Leu Gly Xaa Gly Leu Gly Thr Xaa Glu
 50                  55                  60

Asn Lys Leu Cys Xaa Lys Leu Gly Xaa Gly Leu Thr Phe Asn Ser Asn
 65                  70                  75                  80

Asn Ile Cys Ile Xaa Asp Asn Ile Asn Thr Leu
                 85                  90

<210> SEQ ID NO 13
<211> LENGTH: 193
<212> TYPE: PRT
<213> ORGANISM: Homo sapiens
<220> FEATURE:
<221> NAME/KEY: MISC_FEATURE
```

```
<222> LOCATION: (4)..(4)
<223> OTHER INFORMATION: X is V or P
<220> FEATURE:
<221> NAME/KEY: MISC_FEATURE
<222> LOCATION: (5)..(5)
<223> OTHER INFORMATION: X is N or K
<220> FEATURE:
<221> NAME/KEY: MISC_FEATURE
<222> LOCATION: (7)..(7)
<223> OTHER INFORMATION: X is T or absent
<220> FEATURE:
<221> NAME/KEY: MISC_FEATURE
<222> LOCATION: (8)..(8)
<223> OTHER INFORMATION: X is E or R
<220> FEATURE:
<221> NAME/KEY: MISC_FEATURE
<222> LOCATION: (12)..(12)
<223> OTHER INFORMATION: X is Q or I
<220> FEATURE:
<221> NAME/KEY: MISC_FEATURE
<222> LOCATION: (13)..(13)
<223> OTHER INFORMATION: X is M or I
<220> FEATURE:
<221> NAME/KEY: MISC_FEATURE
<222> LOCATION: (14)..(14)
<223> OTHER INFORMATION: X is M or E
<220> FEATURE:
<221> NAME/KEY: MISC_FEATURE
<222> LOCATION: (15)..(15)
<223> OTHER INFORMATION: X is Y, A, N or D
<220> FEATURE:
<221> NAME/KEY: MISC_FEATURE
<222> LOCATION: (16)..(16)
<223> OTHER INFORMATION: X is S or G
<220> FEATURE:
<221> NAME/KEY: MISC_FEATURE
<222> LOCATION: (17)..(17)
<223> OTHER INFORMATION: X is S or K
<220> FEATURE:
<221> NAME/KEY: MISC_FEATURE
<222> LOCATION: (18)..(18)
<223> OTHER INFORMATION: X is E or Q
<220> FEATURE:
<221> NAME/KEY: MISC_FEATURE
<222> LOCATION: (19)..(19)
<223> OTHER INFORMATION: X is S or N
<220> FEATURE:
<221> NAME/KEY: MISC_FEATURE
<222> LOCATION: (20)..(20)
<223> OTHER INFORMATION: X is N or P
<220> FEATURE:
<221> NAME/KEY: MISC_FEATURE
<222> LOCATION: (22)..(22)
<223> OTHER INFORMATION: X is C or S
<220> FEATURE:
<221> NAME/KEY: MISC_FEATURE
<222> LOCATION: (25)..(25)
<223> OTHER INFORMATION: X is I or T
<220> FEATURE:
<221> NAME/KEY: MISC_FEATURE
<222> LOCATION: (27)..(27)
<223> OTHER INFORMATION: X is I or T
<220> FEATURE:
<221> NAME/KEY: MISC_FEATURE
<222> LOCATION: (31)..(31)
<223> OTHER INFORMATION: X is T or N
<220> FEATURE:
<221> NAME/KEY: MISC_FEATURE
<222> LOCATION: (33)..(33)
<223> OTHER INFORMATION: X is A or G
<220> FEATURE:
<221> NAME/KEY: MISC_FEATURE
<222> LOCATION: (34)..(34)
<223> OTHER INFORMATION: X is L or I
<220> FEATURE:
<221> NAME/KEY: MISC_FEATURE
<222> LOCATION: (36)..(36)
<223> OTHER INFORMATION: X is T or N
<220> FEATURE:
```

```
<221> NAME/KEY: MISC_FEATURE
<222> LOCATION: (37)..(37)
<223> OTHER INFORMATION: X is A or G
<220> FEATURE:
<221> NAME/KEY: MISC_FEATURE
<222> LOCATION: (38)..(38)
<223> OTHER INFORMATION: X is F or Y
<220> FEATURE:
<221> NAME/KEY: MISC_FEATURE
<222> LOCATION: (40)..(40)
<223> OTHER INFORMATION: X is Y or T
<220> FEATURE:
<221> NAME/KEY: MISC_FEATURE
<222> LOCATION: (41)..(41)
<223> OTHER INFORMATION: X is V or L
<220> FEATURE:
<221> NAME/KEY: MISC_FEATURE
<222> LOCATION: (42)..(42)
<223> OTHER INFORMATION: X is I or M
<220> FEATURE:
<221> NAME/KEY: MISC_FEATURE
<222> LOCATION: (44)..(44)
<223> OTHER INFORMATION: X is V or A
<220> FEATURE:
<221> NAME/KEY: MISC_FEATURE
<222> LOCATION: (46)..(46)
<223> OTHER INFORMATION: X is N or D
<220> FEATURE:
<221> NAME/KEY: MISC_FEATURE
<222> LOCATION: (47)..(47)
<223> OTHER INFORMATION: X is N, D or Y
<220> FEATURE:
<221> NAME/KEY: MISC_FEATURE
<222> LOCATION: (48)..(48)
<223> OTHER INFORMATION: X is F or V
<220> FEATURE:
<221> NAME/KEY: MISC_FEATURE
<222> LOCATION: (50)..(50)
<223> OTHER INFORMATION: X is M or T
<220> FEATURE:
<221> NAME/KEY: MISC_FEATURE
<222> LOCATION: (52)..(52)
<223> OTHER INFORMATION: X is T or F
<220> FEATURE:
<221> NAME/KEY: MISC_FEATURE
<222> LOCATION: (53)..(53)
<223> OTHER INFORMATION: X is T or K
<220> FEATURE:
<221> NAME/KEY: MISC_FEATURE
<222> LOCATION: (54)..(54)
<223> OTHER INFORMATION: X is Y, H or N
<220> FEATURE:
<221> NAME/KEY: MISC_FEATURE
<222> LOCATION: (55)..(55)
<223> OTHER INFORMATION: X is R or K
<220> FEATURE:
<221> NAME/KEY: MISC_FEATURE
<222> LOCATION: (57)..(57)
<223> OTHER INFORMATION: X is I or V
<220> FEATURE:
<221> NAME/KEY: MISC_FEATURE
<222> LOCATION: (58)..(58)
<223> OTHER INFORMATION: X is N or S
<220> FEATURE:
<221> NAME/KEY: MISC_FEATURE
<222> LOCATION: (59)..(59)
<223> OTHER INFORMATION: X is F or I
<220> FEATURE:
<221> NAME/KEY: MISC_FEATURE
<222> LOCATION: (60)..(60)
<223> OTHER INFORMATION: X is T or N
<220> FEATURE:
<221> NAME/KEY: MISC_FEATURE
<222> LOCATION: (61)..(61)
<223> OTHER INFORMATION: X is A or V
<220> FEATURE:
<221> NAME/KEY: MISC_FEATURE
<222> LOCATION: (64)..(64)
<223> OTHER INFORMATION: X is F or Y
```

```
<220> FEATURE:
<221> NAME/KEY: MISC_FEATURE
<222> LOCATION: (67)..(67)
<223> OTHER INFORMATION: X is S or A
<220> FEATURE:
<221> NAME/KEY: MISC_FEATURE
<222> LOCATION: (68)..(68)
<223> OTHER INFORMATION: X is A or T
<220> FEATURE:
<221> NAME/KEY: MISC_FEATURE
<222> LOCATION: (70)..(70)
<223> OTHER INFORMATION: X is N or H
<220> FEATURE:
<221> NAME/KEY: MISC_FEATURE
<222> LOCATION: (71)..(71)
<223> OTHER INFORMATION: X is L or I
<220> FEATURE:
<221> NAME/KEY: MISC_FEATURE
<222> LOCATION: (73)..(73)
<223> OTHER INFORMATION: X is T or P
<220> FEATURE:
<221> NAME/KEY: MISC_FEATURE
<222> LOCATION: (74)..(74)
<223> OTHER INFORMATION: X is S, R or D
<220> FEATURE:
<221> NAME/KEY: MISC_FEATURE
<222> LOCATION: (75)..(75)
<223> OTHER INFORMATION: X is L or S
<220> FEATURE:
<221> NAME/KEY: MISC_FEATURE
<222> LOCATION: (81)..(81)
<223> OTHER INFORMATION: X is P or D
<220> FEATURE:
<221> NAME/KEY: MISC_FEATURE
<222> LOCATION: (83)..(83)
<223> OTHER INFORMATION: X is N or E
<220> FEATURE:
<221> NAME/KEY: MISC_FEATURE
<222> LOCATION: (84)..(84)
<223> OTHER INFORMATION: X is H or L
<220> FEATURE:
<221> NAME/KEY: MISC_FEATURE
<222> LOCATION: (86)..(86)
<223> OTHER INFORMATION: X is S or Y
<220> FEATURE:
<221> NAME/KEY: MISC_FEATURE
<222> LOCATION: (87)..(87)
<223> OTHER INFORMATION: X is G or K
<220> FEATURE:
<221> NAME/KEY: MISC_FEATURE
<222> LOCATION: (89)..(89)
<223> OTHER INFORMATION: X is N or T
<220> FEATURE:
<221> NAME/KEY: MISC_FEATURE
<222> LOCATION: (90)..(90)
<223> OTHER INFORMATION: X is M or absent
<220> FEATURE:
<221> NAME/KEY: MISC_FEATURE
<222> LOCATION: (91)..(91)
<223> OTHER INFORMATION: X is A or absent
<220> FEATURE:
<221> NAME/KEY: MISC_FEATURE
<222> LOCATION: (92)..(92)
<223> OTHER INFORMATION: X is T or absent
<220> FEATURE:
<221> NAME/KEY: MISC_FEATURE
<222> LOCATION: (93)..(93)
<223> OTHER INFORMATION: X is G or absent
<220> FEATURE:
<221> NAME/KEY: MISC_FEATURE
<222> LOCATION: (95)..(95)
<223> OTHER INFORMATION: X is I, L or D
<220> FEATURE:
<221> NAME/KEY: MISC_FEATURE
<222> LOCATION: (96)..(96)
<223> OTHER INFORMATION: X is T or F
<220> FEATURE:
<221> NAME/KEY: MISC_FEATURE
<222> LOCATION: (97)..(97)
```

```
<223> OTHER INFORMATION: X is N or S
<220> FEATURE:
<221> NAME/KEY: MISC_FEATURE
<222> LOCATION: (99)..(99)
<223> OTHER INFORMATION: X is K or R
<220> FEATURE:
<221> NAME/KEY: MISC_FEATURE
<222> LOCATION: (100)..(100)
<223> OTHER INFORMATION: X is S or G
<220> FEATURE:
<221> NAME/KEY: MISC_FEATURE
<222> LOCATION: (111)..(111)
<223> OTHER INFORMATION: X is V or absent
<220> FEATURE:
<221> NAME/KEY: MISC_FEATURE
<222> LOCATION: (112)..(112)
<223> OTHER INFORMATION: X is L or absent
<220> FEATURE:
<221> NAME/KEY: MISC_FEATURE
<222> LOCATION: (113)..(113)
<223> OTHER INFORMATION: X is N or P
<220> FEATURE:
<221> NAME/KEY: MISC_FEATURE
<222> LOCATION: (114)..(114)
<223> OTHER INFORMATION: X is N, D or V
<220> FEATURE:
<221> NAME/KEY: MISC_FEATURE
<222> LOCATION: (115)..(115)
<223> OTHER INFORMATION: X is N or A
<220> FEATURE:
<221> NAME/KEY: MISC_FEATURE
<222> LOCATION: (116)..(116)
<223> OTHER INFORMATION: X is S or G
<220> FEATURE:
<221> NAME/KEY: MISC_FEATURE
<222> LOCATION: (117)..(117)
<223> OTHER INFORMATION: X is R or T
<220> FEATURE:
<221> NAME/KEY: MISC_FEATURE
<222> LOCATION: (118)..(118)
<223> OTHER INFORMATION: X is E or H
<220> FEATURE:
<221> NAME/KEY: MISC_FEATURE
<222> LOCATION: (119)..(119)
<223> OTHER INFORMATION: X is N, K or absent
<220> FEATURE:
<221> NAME/KEY: MISC_FEATURE
<222> LOCATION: (120)..(120)
<223> OTHER INFORMATION: X is E or absent
<220> FEATURE:
<221> NAME/KEY: MISC_FEATURE
<222> LOCATION: (124)..(124)
<223> OTHER INFORMATION: X is Y or F
<220> FEATURE:
<221> NAME/KEY: MISC_FEATURE
<222> LOCATION: (126)..(126)
<223> OTHER INFORMATION: X is T or Q
<220> FEATURE:
<221> NAME/KEY: MISC_FEATURE
<222> LOCATION: (128)..(128)
<223> OTHER INFORMATION: X is H or Y
<220> FEATURE:
<221> NAME/KEY: MISC_FEATURE
<222> LOCATION: (130)..(130)
<223> OTHER INFORMATION: X is T or K
<220> FEATURE:
<221> NAME/KEY: MISC_FEATURE
<222> LOCATION: (134)..(134)
<223> OTHER INFORMATION: X is H or G
<220> FEATURE:
<221> NAME/KEY: MISC_FEATURE
<222> LOCATION: (135)..(135)
<223> OTHER INFORMATION: X is T or A
<220> FEATURE:
<221> NAME/KEY: MISC_FEATURE
<222> LOCATION: (136)..(136)
<223> OTHER INFORMATION: X is A or L
<220> FEATURE:
<221> NAME/KEY: MISC_FEATURE
```

```
<222> LOCATION: (139)..(139)
<223> OTHER INFORMATION: X is I or L
<220> FEATURE:
<221> NAME/KEY: MISC_FEATURE
<222> LOCATION: (140)..(140)
<223> OTHER INFORMATION: X is D or E
<220> FEATURE:
<221> NAME/KEY: MISC_FEATURE
<222> LOCATION: (141)..(141)
<223> OTHER INFORMATION: X is I or V
<220> FEATURE:
<221> NAME/KEY: MISC_FEATURE
<222> LOCATION: (142)..(142)
<223> OTHER INFORMATION: X is S or T
<220> FEATURE:
<221> NAME/KEY: MISC_FEATURE
<222> LOCATION: (147)..(147)
<223> OTHER INFORMATION: X is Q, R or K
<220> FEATURE:
<221> NAME/KEY: MISC_FEATURE
<222> LOCATION: (149)..(149)
<223> OTHER INFORMATION: X is A or L
<220> FEATURE:
<221> NAME/KEY: MISC_FEATURE
<222> LOCATION: (150)..(150)
<223> OTHER INFORMATION: X is I, L or P
<220> FEATURE:
<221> NAME/KEY: MISC_FEATURE
<222> LOCATION: (151)..(151)
<223> OTHER INFORMATION: X is R, N or D
<220> FEATURE:
<221> NAME/KEY: MISC_FEATURE
<222> LOCATION: (152)..(152)
<223> OTHER INFORMATION: X is A, D, N or S
<220> FEATURE:
<221> NAME/KEY: MISC_FEATURE
<222> LOCATION: (153)..(153)
<223> OTHER INFORMATION: X is D, E or R
<220> FEATURE:
<221> NAME/KEY: MISC_FEATURE
<222> LOCATION: (157)..(157)
<223> OTHER INFORMATION: X is C or V
<220> FEATURE:
<221> NAME/KEY: MISC_FEATURE
<222> LOCATION: (158)..(158)
<223> OTHER INFORMATION: X is I or M
<220> FEATURE:
<221> NAME/KEY: MISC_FEATURE
<222> LOCATION: (159)..(159)
<223> OTHER INFORMATION: X is R or T
<220> FEATURE:
<221> NAME/KEY: MISC_FEATURE
<222> LOCATION: (160)..(160)
<223> OTHER INFORMATION: X is I, V or F
<220> FEATURE:
<221> NAME/KEY: MISC_FEATURE
<222> LOCATION: (161)..(161)
<223> OTHER INFORMATION: X is T or L
<220> FEATURE:
<221> NAME/KEY: MISC_FEATURE
<222> LOCATION: (164)..(164)
<223> OTHER INFORMATION: X is W or L
<220> FEATURE:
<221> NAME/KEY: MISC_FEATURE
<222> LOCATION: (166)..(166)
<223> OTHER INFORMATION: X is T or A
<220> FEATURE:
<221> NAME/KEY: MISC_FEATURE
<222> LOCATION: (168)..(168)
<223> OTHER INFORMATION: X is D, L or V
<220> FEATURE:
<221> NAME/KEY: MISC_FEATURE
<222> LOCATION: (172)..(172)
<223> OTHER INFORMATION: X is G, V or absent
<220> FEATURE:
<221> NAME/KEY: MISC_FEATURE
<222> LOCATION: (173)..(173)
<223> OTHER INFORMATION: X is Q or absent
<220> FEATURE:
```

```
<221> NAME/KEY: MISC_FEATURE
<222> LOCATION: (175)..(175)
<223> OTHER INFORMATION: X is S or T
<220> FEATURE:
<221> NAME/KEY: MISC_FEATURE
<222> LOCATION: (176)..(176)
<223> OTHER INFORMATION: X is A or Q
<220> FEATURE:
<221> NAME/KEY: MISC_FEATURE
<222> LOCATION: (177)..(177)
<223> OTHER INFORMATION: X is T or A
<220> FEATURE:
<221> NAME/KEY: MISC_FEATURE
<222> LOCATION: (180)..(180)
<223> OTHER INFORMATION: X is V or I
<220> FEATURE:
<221> NAME/KEY: MISC_FEATURE
<222> LOCATION: (187)..(187)
<223> OTHER INFORMATION: X is Y or S

<400> SEQUENCE: 13

Trp Thr Gly Xaa Xaa Pro Xaa Xaa Ala Asn Cys Xaa Xaa Xaa Xaa
 1               5                  10                  15

Xaa Xaa Xaa Xaa Asp Xaa Lys Leu Xaa Leu Xaa Leu Val Lys Xaa Gly
                 20                  25                  30

Xaa Xaa Val Xaa Xaa Xaa Val Xaa Xaa Xaa Gly Xaa Ser Xaa Xaa Xaa
             35                  40                  45

Asn Xaa Leu Xaa Xaa Xaa Xaa Asn Xaa Xaa Xaa Xaa Xaa Glu Leu Xaa
 50                  55                  60

Phe Asp Xaa Xaa Gly Xaa Xaa Leu Xaa Xaa Xaa Ser Ser Leu Lys Thr
 65                  70                  75                  80

Xaa Leu Xaa Xaa Lys Xaa Xaa Gln Xaa Xaa Xaa Xaa Ala Xaa Xaa
                 85                  90                  95

Xaa Ala Xaa Xaa Phe Met Pro Ser Thr Thr Ala Tyr Pro Phe Xaa Xaa
            100                 105                 110

Xaa Xaa Xaa Xaa Xaa Xaa Xaa Asn Tyr Ile Xaa Gly Xaa Cys Xaa
            115                 120                 125

Tyr Xaa Ala Ser Asp Xaa Xaa Xaa Phe Pro Xaa Xaa Xaa Xaa Val Met
130                 135                 140

Leu Asn Xaa Arg Xaa Xaa Xaa Xaa Thr Ser Tyr Xaa Xaa Xaa Xaa
145                 150                 155                 160

Xaa Trp Ser Xaa Asn Xaa Gly Xaa Ala Pro Glu Xaa Xaa Thr Xaa Xaa
                165                 170                 175

Xaa Thr Leu Xaa Thr Ser Pro Phe Thr Phe Xaa Tyr Ile Arg Glu Asp
                180                 185                 190

Asp

<210> SEQ ID NO 14
<211> LENGTH: 191
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: X is E or R
<220> FEATURE:
<221> NAME/KEY: MISC_FEATURE
<222> LOCATION: (13)..(14)
<223> OTHER INFORMATION: X is M or I
<220> FEATURE:
<221> NAME/KEY: MISC_FEATURE
<222> LOCATION: (15)..(15)
<223> OTHER INFORMATION: X is D, N or A
<220> FEATURE:
<221> NAME/KEY: MISC_FEATURE
```

```
<222> LOCATION: (47)..(47)
<223> OTHER INFORMATION: X is N or D
<220> FEATURE:
<221> NAME/KEY: MISC_FEATURE
<222> LOCATION: (54)..(54)
<223> OTHER INFORMATION: X is Y or H
<220> FEATURE:
<221> NAME/KEY: MISC_FEATURE
<222> LOCATION: (55)..(55)
<223> OTHER INFORMATION: X is R or K
<220> FEATURE:
<221> NAME/KEY: MISC_FEATURE
<222> LOCATION: (68)..(68)
<223> OTHER INFORMATION: X is A or T
<220> FEATURE:
<221> NAME/KEY: MISC_FEATURE
<222> LOCATION: (74)..(74)
<223> OTHER INFORMATION: X is S or R
<220> FEATURE:
<221> NAME/KEY: MISC_FEATURE
<222> LOCATION: (95)..(95)
<223> OTHER INFORMATION: X is I or L
<220> FEATURE:
<221> NAME/KEY: MISC_FEATURE
<222> LOCATION: (100)..(100)
<223> OTHER INFORMATION: X is S or G
<220> FEATURE:
<221> NAME/KEY: MISC_FEATURE
<222> LOCATION: (112)..(112)
<223> OTHER INFORMATION: X is N, D or V
<220> FEATURE:
<221> NAME/KEY: MISC_FEATURE
<222> LOCATION: (117)..(117)
<223> OTHER INFORMATION: X is K or absent
<220> FEATURE:
<221> NAME/KEY: MISC_FEATURE
<222> LOCATION: (118)..(118)
<223> OTHER INFORMATION: X is E or absent
<220> FEATURE:
<221> NAME/KEY: MISC_FEATURE
<222> LOCATION: (126)..(126)
<223> OTHER INFORMATION: X is H or Y
<220> FEATURE:
<221> NAME/KEY: MISC_FEATURE
<222> LOCATION: (132)..(132)
<223> OTHER INFORMATION: X is H or R
<220> FEATURE:
<221> NAME/KEY: MISC_FEATURE
<222> LOCATION: (145)..(145)
<223> OTHER INFORMATION: X is Q or R
<220> FEATURE:
<221> NAME/KEY: MISC_FEATURE
<222> LOCATION: (148)..(148)
<223> OTHER INFORMATION: X is I or L
<220> FEATURE:
<221> NAME/KEY: MISC_FEATURE
<222> LOCATION: (149)..(149)
<223> OTHER INFORMATION: X is R or N
<220> FEATURE:
<221> NAME/KEY: MISC_FEATURE
<222> LOCATION: (150)..(150)
<223> OTHER INFORMATION: X is A, D or N
<220> FEATURE:
<221> NAME/KEY: MISC_FEATURE
<222> LOCATION: (151)..(151)
<223> OTHER INFORMATION: X is D or E
<220> FEATURE:
<221> NAME/KEY: MISC_FEATURE
<222> LOCATION: (158)..(158)
<223> OTHER INFORMATION: X is I or V
<220> FEATURE:
<221> NAME/KEY: MISC_FEATURE
<222> LOCATION: (166)..(166)
<223> OTHER INFORMATION: X is D or V
<220> FEATURE:
<221> NAME/KEY: MISC_FEATURE
<222> LOCATION: (170)..(170)
<223> OTHER INFORMATION: X is G or V
```

<400> SEQUENCE: 14

Trp Thr Gly Val Asn Pro Thr Xaa Ala Asn Cys Gln Xaa Xaa Xaa Ser
1               5                   10                  15

Ser Glu Ser Asn Asp Cys Lys Leu Ile Leu Thr Leu Val Lys Thr Gly
            20                  25                  30

Ala Leu Val Thr Ala Phe Val Tyr Val Ile Gly Val Ser Asn Xaa Phe
        35                  40                  45

Asn Met Leu Thr Thr Xaa Xaa Asn Ile Asn Phe Thr Ala Glu Leu Phe
    50                  55                  60

Phe Asp Ser Xaa Gly Asn Leu Leu Thr Xaa Leu Ser Ser Leu Lys Thr
65                  70                  75                  80

Pro Leu Asn His Lys Ser Gly Gln Asn Met Ala Thr Gly Ala Xaa Thr
                85                  90                  95

Asn Ala Lys Xaa Phe Met Pro Ser Thr Thr Ala Tyr Pro Phe Asn Xaa
            100                 105                 110

Asn Ser Arg Glu Xaa Xaa Asn Tyr Ile Tyr Gly Thr Cys Xaa Tyr Thr
            115                 120                 125

Ala Ser Asp Xaa Thr Ala Phe Pro Ile Asp Ile Ser Val Met Leu Asn
            130                 135                 140

Xaa Arg Ala Xaa Xaa Xaa Xaa Thr Ser Tyr Cys Ile Arg Xaa Thr Trp
145                 150                 155                 160

Ser Trp Asn Thr Gly Xaa Ala Pro Glu Xaa Gln Thr Ser Ala Thr Thr
                165                 170                 175

Leu Val Thr Ser Pro Phe Thr Phe Tyr Tyr Ile Arg Glu Asp Asp
            180                 185                 190

<210> SEQ ID NO 15
<211> LENGTH: 319
<212> TYPE: PRT
<213> ORGANISM: Homo sapiens

<400> SEQUENCE: 15

Met Ala Lys Arg Ala Arg Leu Ser Thr Ser Phe Asn Pro Val Tyr Pro
1               5                   10                  15

Tyr Glu Asp Glu Ser Ser Ser Gln His Pro Phe Ile Asn Pro Gly Phe
            20                  25                  30

Ile Ser Pro Asp Gly Phe Thr Gln Ser Pro Asn Gly Val Leu Ser Leu
        35                  40                  45

Lys Cys Val Asn Pro Leu Thr Thr Ala Ser Gly Ser Leu Gln Leu Lys
    50                  55                  60

Val Gly Ser Gly Leu Thr Val Asp Thr Thr Asp Gly Ser Leu Glu Glu
65                  70                  75                  80

Asn Ile Lys Val Asn Thr Pro Leu Thr Lys Ser Asn His Ser Ile Asn
                85                  90                  95

Leu Pro Ile Gly Asn Gly Leu Gln Ile Glu Gln Asn Lys Leu Cys Ser
            100                 105                 110

Lys Leu Gly Asn Gly Leu Thr Phe Asp Ser Ser Asn Ser Ile Ala Leu
            115                 120                 125

Lys Asn Asn Thr Leu Trp Thr Gly Pro Lys Pro Glu Ala Asn Cys Ile
            130                 135                 140

Ile Glu Tyr Gly Lys Gln Asn Pro Asp Ser Lys Leu Thr Leu Ile Leu
145                 150                 155                 160

Val Lys Asn Gly Gly Ile Val Asn Gly Tyr Val Thr Leu Met Gly Ala
                165                 170                 175

```
Ser Asp Tyr Val Asn Thr Leu Phe Lys Asn Lys Asn Val Ser Ile Asn
            180                 185                 190

Val Glu Leu Tyr Phe Asp Ala Thr Gly His Ile Leu Pro Asp Ser Ser
        195                 200                 205

Ser Leu Lys Thr Asp Leu Glu Leu Lys Tyr Lys Gln Thr Ala Asp Phe
    210                 215                 220

Ser Ala Arg Gly Phe Met Pro Ser Thr Thr Ala Tyr Pro Phe Val Leu
225                 230                 235                 240

Pro Asn Ala Gly Thr His Asn Glu Asn Tyr Ile Phe Gly Gln Cys Tyr
                245                 250                 255

Tyr Lys Ala Ser Asp Gly Ala Leu Phe Pro Leu Glu Val Thr Val Met
            260                 265                 270

Leu Asn Lys Arg Leu Pro Asp Ser Arg Thr Ser Tyr Val Met Thr Phe
        275                 280                 285

Leu Trp Ser Leu Asn Ala Gly Leu Ala Pro Glu Thr Thr Gln Ala Thr
    290                 295                 300

Leu Ile Thr Ser Pro Phe Thr Phe Ser Tyr Ile Arg Glu Asp Asp
305                 310                 315

<210> SEQ ID NO 16
<211> LENGTH: 325
<212> TYPE: PRT
<213> ORGANISM: Homo sapiens

<400> SEQUENCE: 16

Met Thr Lys Arg Val Arg Leu Ser Asp Ser Phe Asn Pro Val Tyr Pro
1               5                   10                  15

Tyr Glu Asp Glu Ser Thr Ser Gln His Pro Phe Ile Asn Pro Gly Phe
            20                  25                  30

Ile Ser Pro Asn Gly Phe Thr Gln Ser Pro Asp Gly Val Leu Thr Leu
        35                  40                  45

Lys Cys Leu Thr Pro Leu Thr Thr Thr Gly Gly Ser Leu Gln Leu Lys
    50                  55                  60

Val Gly Gly Gly Leu Thr Ile Asp Asp Thr Asp Gly Phe Leu Lys Glu
65                  70                  75                  80

Asn Ile Ser Ala Thr Thr Pro Leu Val Lys Thr Gly His Ser Ile Gly
                85                  90                  95

Leu Ser Leu Gly Pro Gly Leu Gly Thr Asn Glu Asn Lys Leu Cys Ala
            100                 105                 110

Lys Leu Gly Glu Gly Leu Thr Phe Asn Ser Asn Asn Ile Cys Ile Asn
        115                 120                 125

Asp Asn Ile Asn Thr Leu Trp Thr Gly Val Asn Pro Thr Arg Ala Asn
    130                 135                 140

Cys Gln Ile Met Ala Ser Ser Glu Ser Asn Asp Cys Lys Leu Ile Leu
145                 150                 155                 160

Thr Leu Val Lys Thr Gly Ala Leu Val Thr Ala Phe Val Tyr Val Ile
                165                 170                 175

Gly Val Ser Asn Asp Phe Asn Met Leu Thr Thr His Lys Asn Ile Asn
            180                 185                 190

Phe Thr Ala Glu Leu Phe Asp Ser Thr Gly Asn Leu Leu Thr Ser
        195                 200                 205

Leu Ser Ser Leu Lys Thr Pro Leu Asn His Lys Ser Gly Gln Asn Met
    210                 215                 220

Ala Thr Gly Ala Leu Thr Asn Ala Lys Gly Phe Met Pro Ser Thr Thr
225                 230                 235                 240
```

```
Ala Tyr Pro Phe Asn Val Asn Ser Arg Glu Lys Glu Asn Tyr Ile Tyr
                245                 250                 255

Gly Thr Cys Tyr Tyr Thr Ala Ser Asp His Thr Ala Phe Pro Ile Asp
            260                 265                 270

Ile Ser Val Met Leu Asn Gln Arg Ala Leu Asn Asn Glu Thr Ser Tyr
        275                 280                 285

Cys Ile Arg Val Thr Trp Ser Trp Asn Thr Gly Val Ala Pro Glu Val
    290                 295                 300

Gln Thr Ser Ala Thr Thr Leu Val Thr Ser Pro Phe Thr Phe Tyr Tyr
305                 310                 315                 320

Ile Arg Glu Asp Asp
                325

<210> SEQ ID NO 17
<211> LENGTH: 325
<212> TYPE: PRT
<213> ORGANISM: Homo sapiens

<400> SEQUENCE: 17

Met Thr Lys Arg Val Arg Leu Ser Asp Ser Phe Asn Pro Val Tyr Pro
1               5                   10                  15

Tyr Glu Asp Glu Ser Thr Ser Gln His Pro Phe Ile Asn Pro Gly Phe
            20                  25                  30

Ile Ser Pro Asn Gly Phe Thr Gln Ser Pro Asn Gly Val Leu Thr Leu
        35                  40                  45

Lys Cys Leu Thr Pro Leu Thr Thr Thr Gly Gly Ser Leu Gln Leu Lys
    50                  55                  60

Val Gly Gly Gly Leu Thr Val Asp Asp Thr Asn Gly Phe Leu Lys Glu
65                  70                  75                  80

Asn Ile Ser Ala Thr Thr Pro Leu Val Lys Thr Gly His Ser Ile Gly
                85                  90                  95

Leu Pro Leu Gly Ala Gly Leu Gly Thr Asn Glu Asn Lys Leu Cys Ile
            100                 105                 110

Lys Leu Gly Gln Gly Leu Thr Phe Asn Ser Asn Asn Ile Cys Ile Asp
        115                 120                 125

Asp Asn Ile Asn Thr Leu Trp Thr Gly Val Asn Pro Thr Glu Ala Asn
    130                 135                 140

Cys Gln Ile Met Asn Ser Ser Glu Ser Asn Asp Cys Lys Leu Ile Leu
145                 150                 155                 160

Thr Leu Val Lys Thr Gly Ala Leu Val Thr Ala Phe Val Tyr Val Ile
                165                 170                 175

Gly Val Ser Asn Asn Phe Asn Met Leu Thr Thr His Arg Asn Ile Asn
            180                 185                 190

Phe Thr Ala Glu Leu Phe Phe Asp Ser Thr Gly Asn Leu Leu Thr Arg
        195                 200                 205

Leu Ser Ser Leu Lys Thr Pro Leu Asn His Lys Ser Gly Gln Asn Met
    210                 215                 220

Ala Thr Gly Ala Ile Thr Asn Ala Lys Gly Phe Met Pro Ser Thr Thr
225                 230                 235                 240

Ala Tyr Pro Phe Asn Asp Asn Ser Arg Glu Lys Glu Asn Tyr Ile Tyr
                245                 250                 255

Gly Thr Cys Tyr Tyr Thr Ala Ser Asp Arg Thr Ala Phe Pro Ile Asp
            260                 265                 270

Ile Ser Val Met Leu Asn Arg Arg Ala Ile Asn Asp Glu Thr Ser Tyr
```

```
            275                 280                 285
Cys Ile Arg Ile Thr Trp Ser Trp Asn Thr Gly Asp Ala Pro Glu Val
    290                 295                 300
Gln Thr Ser Ala Thr Thr Leu Val Thr Ser Pro Phe Thr Phe Tyr Tyr
305                 310                 315                 320
Ile Arg Glu Asp Asp
                325

<210> SEQ ID NO 18
<211> LENGTH: 325
<212> TYPE: PRT
<213> ORGANISM: Homo sapiens

<400> SEQUENCE: 18

Met Thr Lys Arg Val Arg Leu Ser Asp Ser Phe Asn Pro Val Tyr Pro
1               5                   10                  15
Tyr Glu Asp Glu Ser Thr Ser Gln His Pro Phe Ile Asn Pro Gly Phe
                20                  25                  30
Ile Ser Pro Asn Gly Phe Thr Gln Ser Pro Asp Gly Val Leu Thr Leu
            35                  40                  45
Lys Cys Leu Thr Pro Leu Thr Thr Thr Gly Gly Ser Leu Gln Leu Lys
50                  55                  60
Val Gly Gly Gly Leu Thr Val Asp Asp Thr Asp Gly Thr Leu Gln Glu
65                  70                  75                  80
Asn Ile Gly Ala Thr Thr Pro Leu Val Lys Thr Gly His Ser Ile Gly
                85                  90                  95
Leu Ser Leu Gly Ala Gly Leu Gly Thr Asp Glu Asn Lys Leu Cys Thr
                100                 105                 110
Lys Leu Gly Glu Gly Leu Thr Phe Asn Ser Asn Asn Ile Cys Ile Asp
            115                 120                 125
Asp Asn Ile Asn Thr Leu Trp Thr Gly Val Asn Pro Thr Glu Ala Asn
130                 135                 140
Cys Gln Met Met Asp Ser Ser Glu Ser Asn Asp Cys Lys Leu Ile Leu
145                 150                 155                 160
Thr Leu Val Lys Thr Gly Ala Leu Val Thr Ala Phe Val Tyr Val Ile
                165                 170                 175
Gly Val Ser Asn Asn Phe Asn Met Leu Thr Thr Tyr Arg Asn Ile Asn
                180                 185                 190
Phe Thr Ala Glu Leu Phe Phe Asp Ser Ala Gly Asn Leu Leu Thr Ser
            195                 200                 205
Leu Ser Ser Leu Lys Thr Pro Leu Asn His Lys Ser Gly Gln Asn Met
210                 215                 220
Ala Thr Gly Ala Ile Thr Asn Ala Lys Ser Phe Met Pro Ser Thr Thr
225                 230                 235                 240
Ala Tyr Pro Phe Asn Asn Ser Arg Glu Lys Glu Asn Tyr Ile Tyr
                245                 250                 255
Gly Thr Cys His Tyr Thr Ala Ser Asp His Thr Ala Phe Pro Ile Asp
                260                 265                 270
Ile Ser Val Met Leu Asn Gln Arg Ala Ile Arg Ala Asp Thr Ser Tyr
            275                 280                 285
Cys Ile Arg Ile Thr Trp Ser Trp Asn Thr Gly Asp Ala Pro Glu Gly
    290                 295                 300
Gln Thr Ser Ala Thr Thr Leu Val Thr Ser Pro Phe Thr Phe Tyr Tyr
305                 310                 315                 320
```

```
Ile Arg Glu Asp Asp
                325

<210> SEQ ID NO 19
<211> LENGTH: 323
<212> TYPE: PRT
<213> ORGANISM: Homo sapiens

<400> SEQUENCE: 19

Met Thr Lys Arg Val Arg Leu Ser Asp Ser Phe Asn Pro Val Tyr Pro
1               5                   10                  15

Tyr Glu Asp Glu Ser Thr Ser Gln His Pro Phe Ile Asn Pro Gly Phe
            20                  25                  30

Ile Ser Pro Asn Gly Phe Thr Gln Ser Pro Asp Gly Val Leu Thr Leu
        35                  40                  45

Lys Cys Leu Thr Pro Leu Thr Thr Thr Gly Gly Ser Leu Gln Leu Lys
    50                  55                  60

Val Gly Gly Gly Leu Thr Val Asp Asp Thr Asp Gly Thr Leu Gln Glu
65                  70                  75                  80

Asn Ile Gly Ala Thr Thr Pro Leu Val Lys Thr Gly His Ser Ile Gly
                85                  90                  95

Leu Ser Leu Gly Ala Gly Leu Gly Thr Asp Glu Asn Lys Leu Cys Thr
            100                 105                 110

Lys Leu Gly Glu Gly Leu Thr Phe Asn Ser Asn Ile Cys Ile Asp
        115                 120                 125

Asp Asn Ile Asn Thr Leu Trp Thr Gly Val Asn Pro Thr Glu Ala Asn
    130                 135                 140

Cys Gln Met Met Asp Ser Ser Glu Ser Asn Asp Cys Lys Leu Ile Leu
145                 150                 155                 160

Thr Leu Val Lys Thr Gly Ala Leu Val Thr Ala Phe Val Tyr Val Ile
                165                 170                 175

Gly Val Ser Asn Asn Phe Asn Met Leu Thr Thr Tyr Arg Asn Ile Asn
            180                 185                 190

Phe Thr Ala Glu Leu Phe Phe Asp Ser Ala Gly Asn Leu Leu Thr Ser
        195                 200                 205

Leu Ser Ser Leu Lys Thr Pro Leu Asn His Lys Ser Gly Gln Asn Met
    210                 215                 220

Ala Thr Gly Ala Ile Thr Asn Ala Lys Ser Phe Met Pro Ser Thr Thr
225                 230                 235                 240

Ala Tyr Pro Phe Asn Asn Asn Ser Arg Glu Asn Tyr Ile Tyr Gly Thr
                245                 250                 255

Cys His Tyr Thr Ala Ser Asp His Thr Ala Phe Pro Ile Asp Ile Ser
            260                 265                 270

Val Met Leu Asn Gln Arg Ala Ile Arg Ala Asp Thr Ser Tyr Cys Ile
        275                 280                 285

Arg Ile Thr Trp Ser Trp Asn Thr Gly Asp Ala Pro Glu Gly Gln Thr
    290                 295                 300

Ser Ala Thr Thr Leu Val Thr Ser Pro Phe Thr Phe Tyr Tyr Ile Arg
305                 310                 315                 320

Glu Asp Asp

<210> SEQ ID NO 20
<211> LENGTH: 246
<212> TYPE: PRT
<213> ORGANISM: Homo sapiens
```

```
<400> SEQUENCE: 20

Met Lys Val Ser Ala Leu Lys Glu Lys Val Ser Ala Leu Lys Glu Lys
1               5                   10                  15

Val Ser Ala Leu Lys Glu Lys Val Ser Ala Leu Lys Glu Lys Val Ser
            20                  25                  30

Ala Leu Lys Glu Gly Ser Gly Gly Ser Gly Gly Ser Gly Gly Ser Gly
        35                  40                  45

Gly Ser Asn Ser Ile Ala Leu Lys Asn Thr Leu Trp Thr Gly Pro
    50                  55                  60

Lys Pro Glu Ala Asn Cys Ile Ile Glu Tyr Gly Lys Gln Asn Pro Asp
65                  70                  75                  80

Ser Lys Leu Thr Leu Ile Leu Val Lys Asn Gly Gly Ile Val Asn Gly
                85                  90                  95

Tyr Val Thr Leu Met Gly Ala Ser Asp Tyr Val Asn Thr Leu Phe Lys
                100                 105                 110

Asn Lys Asn Val Ser Ile Asn Val Glu Leu Tyr Phe Asp Ala Thr Gly
            115                 120                 125

His Ile Leu Pro Asp Ser Ser Leu Lys Thr Asp Leu Glu Leu Lys
    130                 135                 140

Tyr Lys Gln Thr Ala Asp Phe Ser Ala Arg Gly Phe Met Pro Ser Thr
145                 150                 155                 160

Thr Ala Tyr Pro Phe Val Leu Pro Asn Ala Gly Thr His Asn Glu Asn
                165                 170                 175

Tyr Ile Phe Gly Gln Cys Tyr Tyr Lys Ala Ser Asp Gly Ala Leu Phe
            180                 185                 190

Pro Leu Glu Val Thr Val Met Leu Asn Lys Arg Leu Pro Asp Ser Arg
        195                 200                 205

Thr Ser Tyr Val Met Thr Phe Leu Trp Ser Leu Asn Ala Gly Leu Ala
    210                 215                 220

Pro Glu Thr Thr Gln Ala Thr Leu Ile Thr Ser Pro Phe Thr Phe Ser
225                 230                 235                 240

Tyr Ile Arg Glu Asp Asp
                245

<210> SEQ ID NO 21
<211> LENGTH: 257
<212> TYPE: PRT
<213> ORGANISM: Homo sapiens

<400> SEQUENCE: 21

Met Arg Gly Ser His His His His His His Gly Ser Lys Val Ser Ala
1               5                   10                  15

Leu Lys Glu Lys Val Ser Ala Leu Lys Glu Lys Val Ser Ala Leu Lys
            20                  25                  30

Glu Lys Val Ser Ala Leu Lys Glu Lys Val Ser Ala Leu Lys Glu Gly
        35                  40                  45

Ser Gly Gly Ser Gly Gly Ser Gly Gly Ser Asn Ser Ile
    50                  55                  60

Ala Leu Lys Asn Asn Thr Leu Trp Thr Gly Pro Lys Pro Glu Ala Asn
65                  70                  75                  80

Cys Ile Ile Glu Tyr Gly Lys Gln Asn Pro Asp Ser Lys Leu Thr Leu
                85                  90                  95

Ile Leu Val Lys Asn Gly Gly Ile Val Asn Gly Tyr Val Thr Leu Met
            100                 105                 110
```

Gly Ala Ser Asp Tyr Val Asn Thr Leu Phe Lys Asn Lys Asn Val Ser
            115                 120                 125

Ile Asn Val Glu Leu Tyr Phe Asp Ala Thr Gly His Ile Leu Pro Asp
    130                 135                 140

Ser Ser Ser Leu Lys Thr Asp Leu Glu Leu Lys Tyr Lys Gln Thr Ala
145                 150                 155                 160

Asp Phe Ser Ala Arg Gly Phe Met Pro Ser Thr Thr Ala Tyr Pro Phe
                165                 170                 175

Val Leu Pro Asn Ala Gly Thr His Asn Glu Asn Tyr Ile Phe Gly Gln
            180                 185                 190

Cys Tyr Tyr Lys Ala Ser Asp Gly Ala Leu Phe Pro Leu Glu Val Thr
        195                 200                 205

Val Met Leu Asn Lys Arg Leu Pro Asp Ser Arg Thr Ser Tyr Val Met
    210                 215                 220

Thr Phe Leu Trp Ser Leu Asn Ala Gly Leu Ala Pro Glu Thr Thr Gln
225                 230                 235                 240

Ala Thr Leu Ile Thr Ser Pro Phe Thr Phe Ser Tyr Ile Arg Glu Asp
                245                 250                 255

Asp

<210> SEQ ID NO 22
<211> LENGTH: 7
<212> TYPE: PRT
<213> ORGANISM: Homo sapiens

<400> SEQUENCE: 22

Glu Val Ser Ala Leu Glu Lys
1               5

<210> SEQ ID NO 23
<211> LENGTH: 7
<212> TYPE: PRT
<213> ORGANISM: Homo sapiens

<400> SEQUENCE: 23

Lys Val Ser Ala Leu Lys Glu
1               5

<210> SEQ ID NO 24
<211> LENGTH: 16
<212> TYPE: PRT
<213> ORGANISM: Artificial Sequence
<220> FEATURE:
<223> OTHER INFORMATION: Synthetic

<400> SEQUENCE: 24

Asp Phe Leu Val Ile Tyr Ile Glu Glu Ala His Ala Ser Asp Gly Trp
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(6)
<223> OTHER INFORMATION: X can be any amino acid
<220> FEATURE:
<221> NAME/KEY: MISC_FEATURE
<222> LOCATION: (9)..(9)
<223> OTHER INFORMATION: X can be any amino acid

```
<220> FEATURE:
<221> NAME/KEY: MISC_FEATURE
<222> LOCATION: (13)..(14)
<223> OTHER INFORMATION: X can be any amino acid

<400> SEQUENCE: 25

Ala Asp Phe Leu Xaa Xaa Tyr Ile Xaa Glu Ala His Xaa Xaa Asp Gly
1               5                   10                  15

Trp

<210> SEQ ID NO 26
<211> LENGTH: 20
<212> TYPE: PRT
<213> ORGANISM: Artificial Sequence
<220> FEATURE:
<223> OTHER INFORMATION: Synthetic

<400> SEQUENCE: 26

Gln Gly Pro Lys Glu Pro Phe Arg Asp Tyr Val Asp Arg Phe Tyr Lys
1               5                   10                  15

Thr Leu Arg Ala
            20

<210> SEQ ID NO 27
<211> LENGTH: 25
<212> TYPE: PRT
<213> ORGANISM: Artificial Sequence
<220> FEATURE:
<223> OTHER INFORMATION: Synthetic

<400> SEQUENCE: 27

His Met Lys Gln Leu Asp Val Glu Glu Leu Ser Asn Tyr His Leu Asn
1               5                   10                  15

Val Ala Arg Leu Lys Val Gly Glu Arg
            20                  25

<210> SEQ ID NO 28
<211> LENGTH: 32
<212> TYPE: PRT
<213> ORGANISM: Artificial Sequence
<220> FEATURE:
<223> OTHER INFORMATION: Synthetic

<400> SEQUENCE: 28

Gly Val Thr Gln Leu Met Arg Glu Met Leu Gln Leu Ile Lys Phe Gln
1               5                   10                  15

Phe Ser Leu Asn Tyr Gln Glu Glu Ser Leu Ser Tyr Gln Arg Leu Val
            20                  25                  30

<210> SEQ ID NO 29
<211> LENGTH: 19
<212> TYPE: RNA
<213> ORGANISM: Artificial Sequence
<220> FEATURE:
<223> OTHER INFORMATION: Synthetic

<400> SEQUENCE: 29
caauauaccu guaguagaa                                              19

<210> SEQ ID NO 30
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 30
gagaggaucu guccaagaa                                                     19

<210> SEQ ID NO 31
<211> LENGTH: 19
<212> TYPE: RNA
<213> ORGANISM: Artificial Sequence
<220> FEATURE:
<223> OTHER INFORMATION: Synthetic

<400> SEQUENCE: 31
ccuuagagcu acgcauuaa                                                     19

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32
ccaguguucu accuaaaua                                                     19

<210> SEQ ID NO 33
<211> LENGTH: 47
<212> TYPE: DNA
<213> ORGANISM: Artificial Sequence
<220> FEATURE:
<223> OTHER INFORMATION: Synthetic

<400> SEQUENCE: 33
ctgatgaatt cttgatcagg ggttttaagt cttaaatgtg ttaatcc                      47

<210> SEQ ID NO 34
<211> LENGTH: 51
<212> TYPE: DNA
<213> ORGANISM: Artificial Sequence
<220> FEATURE:
<223> OTHER INFORMATION: Synthetic

<400> SEQUENCE: 34
ttactgatga attcttgatc aggctccctc caacttaaag tgggaagtgg t                 51

<210> SEQ ID NO 35
<211> LENGTH: 47
<212> TYPE: DNA
<213> ORGANISM: Artificial Sequence
<220> FEATURE:
<223> OTHER INFORMATION: Synthetic

<400> SEQUENCE: 35
ttactgatga attctggatc cttagaagaa aacatcaaag ttaacac                      47

<210> SEQ ID NO 36
<211> LENGTH: 51
<212> TYPE: DNA
<213> ORGANISM: Artificial Sequence
<220> FEATURE:
<223> OTHER INFORMATION: Synthetic

<400> SEQUENCE: 36
ttactgatga attctggatc ccattctata aatttaccaa taggaaacgg t                 51

<210> SEQ ID NO 37
```

<211> LENGTH: 50
<212> TYPE: DNA
<213> ORGANISM: Artificial Sequence
<220> FEATURE:
<223> OTHER INFORMATION: Synthetic

<400> SEQUENCE: 37
ttactgatga attctggatc caacaaactt tgcagtaaac tcggaaatgg       50

<210> SEQ ID NO 38
<211> LENGTH: 31
<212> TYPE: DNA
<213> ORGANISM: Artificial Sequence
<220> FEATURE:
<223> OTHER INFORMATION: Synthetic

<400> SEQUENCE: 38
accatcacgg atccaattct attgcactga a                            31

<210> SEQ ID NO 39
<211> LENGTH: 35
<212> TYPE: DNA
<213> ORGANISM: Artificial Sequence
<220> FEATURE:
<223> OTHER INFORMATION: Synthetic

<400> SEQUENCE: 39
agctaattaa gcttagtcat cttctctaat atagg                        35

<210> SEQ ID NO 40
<211> LENGTH: 110
<212> TYPE: DNA
<213> ORGANISM: Artificial Sequence
<220> FEATURE:
<223> OTHER INFORMATION: Synthetic

<400> SEQUENCE: 40
atcaaaggta agcgctttaa aggagaaagt ttcagcactt aaagaaaagg tatccgcttt       60
aaaggagaaa gtttcagcac ttaaagaaaa agtgtccgct ctgaaagaag               110

<210> SEQ ID NO 41
<211> LENGTH: 111
<212> TYPE: DNA
<213> ORGANISM: Artificial Sequence
<220> FEATURE:
<223> OTHER INFORMATION: Synthetic

<400> SEQUENCE: 41
gatccttctt tcagagcgga cacttttcct ttaagtgctg aaactttctc ctttaaagcg       60 gataccttt ctttaagtgc tgaaactttc tcctttaaag cgcttacctt t              111

<210> SEQ ID NO 42
<211> LENGTH: 110
<212> TYPE: DNA
<213> ORGANISM: Artificial Sequence
<220> FEATURE:
<223> OTHER INFORMATION: Synthetic

<400> SEQUENCE: 42
atcagaggta agcgctttag agaaagaagt ttcagcactt gagaaggagg tatccgcttt       60
agagaaagaa gtttcagcac ttgagaagga agtgtccgct ctggaaaaag              110

<210> SEQ ID NO 43
<211> LENGTH: 111

```
<212> TYPE: DNA
<213> ORGANISM: Artificial Sequence
<220> FEATURE:
<223> OTHER INFORMATION: Synthetic

<400> SEQUENCE: 43
gatccttttt ccagagcgga cacttccttc tcaagtgctg aaacttcttt ctctaaagcg    60
gatacctcct tctcaagtgc tgaaacttct ttctctaaag cgcttacctc t            111

<210> SEQ ID NO 44
<211> LENGTH: 90
<212> TYPE: DNA
<213> ORGANISM: Artificial Sequence
<220> FEATURE:
<223> OTHER INFORMATION: Synthetic

<400> SEQUENCE: 44
atctaggatc cggtggcggt tctggcggtg gctccggtgg cggttctaac aaactttgca    60
gtaaactcgg aaatggtctt acatttgact                                    90

<210> SEQ ID NO 45
<211> LENGTH: 35
<212> TYPE: DNA
<213> ORGANISM: Artificial Sequence
<220> FEATURE:
<223> OTHER INFORMATION: Synthetic

<400> SEQUENCE: 45
agctaattaa gcttagtcat cttctctaat atagg                              35

<210> SEQ ID NO 46
<211> LENGTH: 79
<212> TYPE: DNA
<213> ORGANISM: Artificial Sequence
<220> FEATURE:
<223> OTHER INFORMATION: Synthetic

<400> SEQUENCE: 46
ttattgctac tggatccggt ggcggttctg gcggtggctc cggtggcggt tctaattcta    60
ttgcactgaa aaataacac                                                79

<210> SEQ ID NO 47
<211> LENGTH: 35
<212> TYPE: DNA
<213> ORGANISM: Artificial Sequence
<220> FEATURE:
<223> OTHER INFORMATION: Synthetic

<400> SEQUENCE: 47
agctaattaa gcttagtcat cttctctaat atagg                              35

<210> SEQ ID NO 48
<211> LENGTH: 41
<212> TYPE: DNA
<213> ORGANISM: Artificial Sequence
<220> FEATURE:
<223> OTHER INFORMATION: Synthetic

<400> SEQUENCE: 48
gacacggaaa ccggtcctcc aactgtgcct tttcttactc c                       41

<210> SEQ ID NO 49
<211> LENGTH: 60
<212> TYPE: DNA
```

```
<213> ORGANISM: Artificial Sequence
<220> FEATURE:
<223> OTHER INFORMATION: Synthetic

<400> SEQUENCE: 49
gcagttggct tctggttttg gacctgtcca caaagttagc ttatcattat ttttgtttcc    60

<210> SEQ ID NO 50
<211> LENGTH: 60
<212> TYPE: DNA
<213> ORGANISM: Artificial Sequence
<220> FEATURE:
<223> OTHER INFORMATION: Synthetic

<400> SEQUENCE: 50
ggaaacaaaa ataatgataa gctaactttg tggacaggtc caaaaccaga agccaactgc    60

<210> SEQ ID NO 51
<211> LENGTH: 89
<212> TYPE: DNA
<213> ORGANISM: Artificial Sequence
<220> FEATURE:
<223> OTHER INFORMATION: Synthetic

<400> SEQUENCE: 51
tgaaaaataa acacgttgaa acataacaca actagttctt tattcttggg cattttagtc    60
atcttctcta ataggaaa aggtaaatg                                        89

<210> SEQ ID NO 52
<211> LENGTH: 89
<212> TYPE: DNA
<213> ORGANISM: Artificial Sequence
<220> FEATURE:
<223> OTHER INFORMATION: Synthetic

<400> SEQUENCE: 52
catttacctt ttcctatatt agagaagatg actaaaatgc ccaagaataa agaactagtt    60
gtgttatgtt tcaacgtgtt tattttca                                       89

<210> SEQ ID NO 53
<211> LENGTH: 46
<212> TYPE: DNA
<213> ORGANISM: Artificial Sequence
<220> FEATURE:
<223> OTHER INFORMATION: Synthetic

<400> SEQUENCE: 53
atacttaggg taccaatcga tatggccacg tgggttctgt ggtccc                   46

<210> SEQ ID NO 54
<211> LENGTH: 100
<212> TYPE: DNA
<213> ORGANISM: Artificial Sequence
<220> FEATURE:
<223> OTHER INFORMATION: Synthetic

<400> SEQUENCE: 54
acggaaaccg gtcctccaac tgtgcctttt cttactcctc cctttgtatc ccccaatggg    60
tttcaagaga gtcccctgg ggttttaagt cttaaatgtg                          100

<210> SEQ ID NO 55
<211> LENGTH: 88
<212> TYPE: DNA
<213> ORGANISM: Artificial Sequence
```

```
<220> FEATURE:
<223> OTHER INFORMATION: Synthetic

<400> SEQUENCE: 55
gaaaaataaa cacgttgaaa cataacacac tcgagtcttt attcttgggc attttagtca    60
tcttctctaa tataggaaaa ggtaaatg                                       88

<210> SEQ ID NO 56
<211> LENGTH: 88
<212> TYPE: DNA
<213> ORGANISM: Artificial Sequence
<220> FEATURE:
<223> OTHER INFORMATION: Synthetic

<400> SEQUENCE: 56
catttacctt ttcctatatt agagaagatg actaaaatgc ccaagaataa agactcgagt    60
gtgttatgtt tcaacgtgtt tattttc                                        88

<210> SEQ ID NO 57
<211> LENGTH: 46
<212> TYPE: DNA
<213> ORGANISM: Artificial Sequence
<220> FEATURE:
<223> OTHER INFORMATION: Synthetic

<400> SEQUENCE: 57
atacttaggg taccaatcga tatggccacg tgggttctgt ggtccc                   46

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
atgacggcta ggaacaccac                                                20

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
tcaggtacat tggaaacatg aaa                                            23

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
tgcaccacca actgcttagc                                                20

<210> SEQ ID NO 61
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 61
ggcatggact gtggtcatga                                                    20

<210> SEQ ID NO 62
<211> LENGTH: 4
<212> TYPE: PRT
<213> ORGANISM: Artificial Sequence
<220> FEATURE:
<223> OTHER INFORMATION: Synthetic

<400> SEQUENCE: 62

Gly Gly Gly Ser
1
```